US009925231B2

(12) United States Patent
Comiskey et al.

(10) Patent No.: US 9,925,231 B2
(45) Date of Patent: *Mar. 27, 2018

(54) FORMULATIONS OF GUANYLATE CYCLASE C AGONISTS AND METHODS OF USE

(71) Applicant: SYNERGY PHARMACEUTICALS, INC., New York, NY (US)

(72) Inventors: Stephen Comiskey, Doylestown, PA (US); Rong Feng, Langhorne, PA (US); John Foss, Doylestown, PA (US); Kunwar Shailubhai, Audubon, PA (US)

(73) Assignee: SYNERGY PHARMACEUTICALS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,631

(22) Filed: Mar. 23, 2017

(65) Prior Publication Data

US 2017/0202903 A1 Jul. 20, 2017

Related U.S. Application Data

(63) Continuation of application No. 14/845,644, filed on Sep. 4, 2015, now Pat. No. 9,610,321, which is a continuation of application No. 14/661,299, filed on Mar. 18, 2015, now abandoned, which is a continuation of application No. 13/421,769, filed on Mar. 15, 2012, now Pat. No. 9,616,097, which is a continuation-in-part of application No. PCT/US2011/051805, filed on Sep. 15, 2011.

(60) Provisional application No. 61/392,186, filed on Oct. 12, 2010, provisional application No. 61/387,636, filed on Sep. 29, 2010, provisional application No. 61/383,156, filed on Sep. 15, 2010.

(51) Int. Cl.

| A61K 38/10 | (2006.01) |
|---|---|
| A61K 47/12 | (2006.01) |
| A61K 47/38 | (2006.01) |
| A61K 9/16 | (2006.01) |
| A61K 45/06 | (2006.01) |
| A61K 9/48 | (2006.01) |
| C07K 7/08 | (2006.01) |
| C07K 7/64 | (2006.01) |

(52) U.S. Cl.
CPC .......... *A61K 38/10* (2013.01); *A61K 9/1623* (2013.01); *A61K 9/1652* (2013.01); *A61K 9/1676* (2013.01); *A61K 9/4858* (2013.01); *A61K 9/4866* (2013.01); *A61K 45/06* (2013.01); *A61K 47/12* (2013.01); *A61K 47/38* (2013.01); *C07K 7/08* (2013.01); *C07K 7/64* (2013.01)

(58) Field of Classification Search
None
See application file for complete search history.

(56) References Cited

U.S. PATENT DOCUMENTS

| 5,106,834 A | 4/1992 | Bovy et al. |
|---|---|---|
| 5,130,333 A | 7/1992 | Pan et al. |
| 5,489,670 A | 2/1996 | Currie et al. |
| 5,518,888 A | 5/1996 | Waldman et al. |
| 5,578,709 A | 11/1996 | Woiszwillo et al. |
| 5,601,990 A | 2/1997 | Waldman et al. |
| 5,721,238 A | 2/1998 | Heiker et al. |
| 5,731,159 A | 3/1998 | Waldman et al. |
| 5,817,624 A | 10/1998 | Yang et al. |
| 5,879,656 A | 3/1999 | Waldman et al. |
| 5,928,873 A | 7/1999 | Waldman et al. |
| 5,969,097 A | 10/1999 | Wiegand et al. |
| 6,060,037 A | 5/2000 | Waldman et al. |
| 6,235,782 B1 | 5/2001 | Pamukcu et al. |
| 7,041,786 B2 | 5/2006 | Shailubhai et al. |
| 7,067,748 B1 | 7/2006 | Whitmore, Jr. et al. |
| 7,375,083 B2 | 5/2008 | Mickle et al. |
| 7,494,979 B2 | 2/2009 | Currie et al. |
| 7,799,897 B2 | 9/2010 | Jacob et al. |
| 7,879,802 B2 | 2/2011 | Shailubhai et al. |
| 8,034,782 B2 | 10/2011 | Shailubhai |
| 8,114,831 B2 | 2/2012 | Shailubhai et al. |
| 8,207,295 B2 | 6/2012 | Shailubhai et al. |
| 8,357,775 B2 | 1/2013 | Shailubhai et al. |
| 8,367,800 B2 | 2/2013 | Shailubhai |
| 8,497,348 B2 | 7/2013 | Shailubhai et al. |
| 8,569,246 B2 | 10/2013 | Shailubhai |
| 8,637,451 B2 | 1/2014 | Shailubhai et al. |
| 8,664,354 B2 | 3/2014 | Shailubhai |
| 8,716,224 B2 | 5/2014 | Shailubhai et al. |
| 8,901,075 B2 | 12/2014 | Shailubhai et al. |
| 8,969,514 B2 | 3/2015 | Shailubhai |
| 9,238,677 B2 | 1/2016 | Shailubhai et al. |
| 9,266,926 B2 | 2/2016 | Shailubhai et al. |
| 9,486,494 B2 | 11/2016 | Shailubhai |
| 9,545,446 B2 | 1/2017 | Riff et al. |
| 9,610,321 B2 * | 4/2017 | Comiskey ............ A61K 9/1623 |
| 9,616,097 B2 * | 4/2017 | Comiskey ............ A61K 9/1623 |

(Continued)

FOREIGN PATENT DOCUMENTS

| JP | 2009-519343 A | 5/2009 |
|---|---|---|
| JP | 2009-537535 A | 10/2009 |

(Continued)

OTHER PUBLICATIONS

Shailubhai et al., "A randomized, double-blind, u placebo-controlled, single-, ascending-, oral-dose safety, tolerability and pharmacokinetic study of SP-304 in healthy adult human male and female volunteers." Digestive Disease Week. San Diego: 2008.*

(Continued)

*Primary Examiner* — Satyanarayana R Gudibande
*Assistant Examiner* — Jia-Hai Lee
(74) *Attorney, Agent, or Firm* — Cynthia A. Kozakiewicz; Ivor Elrifi

(57) ABSTRACT

The invention provides low-dose formulations of guanylate cyclase-C ("GCC") agonist peptides and methods for their use. The formulations of the invention can be administered either alone or in combination with one or more additional therapeutic agents, preferably an inhibitor of cGMP-dependent phosphodiesterase or a laxative.

12 Claims, 6 Drawing Sheets

(56) References Cited

U.S. PATENT DOCUMENTS

| | | |
|---|---|---|
| 2002/0128176 A1 | 9/2002 | Forssmann et al. |
| 2002/0133168 A1 | 9/2002 | Smeldley et al. |
| 2002/0143015 A1 | 10/2002 | Fryburg et al. |
| 2003/0073628 A1 | 4/2003 | Shailubhai et al. |
| 2004/0015140 A1 | 1/2004 | Shields |
| 2005/0016244 A1 | 1/2005 | Hergemoller |
| 2005/0032684 A1 | 2/2005 | Cetin et al. |
| 2005/0107734 A1 | 5/2005 | Coroneo |
| 2005/0145351 A1 | 7/2005 | Schaible et al. |
| 2005/0266047 A1 | 12/2005 | Tu et al. |
| 2005/0267297 A1 | 12/2005 | Berlin |
| 2006/0086653 A1 | 4/2006 | St. Germain |
| 2006/0094658 A1 | 5/2006 | Currie |
| 2007/0101158 A1 | 5/2007 | Elliott |
| 2008/0137318 A1 | 6/2008 | Rangaraj et al. |
| 2008/0151257 A1 | 6/2008 | Yasuda et al. |
| 2009/0048175 A1 | 2/2009 | Shailubhai et al. |
| 2009/0192083 A1 | 7/2009 | Currie |
| 2009/0253634 A1 | 10/2009 | Currie et al. |
| 2010/0048489 A1 | 2/2010 | Fretzen |
| 2010/0069306 A1 | 3/2010 | Shailubhai et al. |
| 2010/0093635 A1 | 4/2010 | Shailubhai |
| 2010/0120694 A1 | 5/2010 | Shailubhai et al. |
| 2010/0152118 A1 | 6/2010 | Shailubhai |
| 2010/0221329 A1 | 9/2010 | Shailubhai et al. |
| 2012/0196797 A1 | 8/2012 | Currie et al. |
| 2012/0237593 A1 | 9/2012 | Comiskey et al. |
| 2012/0289460 A1 | 11/2012 | Shailubhai |
| 2013/0274204 A1 | 10/2013 | Shailubhai et al. |
| 2014/0024605 A1 | 1/2014 | Shailubhai et al. |
| 2014/0121169 A1 | 5/2014 | Shailubhai et al. |
| 2014/0135274 A1 | 5/2014 | Shailubhai |
| 2014/0187470 A1 | 7/2014 | Jacob et al. |
| 2014/0287002 A1 | 9/2014 | Shailubhai |
| 2014/0329738 A1 | 11/2014 | Shailubhai et al. |
| 2015/0359749 A1 | 12/2015 | Shailubhai et al. |
| 2015/0366935 A1 | 12/2015 | Comiskey et al. |
| 2016/0367623 A1 | 12/2016 | Shailubhai |
| 2017/0202904 A1 | 7/2017 | Comiskey et al. |

FOREIGN PATENT DOCUMENTS

| | | |
|---|---|---|
| JP | 2010-519217 A | 6/2010 |
| WO | WO 1999/026567 A1 | 6/1999 |
| WO | WO 2001/025266 A1 | 4/2001 |
| WO | WO 2002/062369 A2 | 8/2002 |
| WO | WO 2002/078683 A1 | 10/2002 |
| WO | WO 2002/098912 A3 | 12/2002 |
| WO | WO 2004/069165 A2 | 8/2004 |
| WO | WO2005016244 A1 * | 2/2005 |
| WO | WO 2005/087797 A1 | 9/2005 |
| WO | WO 2006/086653 A2 | 8/2006 |
| WO | WO 2007/022531 A2 | 2/2007 |
| WO | WO 2007/070562 A2 | 6/2007 |
| WO | WO 2007/101158 A2 | 9/2007 |
| WO | WO 2007/133796 A2 | 11/2007 |
| WO | WO 2008/102264 A2 | 8/2008 |
| WO | WO 2008/106429 A2 | 9/2008 |
| WO | WO 2008/137318 A1 | 11/2008 |
| WO | WO 2008/151257 A2 | 12/2008 |
| WO | WO 2009/149278 A1 | 12/2009 |
| WO | WO 2009/149279 A2 | 12/2009 |
| WO | WO 2010/009319 A2 | 1/2010 |
| WO | WO 2010/027404 A2 | 3/2010 |
| WO | WO 2010/065751 A2 | 6/2010 |
| WO | WO 2011/020054 A1 | 2/2011 |
| WO | WO 2012/037380 A2 | 3/2012 |
| WO | WO 2013/138352 A1 | 9/2013 |

OTHER PUBLICATIONS

Advisory Committee Briefing document for Merida [sibutramine hydrochloride monohydrate], Abbott, Aug. 13, 2010 (205 pages).

Alrefai, "Cholesterol modulates human intestinal sodium-dependent bile acid transporter," Am. J. Physiol. Gastrointest. Liver Physiol. 288:G978-G985 (2005).

Askling "Colorectal cancer rates among first degree relatives of patients with inflammatory bowel disease: A population-based cohort study" Lancet 357:262-266 (2001).

Bakre et al. "Expression and regulation of the cGMP-binding, cGMP-specific phosphodiesterase (PDE5) in human colonic epithelial cells: role in the induction of cellular refractoriness to the heat-stable enterotoxin peptide" J. Cell Biol. 77:159-167 (2000).

Barbara "A role for inflammation in irritable bowel syndrome": Gut, 51(Suppl. 1): 141-144 (2002).

Basoglu In: Proceedings of the Second Feps Congress, Jun. 29-Jul. 4, 1999, Prague, Czech Republic, If2.cuni.cz/physiolres/feps/basoglu.htm. (3 pages).

Baxter "The natriuretic peptides: An introduction" Basic Res. Cardiol. 99(2):71-75 (2004).

Beltowski "Guanylin and related peptides" J. Physiol. Pharmacol 52(3):351-375 (2001).

Bergers "Extrinsic regulators of epithelial tumor progression: metalloproteinases" Cur. Opin. Gen. and Develop. 10:120-127 (2000).

Bhakdi "Release of interleukin-1 beta associated with potent cytocidal action of staphylococcal alpha-toxin on human monocytes" Infect. Immun. 57(11): 3512-3519 (1989).

Brown "A receptor-mediated pathway for cholesterol homeostasis" Sci. 232:34-47 (1986).

Burnham "Polymers for delivering peptides and proteins" Am. J. Hosp. Pharm. 51:210-218 (1994).

Caliceti "Synthesis and biopharmaceutical characterisation of new poly(hydroxethylaspartamide) copolymers as drug carriers" Biochimica et Biophysics Acta 1528:177-189 (2001).

Camilleri "Management of the irritable bowel syndrome" Gastroentrerol. 120:652-668 (2001).

Carrithers, "Guanylyl cyclase C is a selective marker for metastatic colorectal tumors in human extraintestinal tissues" Proc. Natl. Acad. Sci. USA 93:14827-14832. (1996).

Cermak "Natriuretic peptides increase a K+ conductance in rat mesangial cells" Pfugers Arch. Eur. J. Physiol. 431:571-577 (1996).

Cheng "Defective intracellular transport and processing of CFTR is the molecular basis of most cystic fibrosis" Cell, 63:827-834 (1990).

Chino "Topological isomers of human uroguanylin: interconversion between biologically active and inactive isomers" FEBS Letters 421:27-31 (1998).

Cohen "Guanylin mRNA expression in human intestine and colorectal adenocarcinoma" Lab. Invest. 78:101-108 (1998).

Collins "The relationship of enteric microbial infection and functional bowel disorders" J. Clin. Gastroenterol 41 Suppl. 1:S30-32 (2007).

Cui The permissive effect of zinc deficiency on uroguanylin and inducible nitric oxide synthase gene upregulation in rat intestine induced by interleukin 1α is rapidly reversed by zinc repletion. J. Nutri. 133(1):51-56 (2003).

Currie, "Guanylin: An endogenous activator of intestinal guanylate cyclase," Proc. Natl. Acad. Sci. USA 89:947-951 (1992).

Database BIOSIS (Online), biosciences Information Service, Philadelphia, PA, U.S., Apr. 2006, Refaat "SP304, an analog of uroguanylin, ameliorates inflammation in a model of experimental colitis" XP002540570, Database Accession No. PREV200600503788, 2 pages.

De Luca "Inflammation and insulin resistance" FEBS Letter 582:97-105 (2008).

Delvaux "Effect of alosetron on responses to colonic distension in patients with irritable bowel syndrome" Aliment Pharmacol. Ther 12:849-855 (1998).

Dennis "Off by a whisker" Nature 442:739-741 (2006).

DeSAUVAGE "Precursor structure, expression and tissue distribution of human guanylin" Proc. Natl. Acad. Sci USA 89:9089-9093 (1992).

Deschner "Proliferative defects in ulcerative colitis patients" Can. Invest 1:41-47 (1983).

Duncan "Drug-polymer Conjugates: Potential for improved chemotherapy" Anti-Can. Drugs 3:175-210 (1992).

(56) References Cited

OTHER PUBLICATIONS

Dunfield "Energy parameters in polypeptides. 8. Empirical potential energy algorithm for the conformational analysis of large molecules" J. Phys. Chem. 82:2609-2616 (1978).
Eastwood "Epithelial renewal in premalignant conditions of the gastrointestinal tract: A review" J. Clin. Gastroenterol 14(1):S29-S33 (1992).
Ettorre "Mucosal changes in ileal pouches after restorative proctocolectomy for ulcerative and Crohn's colitis" Dis. Colon Rectum 43:1743-1748 (2000).
European Application No. 02721604.3: Office Communication dated Aug. 12, 2008 (3 pages).
European Application No. 02721604.3: Response to European Patent Office Communication dated Mar. 16, 2007 (5 pages).
European Patent 1,379,224: CombiMab, Inc. Annex to Notice of Opposition dated Apr. 22, 2010 (41 pages).
European Patent 1,379,224: Opposition dated Apr. 22, 2010 (19 pages).
European Patent 1,379,224: Response to Communication from Opposition division dated Oct. 8, 2010 (44 pages).
European Patent 1,379,224: Written submission dated Dec. 7, 2011 (6 pages).
European Patent 1,379,224: Written submission dated Nov. 18, 2011 by Ironwood (14 pages).
European Patent 1,379,224: Written submission dated Nov. 22, 2011 (18 pages).
European Patent 1,379,224: Written submission dated Oct. 14, 2011 (7 pages).
European Patent 1,379,224: Written submission dated Oct. 14, 2011 by Ironwood (27 pages).
European Patent 1,379,224: Written submission dated Oct. 25, 2011(5 pages).
European Patent 1,379,224: Written submission dated Oct. 7, 2011 in response to the Jun. 24, 2011 preliminary opinion of the Opposition Division (7 pages).
European Patent 1,379,224: Summons to attend oral hearing dated Jun. 24, 2011 (23 pages).
European Patent Application No. 11825961.3, Extended European Search Report dated Jun. 30, 2016, 6 pages.
Evan "Proliferation, cell cycle and apoptosis in cancer" Nature (London) 411:342-348 (2001).
Fan "Structure and activity of uroguanylin and guanylin from the intestine and urine of rats" Am. J. Physiol. Endocrinol. Metab. 273:957-964 (1997).
Field , "Ezetimibe interferes with cholesterol trafficking from the plasma membrane to the endoplasmic reticulum in CaCo-2 cells," Journal of Lipid Research, 48:1735-1745 (2007).
FMC BioPolymer of Avicel PH Production Instruction, 21 pages (2005).
Fonteles "Natruiretic and kalliuretic activities of guanylin and uroguanylin in isolated perfused rat kidney" Am. J. Physiol. Renal Physiol. 275: 191-197 (1998).
Forte, "Guanylin regulatory peptides: structures, biological activities mediated by cyclic GMP and pathobiology," Regul. Pept., 81.1-3: 25-39 (1999).
Forte, Jr., "Uroguanylin and guanylin peptides: pharmacology and experimental therapeutics," Pharmacol. Ther. 104(2):137-162 (2004).
Galt et al., "In Vivo Evaluation of an 111 In—Labeled ST-Peptide Analog for Specific-Targeting of Human Colon Cancers." Nuc. Med. Biol., 28.8: 903-909 (2001).
Garcia "Processing and characterization of human proguanylin expressed in *Escherichia coli*." J. Biol. Chem. 268:22397-22401 (1993).
Genbank 1 UYAA—Chain A, Solution Structure A—Form uroguanylin. Mar. 15, 2010. 2 pages.
Genbank 1UYBA—Chain A, Solution Structure B—Form uroguanylin. Mar. 15, 2010. 2 pages.
Genbank AAB18760.1 (rat, 1995) Mar. 11, 2010.2 pages.
Genbank AAB30324.1 Guca2B (human, 1994) Mar. 11, 2010. 2 pages.
Genbank AAC50416.1; GUCA2B (human, 1994) Mar. 11, 2010. 2 pages.
Genbank: AAD09215.1 (mouse, 1996) Mar. 11, 2010. 2 pages.
Genbank: CAA98994.1 (guinea pig, 1996) Mar. 11, 2010.2 pages.
Genbank: CAB0642.1 (pig, 1996) Mar. 11, 2010. 2 pages.
Genbank: PRF.738946 (opossum, 1993) Mar. 15, 2010. 1 page.
Greenberg "Comparison of effects of uroguanylin, guanylin, and Escherichia coli heat-stable enterotoxin Sta in mouse intestine and kidney: evidence that uroguanylin is an intestinal natruiretic hormone" J. Invest. Med. 45(5):276-282 (1997).
Guba et al., "Guanylin Strongly Stimulates Rat Duodenal HCO3- Secretion: Proposed Mechanism and Comparison With Other Secretagogues." Gastroenterology, 111.6: 1558-1568 (1996).
Gulcan "Increased frequency of prediabetes in patients with irritable bowel syndrome" Am. J. Med. Sci 338:116-119 (2009).
Gulcan The predictive value of CRP levels on future severe renal disease in overweight and obese subjects without diabetes mellitus and hypertension. Am. J. Med. Sci 334:444-451 (2007).
Gura, "Systems for Identifying New Drugs Are Often Faulty," Science 278:1041-1042 (1997).
Hamman et al., "Oral Delivery of Peptide Drugs." Biodrugs, 19.3: 165-177 (2005).
Hamra et al., "Uroguanylin: Structure and Activity of a Second Endogenous Peptide That Stimulates Intestinal Guanylate Cyclase." PNAS, 90.22: 10464-10468 (1993).
Harris et al., "Drug Evaluation: Linaclotide, a New Direction in the Treatment of Irritable Bowel Syndrome and Chronic Constipation." Curr. Opin. Mol. Ther., 9.4: 403-410 (2007).
Hess , "Gcap-II: isolation and characterization of the circulating form of human uroguanylin," FEBS Letters 374:34-38 (1995).
Hidaka "Dual Function of the Propeptide of Prouroguanylin in the Folding of the Mature Peptide" J. Biol. Chem. 275:25155-25162 (2000).
Hidaka "In Vitro Disulfide-Coupled Folding of Guanylyl Cyclase-Activating Peptide and Its Precursor Protein" Biochem. 37:8498-8507 (1998).
Hill , "Analysis of the human guanylin gene and the processing and cellular localization of the peptide" Proc. Natl. Acad. Sci USA 92:2046-2050 (1995).
Hill et al., "A New Human Guanylate Cyclase-Activating Peptide (Gcap-II, Uroguanylin): Precursor cDNA and Colonic Expression." Biochim. Biophys. Acta., 1253: 146-149 (1995).
Hinds "Synthesis and Characterization of Poly (ethylene glycol)—Insulin Conjugates" Bioconjug. Chem. 11:195-201 (2000).
Howard "Obesity and dyslipidemia" Endocrinol. Metab. Clin. N. Am. 32:855-867 (2003).
http://www.merckmanuals.com/home/childrens_health_issues/ hereditary_metabolic_disorders/disorders_of _Lipid_metabolism. html: last updated 2009; last visited Sep. 25, 2012 (1 page).
http:www.nlm.nih.gov/medlineplus/obesity.html: 1999-2011; last visited Sep. 25, 2012 (6 pages).
Hudson "Rethinking cystic fibrosis pathology: the critical role of abnormal reduced glutathione (GSH) transport caused by CFTR mutation" Free Rad. Biol. Med. 30:1441-1461 (2001).
Huff , "Inhibition of the Apical Sodium-Dependent Bile Acid Transporter Reduces LDL Cholesterol and ApoB by Enhanced Plasma Clearance of LDL ApoB," Arterioscler. Thromb. Vasc. Biol 22:1884-1891 (2002).
Hughes "Intracellular K+ suppresses the activation of apoptosis in lymphocytes" J. Biol. Chem 272(48):30567-30576 (1997).
Hui , "Developmental and Physiological Regulation of Intestinal Lipid Absorption. III. Intestinal transporters and cholesterol absorption," Am. J. Physiol. Gastrointest. Liver Physiol. 294:G839-G843 (2008).
International Preliminary Report on Patentability, PCT Appl. No. PCT/US2011/051805, 17 pages (dated Dec. 15, 2012).
International Preliminary Report on Patentability, PCT Appl. No. PCT/US2013/030551, 7 pages (dated Sep. 16, 2014).
International Search Report in International Application No. PCT/US2009/046287, 5 pages (dated Nov. 10, 2009).

(56) References Cited

OTHER PUBLICATIONS

International Search Report in International Application No. PCT/US2009/046288, 9 pages (dated Dec. 9, 2009).
International Search Report, PCT Appl. No. PCT/US2011/051805, 6 pages (dated Jun. 21, 2012).
International Search Report, PCT Appl. No. PCT/US2013/030551, 5 pages (dated Jun. 18, 2013).
Joo et al., "Regulation of Intestinal Cl and HCO3 Secretion by Uroguanylin." Am. J. Physio., 274.4: G633G644 (1998).
Kelland "'Of mice and men': values and liabilities of the athymic nude mouse model in anticancer drug development" Eur. J. Cancer 40(6):827-836 (2004).
Kita :Characterization of human uroguanylin: A member of the guanylin peptide family Am. J. Physiol. 266:F342-8(1994).
Klodt , "Synthesis, biological activity and isomerism of guanylate cyclase C-activating peptides guanylin and uroguanylin," J. Pep. Res. 50(2):222-230 (1997).
Krause "The guanylin and uroguanylin peptide hormones and their receptors" Acta Anat. 160:213-231 (1997).
Lam "Serotonin and energy balance: molecular mechanisms and implications for type 2 diabetes" Expert Rev. Mol. Med. 9:1-24 (2007).
Leister "Human colorectal cancer: High frequency of deletions at chromosome 1p35" Can. Res. 50:7232-7235 (1990).
Li "Purification, cDNA sequence and tissue distribution of rat uroguanylin" Reg. Pep. 68:45-56 (1997).
Li and Chiang, "Bile Acid Signaling in Liver Metabolism and Diseases", Journal of Lipids, Hindawi Publishing Corporation, 2012:1-9, Article ID 754067 (2011).
Lipkin "Gastric cell regeneration" Arch. Fr. Mal. Appl. Dig. (Paris) 61(10-11):691-693 (1972).
Lorenz "Uroguanylin knockout mice have increased blood pressure and impaired natriuretic response to enteral NaCl load" J. Clin. Invest. 112(8):1244-1254 (2003).
MacFarlane and MacFarlane, "Factors affecting fermentation reactions in the large bowel," Proc. Nutr. Soc. 52(2):367-373 (1993).
Magert Porcine guanylin and uroguanylin: cDNA sequences, deduced amino acid sequences, and biological activity of the chemically synthesized peptides' Biochem. Biophys. Res. Comm. 259:141-148 (1999).
Mahato et al., "Emerging Trends in Oral Delivery of Peptide and Protein Drugs." Crit. Rev. Therapeutic Drug Carrier Sys., 20.2-3: 153-214 (2003).
Marx et al., "One Peptide, Two Topologies: Structure and Interconversion Dynamics of Human Uroguanylin Isomers." J. Pept. Res., 52: 229-240 (1998).
Mihranyan et al., "Moisture sorption by cellulose powders of varying crystallinity", International Journal of Pharmaceutics, 269(2): 433-442 (2004).
Miyazato "Uroguanylin gene expression in the alimentary tract and extra-gastrointestinal tissues" FEBS Letters, 398:170-174 (1996).
Miyazato "Cloning and characterization of a cDNA encoding a precursor for human uroguanylin" Biochem Biophys Res. Comm. 219:644-648 (1996).
Moon "Effects of age, ambient temperature, and heat-stable *Escherichia coli* enterotoxin of intestinal transit in infant mice" Infect. Immun. 25(1):127-132 (1979).
Muller-Lissner "Safety, tolerability, and efficacy of tegaserod over 13 months in patients with chronic constipation" Am. J. Gastroenterol. 101:2558-2569 (2006).
Nakazato "Tissue distribution, cellular source, and structural analysis of rat immunoreactive uroguanylin" Endocrinol. 139:5247-5254 (1998).
Nathan "Copolymers of lysine and polyethylene glycol: a new family of functionalized drug carriers" Bioconjug Chem. 4(1):54-62 (1993).
Nemethy "Energy parameters in polypeptides. 9. Updating of geometrical parameters non-bonded interactions, and hydrogen bond interactions for the naturally occurring amino acids" J. Phys. Chem. 87:1883-1887 (1983).

Nikiforovich "Computation molecular modeling in peptide design" Int. J. Pep. Prot. Res. 44:513-531 (1994).
Nikiforovich "Topographical requirements for 6-selective opioid peptides" Biopolymers, 31:942-955 (1991).
Nyburg "Some uses of best molecular fit routine" Acta Crystallographica B30 (Part 1):251-253 (1974).
Ohbayashi , "Effects of uroguanylin and guanylin against antigen-induced bronchoconstriction and airway microvascular leakage in sensitized guinea-pigs" Life Sci., 62(20:1883-1844 (1998).
Perkins "Uroguanylin is expressed by enterochromaffin cells in the rat gastrointestinal tract" Gastroenterol 113:1007-1014 (1997).
Peterson "Integrating pharmacology and in vivo cancer models in preclinical and clinical drug development" Eur. J. Cancer 40:837-844 (2004).
Pitari "Guanylyl cyclase C agonists regulate progression through the cell cycle of human colon carcinoma cells", Proc. Natl. Acad. Sci. USA 98(14):7546-7851 (2001).
Potten "Regulation and significance of apoptosis in the stem cells of the gastrointestinal epithelium" Stem Cells 15:82-93 (2001).
Provenzale "Surveillance issues in inflammatory bowel disease: ulcerative colitis" J. Clin. Gastroenterol 32:99-105 (2001).
PubChem, CID 469, http://pubchem.ncbi.nlm.nih.gov/summary/summary.cgi?cid=469#x27, (last visited Oct. 18, 2014). 19 pages.
Ramamoorthy "Phosphorylation of threonine residue 276 is required for acute regulation of serotonin transporter by cyclic GMP" J. Biol. Chem. 282(16):11639-11647 (2007).
Reddy and Rao "Lipid metabolism and liver inflammation II fatty liver disease and fatty acid oxidation" Am. J. Physiol. Gastrointest. Liver Physiol. 290:G852-G858 (2006).
Remington, JP "Remington's Pharmaceutical Sciences" Mack Pub. Co. 16th edition (1980) 7 pages.
Roberts "Chemistry of peptide and protein PEGylation" Adv. Drug. Deliv. Rev. 54:459-476 (2002).
Rolfe and Milla, "Nitric oxide stimulates cyclic guanosine monophosphate production and electrogenic secretion in Caco-2 colonocytes," Clin. Sci. (Lond). 96(2):165-170 (1999).
Samuel "Absorption of bile acids from the large bowel in man" J. Clin. Invest. 47:2070-2978 (1968).
Schulz et al., "Guanylyl Cyclase is a Heat-Stable Enterotoxin Receptor." Cell, 63.5: 941-948 (1990).
Schulz et al., "Side Chain Contributions to the Interconversion of the Topological Isomers of Guanylin-Like Peptides." J. Peptide Sci., 11.6: 319-330 (2005).
Sciaky "Mapping of guanylin to murine chromosome 4 and human chromosome 1p34p35" Genomics 26:427-429 (1995).
Sellers "heat-stable enterotoxin of *Escherichia coli* stimulates a non-CFTR-mediated duodenal bicarbonate secretory pathway" Am J. Physiol. Gastrointest. Liver Physiol. 288:G654-G663 (2005).
Shailubhai "Gaunilib, an antagonist of guanylate C, is a new class of oral drug candidate that ameliorates inflammation in models of experimental colitis" [Abstract]: In Charon's and colitis foundation of America (2007) 1 page.
Shailubhai "Guanilib, an agonist of Guanylate C, is a new class of oral drug candidate for GI disorders and colon cancer" [abstract] in GTCbio, 2008. 1 page.
Shailubhai "Guanylate cyclase-C agonists as a new class of drug candidates for GI motility and inflammatory bowel disease" [Abstract] 2009 (1 page).
Shailubhai "Guanylin Peptides: New class of oral drug candidates" [Abstract]: In World Congress 2008 (2 pages).
Shailubhai "Inflammatory bowel disease" Feb. 2008: S5 2007 IBD Abstract: Oral Presentation (1 page).
Shailubhai "Phase II Clinical Evaluation of SP-304, a Guanylate Cyclase-C Agonist, for Treatment of Chronic Constipation," Am. J. Gastroenterol. 105(Suppl. 1):3487-S488 (2010).
Shailubhai "SP-304 to treat GI disorders—effects of a single, oral dose of SP-304 in safety, tolerability, pharmacokinetics and pharmacodynamics in healthy volunteers" [Abstract]: in Digestive Disease Week, (2009) 1 page.
Shailubhai "Therapeutic applications of guanylate cyclase-c receptor agonists" Curr. Opin. Drug Disc. Devel. 5(2):261-268 (2002).

(56) References Cited

OTHER PUBLICATIONS

Shailubhai et al., "Uroguanylin Treatment Suppresses Polyp Formation in the ApcMin/+Mouse and Induces Apoptosis in Human Colon Adenocarcinoma Cells via Cyclic GMP." Cancer Res., 60: 5151-5157 (2000).
Shinozaki "High proliferative activity is associated with dysplasia in ulcerative colitis" Dis. Colon Rectum 43:S34-S39(2000).
Sindice "Guanylin, Uroguanylin, and Heat-stable Enterotoxin Activate Guanylate Cyclase C and/or a Pertussis Toxin-sensitive G Protein in Human Proximal Tubule Cells". J. Biol. Chem. 277:17758-17764 (2002).
Spranger "Inflammatory cytokines and the risk to develop Type 2 Diabetes: Results of the prospective population-based European prospective investigation into cancer and nutrition (EPIC)-Potsdam study" Diabetes, 52:812-817 (2003).
St. John's Providence Health Center; Preventing Obesity, http:www.stjohnprovidence.org/healthInfoLib/swArticle.aspx?85. P07863; last visited Sep. 25, 2012 (2 pages).
Takada , "Alteration of a Single Amino Acid in Peroxisome Proliferator-Activated Receptor-a (PPARa) Generates a PPARd Phenotype" Mol. Endocrinol. 14(5):733-740 (2000).
Talley "Medical costs in community subjects with irritable bowel syndrome" Gastroenterol. 109:17361741 (1995).
Thomas , "Cholesterol dependent downregulation of mouse and human apical sodium dependent bile acid transporter (ASBT) gene expression: molecular mechanism and physiological consequences," GUT 55:1321-1331 (2006).
Tian "STa peptide analogs for probing guanylyl cyclase C" Biopolymers (Pept. Sci). 90(5):713-723 (2008).
Tilg "Inflammatory mechanisms in the regulation of insulin resistance" Mol. Med. 14:222-231 (2008).
Vaandrager, "Structure and Function of the Heat-Stable Enterotoxin Receptor/Guanylyl Cyclase C." Mal. Cell. Biochem., 230.1-2: 73-83 (2002).
Variyam, "Luminal bacteria and proteases together decrease adherence of Entamoeba histolytica trophozoites to Chinese hamster ovary epithelial cells: A novel host defense against an enteric pathogen," GUT 39(4):521-527 (1996).
Venkatakrishnan Exaggerated activation of nuclear factor-B and altered I B-processing in cystic fibrosis bronchial epithelial cells. Am. J. Resp. Cell Mol. Biol. 23(3):396-403 (2000).
Veronese "Bioconjugation in pharmaceutical chemistry" Farmaco, 54:497-516 (1999).
Veronese "PEGylation, successful approach to drug delivery" Drug. Disc. Today. 10(21):1451-1458 (2005).
Veronese "Peptide and protein PEGylation: a review of problems and solutions" Biomaterial, 22:405-417 (2001).
Waldman "Heterogeneity of guanylyl cylcase C expressed by human colorectal cancer cell lines in vitro" Can. Epidemiol. Biomarkers & Prevention 7:505-514 (1998).
Weber "Activation of NF-kB in airway epithelial cells is dependent on CFTR trafficking and CI channel function" Am. J. Physiol. Lung Cell Mol. Biol. 281(1):L71-78 (2001).
Welsh "Molecular mechanisms of CFTR chloride channel dysfunction in cystic fibrosis" Cell 73:1251- 1254 (1993).
Whitaker "The uroguanulin gene (Bucalb) is linked to guanylin (Guca2) on mouse chromosome 4" Genomics 45:348-354 (2002).
Wong "Cell proliferation in gastrointestinal mucosa" J. Clin. Pathol. 52:321-333 (1999).
Wong "Histogenesis of human colorectal adenomas and hyperplastic polyps: the role of cell proliferation and crypt fission" GUT 50:212-217 (2002).
Written Opinion of the International Searching Authority, PCT Appl. No. PCT/US2011/051805, 5 pages (dated Jun. 21, 2012).
Written Opinion of the International Searching Authority, PCT Appl. No. PCT/US2013/030551, 6 pages (dated Jun. 18, 2013).
Wu "Atrial natriuretic peptide induces apoptosis in neonatal rat cardia myocytes" J. Biol. Chem. 272(23):14860-14866 (1997).
Zhang "Gene expression profiles in normal and cancer cells" Science 276:1268-1272 (1997).
Zimmerman "Influence of local interactions on protein structure. I. Conformational energy studies of Nacetyl-N-methylamides of pro-X and X-pro dipeptides" Biopolymers, 16:811-843 (1977).

* cited by examiner

```
                        SEQUENCE LISTING

<160> NUMBER OF SEQ ID NOS: 261

<210> SEQ ID NO 1
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1

Asn Asp Glu Cys Glu Leu Cys Val Asn Val Ala Cys Thr Gly Cys Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 2

Asp Glu Cys Glu Leu Cys Val Asn Val Ala Cys Thr Gly Cys Leu
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 3

Asp Glu Cys Glu Leu Cys Val Asn Val Ala Cys Thr Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 4

Glu Cys Glu Leu Cys Val Asn Val Ala Cys Thr Gly Cys Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 5

Glu Cys Glu Leu Cys Val Asn Val Ala Cys Thr Gly Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Chemically Synthesized
```

```
<400> SEQUENCE: 6

Cys Glu Leu Cys Val Asn Val Ala Cys Thr Gly Cys Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 7

Cys Glu Leu Cys Val Asn Val Ala Cys Thr Gly Cys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 8

Asn Asp Glu Cys Glu Leu Cys Val Asn Val Ala Cys Thr Gly Cys Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 9

Asn Asp Glu Cys Glu Leu Cys Val Asn Val Ala Cys Thr Gly Cys Leu
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (16)..(16)
<223> OTHER INFORMATION: wherein LEU is a D-amino acid
```

-continued

```
<400> SEQUENCE: 10

Asn Asp Glu Cys Glu Leu Cys Val Asn Val Ala Cys Thr Gly Cys Leu
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 11

Asn Asp Glu Cys Glu Leu Cys Val Asn Val Ala Cys Thr Gly Cys Leu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid

<400> SEQUENCE: 12

Asn Asp Glu Cys Glu Leu Cys Val Asn Val Ala Cys Thr Gly Cys Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (6)..(6)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 13

Asn Asp Glu Cys Glu Leu Cys Val Asn Val Ala Cys Thr Gly Cys Leu
1               5                   10                  15

<210> SEQ ID NO 14
<211> LENGTH: 15
```

-continued

```
<212> TYPE: PRT
<213> ORGANISM: Artificial Sequence
<220> FEATURE:
<223> OTHER INFORMATION: Chemically Synthesized

<400> SEQUENCE: 14

Asn Asp Glu Cys Glu Leu Cys Val Asn Val Ala Cys Thr Gly Cys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 15

Asn Asp Glu Cys Glu Leu Cys Val Asn Val Ala Cys Thr Gly Cys Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 16

Asn Asp Glu Cys Glu Leu Cys Val Asn Val Ala Cys Thr Gly Cys Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
```

```
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 17

Asn Asp Glu Cys Glu Leu Cys Val Asn Val Ala Cys Thr Gly Cys Leu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 18

Asn Asp Glu Cys Glu Leu Cys Val Asn Val Ala Cys Thr Gly Cys Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 19

Asn Asp Glu Cys Glu Leu Cys Val Asn Val Ala Cys Thr Gly Cys Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemically Synthesized
```

```
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 20

Asn Asp Glu Cys Glu Leu Cys Val Asn Val Ala Cys Thr Gly Cys Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 21

Asn Asp Glu Cys Glu Leu Cys Val Asn Val Ala Cys Thr Gly Cys Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 22

Asn Asp Glu Cys Glu Leu Cys Val Asn Val Ala Cys Thr Gly Cys Leu
1               5                   10                  15
```

```
<210> SEQ ID NO 23
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 23

Asn Asp Glu Cys Glu Leu Cys Val Asn Val Ala Cys Thr Gly Cys Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 24

Asn Asp Glu Cys Glu Leu Cys Val Asn Val Ala Cys Thr Gly Cys Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
```

```
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 25

Asn Asp Glu Cys Glu Leu Cys Val Asn Val Ala Cys Thr Gly Cys Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 26

Asn Asp Glu Cys Glu Leu Cys Val Asn Val Ala Cys Thr Gly Cys Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein x is 3-(2-naphthyl)alanine
<220> FEATURE:
<221> NAME/KEY: MISC_FEATURE
<222> LOCATION: (16)..(16)
<223> OTHER INFORMATION: wherein x is a D-amino acid

<400> SEQUENCE: 27

Asn Asp Glu Cys Glu Leu Cys Val Asn Val Ala Cys Thr Gly Cys Xaa
1               5                   10                  15

<210> SEQ ID NO 28
<211> LENGTH: 16
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MOD_RES
<222> LOCATION: (8)..(8)
<223> OTHER INFORMATION: wherein the x is a 2-aminoisobutyric acid, Aib
<220> FEATURE:
<221> NAME/KEY: MOD_RES
<222> LOCATION: (10)..(10)
<223> OTHER INFORMATION: wherein the x is a 2-aminoisobutyric acid, Aib
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 28

Asn Asp Glu Cys Glu Leu Cys Xaa Asn Xaa Ala Cys Thr Gly Cys Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (7)..(7)
<223> OTHER INFORMATION: wherein ASP at position 7 is attached to a
      Lactam bridge
<220> FEATURE:
<221> NAME/KEY: MISC_FEATURE
<222> LOCATION: (15)..(15)
<223> OTHER INFORMATION: wherein x at position 15 is ornithine
<220> FEATURE:
<221> NAME/KEY: MOD_RES
<222> LOCATION: (15)..(15)
<223> OTHER INFORMATION: wherein x is an ornithine, Orn
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 29

Asn Asp Glu Cys Glu Leu Asp Val Asn Val Ala Cys Thr Gly Xaa Leu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 30

Asn Asp Glu Cys Glu Tyr Cys Val Asn Val Ala Cys Thr Gly Cys Leu
1               5                   10                  15
```

```
<210> SEQ ID NO 31
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 31

Asn Asp Glu Cys Glu Ser Cys Val Asn Val Ala Cys Thr Gly Cys Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 32

Asn Asp Glu Cys Glu Tyr Cys Val Asn Val Ala Cys Thr Gly Cys Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 33

Asn Asp Glu Cys Glu Tyr Cys Val Asn Val Ala Cys Thr Gly Cys Leu
1               5                   10                  15
```

<210> SEQ ID NO 34
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 34

Asn Asp Glu Cys Glu Tyr Cys Val Asn Val Ala Cys Thr Gly Cys Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 35

Asn Asp Glu Cys Glu Ser Cys Val Asn Val Ala Cys Thr Gly Cys Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 36

```
Asn Asp Glu Cys Glu Ser Cys Val Asn Val Ala Cys Thr Gly Cys Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 37

Asn Asp Glu Cys Glu Ser Cys Val Asn Val Ala Cys Thr Gly Cys Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 38

Asn Asp Glu Cys Glu Leu Cys Val Asn Val Ala Cys Thr Gly Cys Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 39

Asn Asp Glu Cys Glu Leu Cys Val Asn Val Ala Cys Thr Gly Cys Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
```

```
<400> SEQUENCE: 40

Asn Asp Glu Cys Glu Leu Cys Val Asn Val Ala Cys Thr Gly Cys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 41

Asn Asp Glu Cys Glu Leu Cys Val Asn Val Ala Cys Thr Gly Cys Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER is a D-amino acid
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 42

Asn Asp Glu Cys Glu Leu Cys Val Asn Val Ala Cys Thr Gly Cys Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER is a D-amino acid

<400> SEQUENCE: 43

Asn Asp Glu Cys Glu Leu Cys Val Asn Val Ala Cys Thr Gly Cys Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Chemically Synthesized
```

```
<220> FEATURE:
<221> NAME/KEY: MISC_FEATURE
<222> LOCATION: (16)..(16)
<223> OTHER INFORMATION: wherein SER at position 16 is attached to
      polyethylene glycol
<220> FEATURE:
<221> NAME/KEY: MISC_FEATURE
<222> LOCATION: (16)..(16)
<223> OTHER INFORMATION: wherein SER is a D-amino acid

<400> SEQUENCE: 44

Asn Asp Glu Cys Glu Leu Cys Val Asn Val Ala Cys Thr Gly Cys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (8)..(11)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue, and may be an L-amino acid, or a
      D-amino acid, or a methylated or an unmethylated amino acid

<400> SEQUENCE: 45

Asn Asp Glu Cys Xaa Xaa Cys Xaa Xaa Xaa Xaa Cys Xaa Xaa Cys Xaa
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (2)..(2)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid
<220> FEATURE:
<221> NAME/KEY: MISC_FEATURE
<222> LOCATION: (3)..(3)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid
```

```
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (8)..(11)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue that is zero or one residue in
      length and may be an L-amino acid, or a D-amino acid, or a
      methylated or an unmethylated amino acid

<400> SEQUENCE: 46

Xaa Xaa Xaa Cys Xaa Xaa Cys Xaa Xaa Xaa Xaa Cys Xaa Xaa Cys Xaa
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (2)..(2)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid
<220> FEATURE:
<221> NAME/KEY: MISC_FEATURE
<222> LOCATION: (3)..(3)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (6)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
```

```
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid

<400> SEQUENCE: 47

Xaa Xaa Xaa Xaa Glu Xaa Xaa Val Asn Val Ala Xaa Thr Gly Xaa Xaa
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (2)..(2)
<223> OTHER INFORMATION: wherein x is any natural, or unnatural amino
      acid or amino acid
      analogue that is zero or one residue in length and may be an
      L-amino acid, or a D-amino acid, or a methylated or an
      unmethylated amino acid
<220> FEATURE:
<221> NAME/KEY: MISC_FEATURE
<222> LOCATION: (3)..(3)
<223> OTHER INFORMATION: wherein x is any natural, or unnatural amino
      acid or amino acid analogue that is zero or one residue in length
      and may be an L-amino acid, or a D-amino acid, or a methylated or
      an unmethylated amino acid
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (8)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
      D-amino acid, or a methylated or an unmethylated amino acid
```

```
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue that is zero or one residue in length
      and may be an L-amino acid, or a D-amino acid, or a methylated or
      an unmethylated amino acid

<400> SEQUENCE: 48

Xaa Xaa Xaa Xaa Xaa Xaa Xaa Xaa Xaa Xaa Xaa Xaa Xaa Xaa Xaa Xaa
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (8)..(8)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 49

Asn Asp Asp Cys Xaa Xaa Cys Xaa Asn Xaa Xaa Cys Xaa Xaa Cys Xaa
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
```

```
<221> NAME/KEY: MISC_FEATURE
<222> LOCATION: (8)..(8)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue and may be an L-amino acid, or a
      D-amino acid, or a methylated or an unmethylated amino acid

<400> SEQUENCE: 50

Asn Glu Glu Cys Xaa Xaa Cys Xaa Asn Xaa Xaa Cys Xaa Xaa Cys Xaa
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein GLU is a D-amino acid
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (8)..(8)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue and may be an L-amino acid, or a
      D-amino acid, or a methylated or an unmethylated amino acid

<400> SEQUENCE: 51

Asn Glu Asp Cys Xaa Xaa Cys Xaa Asn Xaa Xaa Cys Xaa Xaa Cys Xaa
1               5                   10                  15
```

<210> SEQ ID NO 52
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (8)..(8)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue and may be an L-amino acid, or a
      D-amino acid, or a methylated or an unmethylated amino acid

<400> SEQUENCE: 52

Asn Asp Glu Cys Xaa Xaa Cys Xaa Asn Xaa Xaa Cys Xaa Xaa Cys Xaa
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein ASP is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE

```
<222> LOCATION: (8)..(8)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue and may be an L-amino acid, or a
      D-amino acid, or a methylated or an unmethylated amino acid

<400> SEQUENCE: 53

Asn Asp Glu Cys Xaa Xaa Cys Xaa Tyr Xaa Xaa Cys Xaa Xaa Cys Xaa
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (2)..(2)
<223> OTHER INFORMATION: wherein GLU is a D-amino acid
<220> FEATURE:
<221> NAME/KEY: MISC_FEATURE
<222> LOCATION: (3)..(3)
<223> OTHER INFORMATION: wherein GLU is a D-amino acid
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue and may be an L-amino acid, or a
      D-amino acid, a methylated or an unmethylated amino acid
<220> FEATURE:
<221> NAME/KEY: MISC_FEATURE
<222> LOCATION: (8)..(8)
<223> OTHER INFORMATION: wherein x is any natural, or unnatural amino
      acid, or amino acid analogue and may be an L-amino acid, or a
      D-amino acid, a methylated or an unmethylated amino acid
<220> FEATURE:
<221> NAME/KEY: MISC_FEATURE
<222> LOCATION: (10)..(11)
<223> OTHER INFORMATION: wherein x is any natural, or unnatural amino
      acid, or amino acid analogue and may be an L-amino acid, or a
      D-amino acid, a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue and may be an L-amino acid, or a
      D-amino acid, a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue and may be an L-amino acid, or a
      D-amino acid, a methylated or an unmethylated amino acid

<400> SEQUENCE: 54
```

Asn Glu Glu Cys Xaa Xaa Cys Xaa Tyr Xaa Xaa Cys Xaa Xaa Cys Xaa
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 55

Cys Cys Glu Tyr Cys Cys Asn Pro Ala Cys Thr Gly Cys Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 56

Cys Cys Glu Tyr Cys Cys Asn Pro Ala Cys Thr Gly Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 57

Cys Cys Glu Tyr Cys Cys Asn Pro Ala Cys Thr Gly Cys Tyr
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 58

Asn Phe Cys Cys Glu Ser Cys Cys Asn Pro Ala Cys Thr Gly Cys Tyr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 59

Asn Phe Cys Cys Glu Phe Cys Cys Asn Pro Ala Cys Thr Gly Cys Tyr
1               5                   10                  15

```
<210> SEQ ID NO 60
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein TYR is a D-amino acid

<400> SEQUENCE: 60

Cys Cys Glu Tyr Cys Cys Asn Pro Ala Cys Thr Gly Cys Tyr
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 61

Cys Cys Glu Tyr Cys Cys Asn Pro Ala Cys Thr Gly Cys Tyr
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 62

Asn Phe Cys Cys Glu Thr Cys Cys Asn Pro Ala Cys Thr Gly Cys Tyr
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 63

Asn Phe Cys Cys Glu Ser Cys Cys Asn Pro Ala Cys Thr Gly Cys Tyr
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid

<400> SEQUENCE: 64
```

```
Asn Phe Cys Cys Glu Ser Cys Cys Asn Pro Ala Cys Thr Gly Cys Tyr
1               5                   10                  15
```

<210> SEQ ID NO 65
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 65

```
Asn Phe Cys Cys Glu Ser Cys Cys Asn Pro Ala Cys Thr Gly Cys Tyr
1               5                   10                  15
```

<210> SEQ ID NO 66
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 66

```
Asn Phe Cys Cys Glu Thr Cys Cys Asn Pro Ala Cys Thr Gly Cys Tyr
1               5                   10                  15
```

<210> SEQ ID NO 67
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid

<400> SEQUENCE: 67

```
Asn Phe Cys Cys Glu Thr Cys Cys Asn Pro Ala Cys Thr Gly Cys Tyr
1               5                   10                  15
```

<210> SEQ ID NO 68
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 68

```
Asn Phe Cys Cys Glu Thr Cys Cys Asn Pro Ala Cys Thr Gly Cys Tyr
1               5                   10                  15
```

<210> SEQ ID NO 69
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 69

Asn Phe Cys Cys Glu Phe Cys Cys Asn Pro Ala Cys Thr Gly Cys Tyr
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid

<400> SEQUENCE: 70

Asn Phe Cys Cys Glu Phe Cys Cys Asn Pro Ala Cys Thr Gly Cys Tyr
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 71

Asn Phe Cys Cys Glu Phe Cys Cys Asn Pro Ala Cys Thr Gly Cys Tyr
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 72

Cys Cys Glu Tyr Cys Cys Asn Pro Ala Cys Thr Gly Cys Tyr
1               5                   10

<210> SEQ ID NO 73
<211> LENGTH: 13
<212> TYPE: PRT
<213> ORGANISM: Artificial Sequence
<220> FEATURE:

<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 73

Cys Cys Glu Tyr Cys Cys Asn Pro Ala Cys Thr Gly Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 74

Cys Cys Glu Tyr Cys Cys Asn Pro Ala Cys Thr Gly Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 75

Cys Cys Glu Tyr Cys Cys Asn Pro Ala Cys Thr Gly Cys
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 76

Asn Phe Cys Cys Glu Ser Cys Cys Asn Pro Ala Cys Thr Gly Cys Tyr
1               5                   10                  15

<210> SEQ ID NO 77
<211> LENGTH: 16

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 77

Asn Phe Cys Cys Glu Ser Cys Cys Asn Pro Ala Cys Thr Gly Cys Tyr
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 78

Asn Phe Cys Cys Glu Ser Cys Cys Asn Pro Ala Cys Thr Gly Cys Tyr
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 79

Asn Phe Cys Cys Glu Phe Cys Cys Asn Pro Ala Cys Thr Gly Cys Tyr
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 80

Asn Phe Cys Cys Glu Phe Cys Cys Asn Pro Ala Cys Thr Gly Cys Tyr
1               5                   10                  15

<210> SEQ ID NO 81
<211> LENGTH: 16
<212> TYPE: PRT
<213> ORGANISM: Artificial Sequence
```

```
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 81

Asn Phe Cys Cys Glu Phe Cys Cys Asn Pro Ala Cys Thr Gly Cys Tyr
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 82

Asn Phe Cys Cys Glu Tyr Cys Cys Asn Pro Ala Cys Thr Gly Cys Tyr
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 83

Asn Phe Cys Cys Glu Tyr Cys Cys Asn Pro Ala Cys Thr Gly Cys Tyr
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 84

Asn Phe Cys Cys Glu Tyr Cys Cys Asn Pro Ala Cys Thr Gly Cys Tyr
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: Chemically Synthesized
```

<400> SEQUENCE: 85

Cys Cys Glu Ser Cys Cys Asn Pro Ala Cys Thr Gly Cys Tyr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 86

Cys Cys Glu Phe Cys Cys Asn Pro Ala Cys Thr Gly Cys Tyr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 87

Cys Cys Glu Ser Cys Cys Asn Pro Ala Cys Thr Gly Cys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 88

Cys Cys Glu Phe Cys Cys Asn Pro Ala Cys Thr Gly Cys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is penicillamine
<220> FEATURE:
<221> NAME/KEY: MISC_FEATURE
<222> LOCATION: (5)..(6)
<223> OTHER INFORMATION: wherein x is penicillamine
<220> FEATURE:
<221> NAME/KEY: MISC_FEATURE
<222> LOCATION: (10)..(10)
<223> OTHER INFORMATION: wherein x is penicillamine
<220> FEATURE:
<221> NAME/KEY: MISC_FEATURE
<222> LOCATION: (13)..(13)
<223> OTHER INFORMATION: wherein x is penicillamine

<400> SEQUENCE: 89

Xaa Xaa Glu Tyr Xaa Xaa Asn Pro Ala Xaa Thr Gly Xaa Tyr
1               5                   10

<210> SEQ ID NO 90
<211> LENGTH: 13
<212> TYPE: PRT
<213> ORGANISM: Artificial Sequence

```
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is penicillamine
<220> FEATURE:
<221> NAME/KEY: MISC_FEATURE
<222> LOCATION: (5)..(6)
<223> OTHER INFORMATION: wherein x is penicillamine
<220> FEATURE:
<221> NAME/KEY: MISC_FEATURE
<222> LOCATION: (10)..(10)
<223> OTHER INFORMATION: wherein x is penicillamine
<220> FEATURE:
<221> NAME/KEY: MISC_FEATURE
<222> LOCATION: (13)..(13)
<223> OTHER INFORMATION: wherein x is penicillamine

<400> SEQUENCE: 90

Xaa Xaa Glu Tyr Xaa Xaa Asn Pro Ala Xaa Thr Gly Xaa
1               5                   10

<210> SEQ ID NO 91
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (11)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (15)..(17)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (19)..(20)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (22)..(22)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 91

Xaa Xaa Xaa Xaa Xaa Xaa Asn Tyr Cys Cys Xaa Tyr Cys Cys Xaa Xaa
1               5                   10                  15

Xaa Cys Xaa Xaa Cys Xaa
            20

<210> SEQ ID NO 92
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
```

```
<222> LOCATION: (1)..(6)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (11)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (15)..(17)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (19)..(20)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (22)..(22)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 92

Xaa Xaa Xaa Xaa Xaa Xaa Asn Phe Cys Cys Xaa Phe Cys Cys Xaa Xaa
1               5                   10                  15

Xaa Cys Xaa Xaa Cys Xaa
            20

<210> SEQ ID NO 93
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(5)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (9)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 93

Asn Phe Cys Cys Xaa Phe Cys Cys Xaa Xaa Xaa Cys Xaa Xaa Cys Xaa
1               5                   10                  15

<210> SEQ ID NO 94
<211> LENGTH: 16
<212> TYPE: PRT
<213> ORGANISM: Artificial Sequence
```

```
<220> FEATURE:
<223> OTHER INFORMATION: Chemically Synthesized
<220> FEATURE:
<221> NAME/KEY: MISC_FEATURE
<222> LOCATION: (3)..(3)
<223> OTHER INFORMATION: wherein x is penicillamine
<220> FEATURE:
<221> NAME/KEY: MISC_FEATURE
<222> LOCATION: (5)..(5)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (8)..(8)
<223> OTHER INFORMATION: wherein x is penicillamine
<220> FEATURE:
<221> NAME/KEY: MISC_FEATURE
<222> LOCATION: (9)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 94

Asn Phe Xaa Cys Xaa Phe Cys Xaa Xaa Xaa Xaa Cys Xaa Xaa Cys Xaa
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (3)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (7)..(8)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (9)..(11)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue and may be an L-amino acid, or a
```

```
      D-amino acid, or a methylated or an unmethylated amino acid
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue and may be an L-amino acid, or a
      D-amino acid, or a methylated or an unmethylated amino acid

<400> SEQUENCE: 95

Asn Phe Xaa Xaa Xaa Xaa Xaa Xaa Xaa Xaa Xaa Xaa Xaa Xaa Xaa Xaa
1               5                   10                  15

<210> SEQ ID NO 96
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (4)..(4)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (5)..(6)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (10)..(10)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(13)
<223> OTHER INFORMATION: wherein x is a cysteine, penicillamine
      homocysteine, or 3-mercaptoproline

<400> SEQUENCE: 96

Xaa Xaa Glu Xaa Xaa Xaa Asn Pro Ala Xaa Thr Gly Xaa Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein x is a cysteine, or penicillamine,
      homocysteine, or 3-mercaptoproline
<220> FEATURE:
<221> NAME/KEY: MISC_FEATURE
<222> LOCATION: (4)..(4)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (5)..(6)
<223> OTHER INFORMATION: wherein x is a cysteine, or penicillamine,
```

-continued homocysteine, or 3-mercaptoproline
<220> FEATURE:
<221> NAME/KEY: MISC_FEATURE
<222> LOCATION: (10)..(10)
<223> OTHER INFORMATION: wherein x is a cysteine, or penicillamine,
      homocysteine, or 3-mercaptoproline
<220> FEATURE:
<221> NAME/KEY: MISC_FEATURE
<222> LOCATION: (13)..(13)
<223> OTHER INFORMATION: wherein x is a cysteine, or penicillamine,
      homocysteine, or 3-mercaptoproline

<400> SEQUENCE: 97

Xaa Xaa Glu Xaa Xaa Xaa Asn Pro Ala Xaa Thr Gly Xaa
1               5                   10

<210> SEQ ID NO 98
<211> LENGTH: 20
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (2)..(2)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (3)..(3)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (4)..(4)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (5)..(5)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (6)..(6)
<223> OTHER INFORMATION: wherein x is any natural, or unnatural amino
      acid or amino acid analogue, and  may be zero or one residue in
      length, and may be an L-amino acid, or a D-amino acid, or a
      methylated or an unmethylated amino acid
<220> FEATURE:
<221> NAME/KEY: MISC_FEATURE
<222> LOCATION: (7)..(8)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (9)..(10)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE

```
<222> LOCATION: (11)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(15)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (16)..(16)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (17)..(18)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (19)..(19)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (20)..(20)
<223> OTHER INFORMATION: wherein x is any natural, or unnatural amino
      acid or amino acid analogue, and may be zero or one residue in
      length, and may be an L-amino acid, or a D-amino acid, or a
      methylated or an unmethylated amino acid

<400> SEQUENCE: 98

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 99
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein LEU is a D-amino acid
<220> FEATURE:
<221> NAME/KEY: MISC_FEATURE
<222> LOCATION: (16)..(16)
<223> OTHER INFORMATION: wherein LEU is conjugated to an AMIDE

<400> SEQUENCE: 99

Asn Asp Glu Cys Glu Leu Cys Val Asn Val Ala Cys Thr Gly Cys Leu
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
```

```
<222> LOCATION: (16)..(16)
<223> OTHER INFORMATION: wherein SER is a D-amino acid

<400> SEQUENCE: 100

Asn Asp Glu Cys Glu Leu Cys Val Asn Val Ala Cys Thr Gly Cys Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein SER is a D-amino acid
<220> FEATURE:
<221> NAME/KEY: MISC_FEATURE
<222> LOCATION: (16)..(16)
<223> OTHER INFORMATION: wherein SER is conjugated to an AMIDE

<400> SEQUENCE: 101

Asn Asp Glu Cys Glu Leu Cys Val Asn Val Ala Cys Thr Gly Cys Ser
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 102

Asn Asp Glu Cys Glu Leu Cys Val Asn Val Ala Cys Thr Gly Cys Tyr
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid
<220> FEATURE:
<221> NAME/KEY: MISC_FEATURE
<222> LOCATION: (16)..(16)
<223> OTHER INFORMATION: wherein TYR is conjugated to an AMIDE

<400> SEQUENCE: 103

Asn Asp Glu Cys Glu Leu Cys Val Asn Val Ala Cys Thr Gly Cys Tyr
1               5                   10                  15
```

```
<210> SEQ ID NO 104
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein x is Pyroglutamic acid
<220> FEATURE:
<221> NAME/KEY: MISC_FEATURE
<222> LOCATION: (16)..(16)
<223> OTHER INFORMATION: wherein LEU is conjugated to an AMIDE
<220> FEATURE:
<221> NAME/KEY: MISC_FEATURE
<222> LOCATION: (16)..(16)
<223> OTHER INFORMATION: wherein LEU is a D-amino acid

<400> SEQUENCE: 104

Xaa Asp Glu Cys Glu Leu Cys Val Asn Val Ala Cys Thr Gly Cys Leu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol
<220> FEATURE:
<221> NAME/KEY: MISC_FEATURE
<222> LOCATION: (16)..(16)
<223> OTHER INFORMATION: wherein LEU is attached to polyethylene glycol

<400> SEQUENCE: 105

Asn Asp Glu Cys Glu Leu Cys Val Asn Val Ala Cys Thr Gly Cys Leu
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol

<400> SEQUENCE: 106

Asn Asp Glu Cys Glu Leu Cys Val Asn Val Ala Cys Thr Gly Cys Leu
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU is attached to polyethylene glycol

<400> SEQUENCE: 107

Asn Asp Glu Cys Glu Leu Cys Val Asn Val Ala Cys Thr Gly Cys Leu
1               5                   10                  15
```

```
<210> SEQ ID NO 108
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, or unnatural amino
      acid or amino acid analogue and may be an L-amino acid, or a
      D-amino acid, or a methylated or an unmethylated amino acid
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (8)..(11)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, or unnatural amino
      acid or amino acid analogue, and may be an L-amino acid, or a
      D-amino acid, or a methylated or an unmethylated amino acid
<220> FEATURE:
<221> NAME/KEY: MISC_FEATURE
<222> LOCATION: (15)..(15)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (16)..(16)
<223> OTHER INFORMATION: wherein x is any natural, or unnatural amino
      acid or amino acid analogue, and may be an L-amino acid, or a
      D-amino acid, or a methylated or an unmethylated amino acid

<400> SEQUENCE: 108

Xaa Xaa Xaa Xaa Xaa Xaa Xaa Xaa Xaa Xaa Xaa Xaa Xaa Xaa Xaa Xaa
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 109

Asn Asp Asp Cys Glu Leu Cys Val Asn Val Ala Cys Thr Gly Cys Leu
1               5                   10                  15

<210> SEQ ID NO 110
```

```
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 110

Glu Asp Asp Cys Glu Leu Cys Val Asn Val Ala Cys Thr Gly Cys Leu
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 111

Glu Asp Glu Cys Glu Leu Cys Val Asn Val Ala Cys Thr Gly Cys Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 112

Glu Glu Asp Cys Glu Leu Cys Val Asn Val Ala Cys Thr Gly Cys Leu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 113

Glu Glu Glu Cys Glu Leu Cys Val Asn Val Ala Cys Thr Gly Cys Leu
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 114

Asp Asp Asp Cys Glu Leu Cys Val Asn Val Ala Cys Thr Gly Cys Leu
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 115

Asp Asp Glu Cys Glu Leu Cys Val Asn Val Ala Cys Thr Gly Cys Leu
1               5                   10                  15

<210> SEQ ID NO 116
<211> LENGTH: 16
```

```
<212> TYPE: PRT
<213> ORGANISM: Artificial Sequence
<220> FEATURE:
<223> OTHER INFORMATION: Chemically Synthesized

<400> SEQUENCE: 116

Asp Glu Asp Cys Glu Leu Cys Val Asn Val Ala Cys Thr Gly Cys Leu
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 117

Asp Glu Glu Cys Glu Leu Cys Val Asn Val Ala Cys Thr Gly Cys Leu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 118

Gln Asp Asp Cys Glu Leu Cys Val Asn Val Ala Cys Thr Gly Cys Leu
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 119

Gln Asp Glu Cys Glu Leu Cys Val Asn Val Ala Cys Thr Gly Cys Leu
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 120

Gln Glu Asp Cys Glu Leu Cys Val Asn Val Ala Cys Thr Gly Cys Leu
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 121

Gln Glu Glu Cys Glu Leu Cys Val Asn Val Ala Cys Thr Gly Cys Leu
1               5                   10                  15

<210> SEQ ID NO 122
<211> LENGTH: 16
<212> TYPE: PRT
```

```
<213> ORGANISM: Artificial Sequence
<220> FEATURE:
<223> OTHER INFORMATION: Chemically Synthesized

<400> SEQUENCE: 122

Lys Asp Asp Cys Glu Leu Cys Val Asn Val Ala Cys Thr Gly Cys Leu
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 123

Lys Asp Glu Cys Glu Leu Cys Val Asn Val Ala Cys Thr Gly Cys Leu
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 124

Lys Glu Asp Cys Glu Leu Cys Val Asn Val Ala Cys Thr Gly Cys Leu
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 125

Lys Glu Glu Cys Glu Leu Cys Val Asn Val Ala Cys Thr Gly Cys Leu
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 126

Glu Asp Asp Cys Glu Leu Cys Val Asn Val Ala Cys Thr Gly Cys Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 127

Glu Asp Glu Cys Glu Leu Cys Val Asn Val Ala Cys Thr Gly Cys Ser
1               5                   10                  15

<210> SEQ ID NO 128
<211> LENGTH: 16
<212> TYPE: PRT
<213> ORGANISM: Artificial Sequence
```

<220> FEATURE:
<223> OTHER INFORMATION: Chemically Synthesized

<400> SEQUENCE: 128

Glu Glu Asp Cys Glu Leu Cys Val Asn Val Ala Cys Thr Gly Cys Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 129

Glu Glu Glu Cys Glu Leu Cys Val Asn Val Ala Cys Thr Gly Cys Ser
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 130

Asp Asp Asp Cys Glu Leu Cys Val Asn Val Ala Cys Thr Gly Cys Ser
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 131

Asp Asp Glu Cys Glu Leu Cys Val Asn Val Ala Cys Thr Gly Cys Ser
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 132

Asp Glu Asp Cys Glu Leu Cys Val Asn Val Ala Cys Thr Gly Cys Ser
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 133

Asp Glu Glu Cys Glu Leu Cys Val Asn Val Ala Cys Thr Gly Cys Ser
1               5                   10                  15

<210> SEQ ID NO 134
<211> LENGTH: 16
<212> TYPE: PRT
<213> ORGANISM: Artificial Sequence
<220> FEATURE:

<223> OTHER INFORMATION: Chemically Synthesized

<400> SEQUENCE: 134

Gln Asp Asp Cys Glu Leu Cys Val Asn Val Ala Cys Thr Gly Cys Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 135

Gln Asp Glu Cys Glu Leu Cys Val Asn Val Ala Cys Thr Gly Cys Ser
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 136

Gln Glu Asp Cys Glu Leu Cys Val Asn Val Ala Cys Thr Gly Cys Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 137

Gln Glu Glu Cys Glu Leu Cys Val Asn Val Ala Cys Thr Gly Cys Ser
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 138

Lys Asp Asp Cys Glu Leu Cys Val Asn Val Ala Cys Thr Gly Cys Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 139

Lys Asp Glu Cys Glu Leu Cys Val Asn Val Ala Cys Thr Gly Cys Ser
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 140

Lys Glu Asp Cys Glu Leu Cys Val Asn Val Ala Cys Thr Gly Cys Ser
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 141

Lys Glu Glu Cys Glu Leu Cys Val Asn Val Ala Cys Thr Gly Cys Ser
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 142

Glu Asp Asp Cys Glu Leu Cys Ile Asn Met Ala Cys Thr Gly Cys Leu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 143

Glu Asp Glu Cys Glu Leu Cys Ile Asn Met Ala Cys Thr Gly Cys Leu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 144

Glu Glu Asp Cys Glu Leu Cys Ile Asn Met Ala Cys Thr Gly Cys Leu
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 145

Glu Glu Glu Cys Glu Leu Cys Ile Asn Met Ala Cys Thr Gly Cys Leu
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Chemically Synthesized

```
<400> SEQUENCE: 146

Asp Asp Asp Cys Glu Leu Cys Ile Asn Met Ala Cys Thr Gly Cys Leu
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 147

Asp Asp Glu Cys Glu Leu Cys Ile Asn Met Ala Cys Thr Gly Cys Leu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 148

Asp Glu Asp Cys Glu Leu Cys Ile Asn Met Ala Cys Thr Gly Cys Leu
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 149

Asp Glu Glu Cys Glu Leu Cys Ile Asn Met Ala Cys Thr Gly Cys Leu
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 150

Gln Asp Asp Cys Glu Leu Cys Ile Asn Met Ala Cys Thr Gly Cys Leu
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 151

Gln Asp Glu Cys Glu Leu Cys Ile Asn Met Ala Cys Thr Gly Cys Leu
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 152
```

```
Gln Glu Asp Cys Glu Leu Cys Ile Asn Met Ala Cys Thr Gly Cys Leu
1               5                   10                  15
```

<210> SEQ ID NO 153
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 153

```
Gln Glu Glu Cys Glu Leu Cys Ile Asn Met Ala Cys Thr Gly Cys Leu
1               5                   10                  15
```

<210> SEQ ID NO 154
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 154

```
Lys Asp Asp Cys Glu Leu Cys Ile Asn Met Ala Cys Thr Gly Cys Leu
1               5                   10                  15
```

<210> SEQ ID NO 155
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 155

```
Lys Asp Glu Cys Glu Leu Cys Ile Asn Met Ala Cys Thr Gly Cys Leu
1               5                   10                  15
```

<210> SEQ ID NO 156
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 156

```
Lys Glu Asp Cys Glu Leu Cys Ile Asn Met Ala Cys Thr Gly Cys Leu
1               5                   10                  15
```

<210> SEQ ID NO 157
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 157

```
Lys Glu Glu Cys Glu Leu Cys Ile Asn Met Ala Cys Thr Gly Cys Leu
1               5                   10                  15
```

<210> SEQ ID NO 158
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 158

Glu Asp Asp Cys Glu Leu Cys Ile Asn Met Ala Cys Thr Gly Cys Ser
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 159

Glu Asp Glu Cys Glu Leu Cys Ile Asn Met Ala Cys Thr Gly Cys Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 160

Glu Glu Asp Cys Glu Leu Cys Ile Asn Met Ala Cys Thr Gly Cys Ser
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 161

Glu Glu Glu Cys Glu Leu Cys Ile Asn Met Ala Cys Thr Gly Cys Ser
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 162

Asp Asp Asp Cys Glu Leu Cys Ile Asn Met Ala Cys Thr Gly Cys Ser
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 163

Asp Asp Glu Cys Glu Leu Cys Ile Asn Met Ala Cys Thr Gly Cys Ser
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 164

Asp Glu Asp Cys Glu Leu Cys Ile Asn Met Ala Cys Thr Gly Cys Ser

```
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 165

Asp Glu Glu Cys Glu Leu Cys Ile Asn Met Ala Cys Thr Gly Cys Ser
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 166

Gln Asp Asp Cys Glu Leu Cys Ile Asn Met Ala Cys Thr Gly Cys Ser
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 167

Gln Asp Glu Cys Glu Leu Cys Ile Asn Met Ala Cys Thr Gly Cys Ser
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 168

Gln Glu Asp Cys Glu Leu Cys Ile Asn Met Ala Cys Thr Gly Cys Ser
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 169

Gln Glu Glu Cys Glu Leu Cys Ile Asn Met Ala Cys Thr Gly Cys Ser
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 170

Lys Asp Asp Cys Glu Leu Cys Ile Asn Met Ala Cys Thr Gly Cys Ser
1               5                   10                  15
```

<210> SEQ ID NO 171
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 171

Lys Asp Glu Cys Glu Leu Cys Ile Asn Met Ala Cys Thr Gly Cys Ser
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 172

Lys Glu Asp Cys Glu Leu Cys Ile Asn Met Ala Cys Thr Gly Cys Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 173

Lys Glu Glu Cys Glu Leu Cys Ile Asn Met Ala Cys Thr Gly Cys Ser
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, or unnatural amino
      acid, or amino acid analogue, and may be an L-amino acid, or a
      D-amino acid, or a methylated or an unmethylated amino acid
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue, and may be an L-amino acid, or a
      D-amino acid, or a methylated or an unmethylated amino acid
<220> FEATURE:
<221> NAME/KEY: MISC_FEATURE
<222> LOCATION: (7)..(7)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (8)..(11)
<223> OTHER INFORMATION: wherein x is any natural, or unnatural amino
      acid, or amino acid analogue, and may be an L-amino acid, or a
      D-amino acid, or a methylated or an unmethylated amino acid
<220> FEATURE:
<221> NAME/KEY: MISC_FEATURE
<222> LOCATION: (12)..(12)
<223> OTHER INFORMATION: wherein x is a cysteine, penicillamine

```
       homocysteine, or 3-mercaptoproline
<220> FEATURE:
<221> NAME/KEY: MISC_FEATURE
<222> LOCATION: (13)..(14)
<223> OTHER INFORMATION: wherein x is any natural, or unnatural amino
       acid, or amino acid analogue, and may be an L-amino acid, or a
       D-amino acid, or a methylated or an unmethylated amino acid
<220> FEATURE:
<221> NAME/KEY: MISC_FEATURE
<222> LOCATION: (15)..(15)
<223> OTHER INFORMATION: wherein x is a cysteine, penicillamine
       homocysteine, or 3-mercaptoproline

<400> SEQUENCE: 174

Xaa Xaa Xaa Xaa Xaa Xaa Xaa Xaa Xaa Xaa Xaa Xaa Xaa Xaa Xaa
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 175

Ser His Thr Cys Glu Ile Cys Ala Phe Ala Ala Cys Ala Gly Cys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 176

Ser His Thr Cys Glu Ile Cys Ala Asn Ala Ala Cys Ala Gly Cys
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 177

Ser His Thr Cys Glu Leu Cys Ala Asn Ala Ala Cys Ala Gly Cys
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 178

Ser His Thr Cys Glu Val Cys Ala Asn Ala Ala Cys Ala Gly Cys
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 179
```

Ser His Thr Cys Glu Tyr Cys Ala Asn Ala Ala Cys Ala Gly Cys
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 180

Ser His Thr Cys Glu Ile Cys Ala Asn Ala Ala Cys Ala Gly Cys
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 181

Ser His Thr Cys Glu Leu Cys Ala Asn Ala Ala Cys Ala Gly Cys
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 182

Ser His Thr Cys Glu Val Cys Ala Asn Ala Ala Cys Ala Gly Cys
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 183

Ser His Thr Cys Glu Tyr Cys Ala Asn Ala Ala Cys Ala Gly Cys
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 184

Ser His Thr Cys Glu Ile Cys Ala Asn Ala Ala Cys Ala Gly Cys
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 185

```
Ser His Thr Cys Glu Leu Cys Ala Asn Ala Ala Cys Ala Gly Cys
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 186

Ser His Thr Cys Glu Val Cys Ala Asn Ala Ala Cys Ala Gly Cys
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 187

Ser His Thr Cys Glu Tyr Cys Ala Asn Ala Ala Cys Ala Gly Cys
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 188

Ser His Thr Cys Glu Ile Cys Ala Asn Ala Ala Cys Ala Gly Cys
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 189

Ser His Thr Cys Glu Leu Cys Ala Asn Ala Ala Cys Ala Gly Cys
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 190

Ser His Thr Cys Glu Val Cys Ala Asn Ala Ala Cys Ala Gly Cys
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 191

Ser His Thr Cys Glu Tyr Cys Ala Asn Ala Ala Cys Ala Gly Cys
```

```
1               5                   10                  15
```

<210> SEQ ID NO 192
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 192

```
Asn Asp Glu Cys Glu Ile Cys Ala Asn Ala Ala Cys Ala Gly Cys
1               5                   10                  15
```

<210> SEQ ID NO 193
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 193

```
Asn Asp Glu Cys Glu Leu Cys Ala Asn Ala Ala Cys Ala Gly Cys
1               5                   10                  15
```

<210> SEQ ID NO 194
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 194

```
Asn Asp Glu Cys Glu Val Cys Ala Asn Ala Ala Cys Ala Gly Cys
1               5                   10                  15
```

<210> SEQ ID NO 195
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 195

```
Asn Asp Glu Cys Glu Tyr Cys Ala Asn Ala Ala Cys Ala Gly Cys
1               5                   10                  15
```

<210> SEQ ID NO 196
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 196

```
Asn Asp Glu Cys Glu Ile Cys Ala Asn Ala Ala Cys Ala Gly Cys
1               5                   10                  15
```

<210> SEQ ID NO 197
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 197

```
Asn Asp Glu Cys Glu Leu Cys Ala Asn Ala Ala Cys Ala Gly Cys
1               5                   10                  15
```

```
<210> SEQ ID NO 198
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 198

Asn Asp Glu Cys Glu Val Cys Ala Asn Ala Ala Cys Ala Gly Cys
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 199

Asn Asp Glu Cys Glu Tyr Cys Ala Asn Ala Ala Cys Ala Gly Cys
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 200

Asn Asp Glu Cys Glu Ile Cys Ala Asn Ala Ala Cys Ala Gly Cys
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 201

Asn Asp Glu Cys Glu Leu Cys Ala Asn Ala Ala Cys Ala Gly Cys
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 202

Asn Asp Glu Cys Glu Val Cys Ala Asn Ala Ala Cys Ala Gly Cys
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 203

Asn Asp Glu Cys Glu Tyr Cys Ala Asn Ala Ala Cys Ala Gly Cys
1               5                   10                  15
```

```
<210> SEQ ID NO 204
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 204

Asn Asp Glu Cys Glu Ile Cys Ala Asn Ala Ala Cys Ala Gly Cys
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 205

Asn Asp Glu Cys Glu Leu Cys Ala Asn Ala Ala Cys Ala Gly Cys
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 206

Asn Asp Glu Cys Glu Val Cys Ala Asn Ala Ala Cys Ala Gly Cys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 207

Asn Asp Glu Cys Glu Tyr Cys Ala Asn Ala Ala Cys Ala Gly Cys
1               5                   10                  15

<210> SEQ ID NO 208
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: wherein x is any natural, or unnatural amino
      acid, or amino acid analogue, and may be an L-amino acid, or a
      D-amino acid, or a methylated, or an unmethylated amino acid
<220> FEATURE:
<221> NAME/KEY: MISC_FEATURE
<222> LOCATION: (4)..(4)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (5)..(6)
<223> OTHER INFORMATION: wherein x is any natural, or unnatural amino
      acid, or amino acid analogue, and may be an L-amino acid, or a
      D-amino acid, or a methylated, or an unmethylated amino acid
<220> FEATURE:
<221> NAME/KEY: MISC_FEATURE
<222> LOCATION: (7)..(7)
```

```
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (8)..(11)
<223> OTHER INFORMATION: wherein x is any natural, or unnatural amino
      acid, or amino acid analogue, and may be an L-amino acid, or a
      D-amino acid, or a methylated, or an unmethylated amino acid
<220> FEATURE:
<221> NAME/KEY: MISC_FEATURE
<222> LOCATION: (12)..(12)
<223> OTHER INFORMATION: wherein x is a cysteine, penicillamine
      homocysteine, or 3-mercaptoproline
<220> FEATURE:
<221> NAME/KEY: MISC_FEATURE
<222> LOCATION: (13)..(14)
<223> OTHER INFORMATION: wherein x is any natural, or unnatural amino
      acid, or amino acid analogue, and may be an L-amino acid, or a
      D-amino acid, or a methylated, or an unmethylated amino acid
<220> FEATURE:
<221> NAME/KEY: MISC_FEATURE
<222> LOCATION: (15)..(15)
<223> OTHER INFORMATION: wherein x is any natural, or unnatural amino
      acid, or amino acid analogue and may be an L-amino acid, or a
      D-amino acid, or a methylated, or an unmethylated amino acid
<220> FEATURE:
<221> NAME/KEY: MISC_FEATURE
<222> LOCATION: (16)..(16)
<223> OTHER INFORMATION: wherein x is any natural, or unnatural amino
      acid, or amino acid analogue, and may be zero or one residue in
      length, and may be an L-amino acid, or a D-amino acid, or a
      methylated, or an unmethylated amino acid
<220> FEATURE:
<221> NAME/KEY: MISC_FEATURE
<222> LOCATION: (17)..(17)
<223> OTHER INFORMATION: wherein x is any natural, or unnatural amino
      acid, or amino acid analogue, and may be zero or one residue in
      length, and may be an L-amino acid, or a D-amino acid, or a
      methylated, or an unmethylated amino acid

<400> SEQUENCE: 208

Xaa Xaa Xaa Xaa Xaa Xaa Xaa Xaa Xaa Xaa Xaa Xaa Xaa Xaa Xaa
1               5                   10                  15

Xaa

<210> SEQ ID NO 209
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 209

Gln Glu Glu Cys Glu Leu Cys Ile Asn Met Ala Cys Thr Gly Tyr
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 210

Gln Glu Glu Cys Glu Thr Cys Ile Asn Met Ala Cys Thr Gly Tyr
1               5                   10                  15

<210> SEQ ID NO 211
<211> LENGTH: 15
<212> TYPE: PRT
<213> ORGANISM: Artificial Sequence
<220> FEATURE:
```

<223> OTHER INFORMATION: Chemically Synthesized

<400> SEQUENCE: 211

Gln Asp Glu Cys Glu Thr Cys Ile Asn Met Ala Cys Thr Gly Tyr
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 212

Gln Asp Asp Cys Glu Thr Cys Ile Asn Met Ala Cys Thr Gly Tyr
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 213

Gln Glu Asp Cys Glu Thr Cys Ile Asn Met Ala Cys Thr Gly Tyr
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 214

Gln Glu Glu Cys Glu Glu Cys Ile Asn Met Ala Cys Thr Gly Tyr
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 215

Gln Asp Glu Cys Glu Glu Cys Ile Asn Met Ala Cys Thr Gly Tyr
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 216

Gln Asp Asp Cys Glu Glu Cys Ile Asn Met Ala Cys Thr Gly Tyr
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 217

Gln Glu Asp Cys Glu Glu Cys Ile Asn Met Ala Cys Thr Gly Tyr
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 218

Gln Glu Glu Cys Glu Tyr Cys Ile Asn Met Ala Cys Thr Gly Tyr
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 219

Gln Asp Glu Cys Glu Tyr Cys Ile Asn Met Ala Cys Thr Gly Tyr
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 220

Gln Asp Asp Cys Glu Tyr Cys Ile Asn Met Ala Cys Thr Gly Tyr
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 221

Gln Glu Asp Cys Glu Tyr Cys Ile Asn Met Ala Cys Thr Gly Tyr
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 222

Gln Glu Glu Cys Glu Ile Cys Ile Asn Met Ala Cys Thr Gly Tyr
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Chemically Synthesized

```
<400> SEQUENCE: 223

Gln Asp Glu Cys Glu Ile Cys Ile Asn Met Ala Cys Thr Gly Tyr
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 224

Gln Asp Asp Cys Glu Ile Cys Ile Asn Met Ala Cys Thr Gly Tyr
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 225

Gln Glu Asp Cys Glu Ile Cys Ile Asn Met Ala Cys Thr Gly Tyr
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 226

Gln Glu Glu Cys Glu Thr Cys Ile Asn Met Ala Cys Thr Gly Cys Ser
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 227

Gln Asp Glu Cys Glu Thr Cys Ile Asn Met Ala Cys Thr Gly Cys Ser
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 228

Gln Asp Asp Cys Glu Thr Cys Ile Asn Met Ala Cys Thr Gly Cys Ser
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 229
```

Gln Glu Asp Cys Glu Thr Cys Ile Asn Met Ala Cys Thr Gly Cys Ser
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 230

Gln Glu Glu Cys Glu Glu Cys Ile Asn Met Ala Cys Thr Gly Cys Ser
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 231

Gln Asp Glu Cys Glu Glu Cys Ile Asn Met Ala Cys Thr Gly Cys Ser
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 232

Gln Asp Asp Cys Glu Glu Cys Ile Asn Met Ala Cys Thr Gly Cys Ser
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 233

Gln Glu Asp Cys Glu Glu Cys Ile Asn Met Ala Cys Thr Gly Cys Ser
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 234

Gln Glu Glu Cys Glu Tyr Cys Ile Asn Met Ala Cys Thr Gly Cys Ser
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 235

Gln Asp Glu Cys Glu Tyr Cys Ile Asn Met Ala Cys Thr Gly Cys Ser
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 236

Gln Asp Asp Cys Glu Tyr Cys Ile Asn Met Ala Cys Thr Gly Cys Ser
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 237

Gln Glu Asp Cys Glu Tyr Cys Ile Asn Met Ala Cys Thr Gly Cys Ser
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 238

Gln Glu Glu Cys Glu Ile Cys Ile Asn Met Ala Cys Thr Gly Cys Ser
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 239

Gln Asp Glu Cys Glu Ile Cys Ile Asn Met Ala Cys Thr Gly Cys Ser
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 240

Gln Asp Asp Cys Glu Ile Cys Ile Asn Met Ala Cys Thr Gly Cys Ser
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 241

Gln Glu Asp Cys Glu Ile Cys Ile Asn Met Ala Cys Thr Gly Cys Ser

```
1               5                   10                  15

<210> SEQ ID NO 242
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 242

Asn Ser Ser Asn Ser Ser Asn Tyr Cys Cys Glu Lys Cys Cys Asn Pro
1               5                   10                  15

Ala Cys Thr Gly Cys Tyr
            20

<210> SEQ ID NO 243
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol
<220> FEATURE:
<221> NAME/KEY: MISC_FEATURE
<222> LOCATION: (16)..(16)
<223> OTHER INFORMATION: wherein TYR is attached to polyethylene glycol

<400> SEQUENCE: 243

Asn Phe Cys Cys Glu Thr Cys Cys Asn Pro Ala Cys Thr Gly Cys Tyr
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol

<400> SEQUENCE: 244

Asn Phe Cys Cys Glu Thr Cys Cys Asn Pro Ala Cys Thr Gly Cys Tyr
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is attached to polyethylene glycol

<400> SEQUENCE: 245

Asn Phe Cys Cys Glu Thr Cys Cys Asn Pro Ala Cys Thr Gly Cys Tyr
1               5                   10                  15

<210> SEQ ID NO 246
<211> LENGTH: 16
<212> TYPE: PRT
<213> ORGANISM: Artificial Sequence
<220> FEATURE:
```

<223> OTHER INFORMATION: Chemically Synthesized

<400> SEQUENCE: 246

Asn Phe Cys Cys Glu Tyr Cys Cys Asn Pro Ala Cys Thr Gly Cys Tyr
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 247

Asn Phe Cys Cys Glu Tyr Cys Cys Asn Pro Ala Cys Thr Gly Cys Tyr
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D-amino acid

<400> SEQUENCE: 248

Asn Phe Cys Cys Glu Tyr Cys Cys Asn Pro Ala Cys Thr Gly Cys Tyr
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D-amino acid

<400> SEQUENCE: 249

Asn Phe Cys Cys Glu Tyr Cys Cys Asn Pro Ala Cys Thr Gly Cys Tyr
1               5                   10                  15

<210> SEQ ID NO 250
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 250

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

```
<210> SEQ ID NO 251
<211> LENGTH: 27
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein HIS is conjugated to an AMINE having
      the general formula R-NH, and wherein R is a hydrogen or an
      organic compound having one, two, three, four, five, six, seven,
      eight, nine, or ten carbon atoms
<220> FEATURE:
<221> NAME/KEY: MISC_FEATURE
<222> LOCATION: (27)..(27)
<223> OTHER INFORMATION: wherein LYS is conjugated to an AMIDE

<400> SEQUENCE: 251

His Ala Glu Gly Thr Phe Thr Ser Asp Val Ser Tyr Leu Glu Gly Gln
1               5                   10                  15

Ala Ala Lys Glu Phe Ile Ala Trp Leu Val Lys
            20                  25

<210> SEQ ID NO 252
<211> LENGTH: 5
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 252

Gln His Asn Pro Arg
1               5

<210> SEQ ID NO 253
<211> LENGTH: 6
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 253

Val Gln His Asn Pro Arg
1               5

<210> SEQ ID NO 254
<211> LENGTH: 7
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 254

Val Arg Gln His Asn Pro Arg
1               5

<210> SEQ ID NO 255
<211> LENGTH: 8
<212> TYPE: PRT
<213> ORGANISM: Artificial Sequence
<220> FEATURE:
<223> OTHER INFORMATION: Chemically Synthesized Sialorphin-related
      polypeptide
```

```
<400> SEQUENCE: 255

Val Arg Gly Gln His Asn Pro Arg
1               5

<210> SEQ ID NO 256
<211> LENGTH: 9
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 256

Val Arg Gly Pro Gln His Asn Pro Arg
1               5

<210> SEQ ID NO 257
<211> LENGTH: 10
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 257

Val Arg Gly Pro Arg Gln His Asn Pro Arg
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 258

Val Arg Gly Pro Arg Arg Gln His Asn Pro Arg
1               5                   10

<210> SEQ ID NO 259
<211> LENGTH: 6
<212> TYPE: PRT
<213> ORGANISM: Artificial Sequence
<220> FEATURE:
<223> OTHER INFORMATION: Chemically Synthesized Sialorphin-related
      polypeptide

<400> SEQUENCE: 259

Arg Gln His Asn Pro Arg
1               5

<210> SEQ ID NO 260
<211> LENGTH: 5
<212> TYPE: PRT
<213> ORGANISM: Artificial Sequence
<220> FEATURE:
<223> OTHER INFORMATION: Chemically Synthesized Enkephalin Pentapeptide
<220> FEATURE:
<221> NAME/KEY: MISC_FEATURE
<222> LOCATION: (2)..(2)
<223> OTHER INFORMATION: wherein LYS is a D-amino acid
<220> FEATURE:
<221> NAME/KEY: MISC_FEATURE
<222> LOCATION: (5)..(5)
<223> OTHER INFORMATION: wherein x is a L-homoserine
```

```
<400> SEQUENCE: 260

Tyr Lys Gly Phe Xaa
1               5

<210> SEQ ID NO 261
<211> LENGTH: 4
<212> TYPE: PRT
<213> ORGANISM: Artificial Sequence
<220> FEATURE:
<223> OTHER INFORMATION: Chemically Synthesized Frakefamide
<220> FEATURE:
<221> NAME/KEY: MISC_FEATURE
<222> LOCATION: (2)..(2)
<223> OTHER INFORMATION: wherein ALA is a D-amino acid
<220> FEATURE:
<221> NAME/KEY: MOD_RES
<222> LOCATION: (3)..(3)
<223> OTHER INFORMATION: wherein PHE is fluorinated at the phenyl group
      at 4-position
<220> FEATURE:
<221> NAME/KEY: MISC_FEATURE
<222> LOCATION: (4)..(4)
<223> OTHER INFORMATION: wherein PHE is attached to an AMINE

<400> SEQUENCE: 261

Tyr Ala Phe Phe
1
```

FORMULATIONS OF GUANYLATE CYCLASE C AGONISTS AND METHODS OF USE

RELATED APPLICATIONS

This application is a continuation of U.S. application Ser. No. 14/845,644, filed Sep. 4, 2015, now U.S. Pat. No. 9,610,321, which is a continuation of U.S. application Ser. No. 14/661,299 filed Mar. 18, 2015 which is a continuation of U.S. application Ser. No. 13/421,769, filed Mar. 15, 2012, now U.S. Pat. No. 9,616,097, which is a continuation-in-part of PCT/US2011/051805 filed on Sep. 15, 2011, which claims the benefit of priority to U.S. Provisional Application No. 61/383,156 filed on Sep. 15, 2010, U.S. Provisional Application No. 61/387,636 filed on Sep. 29, 2010, and U.S. Provisional Application No. 61/392,186 filed on Oct. 12, 2010, the contents of each of which are incorporated by reference in their entireties.

INCORPORATION OF SEQUENCE LISTING

The contents of the text file named "SYPA_009_C03US_SeqList_ST25.txt", which was created on Mar. 23, 2017 and is 113 KB in size, are hereby incorporated by reference in their entirety.

FIELD OF THE INVENTION

The present invention relates to low-dose formulations of guanylate cyclase C peptide agonists useful for the treatment and prevention of various diseases and disorders.

BACKGROUND OF THE INVENTION

Guanylate cyclase C is a transmembrane form of guanylate cyclase that is expressed on various cells, including gastrointestinal epithelial cells (reviewed in Vaandrager 2002 *Mol. Cell. Biochem.* 230:73-83). It was originally discovered as the intestinal receptor for the heat-stable toxin (ST) peptides secreted by enteric bacteria and which cause diarrhea. The ST peptides share a similar primary amino acid structure with two peptides isolated from intestinal mucosa and urine, guanylin and uroguanylin (Currie, et al., *Proc. Nat'l Acad. Sci. USA* 89:947-951 (1992); Hamra, et al., *Proc. Nat'l Acad. Sci. USA* 90:10464-10468 (1993); Forte, L., *Reg. Pept.* 81:25-39 (1999); Schulz, et al., *Cell* 63:941-948 (1990); Guba, et al., *Gastroenterology* 111:1558-1568 (1996); Joo, et al., *Am. J. Physiol.* 274:G633-G644 (1998)).

In the intestines, guanylin and uroguanylin act as regulators of fluid and electrolyte balance. In response to high oral salt intake, these peptides are released into the intestinal lumen where they bind to guanylate cyclase C localized on the luminal membrane of enterocytes (simple columnar epithelial cells of the small intestines and colon). The binding of the guanylin peptides to guanylate cyclase C induces electrolyte and water excretion into the intestinal lumen via a complex intracellular signaling cascade that is initiated by an increase in cyclic guanosine monophosphate (cGMP).

The cGMP-mediated signaling that is initiated by the guanylin peptides is critical for the normal functioning of the gut. Any abnormality in this process could lead to gastrointestinal disorders such as irritable bowel syndrome (IBS) and inflammatory bowel diseases. Inflammatory bowel disease is a general name given to a group of disorders that cause the intestines to become inflamed, characterized by red and swollen tissue. Examples include ulcerative colitis and Crohn's disease. Crohn's disease is a serious inflammatory disease that predominantly affects the ileum and colon, but can also occur in other sections of the gastrointestinal tract. Ulcerative colitis is exclusively an inflammatory disease of the colon, the large intestine. Unlike Crohn's disease, in which all layers of the intestine are involved, and in which there can be normal healthy bowel in between patches of diseased bowel, ulcerative colitis affects only the innermost lining (mucosa) of the colon in a continuous manner. Depending on which portion of the gastrointestinal tract is involved, Crohn's disease may be referred to as ileitis, regional enteritis, colitis, etc. Crohn's disease and ulcerative colitis differ from spastic colon or irritable bowel syndrome, which are motility disorders of the gastrointestinal tract. Gastrointestinal inflammation can be a chronic condition. It is estimated that as many as 1,000,000 Americans are afflicted with inflammatory bowel disease, with male and female patients appearing to be equally affected. Most cases are diagnosed before age 30, but the disease can occur in the sixth, seventh, and later decades of life.

IBS and chronic idiopathic constipation are pathological conditions that can cause a great deal of intestinal discomfort and distress but unlike the inflammatory bowel diseases, IBS does not cause the serious inflammation or changes in bowel tissue and it is not thought to increase the risk of colorectal cancer. In the past, inflammatory bowel disease, celiac disease and IBS were regarded as completely separate disorders. Now, with the description of inflammation, albeit low-grade, in IBS, and of symptom overlap between IBS and celiac disease, this contention has come under question. Acute bacterial gastroenteritis is the strongest risk factor identified to date for the subsequent development of postinfective irritable bowel syndrome. Clinical risk factors include prolonged acute illness and the absence of vomiting. A genetically determined susceptibility to inflammatory stimuli may also be a risk factor for irritable bowel syndrome. The underlying pathophysiology indicates increased intestinal permeability and low-grade inflammation, as well as altered motility and visceral sensitivity. Serotonin (5-hydroxytryptamine [5-HT]) is a key modulator of gut function and is known to play a major role in pathophysiology of IBS. The activity of 5-HT is regulated by cGMP.

While the precise causes of IBS and inflammatory bowel diseases (IBD) are not known, a disruption in the process of continual renewal of the gastrointestinal mucosa may contribute to disease pathology in IBD and aggravate IBS. The renewal process of the gastrointestinal lining is an efficient and dynamic process involving the continual proliferation and replenishment of unwanted damaged cells. Proliferation rates of cells lining the gastrointestinal mucosa are very high, second only to the hematopoietic system. Gastrointestinal homeostasis depends on both the proliferation and programmed cellular death (apoptosis) of epithelial cells lining the gut mucosa. Cells are continually lost from the villus into the lumen of the gut and are replenished at a substantially equal rate by the proliferation of cells in the crypts, followed by their upward movement to the villus. The rates of cell proliferation and apoptosis in the gut epithelium can be increased or decreased in a variety of circumstances, e.g., in response to physiological stimuli such as aging, inflammatory signals, hormones, peptides, growth factors, chemicals and dietary habits. In addition, an enhanced proliferation rate is frequently associated with a reduction in turnover time and an expansion of the proliferative zone. The proliferation index is much higher in pathological states such as ulcerative colitis and other gastrointestinal disorders. Intestinal hyperplasia is a major promoter of gastrointestinal inflammation. Apoptosis and cell proliferation together regulate cell number and determine the proliferation index. Reduced rates of apoptosis are often associated with abnormal growth, inflammation, and neoplastic transformation. Thus, both increased proliferation and/or reduced cell death may increase the proliferation index of intestinal tissue, which may in turn lead to gastrointestinal inflammatory diseases.

In addition to a role for uroguanylin and guanylin as modulators of intestinal fluid and ion secretion, these peptides may also be involved in the continual renewal of gastrointestinal mucosa by maintaining the balance between proliferation and apoptosis. For example, uroguanylin and guanylin peptides appear to promote apoptosis by controlling cellular ion flux. Given the prevalence of inflammatory conditions in Western societies a need exists to improve the treatment options for inflammatory conditions, particularly of the gastrointestinal tract.

Peptide agonists of guanylate cyclase C agonists ("GCC agonists") are described in U.S. Pat. Nos. 7,041,786, 7,799,897, and U.S. Patent Application Publication Nos. US2009/0048175, US 2010/0069306, US 2010/0120694, US 2010/0093635, and US 2010/0221329. However, the formulation of peptides for pharmaceutical delivery presents a number of special problems. For example, peptides are subject to structural modifications by a variety of degradation mechanisms resulting in problems of chemical and physical instability of the formulation.

SUMMARY OF THE INVENTION

The present invention provides low-dose formulations of peptide agonists of guanylate cyclase C ("GCC") and methods for their use in the treatment and prevention of human diseases and disorders, such as a gastrointestinal motility disorder, irritable bowel syndrome, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction; Crohn's disease, ulcerative colitis, inflammatory bowel disease, colonic pseudo-obstruction, obesity, congestive heart failure, and benign prostatic hyperplasia. In certain embodiments, the formulations are stabilized against chemical degradation of the peptide. The low-dose formulations of the invention have unexpected efficacy in humans in a dosage range that was not predicted based on studies in primates. The formulations of the invention are particularly useful for the treatment or prevention of chronic idiopathic constipation. In certain embodiments, the GCC agonists are analogs of uroguanylin and bacterial ST peptides. In preferred embodiments, the analogs have superior properties compared to the naturally occurring or "wild-type" peptides. Examples of such superior properties include a high resistance to degradation at the N-terminus and C-terminus from carboxypeptidases, aminopeptidases, and/or by other proteolytic enzymes present in the stimulated human intestinal juices and human gastric juices. Examples of GCC agonists that can be used in the formulations and methods of the invention are described in more detail below and in U.S. Pat. Nos. 7,041,786, 7,799,897, and U.S. Patent Application Publication Nos. US2009/0048175, US 2010/0069306, US 2010/0120694, US 2010/0093635, and US 2010/0221329, each of which is incorporated herein by reference in its entirety.

The invention provides an oral dosage formulation comprising one or more pharmaceutically acceptable excipients and at least one GCC agonist peptide, wherein the amount of GCC agonist peptide per unit dose is from 0.01 mg to 10 mg, and wherein the GCC agonist peptide is selected from the group consisting of SEQ ID NOs: 1-54 and 56-249. In one embodiment, the GCC agonist peptide has a chromatographic purity of no less than 90%, no less than 90.5%, no less than 91%, no less than 92%, no less than 93%, no less than 94%, no less than 95%, no less than 96%, no less than 97%, no less than 98%, or no less than 99%. The chromatographic purity of the GCC agonist peptide is determined as area percent by HPLC. In one embodiment, the GCC agonist peptide is selected from the group consisting of SEQ ID NOs: 1, 8, 9, or 56. In one embodiment, the GCC agonist peptide is selected from the group consisting of SEQ ID NOs: 1 and 9. In one embodiment, the GCC agonist peptide is selected from the group consisting of SEQ ID NOs: 8 and 9. In one embodiment, the amount of GCC agonist peptide per unit dose is 0.1 mg, 0.3 mg, 0.6 mg, 1.0 mg, 3.0 mg, 6.0 mg, 9.0 mg or 9.5 mg.

In one embodiment, the GCC agonist peptide has a total impurity content of no greater than 10%, no greater than 9.5%, no greater than 9%, no greater than 8%, no greater than 7%, no greater than 6%, no greater than 5%, no greater than 4%, no greater than 3%, no greater than 2%, or no greater than 1%. The total impurity content is determined as total area percentages of impurities by HPLC. The impurities do not include any pharmaceutically acceptable excipient used for the formulation. In one embodiment, the formulation is substantially free of inorganic acids and carboxylic acids, e.g., HCl, phosphoric acid, or acetic acid. In this context, carboxylic acids do not include amino acids or peptides. In this context "substantially" free of acids means that the acid content of the formulation at the time of packaging is preferably less than 0.2%, less than 0.1%, less than 0.05%, less than 0.01%, less than 0.005%, or less than 0.001% of the total weight of the formulation. In one embodiment, the formulation is free of HCl.

In one embodiment, the formulation is a solid formulation. In one embodiment, the formulation is in the form of a powder, granule, sachet, troche, tablet, or capsule. In another embodiment, the formulation is a liquid formulation and the GCC agonist peptide is in solution or suspension in a lipophilic liquid. In one embodiment, the liquid is a refined specialty oil or a medium chain triglyceride or related ester. In one embodiment, the refined specialty oil is selected from *Arachis* oil, Castor oil, cottonseed oil, maize (corn) oil, olive oil, sesame oil, soybean oil, and sunflower oil. In one embodiment, the medium chain triglyceride or related ester is AKOMED E, AKOMED R, CAPTEX 355, LABRAFAC CC, LABRAFAC PG, LAUROGLYCOL FCC, MIGLYOL 810, MIGLYOL 812, MIGLYOL 829, MIGLYOL 840, and SOFTISAN 645. In one embodiment, the liquid is selected from the group consisting of medium chain triglycerides, propylene glycol dicaprylocaprate, vitamin E, soybean oil, Cremaphor, PG, and PG 400. In one embodiment, the unit dose is a powder, tablet, or capsule. In one embodiment, the unit dose is a liquid-filled capsule. In one embodiment, the capsule or tablet is in a blister pack or strip. Preferably, the blister pack or strip is made of a material that is impermeable to water vapor and oxygen. In one embodiment the blister pack is comprised of a metal foil. In one embodiment the blister pack is a FOIL/FOIL blister pack. In one embodiment, the container of the blister pack is flushed with an inert gas such as nitrogen or argon. In one embodiment, the container further includes a desiccant. In a preferred embodiment the desiccant is a molecular sieve. In one embodiment, the unit dose is in a high density polyethylene bottle having a seal. In one embodiment, the bottle further comprises a desiccant. In one embodiment, the bottle further comprises an oxygen scavenger or molecular sieve. In one embodiment, the bottle is nearly impermeable to oxygen and water vapor (e.g., much more impermeable than a HDPE bottle), such as an OxyGuard bottle.

In one embodiment, the one or more pharmaceutically acceptable excipients include an inert carrier. In one embodiment, the inert carrier is a selected from mannitol, lactose, a microcrystalline cellulose, or starch. In one embodiment, the inert carrier has a particle size of from 50 to 900 microns, from 50 to 800 microns, from 50 to 300 microns, from 50 to 200 microns, from 75 to 150 microns, from 75 to 200 microns, or from 75 to 300 microns.

In one embodiment, the GCC agonist peptide is stabilized against chemical or physical degradation for a period of at least 18 months at 30° C. and 65% relative humidity, or at least 18 months at 25° C. and 60% relative humidity, or at least 18 months at 2-8° C.

In one embodiment, the one or more pharmaceutically acceptable excipients include a divalent cation salt such as calcium chloride. In one embodiment, the one or more pharmaceutically acceptable excipients comprise an amino acid, such as leucine, histidine, or arginine, or an amine such TRIS or TRIS/HCl.

In one embodiment, the oral dosage formulation consists of the GCC agonist peptide described herein, an inert carrier (e.g., Celphere SCP-100, Avicel PH 102, or Avicel PH 112), and a lubricant (e.g., magnesium stearate). In one embodiment, the formulation consists of the GCC agonist peptide, an inert carrier (e.g., Avicel PH 200), a divalent cation salt (e.g., calcium chloride or calcium ascorbate), an amino acid (e.g., leucine, histidine, or arginine) or a protective amine (e.g., TRIS), a coating agent (e.g., Methocel ES Premium LV) and optionally a lubricant (e.g., magnesium stearate) or another additive (e.g., trehalose). In one embodiment, the formulation consists of the GCC agonist peptide, a binder (e.g., Provsolv SMCC 90 LM), and a disintegrant (e.g., Explotab). In one embodiment, the formulation consists of the GCC agonist peptide, a diluent (e.g., Mannogem EZ), a binder (e.g., Provsolv SMCC 90 LM), a disintegrant (e.g., Explotab), a lubricant (e.g., Pruv).

The invention also provides a process for making the oral dosage formulations described herein, wherein the process comprises a step of dry granulation, wet granulation, or spray coating followed by drying. In another embodiment, the process comprises a step of dry mixing. In a preferred embodiment the step of dry mixing includes geometric blending. In one embodiment, the process comprises a step of direct compression. In one embodiment, the process for making the oral dosage formulations described herein is a spray coating-drying process which includes (a) providing an aqueous solution comprising: a GCC agonist peptide selected from the group consisting of SEQ ID NOs: 1-54 and 56-249, and one or more pharmaceutically acceptable excipients, wherein the concentration of the GCC agonist peptide ranges from 10 to 60 mg/mL; and (b) applying the aqueous solution to a pharmaceutically acceptable carrier to generate a GCC agonist peptide-coated carrier.

In one embodiment of the spray coating-drying process above, the one or more pharmaceutically acceptable excipients comprise a divalent cation salt wherein the divalent cation is selected from $Ca^{2+}$, $Mg^{2+}$, $Zn^{2+}$, and $Mn^{2+}$. In one embodiment, the one or more pharmaceutically acceptable excipients comprise an amino acid selected from leucine, isoleucine, and valine. In one embodiment, the one or more pharmaceutically acceptable excipients comprise a coating agent (such as hypromellose Methocel E5 PremLV). In one embodiment, the aqueous solution has a pH greater than 4 (e.g., 4.5-5.5, 5-6, about 5, or greater than 5) or even greater than 7. In one embodiment, the aqueous solution is substantially free of inorganic acids and carboxylic acids. In one embodiment, the GCC agonist peptide is selected from the group consisting of SEQ ID NOs: 1, 8, 9, and 56. In one embodiment, the process further includes drying the GCC agonist peptide-coated carrier.

The invention further provides an oral dosage formulation made by the process described herein. Preferably, the GCC agonist peptide as made is stabilized against chemical or physical degradation for a period of at least 18 months at 30° C. and 65% relative humidity, or at least 18 months at 25° C. and 60% relative humidity, or at least 18 months at 2-8° C.

The invention also provides a method for treating or preventing a disease or disorder in a subject in need thereof, comprising administering to the subject an oral dosage formulation comprising at least one GCC agonist peptide, wherein the amount of GCC agonist peptide per unit dose is from 0.01 mg to 10 mg, and wherein the GCC agonist peptide is selected from the group consisting of SEQ ID NOs: 1-54 and 56-249. Preferably, the subject is a human subject. In one embodiment, the GCC agonist peptide is selected from the group consisting of SEQ ID NOs: 1, 8, 9, or 56. In one embodiment, the GCC agonist peptide is selected from the group consisting of SEQ ID NOs: 1 and 9. In one embodiment, the amount of GCC agonist peptide per unit dose is 0.1 mg, 0.3 mg, 0.6 mg, 1.0 mg, 3.0 mg, 6.0 mg, 9.0 mg, 9.5 mg, or 10 mg.

In one embodiment, the disease or disorder is a gastrointestinal disease or disorder selected from the group consisting of irritable bowel syndrome, non-ulcer dyspepsia, chronic intestinal pseudo-obstruction, functional dyspepsia, colonic pseudo-obstruction, duodenogastric reflux, gastro esophageal reflux disease, constipation, gastroparesis, heartburn, gastric cancer, and *H. pylori* infection. In a preferred embodiment, the gastrointestinal disease or disorder is chronic idiopathic constipation.

In one embodiment, the method further comprises administering to the subject an effective amount of an inhibitor of a cGMP-specific phosphodiesterase. In one embodiment, the cGMP-dependent phosphodiesterase inhibitor is selected from the group consisting of suldinac sulfone, zaprinast, and motapizone, vardenifil, and suldenifil.

In one embodiment, the method further comprises administering to the subject an effective amount of at least one laxative. In one embodiment, the at least one laxative is selected from the group consisting of SENNA, MIRALAX, PEG, or calcium polycarbophil.

In one embodiment, the method further comprises administering to the subject an effective amount of at least one anti-inflammatory agent.

The invention also provides pharmaceutical compositions comprising the formulations described herein.

Other features and advantages of the invention will be apparent from and are encompassed by the following detailed description and claims.

DETAILED DESCRIPTION

Figure 1:
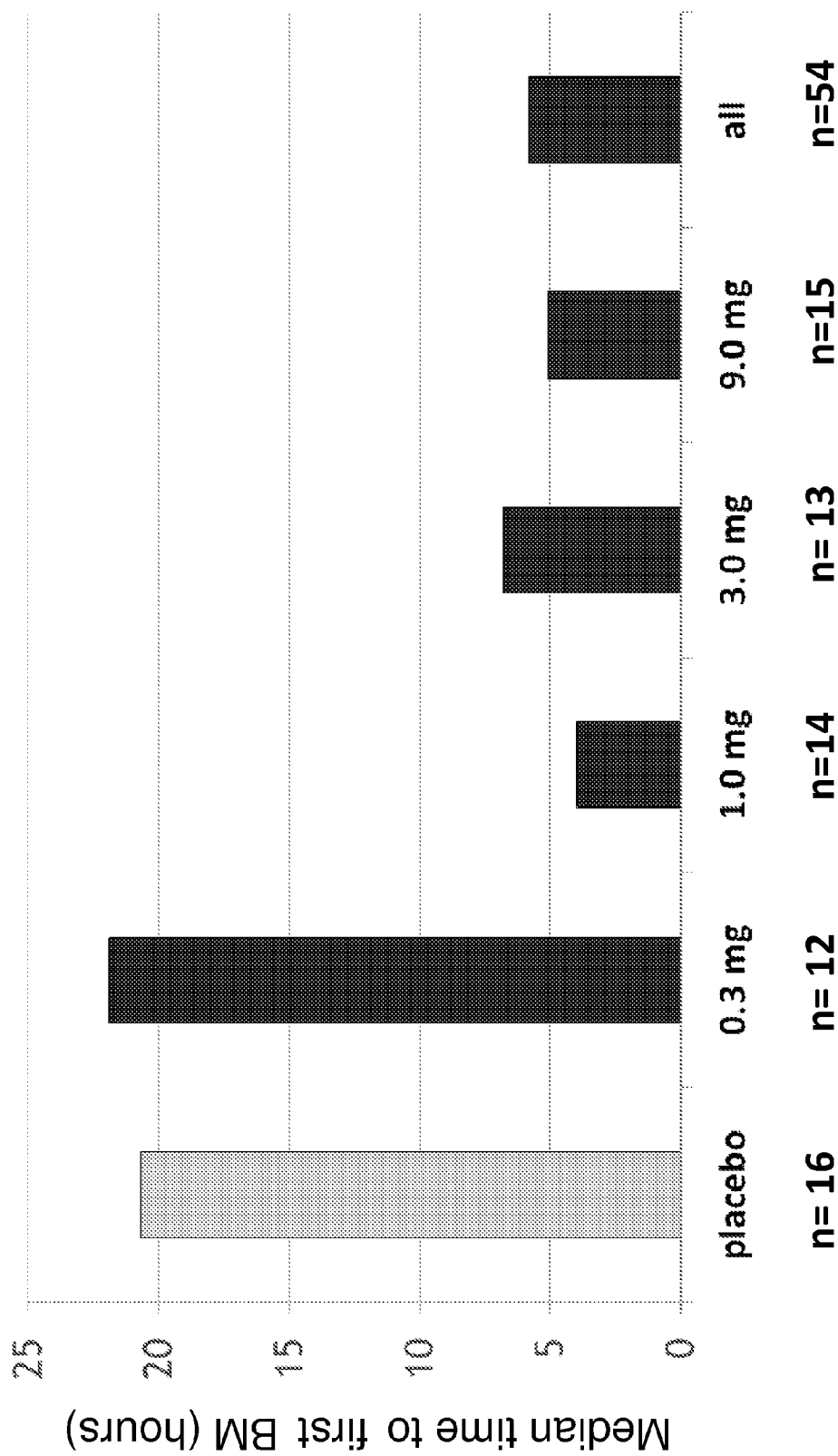
FIG. 1: Plecanatide (SP-304) treatment reduced time to first BM following daily dose.

The invention provides pharmaceutical formulations of peptide GCC agonists. It is intended that the formulations of the invention are "pharmaceutical" formulations, meaning that they are suitable for pharmaceutical use. Accordingly, the term "formulations" as used herein is meant to encompass pharmaceutical formulations even if "pharmaceutical" is not expressly stated. Pharmaceutical compositions comprising the formulations described herein are also provided by the invention. The formulations of the invention preferably provide stability against chemical and physical degradation of the peptide, e.g., plecanatide (i.e., SEQ ID #1).

The invention is based in part upon the discovery that mannitol mixes very effectively with the GCC agonist peptides described herein and provides stability against degradation, allowing the peptides to be formulated at very low doses. The invention is also based in part on the discovery that very low doses of the GCC agonist peptides described herein are effective for the treatment of diseases and disorders in humans. The dosage range found to be effective was not predicted based on animal studies. The invention is also based in part upon the discovery that a divalent cation (e.g., $Ca^{2+}$) and/or an amino acid (e.g., leucine or arginine) stabilize the GCC agonist peptides described herein during a process (e.g., spray coating-drying process) of manufacturing a formulation of the GCC agonist peptides and provides stability against degradation both during the manufacturing process and storage of the formulation.

Plecanatide is a charged peptide due to the presence of four carboxylic acids and single amine group with a calculated pKa of approximately 3.5. Therefore plecanatide is likely to interact with ions in solution or in the solid state. Plecanatide is a hygroscopic peptide requiring the control of water during manufacture and storage to promote long term stability. Plecanatide is prone to degradation by oxidation in the presence of residual peroxides or formaldehyde contaminants that are formed from peroxide reaction with polymeric excipients. The present invention discloses a manufacturing process and dry solid formulation compositions that minimizes water content. The formulations are comprised of components to minimize levels of residual formaldehyde and peroxides commonly found in many pharmaceutical excipients. The invention also discloses additives (i.e. $CaCl_2$) that may function as local desiccants in the formulation. Divalent cation salts such as calcium ascorbate, $MgCl_2$, $ZnCl_2$, $MnCl_2$ and $CaCl_2$ bind plecanatide and sterically hinder reactive species such as water or oxygen from causing plecanatide degradation by molecular displacement. The invention further includes scavengers of residual formaldehyde (amines such as TRIS or TRIS/HCl or amino acids such as leucine, isoleucine and valine), and discloses packaging confirmations to minimize oxygen exposure and water vapor during storage. The invention also discloses a stable manufacturing process comprised of initially dissolving plecanatide in cold water to minimize solution degradation, followed by spray coating the peptide solution on particles and drying to remove moisture.

The formulations of the invention are particularly useful for the treatment or prevention of a gastrointestinal disease or disorder selected from the group consisting of irritable bowel syndrome, non-ulcer dyspepsia, chronic intestinal pseudo-obstruction, functional dyspepsia, colonic pseudo-obstruction, duodenogastric reflux, gastro esophageal reflux disease, chronic idiopathic constipation, gastroparesis, heartburn, gastric cancer, and *H. pylori* infection.

In one embodiment, the formulations of the invention are used in a method for the treatment of constipation. Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining. Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple sclerosis, Parkinson's disease, spinal cord lesions, Neurofibromatosis, autonomic neuropathy, Chagas disease, Hirschsprung disease and cystic fibrosis. Constipation may also be the result of surgery or due to the use of drugs such as analgesics (like opioids), antihypertensives, anticonvulsants, antidepressants, antispasmodics and antipsychotics. In a preferred embodiment, the constipation is chronic idiopathic constipation.

The stabilized formulations of the invention comprise at least one GCC agonist peptide formulated with one or more excipients such that the peptide is stabilized against chemical degradation. Chemical degradation of peptides results from a number of mechanisms including oxidation, water-mediated degradation, and reaction with aldehydes or reducing sugars. The ideal excipient or combination of excipients will be non-hygroscopic, have few or no reducing sugars, and be substantially free of contaminants such as iron, peroxide, and formaldehyde. The formulations of the invention are preferably substantially free of water. In this context "substantially" free of water means that the water content of the formulation at the time of packaging is preferably less than 7%, less than 5%, less than 1%, or less than 0.5% of the total weight of the formulation. In one embodiment the amount of water is between 0.1 to 5% of the total weight of the formulation. In one embodiment, the amount of water in the formulation of the invention manufactured through a spray-coating process is less than 0.5% (e.g., about 0.47%).

In the context of the present formulations, the term "stable" or "stabilized" refers to the resistance of the peptide to chemical or physical degradation over time. Preferably, a stable formulation of the invention retains an amount of the peptide in the formulation over a period of time that is at least 90%, preferably at least 95%, and most preferably at least 99% the amount of peptide initially present in the formulation. In one embodiment, a stable formulation of the invention, over a period of time (e.g., 18 month), has an increase in the total impurity content not greater than 8%, not greater than 7%, not greater than 6%, not greater than 5%, not greater than 4%, not greater than 3%, not greater than 2%, or not greater than 1%. In one embodiment, the peptide is chemically stable in the formulation for a period of time that is at least 18 months, at least 20 months, or at least 24 months when stored at 25 degrees Celsius (25 C)

and 60% relative humidity. In one embodiment, the peptide is chemically stable in the formulation for a period of time that is at least 18 months, at least 20 months, or at least 24 months when stored at 2-8 degrees Celsius (2-8 C). In one embodiment, the peptide is chemically stable in the formulation for a period of time that is at least 3 months, 12 months, 18 months and preferably 24 months when stored at 25 degrees Celsius (25 C) and 60% relative humidity. In one embodiment, the peptide is chemically stable in the formulation for a period of time that is at least 3 months, 18 months and preferably 24 months when stored at 30 degrees Celsius (30 C).

The low-dose formulations of the invention comprise an amount of at least one GCC agonist peptide per unit dose that is less than 10 mg. It is especially advantageous to formulate oral compositions in unit dosage form for ease of administration and uniformity of dosage. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. In one embodiment, the unit dosage form is a tablet or a capsule.

In one embodiment of the low-dose formulations of the invention, the amount of GCC agonist peptide per unit dose is from 0.01 mg to 10 mg. In one embodiment, the amount of GCC agonist peptide per unit dose is 0.1 mg, 0.3 mg, 0.6 mg, 1.0 mg, 3.0 mg, 6.0 mg, 9.0 mg, 9.5 mg, or 10 mg.

In one embodiment, the low-dose formulation contains a carrier that is non-hygroscopic. In one embodiment, the carrier is selected from mannitol and maltose (e.g., ADVANTOSE 100).

In one embodiment, the carrier is cellulose, preferably microcrystalline cellulose (e.g., Avicel PH 102, low moisture Avicel PH 112, Avicel PH 200, or Celphere SCP-100). In one embodiment, the carrier is calcium phosphate or calcium sulphate. In another embodiment, the carrier is a saccharide. The term "saccharide" as used herein also refers to polysaccharides. Thus, the term saccharide is meant to include polysaccharides. In one embodiment, the saccharide is selected from mannitol, trehalose, lactose, sucrose, sorbitol, and maltose. In a preferred embodiment, the saccharide is mannitol. Preferably the saccharide has a low water content, a small particle size and a narrow particle-size distribution.

Carriers having small particle sizes, and/or spherical shape, and narrow size distribution are preferred. Particles of less than 20 microns have a relatively high surface area to volume ratio causing inter-particle attractive forces to dominate and resist bulk flow. Larger particles (greater than 100 microns) tend to roll or slide over one another and exhibit superior bulk flow properties compared with small particles. A narrow particle-size distribution reduces particle packing and increases flow. In one embodiment, the particles are between 20 and 500 microns in size (as measured across the largest diameter of the particle, on average). In one embodiment, a small particle size and a narrow particle size range refers to particles having a size range of from 20-300 microns, 50-200 microns, or 75-150 microns. In certain embodiments, the carrier has a substantially spherical shape such as can be obtained with a spray drying process.

In one embodiment, the low-dose formulation is a solid formulation and the unit dose is in the form of a tablet or capsule. In one embodiment, the low-dose formulation is a liquid formulation and the unit dosage form is a liquid-filled capsule. In one embodiment, the liquid formulation in the form of a solution or suspension of the GCC agonist peptide in an lipophilic liquid. Examples of suitable liquids include medium chain triglycerides (e.g., LABRAFAC Lipophile), propylene glycol dicaprylocaprate (e.g., LABRAFAC PG), vitamin E (e.g., a tocopherol), PEG 400 (e.g., Polyethylene glycol low M.W. (liquid)), propylene glycol, soybean oil, and Castor oil. In one embodiment, the liquid is selected from the group consisting of medium chain triglycerides, propylene glycol dicaprylocaprate, vitamin E, and soybean oil. In one embodiment, the refined specialty oil is selected from Arachis oil, Castor oil, cottonseed oil, maize (corn) oil, olive oil, sesame oil, soybean oil, and sunflower oil. In one embodiment, the medium chain triglyceride or related ester is AKOMED E, AKOMED R, CAPTEX 355, LABRAFAC CC, LABRAFAC PG, LAUROGLYCOL FCC, MIGLYOL 810, MIGLYOL 812, MIGLYOL 829, MIGLYOL 840, and SOFTISAN 645.

A formulation according to the invention may be contained in a blister pack. In a particular embodiment, the powder, tablet, or capsule comprising the formulation is contained in a blister pack. Preferably, the blister pack is made of a material that allows only minimal permeation by water vapor and oxygen. In one embodiment the blister pack is comprised of a metal foil. In one embodiment, the blister pack is comprised of ACLAR. In one embodiment, the container of the blister pack is flushed with an inert gas such as nitrogen or argon. In one embodiment, the container further includes a desiccant. In one embodiment, the desiccant is calcium chloride. In one embodiment the desiccant is a molecular sieve.

While any GCC agonist known in the art can be formulated according to the present invention, analogs of uroguanylin and bacterial ST peptides are preferred. In certain embodiments, the uroguanylin and bacterial ST peptide analogs have superior properties compared to naturally occurring, or "wild-type" peptides. For example, the uroguanylin and bacterial ST peptides for use in the present invention are preferably modified to increase their resistance to degradation at the N-terminus and C-terminus from carboxypeptidases, aminopeptidases, and/or by other proteolytic enzymes present in the stimulated human intestinal juices and human gastric juices. In certain embodiments, the GCC agonist formulation comprises a peptide consisting essentially of an amino acid sequence selected from SEQ ID NOs: 1-249. In a preferred embodiment, the peptide consists essentially of an amino acid sequence selected from SEQ ID NOs: 1, 8, 9, 55 and 56. The term "consists essentially or refers to a peptide that is identical to the reference peptide in its amino acid sequence or to a peptide that does not differ substantially in terms of" either structure or function from the reference peptide. A peptide differs substantially from the reference peptide if its primary amino acid sequence varies by more than three amino acids from the reference peptide or if its activation of cellular cGMP production is reduced by more than 50% compared to the reference peptide. Preferably, substantially similar peptides differ by no more than two amino acids and not by more than about 25% with respect to activating cGMP production. In preferred embodiments, the GCC agonist is a peptide comprising at least 12 amino acid residues, and most preferably comprising between 12 and 26 amino acids. Non-limiting examples of such analogs of uroguanylin and bacterial ST peptides are described in Section 1.2 below.

The invention provides methods for treating or preventing certain diseases and disorders and methods for increasing gastrointestinal motility in a subject in need thereof by administering an effective amount of a GCC agonist formulation to the subject. The term "treating" as used herein refers to a reduction, a partial improvement, amelioration, or a mitigation of at least one clinical symptom associated with the gastrointestinal disorders being treated. The term "preventing" refers to an inhibition or delay in the onset or progression of at least one clinical symptom associated with the gastrointestinal disorders to be prevented. The term "effective amount" as used herein refers to an amount that provides some improvement or benefit to the subject. In certain embodiments, an effective amount is an amount that provides some alleviation, mitigation, and/or decrease in at least one clinical symptom of the gastrointestinal disorder to be treated. In other embodiments, the effective amount is the amount that provides some inhibition or delay in the onset or progression of at least one clinical symptom associated with the gastrointestinal disorder to be prevented. The therapeutic effects need not be complete or curative, as long as some benefit is provided to the subject. The term "subject" preferably refers to a human subject but may also refer to a non-human primate or other mammal preferably selected from among a mouse, a rat, a dog, a cat, a cow, a horse, or a pig.

In accordance with the methods of the present invention, the GCC agonist formulation can be administered alone or in combination with one or more additional therapeutic agents to prevent or treat inflammation, cancer and other disorders, particularly of the gastrointestinal tract. In a preferred embodiment, the GCC agonist formulation is administered for the treatment of chronic constipation. In one embodiment, the GCC agonist formulation is administered in combination with one or more additional therapeutic agents selected from the group consisting of phosphodiesterase inhibitors, cyclic nucleotides (such as cGMP and cAMP), a laxative (such as SENNA, METAMUCIL, MIRALAX, PEG, or calcium polycarbophil), a stool softener, an anti-tumor necrosis factor alpha therapy for IBD (such as REMICADE, ENBREL, or HUMAIRA), and anti-inflammatory drugs (such as COX-2 inhibitors, sulfasalazine, 5-ASA derivatives and NSAIDS). In certain embodiments, the GCC agonist formulation is administered in combination with an effective dose of an inhibitor of cGMP-specific phosphodiesterase (cGMP-PDE) either concurrently or sequentially with said GCC agonist. cGMP-PDE inhibitors include, for example, suldinac sulfone, zaprinast, motapizone, vardenifil, and sildenafil. In another embodiment, the GCC agonist formulation is administered in combination with inhibitors of cyclic nucleotide transporters.

1.1 Formulations

The formulations of the invention contain one or more GCC agonist peptides described herein, in combination with one or more pharmaceutically acceptable carriers (also referred to as diluents) and/or excipients. In a preferred embodiment, the formulations of the invention include an inert carrier. The inert carrier is preferably non-hygroscopic. In one embodiment, the carrier in the formulation contains few or no reducing sugars and is substantially free of contaminants including, but not limited to, iron, peroxide, and formaldehyde. In one embodiment, the carrier is selected from the group consisting of sorbitol, mannitol, EMDEX, and starch. In one embodiment, the carrier is mannitol (e.g., MANNOGEM) or microcrystalline cellulose (e.g. PROSOLV, CELPHERE, CELPHERE beads).

The low-dose formulations of the invention contain no greater than 10 mg per unit dose of a GCC agonist peptide. The remainder of the formulation is comprised of the carrier and one or more optional excipients. In one embodiment, the amount of carrier is at least 90% of the total weight of the formulation. In another embodiment, the amount of carrier is at least 95% or at least 98% of the total weight of the formulation. In one embodiment, the amount of carrier is between 90 and 99.9% of the total weight of the formulation. In one embodiment, the one or more optional excipients comprise a disintegrant which is present at 1 to 5% of the total weight of the formulation. In one embodiment, the one or more optional excipients comprise a lubricant which is present at 0.02 to 5% of the total weight of the formulation. In one embodiment, the one or more optional excipients comprise an amino acid such as arginine, leucine, isoleucine, valine, histidine, phenylalanine, alanine, glutamic acid, aspartic acid, glutamine, methionine, asparagine, tyrosine, threonine, tryptophan, or glycine, which is present at 0.1 to 4% (e.g., 0.1-1%) of the total weight of the formulation. In one embodiment, the molar ratio between the amino acid and the GCC agonist peptide is from about 2:1 to about 30:1 or about 2:1 to about 20:1 (e.g., 5:1). In one embodiment, the one or more optional excipients comprise a stabilizer such as a divalent cation salt, more specifically, a water-soluble divalent cation salt (e.g., calcium chloride, magnesium chloride, zinc chloride, manganese chloride, or calcium ascorbate), which is present at 0.1 to 12% (e.g., 0.1-4%) of the total weight of the formulation. In one embodiment, the molar ratio between the salt and the GCC agonist peptide is from about 5:1 to about 20:1 (e.g., 10:1).

The formulations may contain other additives as needed, including for example lactose, glucose, fructose, galactose, trehalose, sucrose, maltose, raffnose, maltitol, melezitose, stachyose, lactitol, palatinite, starch, xylitol, mannitol, myo-inositol, and the like, and hydrates thereof, and amino acids, for example alanine, glycine and betaine, and polypeptides and proteins, for example albumen.

Further examples of pharmaceutically acceptable carriers and excipients include, but are not limited to binders, fillers, disintegrants, lubricants, anti-microbial agents, antioxidant, and coating agents such as: BINDERS: corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc), methyl cellulose, Methocel, pre-gelatinized starch (e.g., STARCH 1500® and STARCH 1500 LM®, sold by Colorcon, Ltd.), hydroxypropyl methyl cellulose, microcrystalline cellulose (FMC Corporation, Marcus Hook, Pa., USA), Emdex, Plasdone, or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof, DISINTEGRANTS: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ployplasdone, or mixtures thereof, LUBRICANTS: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Plano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, ANTOXIDANTS: ascorbic acid, BHA, BHT, EDTA, or mixture thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation can also include other excipients and categories thereof including but not limited to Pluronic®, Poloxamers (such as Lutrol® and Poloxamer 188), ascorbic acid, glutathione, protease inhibitors (e.g. soybean trypsin inhibitor, organic acids), pH lowering agents, creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

Solid oral dosage forms may optionally be treated with coating systems (e.g. Opadry® fx film coating system, for example Opadry® blue (OY-LS-20921), Opadry® white (YS-2-7063), Opadry® white (YS-1-7040), and black ink (S-1-8106).

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly($\epsilon$-caprolactone) and poly(alkylene oxide) (U.S. 20030068384) to create a sustained release formulation. Other sustained release formulations and polymers for use in the compositions and methods of the invention are described in EP 0 467 389 A2, WO 93/24150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 97/26015, WO 97/04744, and US20020019446. In such sustained release formulations microparticles (Delie and Blanco-Prieto 2005 Molecule 10:65-80) of polypeptide are combined with microparticles of polymer. U.S. Pat. No. 6,011,01 and WO 94/06452 describe a sustained release formulation providing either polyethylene glycols (i.e. PEG 300 and PEG 400) or triacetin. WO 03/053401 describes a formulation which may both enhance bioavailability and provide controlled release of the agent within the GI tract. Additional controlled release formulations are described in WO 02/38129, EP 326151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224 materials which may include those described in WO04041195 (including the seal and enteric coating described therein) and pH-sensitive coatings that achieve delivery in the colon including those described in U.S. Pat. No. 4,910,021 and WO9001329. U.S. Pat. No. 4,910,021 describes using a pH-sensitive material to coat a capsule. WO9001329 describes using pH-sensitive coatings on beads containing acid, where the acid in the bead core prolongs dissolution of the pH-sensitive coating. U.S. Pat. No. 5,175,003 discloses a dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with a drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher.

The GCC peptides described herein may be formulated in the pH triggered targeted control release systems described in WO04052339. The agents described herein may be formulated according to the methodology described in any of WO03105812 (extruded hyrdratable polymers); WO0243767 (enzyme cleavable membrane translocators); WO03007913 and WO03086297 (mucoadhesive systems); WO02072075 (bilayer laminated formulation comprising pH lowering agent and absorption enhancer); WO04064769 (amidated polypeptides); WO05063156 (solid lipid suspension with pseudotropic and/or thixotropic properties upon melting); WO03035029 and WO03035041 (erodible, gastric retentive dosage forms); U.S. Pat. Nos. 5,007,790 and 5,972,389 (sustained release dosage forms); WO041 1271 1 (oral extended release compositions); WO05027878, WO02072033, and WO02072034 (delayed release compositions with natural or synthetic gum); WO05030182 (controlled release formulations with an ascending rate of release); WO05048998 (microencapsulation system); U.S. Pat. No. 5,952,314 (biopolymer); U.S. Pat. No. 5,108,758 (glassy amylose matrix delivery); U.S. Pat. No. 5,840,860 (modified starch based delivery). JP10324642 (delivery system comprising chitosan and gastric resistant material such as wheat gliadin or zein); U.S. Pat. Nos. 5,866,619 and 6,368,629 (saccharide containing polymer); U.S. Pat. No. 6,531,152 (describes a drug delivery system containing a water soluble core (Ca pectinate or other water-insoluble polymers) and outer coat which bursts (e.g. hydrophobic polymer-Eudragrit)); U.S. Pat. Nos. 6,234,464; 6,403,130 (coating with polymer containing casein and high methoxy pectin; WO0174 175 (Maillard reaction product); WO05063206 (solubility increasing formulation); WO040 19872 (transferring fusion proteins).

The GCC peptides described herein may be formulated using gastrointestinal retention system technology (GIRES; Merrion Pharmaceuticals). GIRES comprises a controlled-release dosage form inside an inflatable pouch, which is placed in a drug capsule for oral administration. The capsule shell can be a HPMC capsule shell or Gelatin capsule shell. Upon dissolution of the capsule, a gas-generating system inflates the pouch in the stomach where it is retained for 16-24 hours, all the time releasing agents described herein.

The GCC peptides described herein can also be formulated using the multi matrix system technology (MMX).

The GCC peptides described herein can be formulated in an osmotic device including the ones disclosed in U.S. Pat. Nos. 4,503,030, 5,609,590 and 5,358,502. U.S. Pat. No. 4,503,030 discloses an osmotic device for dispensing a drug to certain pH regions of the gastrointestinal tract. More particularly, the invention relates to an osmotic device comprising a wall formed of a semi-permeable pH sensitive composition that surrounds a compartment containing a drug, with a passageway through the wall connecting the exterior of the device with the compartment. The device delivers the drug at a controlled rate in the region of the gastrointestinal tract having a pH of less than 3.5, and the device self-destructs and releases all its drug in the region of the gastrointestinal tract having a pH greater than 3.5, thereby providing total availability for drug absorption. U.S. Pat. Nos. 5,609,590 and 5,358,502 disclose an osmotic bursting device for dispensing a beneficial agent to an aqueous environment. The device comprises a beneficial agent and osmagent surrounded at least in part by a semi-permeable membrane. The beneficial agent may also function as the osmagent. The semi-permeable membrane is permeable to water and substantially impermeable to the beneficial agent and osmagent. A trigger means is attached to the semi-permeable membrane (e.g., joins two capsule halves). The trigger means is activated by a pH of from 3 to 9 and triggers the eventual, but sudden, delivery of the beneficial agent. These devices enable the pH-triggered release of the beneficial agent core as a bolus by osmotic bursting.

In one embodiment the formulation contains a GCC agonist peptide, mannitol, silicified microcrystalline cellulose, sodium starch glycolate, and sodium stearyl fumarate. The GCC agonist is at a concentration of less than 5% w/w, less than 4%, less than 3% w/w, less than 2% w/w, less than 1% w/w, less than 0.5% w/w, or less than 0.25% w/w. In some embodiments the GCC peptide is at a concentration of about 0.23% w/w. The GCC peptide is preferably SEQ NO: 1 or SEQ NO: 9. The mannitol is at a concentration of at least 60% w/w, at least 65% w/w, at least 70% w/w, at least 75% w/w, or at least 80% w/w. In some embodiments the mannitol is present at about 79% w/w (e.g., 79.77%). The mannitol is preferably Mannogem EZ. The silicified microcrystalline cellulose is at a concentration of at least 5% w/w, at least 10% w/w, or at least 15% w/w. In some embodiments the concentration of the silicified microcrystalline cellulose is about 15% w/w. The silicified microcrystalline cellulose is preferably Prosolv SMCC 90 LM. The sodium starch glycolate is at a concentration of at least 1% w/w, at least 2% w/w, at least 3% w/w, or at least 4% w/w. In some embodiments the concentration of the sodium starch glycolate is about 4% w/w. The sodium starch glycolate is preferably Explotab. The sodium stearyl fumarate is at a concentration of at least 0.2% w/w, at least 0.5% w/w, at least 0.7% w/w, at least 0.8% w/w, at least 0.9, or at least 1% w/w. In some embodiments the concentration of the sodium stearyl fumarate is about 1% w/w. The sodium stearyl fumarate is preferably Pruv.

In one embodiment the formulation contains a GCC agonist peptide, silicified microcrystalline cellulose, and sodium starch glycolate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 0.3% w/w. The GCC peptide is preferably SEQ NO: 1 or SEQ NO: 9. The silicified microcrystalline cellulose is at a concentration of at least 10% w/w, at least 20% w/w, at least 30% w/w, at least 40% w/w, at least 50% w/w, at least 60% w/w, at least 70% w/w, at least 80% w/w, at least 90% w/w, or at least 95% w/w. In some embodiments the concentration of the silicified microcrystalline cellulose is about 95.7% w/w. The silicified microcrystalline cellulose is preferably Prosolv SMCC 90 HD. The sodium starch glycolate is at a concentration of at least 1% w/w, at least 2% w/w, at least 3% w/w, or at least 4% w/w. In some embodiments the concentration of the sodium starch glycolate is 4% w/w. The sodium starch glycolate is preferably Explotab.

In one embodiment the formulation contains a GCC agonist peptide, microcrystalline cellulose, calcium chloride dihydrate, leucine, and hypromellose. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 0.3246% w/w. The GCC peptide is preferably SEQ NO: 1 or SEQ NO: 9. The microcrystalline cellulose is at a concentration of at least 50% w/w, at least 60% w/w, at least 70% w/w, at least 80% w/w, at least 90% w/w, at least 95% w/w, or at least 99% w/w. In some embodiments the concentration of the microcrystalline cellulose is about 99.10% w/w. The microcrystalline cellulose is preferably Celphere SCP-100. The calcium chloride dihydrate is at a concentration of at least 0.1% w/w, at least 0.15% w/w, at least 0.2% w/w, or at least 0.25% w/w. In some embodiments the concentration of the calcium chloride dihydrate is about 0.2622% w/w. The leucine is at a concentration of at least 0.05% w/w, at least 0.1% w/w, at least 0.12% w/w, or at least 0.15% w/w. In some embodiments the concentration of leucine is about 0.12% w/w. The hypromellose is at a concentration of at least 0.1% w/w, at least 0.15% w/w, at least 0.2% w/w, or at least 0.25% w/w. In some embodiments the concentration of the hypromellose is about 0.2% w/w. The hypromellose is preferably Methocel E5 PremLV.

In one embodiment the formulation contains a GCC agonist peptide, microcrystalline cellulose, calcium chloride dihydrate, leucine, hypromellose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 0.36% w/w. The GCC peptide is preferably SEQ NO: 1 or SEQ NO: 9. The microcrystalline cellulose is at a concentration of at least 50% w/w, at least 60% w/w, at least 70% w/w, at least 80% w/w, at least 90% w/w, at least 95% w/w, or at least 99% w/w. In some embodiments the concentration of the microcrystalline cellulose is about 98.75% w/w. The microcrystalline cellulose is preferably Avicel PH 102. The calcium chloride dihydrate is at a concentration of at least 0.1% w/w, at least 0.15% w/w, at least 0.2% w/w, at least 0.25% w/w, or at least 0.3% w/w. In some embodiments the concentration of the calcium chloride dihydrate is about 0.29% w/w. The leucine is at a concentration of at least 0.05% w/w, at least 0.1% w/w, at least 0.12% w/w, or at least 0.15% w/w. In some embodiments the concentration of leucine is about 0.13% w/w. The hypromellose is at a concentration of at least 0.1% w/w, at least 0.15% w/w, at least 0.2% w/w, or at least 0.25% w/w. In some embodiments the concentration of the hypromellose is about 0.22% w/w. The hypromellose is preferably Methocel E5 PremLV. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

In one embodiment the formulation contains a GCC agonist peptide, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 0.32% w/w. The GCC peptide is preferably SEQ NO: 1 or SEQ NO: 9. The microcrystalline cellulose is at a concentration of at least 50% w/w, at least 60% w/w, at least 70% w/w, at least 80% w/w, at least 90% w/w, at least 95% w/w, or at least 99% w/w. In some embodiments the concentration of the microcrystalline cellulose is about 99.43% w/w. The microcrystalline cellulose is preferably Avicel PH 102. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

In one embodiment the formulation contains a GCC agonist peptide, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 0.32% w/w, about 1.18% w/w. The GCC peptide is preferably SEQ NO: 1 or SEQ NO: 9. The microcrystalline cellulose is at a concentration of at least 30% w/w, at least 40% w/w, at least 50% w/w, at least 60% w/w, at least 70% w/w, at least 80% w/w, at least 90% w/w, at least 95% w/w, or at least 99% w/w. In some embodiments the concentration of the microcrystalline cellulose is about 98.57% w/w. The microcrystalline cellulose is preferably Avicel PH 102. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

In one embodiment the formulation contains a GCC agonist peptide, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 1.18% w/w. The GCC peptide is preferably SEQ NO: 1 or SEQ NO: 9. The microcrystalline cellulose is at a concentration of at least 30% w/w, at least 40% w/w, at least 50% w/w, at least 60% w/w, at least 70% w/w, at least 80% w/w, at least 90% w/w, at least 95% w/w, or at least 99% w/w. In some embodiments the concentration of the microcrystalline cellulose is about 97.09% w/w. The microcrystalline cellulose is preferably Avicel PH 112. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

In one embodiment the formulation contains a GCC agonist peptide, trehalose granules, hypromellose, histidine, calcium ascorbate, trehalose powder, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 1.18% w/w. The GCC peptide is preferably SEQ NO: 1 or SEQ NO: 9. The trehalose granules are at a concentration of at least 50% w/w, at least 55% w/w, at least 60% w/w, at least 65% w/w, at least 70% w/w, or at least 75% w/w. In some embodiments the concentration of the trehalose granules is 55-75% w/w. In a particular embodiment, the concentration of the trehalose granules is 70.48% w/w. The hypromellose is at a concentration of at least 0.1% w/w, at least 0.2% w/w, at least 0.3% w/w, at least 0.4% w/w, or at least 0.5% w/w. In some embodiments the concentration of the hypromellose is 0.2-2% w/w. In a particular embodiment the concentration of the hypromellose about 0.5% w/w. The hypromellose is preferably Methocel ES Premium LV. The histine is a concentration of at least 0.6% w/w, at least 0.8% w/w, at least 0.9% w/w, at least 1% w/w, at least 3% w/w, or at least 5% w/w. In some embodiments the concentration of the histidine is 1-6% w/w. In a particular embodiment, the concentration of the arginine is 1.48% w/w. The calcium ascorbate is at a concentration of at least 0.05% w/w, at least 0.07% w/w, at least 0.09% w/w, or at least 0.1% w/w. In some embodiments the concentration of the calcium ascorbate is 0.05-10% w/w. In a particular embodiment, the concentration of the calcium ascorbate is about 0.1% w/w. The trehalose powder is at a concentration of at least 0.5% w/w, at least 0.7% w/w, at least 0.8% w/w, at least 0.9% w/w, at least 1% w/w, or at least 1.2% w/w. In some embodiments the concentration of the trehalose powder is 0.5-4% w/w. In a particular embodiment, the concentration of the trehalose powder is 1.02% w/w. The microcrystalline cellulose is at a concentration of at least 10% w/w, at least 20% w/w, or at least 25% w/w. In some embodiments the concentration of the microcrystalline cellulose is 20-40% w/w. In a particular embodiment, the concentration of the microcrystalline cellulose is 25% w/w. The microcrystalline cellulose is preferably Avicel PH 200. The magnesium stearate is at a concentration of at least 0.1% w/w, at least 0.15% w/w, at least 0.2% w/w, or at least 0.25% w/w. In some embodiments the concentration of the magnesium stearate is 0.2-1% w/w. In a particular embodiment the concentration of the magnesium stearate is about 0.25% w/w.

In one embodiment the formulation contains a GCC agonist peptide, trehalose granules, hypromellose, arginine, calcium ascorbate, trehalose powder, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 1.17% w/w. The GCC peptide is preferably SEQ NO: 1 or SEQ NO: 9. The trehalose granules are at a concentration of at least 50% w/w, at least 55% w/w, at least 60% w/w, at least 65% w/w, at least 70% w/w, or at least 75% w/w. In some embodiments the concentration of the trehalose granules is 55-75% w/w. In a particular embodiment, the concentration of the trehalose granules is 70.31% w/w. The hypromellose is at a concentration of at least 0.1% w/w, at least 0.2% w/w, at least 0.3% w/w, at least 0.4% w/w, or at least 0.5% w/w. In some embodiments the concentration of the hypromellose is 0.2-2% w/w. In a particular embodiment the concentration of the hypromellose about 0.5% w/w. The hypromellose is preferably Methocel ES Premium LV. The arginine is a concentration of at least 0.5% w/w, at least 1% w/w, at least 1.5% w/w, or at least 2% w/w. In some embodiments the concentration of the arginine is 1-6% w/w. In a particular embodiment, the concentration of the arginine is 1.66% w/w. The calcium ascorbate is at a concentration of at least 0.05% w/w, at least 0.07% w/w, at least 0.09% w/w, or at least 0.1% w/w. In some embodiments the concentration of the calcium ascorbate is 0.05-10% w/w. In a particular embodiment, the concentration of the calcium ascorbate is about 0.1% w/w. The trehalose powder is at a concentration of at least 0.5% w/w, at least 0.7% w/w, at least 0.8% w/w, at least 0.9% w/w, at least 1% w/w, or at least 1.2% w/w. In some embodiments the concentration of the trehalose powder is 0.5-4% w/w. In a particular embodiment, the concentration of the trehalose powder is 1.02% w/w. The microcrystalline cellulose is at a concentration of at least 10% w/w, at least 20% w/w, or at least 25% w/w. In some embodiments the concentration of the microcrystalline cellulose is 20-40% w/w. In a particular embodiment, the concentration of the microcrystalline cellulose is 25% w/w. The microcrystalline cellulose is preferably Avicel PH 200. The magnesium stearate is at a concentration of at least 0.1% w/w, at least 0.15% w/w, at least 0.2% w/w, or at least 0.25% w/w. In some embodiments the concentration of the magnesium stearate is 0.2-1% w/w. In a particular embodiment the concentration of the magnesium stearate is about 0.25% w/w.

In one embodiment the formulation contains a GCC agonist peptide, trehalose granules, hypromellose, TRIS, calcium ascorbate, trehalose powder, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 1.17% w/w. The GCC peptide is preferably SEQ NO: 1 or SEQ NO: 9. The trehalose granules are at a concentration of at least 50% w/w, at least 55% w/w, at least 60% w/w, at least 65% w/w, at least 70% w/w, or at least 75% w/w. In some embodiments the concentration of the trehalose granules is 55-75% w/w. In a particular embodiment, the concentration of the trehalose granules is 70.81% w/w. The hypromellose is at a concentration of at least 0.1% w/w, at least 0.2% w/w, at least 0.3% w/w, at least 0.4% w/w, or at least 0.5% w/w. In some embodiments the concentration of the hypromellose is 0.2-2% w/w. In a particular embodiment the concentration of the hypromellose about 0.5% w/w. The hypromellose is preferably Methocel ES Premium LV. The TRIS is a concentration of at least 0.6% w/w, at least 0.8% w/w, at least 0.9% w/w, or at least 1% w/w. In some embodiments the concentration of the TRIS is 0.5-6% w/w. In a particular embodiment, the concentration of the arginine is 1.15% w/w. The calcium ascorbate is at a concentration of at least 0.05% w/w, at least 0.07% w/w, at least 0.1% w/w, or at least 1% w/w. In some embodiments the concentration of the calcium ascorbate is 0.05-10% w/w. In a particular embodiment, the concentration of the calcium ascorbate is about 0.1% w/w. The trehalose powder is at a concentration of at least 0.5% w/w, at least 0.7% w/w, at least 0.8% w/w, at least 0.9% w/w, at least 1% w/w, or at least 1.2% w/w. In some embodiments the concentration of the trehalose powder is 0.5-4% w/w. In a particular embodiment, the concentration of the trehalose powder is 1.02% w/w. The microcrystalline cellulose is at a concentration of at least 10% w/w, at least 20% w/w, or at least 25% w/w. In some embodiments the concentration of the microcrystalline cellulose is 20-40% w/w. In a particular embodiment, the concentration of the microcrystalline cellulose is 25% w/w. The microcrystalline cellulose is preferably Avicel PH 200. The magnesium stearate is at a concentration of at least 0.1% w/w, at least 0.15% w/w, at least 0.2% w/w, or at least 0.25% w/w. In some embodiments the concentration of the magnesium stearate is 0.2-1% w/w. In a particular embodiment the concentration of the magnesium stearate is about 0.25% w/w.

In one embodiment the formulation contains a GCC agonist peptide, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 1.10% w/w. The GCC peptide is preferably SEQ NO: 1 or SEQ NO: 9. The microcrystalline cellulose is at a concentration of at least 30% w/w, at least 40% w/w, at least 50% w/w, at least 60% w/w, at least 70% w/w, at least 80% w/w, at least 90% w/w, at least 95% w/w, or at least 99% w/w. In some embodiments the concentration of the microcrystalline cellulose is about 98.64% w/w. The microcrystalline cellulose is preferably Avicel PH 102. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

In one embodiment the formulation contains a GCC agonist peptide, microcrystalline cellulose, and magnesium stearate. The GCC agonist is at a concentration of less than 5% w/w, less than 4% w/w, less than 3% w/w, less than 2% w/w, less than 1% w/w, less than 0.5% w/w, or less than 0.25% w/w. In some embodiments the GCC peptide is at a concentration of about 3.32% w/w. The GCC peptide is preferably SEQ NO: 1 or SEQ NO: 9. The microcrystalline cellulose is at a concentration of at least 30% w/w, at least 40% w/w, at least 50% w/w, at least 60% w/w, at least 70% w/w, at least 80% w/w, at least 90% w/w, at least 95% w/w, or at least 99% w/w. In some embodiments the concentration of the microcrystalline cellulose is about 96.43% w/w. The microcrystalline cellulose is preferably Avicel PH 102. The magnesium stearate is at a concentration of at least 0.1% w/w, at least 0.15% w/w, at least 0.2% w/w, or at least 0.25% w/w. In some embodiments the concentration of the magnesium stearate is about 0.25% w/w.

1.2 GCC Agonists

The GCC agonists for use in the formulations and methods of the invention bind to guanylate cyclase C and stimulate intracellular production of cGMP. Optionally, the GCC agonists induce apoptosis and inhibit proliferation of epithelial cells. The term, "guanylate cyclase C" refers to a transmembrane form of guanylate cyclase that acts as the intestinal receptor for the heat-stable toxin (ST) peptides secreted by enteric bacteria. Guanylate cyclase C is also the receptor for the naturally occurring peptides guanylin and uroguanylin. The possibility that there may be different receptors for each of these peptides has not been excluded. Hence, the term "guanylate cyclase C" may also encompass a class of transmembrane guanylate cyclase receptors expressed on epithelial cells lining the gastrointestinal mucosa.

The term "GCC agonist" refers to both peptides and non-peptide compounds such as that bind to an intestinal guanylate cyclase C and stimulate the intracellular production of cGMP. Where the GCC agonist is a peptide, the term encompasses biologically active fragments of such peptides and pro-peptides that bind to guanylate cyclase C and stimulate the intracellular production of cGMP.

Preferably, the GCC agonists for use in the formulations and methods of the invention stimulate intracellular cGMP production at higher levels than naturally occurring GCC agonists such as uroguanylin, guanylin, and ST peptides. In some embodiments, the GCC agonists stimulate intracellular cGMP production at higher levels than the peptide designated SP-304 (SEQ ID NO:1). In specific embodiments, a GCC agonist for use in the formulations and methods of the invention stimulates 5%, 10%, 20%, 30%, 40%, 50%, 75%, 90% or more intracellular cGMP compared to uroguanylin, guanylin, lymphoguanylin, linaclotide, ST peptides, or SP-304. The terms "induce" and "stimulate" are used interchangeably throughout the specification.

Preferably, the GCC agonists for use in the formulations and methods of the invention are more stable than naturally occurring GCC agonists such as uroguanylin, guanylin, and ST peptides. In some embodiments, the GCC agonists are more stable than the peptide designated SP-304. "Stability" in this context refers to resistance to degradation in gastrointestinal fluid and/or intestinal fluid (or simulated gastrointestinal or intestinal fluids) compared to the reference peptide. For example, the GCC agonists for use in the formulations and methods of the invention preferably degrade 2%, 3%, 5%, 10%, 15%, 20%, 30%, 40%, 50%, 75%, 90% or less compared to naturally occurring GCC angonists and/or SP-304.

The GCC agonists for use in the formulations and methods of the invention are preferably peptides. In some embodiments, the GCC agonist peptide is less than 30 amino acids in length. In particular embodiments, the GCC agonist peptide is less than or equal to 30, 25, 20, 15, 14, 13, 12, 11, 10, or 5 amino acids in length. Examples of GCC agonist peptides for use in the formulations and methods of the invention include those described in U.S. Ser. No. 12/133,344, filed Jun. 4, 2008, Ser. No. 12/478,505, filed Jun. 4, 2009; Ser. No. 12/478,511, filed Jun. 4, 2009; Ser. No. 12/504,288, filed Jul. 16, 2009; and U.S. Provisional Application Ser. Nos. 60/933,194, filed Jun. 4, 2007; 61/058,888, filed Jun. 4, 2008; 61/058,892, filed Jun. 4, 2008; and 61/081,289, filed Jul. 16, 2008, each of which is incorporated by reference herein in its entirety.

Specific examples of GCC agonist peptides for use in the formulations and methods of the invention include those described in Tables I-VII below. As used Tables I-VII, the terms "PEG3" or "3PEG" refer to a polyethylene glycol such as aminoethyloxy-ethyloxy-acetic acid (AeeA), and polymers thereof. The term "$X_{aa}$" refers to any natural or unnatural amino acid or amino acid analogue. The term "$M_{aa}$" refers to a cysteine (Cys), penicillamine (Pen) homocysteine, or 3-mercaptoproline. The term "$Xaa_{n1}$" is meant to denote an amino acid sequence of any natural or unnatural amino acid or amino acid analogue that is one, two or three residues in length; $Xaa_{n2}$ is meant to denote an amino acid sequence that is zero or one residue in length; and $Xaa_{n3}$ is meant to denote an amino acid sequence zero, one, two, three, four, five or six residues in length. Additionally, any amino acid represented by Xaa, $Xaa_{n1}$, $Xaa_{n2}$, or $Xaa_{n3}$ may be an L-amino acid, a D-amino acid, a methylated amino acid or any combination of thereof. Optionally, any GCC agonist peptide represented by Formulas I to XX in the tables may contain on or more polyethylene glycol residues at the N-terminus, C-terminus or both.

In certain embodiments, a GCC agonist formulation of the invention comprises a peptide selected from SEQ ID NOs: 1-249, the sequences of which are set forth below in Tables I to VII below. In one embodiment, a GCC agonist formulation comprises the peptide designated by SEQ ID NOs:1, 8, 9, 55, or 56.

In certain embodiments, a GCC agonist formulation of the invention comprises a peptide that is substantially equivalent to a peptide selected from SEQ ID NOs: 1-249. The term "substantially equivalent" refers to a peptide that has an amino acid sequence equivalent to that of the binding domain where certain residues may be deleted or replaced with other amino acids without impairing the peptide's ability to bind to an intestinal guanylate cyclase receptor and stimulate fluid and electrolyte transport.

1.2.1 GCC Agonist Peptides

In a preferred embodiment, the GCC agonists for use in the formulations and methods of the invention are GCC agonist peptides. In certain embodiments, the GCC agonist peptides are analogues of uroguanylin or a bacterial ST peptide. Uroguanylin is a circulating peptide hormone with natriuretic activity. An ST peptide is a member of a family of heat stable enterotoxins (ST peptides) secreted by pathogenic strains of *E. coli* and other enteric bacteria that activate guanylate cyclase receptor and cause secretory diarrhea. Unlike bacterial ST peptides, the binding of uroguanylin to guanylate cyclase receptor is dependent on the physiological pH of the gut. Therefore, uroguanylin is expected to regulate fluid and electrolyte transport in a pH dependent manner and without causing severe diarrhea.

The GCC agonist peptides for use in the formulations and methods of the invention can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

The GCC agonist peptides for use in the formulations and methods of the invention are able to induce intracellular cGMP production in cells and tissues expressing guanylate cyclase C. In certain embodiments, the GCC agonist peptide stimulates 5%, 10%, 20%, 30%, 40%, 50%, 75%, 90% or more intracellular cGMP compared to naturally occurring GCC agonists such as uroguanylin, guanylin, or ST peptides. Optionally, the GCC agonist peptide stimulates 5%, 10%, 20%, 30%, 40%, 50%, 75%, 90% or more intracellular cGMP compared SP-304 (SEQ ID NO:1). In further embodiments, the GCC agonist peptide stimulates apoptosis, e.g., programmed cell death, or activate the cystic fibrosis transmembrane conductance regulator (CFTR).

In some embodiments, the GCC agonist peptides for use in the formulations and methods of the invention are more stable than naturally occurring GCC agonists and/or SP-304 (SEQ ID NO:1), SP-339 (linaclotide) (SEQ ID NO: 55) or SP-340 (SEQ ID NO: 56). For example, the GCC agonist peptide degrades 2%, 3%, 5%, 10%, 15%, 20%, 30%, 40%, 50%, 75%, 90% or less compared to naturally occurring GCC agonists and/or SP-304, SP-339 (linaclotide) or SP-340. In certain embodiments, the GCC agonist peptides for use in the formulations and methods of the invention are more stable to proteolytic digestion than naturally occurring GCC agonists and/or SP-304 (SEQ ID NO:1), SP-339 (linaclotide) (SEQ ID NO: 55) or SP-340 (SEQ ID NO: 56). In one embodiment, a GCC agonist peptide is pegylated in order to render the peptides more resistant towards proteayalysis by enzymes of the gastrointestinal tract. In a preferred embodiment, the GCC agonist peptide is pegylated with the aminoethyloxy-ethyloxy-acetic acid (Aeea) group at its C-terminal end, at its N-terminal end, or at both termini.

Specific examples of GCC agonist peptides that can be used in the methods and formulations of the invention include a peptide selected from the group designated by SEQ ID NOs: 1-249.

In one embodiment, the GCC agonist peptide is a peptide having the amino acid sequence of any one of Formulas X-XVII (e.g. SEQ ID NO:87-98).

In some embodiments, GCC agonist peptides include peptides having the amino acid sequence of Formula I, wherein at least one amino acid of Formula I is a D-amino acid or a methylated amino acid and/or the amino acid at position 16 is a serine. Preferably, the amino acid at position 16 of Formula I is a D-amino acid or a methylated amino acid. For example, the amino acid at position 16 of Formula I is a d-leucine or a d-serine. Optionally, one or more of the amino acids at positions 1-3 of Formula I are D-amino acids or methylated amino acids or a combination of D-amino acids or methylated amino acids. For example, $Asn^1$, $Asp^2$ or $Glu^3$ (or a combination thereof) of Formula I is a D-amino acid or a methylated amino acid. Preferably, the amino acid at position $Xaa^6$ of Formula I is a leucine, serine or tyrosine.

In alternative embodiments, GCC agonist peptides include peptides having the amino acid sequence of Formula II, wherein at least one amino acid of Formula II is a D-amino acid or a methylated amino acid. Preferably, the amino acid denoted by $Xaa_{n2}$ of Formula II is a D-amino acid or a methylated amino acid. In some embodiments, the amino acid denoted by $Xaa_{n2}$ of Formula II is a leucine, a d-leucine, a serine, or a d-serine. Preferably, the one or more amino acids denoted by $Xaa_{n1}$ of Formula II is a D-amino acid or a methylated amino acid. Preferably, the amino acid at position $Xaa^6$ of Formula II is a leucine, a serine, or a tyrosine.

In some embodiments, GCC agonist peptides include peptides having the amino acid sequence of Formula III, wherein at least one amino acid of Formula III is a D-amino acid or a methylated amino acid and/or Maa is not a cysteine. Preferably, the amino acid denoted by $Xaa_{n2}$ of Formula III is a D-amino acid or a methylated amino acid. In some embodiments the amino acid denoted by $Xaa_{n2}$ of Formula III is a leucine, a d-leucine, a serine, or a d-serine. Preferably, the one or more amino acids denoted by $Xaa_{n1}$ of Formula III is a D-amino acid or a methylated amino acid. Preferably, the amino acid at position $Xaa^6$ of Formula III is a leucine, a serine, or a tyrosine.

In other embodiments, GCC agonist peptides include peptides having the amino acid sequence of Formula IV, wherein at least one amino acid of Formula IV is a D-amino acid or a methylated amino acid, and/or Maa is not a cysteine. Preferably, the $Xaa_{n2}$ of Formula IV is a D-amino acid or a methylated amino acid. In some embodiments, the amino acid denoted by $Xaa_{n2}$ of Formula IV is a leucine, a d-leucine, a serine, or a d-serine. Preferably, the one or more of the amino acids denoted by $Xaa_{n1}$ of Formula IV is a D-amino acid or a methylated amino acid. Preferably, the amino acid denoted $Xaa^6$ of Formula IV is a leucine, a serine, or a tyrosine.

In further embodiments, GCC agonist peptides include peptides having the amino acid sequence of Formula V, wherein at at least one amino acid of Formula V is a D-amino acid or a methylated amino acid. Preferably, the amino acid at position 16 of Formula V is a D-amino acid or a methylated amino acid. For example, the amino acid at position 16 (i.e., $Xaa^{16}$) of Formula V is a d-leucine or a d-serine. Optionally, one or more of the amino acids at position 1-3 of Formula V are D-amino acids or methylated amino acids or a combination of D-amino acids or methylated amino acids. For example, $Asn^1$, $Asp^2$ or $Glu^3$ (or a combination thereof) of Formula V is a D-amino acids or a methylated amino acid. Preferably, the amino acid denoted at $Xaa^6$ of Formula V is a leucine, a serine, or a tyrosine.

In additional embodiments, GCC agonist peptides include peptides having the amino acid sequence of Formula VI, VII, VIII, or IX. Preferably, the amino acid at position 6 of Formula VI, VII, VIII, or IX is a leucine, a serine, or a tyrosine. In some aspects the amino acid at position 16 of Formula VI, VII, VIII, or IX is a leucine or a serine. Preferably, the amino acid at position 16 of Formula V is a D-amino acid or a methylated amino acid.

In additional embodiments, GCC agonist peptides include peptides having the amino acid sequence of Formula X, XI, XII, XIII, XIV, XV, XVI or XVII. Optionally, one or more amino acids of Formulas X, XI, XII, XIII, XIV, XV, XVI or XVII is a D-amino acid or a methylated amino acid. Preferably, the amino acid at the carboxy terminus of the peptides according to Formulas X, XI, XII, XIII, XIV, XV, XVI or XVII is a D-amino acid or a methylated amino acid. For example the amino acid at the carboxy terminus of the peptides according to Formulas X, XI, XII, XIII, XIV, XV, XVI or XVII is a D-tyrosine.

Preferably, the amino acid denoted by $Xaa^6$ of Formula XIV is a tyrosine, phenylalanine or a serine. Most preferably the amino acid denoted by $Xaa^6$ of Formula XIV is a phenylalanine or a serine. Preferably, the amino acid denoted by $Xaa^4$ of Formula XV, XVI or XVII is a tyrosine, a phenyalanine, or a serine. Most preferably, the amino acid position $Xaa^4$ of Formula V, XVI or XVII is a phenyalanine or a serine.

In some embodiments, GCRA peptides include peptides containing the amino acid sequence of Formula XVIII. Preferably, the amino acid at position 1 of Formula XVIII is a glutamic acid, aspartic acid, glutamine or lysine. Preferably, the amino acid at position 2 and 3 of Formula XVIII is a glutamic acid, or an aspartic acid. Preferably, the amino acid at position 5 a glutamic acid. Preferably, the amino acid at position 6 of Formula XVIII is an isoleucine, valine, serine, threonine or tyrosine. Preferably, the amino acid at position 8 of Formula XVIII is a valine or isoleucine. Preferably, the amino acid at position 9 of Formula XVIII is a an asparagine. Preferably, the amino acid at position 10 of Formula XVIII is a valine or an methionine. Preferably, the amino acid at position 11 of Formula XVIII is an alanine. Preferably, the amino acid at position 13 of Formula XVIII is a threonine. Preferably, the amino acid at position 14 of Formula XVIII is a glycine. Preferably, the amino acid at position 16 of Formula XVIII is a leucine, serine or threonine In alternative embodiments, GCRA peptides include peptides containing the amino acid sequence of Formula XIX. Preferably, the amino acid at position 1 of Formula XIX is a serine or asparagine. Preferably, the amino acid at position 2 of Formula XIX is a histidine or an aspartic acid. Preferably, the amino acid at position 3 of Formula XIX is a threonine or a glutamic acid. Preferably, the amino acid at position 5 of Formula XIX is a glutamic acid. Preferably, the amino acid at position 6 of Formula XIX is an isoleucine, leucine, valine or tyrosine. Preferably, the amino acid at position 8, 10, 11, or 13 of Formula XIX is a alanine. Preferably, the amino acid at position 9 of Formula XIX is an asparagine or a phenylalanine. Preferably, the amino acid at position 14 of Formula XIX is a glycine.

In further embodiments, GCRA peptides include peptides containing the amino acid sequence of Formula XX. Preferably, the amino acid at position 1 of Formula XX is a glutamine. Preferably, the amino acid at position 2 or 3 of Formula XX is a glutamic acid or a aspartic acid. Preferably, the amino acid at position 5 of Formula XX is a glutamic acid. Preferably, the amino acid at position 6 of Formula XX is threonine, glutamine, tyrosine, isoleucine, or leucine. Preferably, the amino acid at position 8 of Formula XX is isoleucine or valine. Preferably, the amino acid at position 9 of Formula XX is asparagine. Preferably, the amino acid at position 10 of Formula XX is methionine or valine. Preferably, the amino acid at position 11 of Formula XX is alanine. Preferably, the amino acid at position 13 of Formula XX is a threonione. Preferably, the amino acid at position 1 of Formula XX is a glycine. Preferably, the amino acid at position 15 of Formula XX is a tyrosine. Optionally, the amino acid at position 15 of Formula XX is two amino acid in length and is Cysteine (Cys), Penicillamine (Pen) homocysteine, or 3-mercaptoproline and serine, leucine or threonine.

In certain embodiments, one or more amino acids of the GCC agonist peptides are replaced by a non-naturally occurring amino acid or a naturally or non-naturally occurring amino acid analog. Such amino acids and amino acid analogs are known in the art. See, for example, Hunt, "The Non-Protein Amino Acids," in *Chemistry and Biochemistry of the Amino Acids*, Barrett, Chapman and Hall, 1985. In some embodiments, an amino acid is replaced by a naturally-occurring, non-essential amino acid, e.g., taurine. Non-limiting examples of naturally occurring amino acids that can be replaced by non-protein amino acids include the following: (1) an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr); (2) Phg and norTyr and other amino acids including Phe and Tyr can be substituted by, e.g., a halogen, —CH3, —OH, —CH2NH3, —C(O)H, —CH2CH3, —CN, —CH2CH2CH3, —SH, or another group; (3) glutamine residues can be substituted with gamma-Hydroxy-Glu or gamma-Carboxy-Glu; (4) tyrosine residues can be substituted with an alpha substituted amino acid such as L-alpha-methylphenylalanine or by analogues such as: 3-Amino-Tyr; Tyr(CH3); Tyr(PO3(CH3)2); Tyr(SO3H); beta-Cyclohexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp; (5) proline residues can be substituted with homopro (L-pipecolic acid); hydroxy-Pro; 3,4-Dehydro-Pro; 4-fluoro-Pro; or alpha-methyl-Pro or an N(alpha)-C(alpha) cyclized amino acid analogues with the structure: n=0, 1, 2, 3; and (6) alanine residues can be substituted with alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of non-natural amino acids include: an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}C$, $^{15}N$, or $^{18}O$); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline; an O-methyl-L-tyrosine; an L-3-(2-naphthyl)alanine; a 3-methyl-phenylalanine; a ρ-acetyl-L-phenylalanine; an O-4-allyl-L-tyrosine; a 4-propyl-L-tyrosine; a tri-O-acetyl-GlcNAc β-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl)alanine; D-3-(2-naphthyl)alanine (dNal); an amino-, isopropyl-, or O-allyl-containing phenylalanine analogue; a dopa, O-methyl-L-tyrosine; a glycosylated amino acid; a p-(propargyloxy) phenylalanine; dimethyl-Lysine; hydroxy-proline; mercaptopropionic acid; methyl-lysine; 3-nitro-tyrosine; norleucine; pyro-glutamic acid; Z (Carbobenzoxyl); ε-Acetyl-Lysine; β-alanine; aminobenzoyl derivative; aminobutyric acid (Abu); citrulline; aminohexanoic acid; aminoisobutyric acid (AIB); cyclohexylalanine; d-cyclohexylalanine; hydroxyproline; nitro-arginine; nitro-phenylalanine; nitro-tyrosine; norvaline; octahydroindole carboxylate; ornithine (Orn); penicillamine (PEN); tetrahydroisoquinoline; acetamidomethyl protected amino acids and pegylated amino acids. Further examples of unnatural amino acids and amino acid analogs can be found in U.S. 20030108885, U.S. 20030082575, US20060019347 (paragraphs 410-418) and the references cited therein. The polypeptides of the invention can include further modifications including those described in US20060019347, paragraph 589. Exempary GCC agonist peptides which include a non-naturally occurring amino acid include for example SP-368 and SP-369.

In some embodiments, the GCC agonist peptides are cyclic peptides. GCC agonist cyclic peptides can be prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., Endocrinology, 137: 5182-5185 (1996)), or between two amino acid side chains, such as cysteine. See, e.g., DeGrado, *Adv Protein Chem*, 39: 51-124 (1988). In various embodiments, the GCC agonist peptides are [4,12; 7,15] bicycles.

In certain embodiments, one or both Cys residues which normally form a disulfide bond in a GCC agonist peptide are replaced with homocysteine, penicillamine, 3-mercaptoproline (Kolodziej et al. 1996 *Int. J. Pept. Protein Res.* 48:274), β,β dimethylcysteine (Hunt et al. 1993 *Int. J. Pept. Protein Res.* 42:249), or diaminopropionic acid (Smith et al. 1978 *J. Med. Chem.* 2 1:117) to form alternative internal cross-links at the positions of the normal disulfide bonds.

In certain embodiments, one or more disulfide bonds in a GCC agonist peptide are replaced by alternative covalent cross-links, e.g., an amide linkage ($-CH_2CH(O)NHCH_2-$ or $-CH_2NHCH(O)CH_2-$), an ester linkage, a thioester linkage, a lactam bridge, a carbamoyl linkage, a urea linkage, a thiourea linkage, a phosphonate ester linkage, an alkyl linkage ($-CH_2CH_2CH_2CH_2-$), an alkenyl linkage ($-CH_2CH=CHCH_2-$), an ether linkage ($-CH_2CH_2OCH_2-$ or $-CH_2OCH_2CH_2-$), a thioether linkage ($-CH_2CH_2SCH_2-$ or $-CH_2SCH_2CH_2-$), an amine linkage ($-CH_2CH_2NHCH_2-$ or $-CH_2NHCH_2CH_2-$) or a thioamide linkage ($-CH_2CH(S)HNHCH_2-$ or $-CH_2NHCH(S)CH_2-$). For example, Ledu et al. (*Proc. Natl. Acad. Sci.* 100:11263-78, 2003) describe methods for preparing lactam and amide cross-links Exemplary GCC agonist peptides which include a lactam bridge include, for example, SP-370.

In certain embodiments, the GCC agonist peptides have one or more conventional polypeptide bonds replaced by an alternative bond. Such replacements can increase the stability of the polypeptide. For example, replacement of the polypeptide bond between a residue amino terminal to an aromatic residue (e.g. Tyr, Phe, Trp) with an alternative bond can reduce cleavage by carboxy peptidases and may increase half-life in the digestive tract. Bonds that can replace polypeptide bonds include: a retro-inverso bond (C(O)—NH instead of NH—C(O); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefine bond (CH=CH); a fluoro substituted trans-olefine bond (CF=CH); a ketomethylene bond (C(O)—CHR or CHR—C(O) wherein R is H or $CH_3$; and a fluoro-ketomethylene bond (C(O)—CFR or CFR—C(O) wherein R is H or F or $CH_3$.

In certain embodiments, the GCC agonist peptides are modified using standard modifications. Modifications may occur at the amino (N—), carboxy (C—) terminus, internally or a combination of any of the preceeding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The GCC agonist peptides described herein may also be modified by 2,4-dinitrophenyl (DNP), DNP-lysine, modification by 7-Amino-4-methyl-coumarin (AMC), flourescein, NBD (7-Nitrobenz-2-Oxa-1,3-Diazole), p-nitro-anilide, rhodamine B, EDANS (5((2-aminoethyl)amino)naphthalene-1-sulfonic acid), dabcyl, dabsyl, dansyl, texas red, FMOC, and Tamra (Tetramethylrhodamine). The GCC agonist peptides described herein may also be conjugated to, for example, polyethylene glycol (PEG); alkyl groups (e.g., C1-C20 straight or branched alkyl groups); fatty acid radicals; combinations of PEG, alkyl groups and fatty acid radicals (See, U.S. Pat. No. 6,309,633; Soltero et al., 2001 Innovations in Pharmaceutical Technology 106-110); BSA and KLH (Keyhole Limpet Hemocyanin). The addition of PEG and other polymers which can be used to modify polypeptides of the invention is described in US20060 19347 section IX.

A GCC agonist peptide can also be a derivatives of a GCC agonist peptide described herein. For example, a derivative includes hybrid and modified forms of GCC agonist peptides in which certain amino acids have been deleted or replaced. A modification may also include glycosylation. Preferably, where the modification is an amino acid substitution, it is a conservative substitution at one or more positions that are predicted to be non-essential amino acid residues for the biological activity of the peptide. A "conservative substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, a GCC agonist peptide described herein is subjected to random mutagenesis in order to identify mutants having biological activity.

In one embodiment, the GCC agonist peptide is substantially homologous is a GCC agonist peptide described herein. Such substantially homologous peptides can be isolated by virtue of cross-reactivity with antibodies to a GCC agonist peptide described herein.

Further examples of GCC agonist peptides that can be used in the methods and formulations of the invention are found in Tables I-VII below.

1.2.2 Preparation of GCC Agonist Peptides

GCC agonist peptides can be prepared using art recognized techniques such as molecular cloning, peptide synthesis, or site-directed mutagenesis.

Peptide synthesis can be performed using standard solution phase or solid phase peptide synthesis techniques or a combination of both process where segments are synthesized by solid phase and condensed in solution phase, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (See, Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor. Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc., 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Alternatively the GCC agonist peptides are produced by modern cloning techniques For example, the GCC agonist peptides are produced either in bacteria including, without limitation, E. coli, or in other existing systems for polypeptide or protein production (e.g., Bacillus subtilis, baculovirus expression systems using Drosophila Sf9 cells, yeast or filamentous fungal expression systems, mammalian cell expression systems), or they can be chemically synthesized. If the GCC agonist peptide or variant peptide is to be produced in bacteria, e.g., E. coli, the nucleic acid molecule encoding the polypeptide may also encode a leader sequence that permits the secretion of the mature polypeptide from the cell. Thus, the sequence encoding the polypeptide can include the pre sequence and the pro sequence of, for example, a naturally-occurring bacterial ST polypeptide. The secreted, mature polypeptide can be purified from the culture medium.

The sequence encoding a GCC agonist peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, E. coli, B subtilis, Pseudomonas, Salmonella. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences.

A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during polypeptide production.

The protein coding sequence that includes a GCC agonist peptide described herein can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the polypeptide of interest to the reading frame of the gene encoding the affinity tag such that a translational fusion is generated. Expression of the fusion gene results in translation of a single polypeptide that includes both the polypeptide of interest and the affinity tag. In some instances where affinity tags are utilized, DNA sequence encoding a protease recognition site will be fused between the reading frames for the affinity tag and the polypeptide of interest.

Genetic constructs and methods suitable for production of immature and mature forms of the GCC agonist peptides and variants described herein in protein expression systems other than bacteria, and well known to those skilled in the art, can also be used to produce polypeptides in a biological system.

The peptides disclosed herein may be modified by attachment of a second molecule that confers a desired property upon the peptide, such as increased half-life in the body, for example, pegylation. Such modifications also fall within the scope of the term "variant" as used herein.

TABLE I

GCRA Peptides (SP-304 and Derivatives)

| Name | Position of Disulfide bonds | Structure | SEQ ID NO |
|---|---|---|---|
| SP-304 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 1 |
| SP-326 | C3:C11, C6:C14 | Asp$^1$-Glu$^2$-Cys$^3$-Glu$^4$-Leu$^5$-Cys$^6$-Val$^7$-Asn$^8$-Val$^9$-Ala$^{10}$-Cys$^{11}$-Thr$^{12}$-Gly$^{13}$-Cys$^{14}$-Leu$^{15}$ | 2 |
| SP-327 | C2:C10, C5:C13 | Asp$^1$-Glu$^2$-Cys$^3$-Glu$^4$-Leu$^5$-Cys$^6$-Val$^7$-Asn$^8$-Val$^9$-Ala$^{10}$-Cys$^{11}$-Thr$^{12}$-Gly$^{13}$-Cys$^{14}$ | 3 |
| SP-328 | C2:C10, C5:C13 | Glu$^1$-Cys$^2$-Glu$^3$-Leu$^4$-Cys$^5$-Val$^6$-Asn$^7$-Val$^8$-Ala$^9$-Cys$^{10}$-Thr$^{11}$-Gly$^{12}$-Cys$^{13}$-Leu$^{14}$ | 4 |
| SP-329 | C2:C10, C5:C13 | Glu$^1$-Cys$^2$-Glu$^3$-Leu$^4$-Cys$^5$-Val$^6$-Asn$^7$-Val$^8$-Ala$^9$-Cys$^{10}$-Thr$^{11}$-Gly$^{12}$-Cys$^{13}$-Leu$^{14}$ | 5 |
| SP-330 | C1:C9, C4:C12 | Cys$^1$-Glu$^2$-Leu$^3$-Cys$^4$-Val$^5$-Asn$^6$-Val$^7$-Ala$^8$-Cys$^9$-Thr$^{10}$-Gly$^{11}$-Cys$^{12}$-Leu$^{13}$ | 6 |
| SP-331 | C1:C9, C4:C12 | Cys$^1$-Glu$^2$-Leu$^3$-Cys$^4$-Val$^5$-Asn$^6$-Val$^7$-Ala$^8$-Cys$^9$-Thr$^{10}$-Gly$^{11}$-Cys$^{12}$ | 7 |
| SP332 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 8 |
| SP-333 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 9 |
| SP-334 | C4:C12, C7:C15 | dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 10 |
| SP-335 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 11 |
| SP-336 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 12 |
| SP-337 | C4:C12, C7:C15 | dAsn$^1$-Asp$^2$-Glu$^3$-Cys$^4$-Glu$^5$-dLeu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 13 |
| SP-338 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$ | 14 |
| SP-342 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 15 |
| SP-343 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 16 |
| SP-344 | C4:C12, C7:C15 | PEG3-dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 17 |
| SP-347 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 18 |
| SP-348 | C4:C12, C7:C15 | PEG3-dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 19 |
| SP-350 | C4:C12, C7:C15 | PEG3-dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 20 |
| SP-352 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 21 |
| SP-358 | C4:C12, C7:C15 | PEG3-dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 22 |

TABLE I-continued

GCRA Peptides (SP-304 and Derivatives)

| Name | Position of Disulfide bonds | Structure | SEQ ID NO |
|---|---|---|---|
| SP-359 | C4:C12, C7:C15 | PEG3-dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 23 |
| SP-360 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 24 |
| SP-361 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 25 |
| SP-362 | C4:C12, C7:C15 | PEG3-dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 26 |
| SP-368 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dNal$^{16}$ | 27 |
| SP-369 | C4:C12, C7:C15 | dAsn$^1$-Asp$^2$-Glu$^3$-Cys$^4$-Glu$^5$-Leu$^6$-Cys$^7$-Val$^8$-Asn$^9$-AIB$^{10}$-Ala$^{11}$-Cys$^{12}$-Thr$^{13}$-Gly$^{14}$-Cys$^{15}$-dLeu$^{16}$ | 28 |
| SP-370 | C4:C12, C7:C15 | dAsn$^1$-Asp$^2$-Glu$^3$-Cys$^4$-Glu$^5$-Leu$^6$-Asp[Lactam]$^7$-Val$^8$-Asn$^9$-Val$^{10}$-Ala$^{11}$-Cys$^{12}$-Thr$^{13}$-Gly$^{14}$-Orn$^{15}$-dLeu$^1$ | 29 |
| SP-371 | C4:C12, C7:C15 | dAsn$^1$-Asp$^2$-Glu$^3$-Cys$^4$-Glu$^5$-Leu$^6$-Cys$^7$-Tyr$^6$-Asn$^9$-Val$^{10}$-Ala$^{11}$-Cys$^{12}$-Thr$^{13}$-Gly$^{14}$-Cys$^{15}$-dLeu$^{16}$ | 30 |
| SP-372 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 31 |
| N1 | C4:C12, C7:C15 | PEG3-dAsn$^1$-Asp$^2$-Glu$^3$-Cys$^4$-Glu$^5$-Leu$^6$-Cys$^7$-Tyr$^6$-Asn$^9$-Val$^{10}$-Ala$^{11}$-Cys$^{12}$-Thr$^{13}$-Gly$^{14}$-Cys$^{15}$-dLeu$^{16}$-PEG3 | 32 |
| N2 | C4:C12, C7:C15 | PEG3-dAsn$^1$-Asp$^2$-Glu$^3$-Cys$^4$-Glu$^5$-Leu$^6$-Cys$^7$-Tyr$^6$-Asn$^9$-Val$^{10}$-Ala$^{11}$-Cys$^{12}$-Thr$^{13}$-Gly$^{14}$-Cys$^{15}$-dLeu$^{16}$ | 33 |
| N3 | C4:C12, C7:C15 | dAsn$^1$-Asp$^2$-Glu$^3$-Cys$^4$-Glu$^5$-Leu$^6$-Cys$^7$-Tyr$^6$-Asn$^9$-Val$^{10}$-Ala$^{11}$-Cys$^{12}$-Thr$^{13}$-Gly$^{14}$-Cys$^{15}$-dLeu$^{16}$ PEG3 | 34 |
| N4 | C4:C12, C7:C15 | PEG3-dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 35 |
| N5 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 36 |
| N6 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 37 |
| N7 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 38 |
| N8 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 39 |
| N9 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 40 |
| N10 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 41 |
| N11 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 42 |
| N12 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 43 |
| N13 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 44 |
| Formula I | C4:C12, C7:C15 | Asn$^1$-Asp$^2$-Glu$^3$-Cys$^4$-Xaa$^5$-Xaa$^6$-Cys$^7$-Val$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 45 |

TABLE I-continued

GCRA Peptides (SP-304 and Derivatives)

| Name | Position of Disulfide bonds | Structure | SEQ ID NO |
|---|---|---|---|
| Formula II | C4:C12, C7:C15 | $Xaa_{n1}$-$Cys^4$-$Xaa^5$-$Xaa^6$-$Cys^7$-$Xaa^8$-$Xaa^9$-$Xaa^{10}$-$Xaa^{11}$-$Cys^{12}$-$Xaa^{13}$-$Xaa^{14}$-$Cys^{15}$-$Xaa_{n2}^{16}$ | 46 |
| Formula III | 4:12, 7:15 | $Xaa_{n1}$-$Maa^4$-$Glu^5$-$Xaa^6$-$Maa^7$-$Val^8$-$Asn^9$-$Val^{10}$-$Ala^{11}$-$Maa^{12}$-$Thr^{13}$-$Gly^{14}$-$Maa^{15}$-$Xaa_{n2}$ | 47 |
| Formula IV | 4:12, 7:15 | $Xaa_{n1}$-$Maa^4$-$Xaa^5$-$Xaa^6$-$Maa^7$-$Xaa^8$-$Xaa^9$-$Xaa^{10}$-$Xaa^{11}$-$Maa^{12}$-$Xaa^{13}$-$Maa^{14}$-$Maa^{15}$-$Xaa_{n2}$ | 48 |
| Formula V | C4:C12, C7:C15 | $Asn^1$-$Asp^2$-$Asp^3$-$Cys^4$-$Xaa^5$-$Xaa^6$-$Cys^7$-$Xaa^8$-$Asn^9$-$Xaa^{10}$-$Xaa^{11}$-$Cys^{12}$-$Xaa^{13}$-$Xaa^{14}$-$Cys^{15}$-$Xaa^{16}$ | 49 |
| Formula VI | C4:C12, C7:C15 | $dAsn^1$-$Glu^2$-$Glu^3$-$Cys^4$-$Xaa^5$-$Xaa^6$-$Cys^7$-$Xaa^8$-$X3^8$-$Asn^9$-$Xaa^{10}$-$Xaa^{11}$-$Cys^{12}$-$Xaa^{13}$-$Xaa^{14}$-$Cys^{15}$-d-$Xaa^{16}$ | 50 |
| Formula VII | C4:C12, C7:C15 | $dAsn^1$-$Glu^2$-$Asp^3$-$Cys^4$-$Xaa^5$-$Xaa^6$-$Cys^7$-$Xaa^8$-$Asn^9$-$Xaa^{10}$-$Xaa^{11}$-$Cys^{12}$-$Xaa^{13}$-$Xaa^{14}$-$Cys^{15}$-d-$Xaa^{16}$ | 51 |
| Formula VII | C4:C12, C7:C15 | $dAsn^1$-$dAsp^2$-$Glu^3$-$Cys^4$-$Xaa^5$-$Xaa^6$-$Cys^7$-$Xaa^8$-$Asn^9$-$Xaa^{10}$-$Xaa^{11}$-$Cys^{12}$-$Xaa^{13}$-$Xaa^{14}$-$Cys^{15}$-d-$Xaa^{16}$ | 52 |
| Formula VIII | C4:C12, C7:C15 | $dAsn^1$-$dAsp^2$-$dAsp^3$-$Cys^4$-$Xaa^5$-$Xaa^6$-$Cys^7$-$Xaa^8$-$Tyr^9$-$Xaa^{10}$-$Xaa^{11}$-$Cys^{12}$-$Xaa^{13}$-$Xaa^{14}$-$Cys^{15}$-d-$Xaa^{16}$ | 53 |
| Formula IX | C4:C12, C7:C15 | $dAsn^1$-$dGlu^2$-$dGlu^3$-$Cys^4$-$Xaa^5$-$Xaa^6$-$Cys^7$-$Xaa^8$-$Tyr^9$-$Xaa^{10}$-$Xaa^{11}$-$Cys^{12}$-$Xaa^{13}$-$Xaa^{14}$-$Cys^{15}$-d-$Xaa^{16}$ | 54 |

TABLE II

Linaclotide and Derivatives

| Name | Position of Disulfide bonds | Structure | SEQ ID NO: |
|---|---|---|---|
| SP-339 (linaclotide) | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 55 |
| SP-340 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$ | 56 |
| SP-349 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$-PEG3 | 57 |
| SP-353 | C3:C8, C4:C12, C7:15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 58 |
| SP-354 | C3:C8, C4:C12, C7:15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 59 |
| SP-355 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$dTyr^{14}$ | 60 |
| SP-357 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 61 |
| SP-374 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 62 |
| SP-375 | C3:C8, C4:C12, C7:15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 63 |
| SP-376 | C3:C8, C4:C12, C7:15 | $dAsn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 64 |
| SP-377 | C3:C8, C4:C12, C7:15 | $dAsn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 65 |
| SP-378 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 66 |
| SP-379 | C3:C8, C4:C12, C7:15 | $dAsn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 67 |
| SP-380 | C3:C8, C4:C12, C7:15 | $dAsn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 68 |

TABLE II-continued

Linaclotide and Derivatives

| Name | Position of Disulfide bonds | Structure | SEQ ID NO: |
|---|---|---|---|
| SP-381 | C3:C8, C4:C12, C7:15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 69 |
| SP-382 | C3:C8, C4:C12, C7:15 | $dAsn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 70 |
| SP-383 | C3:C8, C4:C12, C7:15 | $dAsn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 71 |
| SP384 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$-PEG3 | 72 |
| N14 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-PEG3 | 73 |
| N15 | C1:C6, C2:C10, C5:13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$ | 74 |
| N16 | C1:C6, C2:C10, C5:13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-PEG3 | 75 |
| N17 | C3:C8, C4:C12, C7:15 | PEG3-$Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 76 |
| N18 | C3:C8, C4:C12, C7:15 | PEG3-$Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 77 |
| N19 | C3:C8, C4:C12, C7:15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 78 |
| N20 | C3:C8, C4:C12, C7:15 | PEG3-$Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 79 |
| N21 | C3:C8, C4:C12, C7:15 | PEG3-$Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 80 |
| N22 | C3:C8, C4:C12, C7:15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 81 |
| N23 | C3:C8, C4:C12, C7:15 | PEG3-$Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 82 |
| N24 | C3:C8, C4:C12, C7:15 | PEG3-$Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 83 |
| N25 | C3:C8, C4:C12, C7:15 | $Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 84 |
| N26 | C1:C6, C2:C10, C5:13 | $Cys^1$-$Cys^2$-$Glu3$-$Ser^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 85 |
| N27 | C1:C6, C2:C10, C5:13 | $Cys^1$-$Cys^2$-$Glu3$-$Phe^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 86 |
| N28 | C1:C6, C2:C10, C5:13 | $Cys^1$-$Cys^2$-$Glu3$-$Ser^4$-$Cys^5$-$Cys^6$-$Asn^7$-$Pro^8$-$Ala^9$-$Cys^{10}$-$Thr^{11}$-$Gly^{12}$-$Cys^{13}$- | 87 |

TABLE II-continued

Linaclotide and Derivatives

| Name | Position of Disulfide bonds | Structure | SEQ ID NO: |
|---|---|---|---|
| N29 | C1:C6, C2:C10, C5:13 | Cys$^1$-Cys$^2$-Glu3-Phe$^4$-Cys$^5$-Cys$^6$-Asn$^7$-Pro$^8$-Ala$^9$-Cys$^{10}$-Thr$^{11}$-Gly$^{12}$-Cys$^{13}$ | 88 |
| N30 | 1:6, 2:10, 5:13 | Pen$^1$-Pen$^2$-Glu3-Tyr$^4$-Pen$^5$-Pen$^6$-Asn$^7$-Pro$^8$-Ala$^9$-Pen$^{10}$-Thr$^{11}$-Gly$^{12}$-Pen$^{13}$-Tyr$^{14}$ | 89 |
| N31 | 1:6, 2:10, 5:13 | Pen$^1$-Pen$^2$-Glu3-Tyr$^4$-Pen$^5$-Pen$^6$-Asn$^7$-Pro$^8$-Ala$^9$-Pen$^{10}$-Thr$^{11}$-Gly$^{12}$-Pen$^{13}$ | 90 |
| Formula X | C9:C14, C10:C18, C13:21 | Xaa$^1$-Xaa$^2$-Xaa$^3$-Xaa$^4$-Xaa$^5$-Xaa$^6$-Asn$^7$-Tyr$^8$-Cys$^9$-Cys$^{10}$-Xaa$^{11}$-Tyr$^{12}$-Cys$^{13}$-Cys$^{14}$-Xaa$^{15}$-Xaa$^{16}$-Xaa$^{17}$-Cys$^{18}$-Xaa$^{19}$-Xaa$^{20}$-Cys$^{21}$-Xaa$^{22}$ | 91 |
| Formula XI | C9:C14, C10:C18, C13:21 | Xaa$^1$-Xaa$^2$-Xaa$^3$-Xaa$^4$-Xaa$^5$-Xaa$^6$-Asn$^7$-Phe$^8$-Cys$^9$-Cys$^{10}$-Xaa$^{11}$-Phe$^{12}$-Cys$^{13}$-Cys$^{14}$-Xaa$^{15}$-Xaa$^{16}$-Xaa$^{17}$-Cys$^{18}$-Xaa$^{19}$-Xaa$^{20}$-Cys$^{21}$-Xaa$^{22}$ | 92 |
| Formula XII | C3:C8, C4:C12, C7:15 | Asn$^1$-Phe$^2$-Cys$^3$-Cys$^4$-Xaa$^5$-Phe$^6$-Cys$^7$-Cys$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 93 |
| Formula XIII | 3:8, 4:12, C:15 | Asn$^1$-Phe$^2$-Pen$^3$-Cys$^4$-Xaa$^5$-Phe$^6$-Cys$^7$-Pen$^8$-Xaa$^9$-Xaa$^{10}$-Xaa$^{11}$-Cys12-Xaa$^{13}$-Xaa$^{14}$-Cys$^{15}$-Xaa$^{16}$ | 94 |
| Formula XIV | 3:8, 4:12, 7:15 | Asn$^1$-Phe$^2$-Maa$^3$-Maa$^4$-Xaa$^5$-Maa$^6$-Maa$^7$-Maa$^8$-Xaa$^9$-Xaa$^{10}$-Xaa$^{11}$-Maa$^{12}$-Xaa$^{13}$-Xaa$^{14}$-Maa$^{15}$-Xaa$^{16}$ | 95 |
| Formula XV | 1:6, 2:10, 5:13 | Maa$^1$-Maa$^2$-Glu3-Xaa$^4$-Maa$^5$-Maa$^6$-Asn$^7$-Pro$^8$-Ala$^9$-Maa$^{10}$-Thr$^{11}$-Gly$^{12}$-Maa$^{13}$-Tyr$^{14}$ | 96 |
| Formula XVI | 1:6, 2:10, 5:13 | Maa$^1$-Maa$^2$-Glu3-Xaa$^4$-Maa$^5$-Maa$^6$-Asn$^7$-Pro$^8$-Ala$^9$-Maa$^{10}$-Thr$^{11}$-Gly$^{12}$-Maa$^{13}$- | 97 |
| Formula XVII | 1:6, 2:10, 5:13 | Xaa$_{n3}$-Maa$^1$-Maa$^2$-Xaa$^3$-Xaa$^4$-Maa$^5$-Maa$^6$-Xaa$^7$-Xaa$^8$-Xaa$^9$-Maa$^{10}$-Xaa$^{11}$-Xaa$^{12}$-Maa$^{13}$-Xaa$_{n2}$ | 98 |

TABLE III

GCRA Peptides

| Name | Position of Disulfide bonds | Structure | SEQ ID NO: |
|---|---|---|---|
| SP-363 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-AMIDE$^{16}$ | 99 |
| SP-364 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 100 |
| SP-365 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer-AMIDE$^{16}$ | 101 |
| SP-366 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr$^{16}$ | 102 |
| SP-367 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr-AMIDE$^{16}$ | 103 |
| SP-373 | C4:C12, C7:C15 | Pyglu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-AMIDE$^{16}$ | 104 |
| SP-304 di PEG | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16-PEG3}$ | 105 |
| SP-304 N-PEG | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 106 |
| SP-304 C-PEG | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$-PEG3 | 107 |

TABLE IV

SP-304 Analogs, Uroguanylin, and Uroguanylin Analogs

| Name | Position of Disulfide bonds | Structure | SEQ ID NO |
|---|---|---|---|
| Formula XVIII | C4:C12, C7:C15 | $Xaa^1-Xaa^2-Xaa^3-Maa^4-Xaa^5-Xaa^6-Maa^7-Xaa^8-Xaa^9-Xaa^{10}-Xaa^{11}-Maa^{12}-Xaa^{13}-Xaa^{14}-Maa^{15}-Xaa^{16}$ | 108 |
| Uroguanylin | C4:C12, C7:C15 | $Asn^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 109 |
| N32 | C4:C12, C7:C15 | $Glu^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 110 |
| N33 | C4:C12, C7:C15 | $Glu^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 111 |
| N34 | C4:C12, C7:C15 | $Glu^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 112 |
| N35 | C4:C12, C7:C15 | $Glu^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 113 |
| N36 | C4:C12, C7:C15 | $Asp^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 114 |
| N37 | C4:C12, C7:C15 | $Asp^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 115 |
| N38 | C4:C12, C7:C15 | $Asp^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 116 |
| N39 | C4:C12, C7:C15 | $Glu^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 117 |
| N40 | C4:C12, C7:C15 | $Gln^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 118 |
| N41 | C4:C12, C7:C15 | $Gln^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 119 |
| N42 | C4:C12, C7:C15 | $Gln^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 120 |
| N43 | C4:C12, C7:C15 | $Gln^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 121 |
| N44 | C4:C12, C7:C15 | $Lys^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 122 |
| N45 | C4:C12, C7:C15 | $Lys^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 123 |
| N46 | C4:C12, C7:C15 | $Lys^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 124 |
| N47 | C4:C12, C7:C15 | $Lys^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Leu^{16}$ | 125 |
| N48 | C4:C12, C7:C15 | $Glu^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 126 |
| N49 | C4:C12, C7:C15 | $Glu^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 127 |
| N50 | C4:C12, C7:C15 | $Glu^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 128 |
| N51 | C4:C12, C7:C15 | $Glu^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 129 |
| N52 | C4:C12, C7:C15 | $Asp^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 130 |
| N53 | C4:C12, C7:C15 | $Asp^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 131 |

TABLE IV-continued

SP-304 Analogs, Uroguanylin, and Uroguanylin Analogs

| Name | Position of Disulfide bonds | Structure | SEQ ID NO |
|---|---|---|---|
| N54 | C4:C12, C7:C15 | $Asp^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 132 |
| N55 | C4:C12, C7:C15 | $Asp^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 133 |
| N56 | C4:C12, C7:C15 | $Gln^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 134 |
| N57 | C4:C12, C7:C15 | $Gln^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 135 |
| N58 | C4:C12, C7:C15 | $Gln^1-Glu^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 136 |
| N59 | C4:C12, C7:C15 | $Gln^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 137 |
| N60 | C4:C12, C7:C15 | $Lys^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 138 |
| N61 | C4:C12, C7:C15 | $Lys^1-Asp^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 139 |
| N62 | C4:C12, C7:C15 | $Lys^1-Glu^2-Glu^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 140 |
| N63 | C4:C12, C7:C15 | $Glu^1-Asp^2-Asp^3-Cys^4-Glu^5-Leu^6-Cys^7-Val^8-Asn^9-Val^{10}-Ala^{11}-Cys^{12}-Thr^{13}-Gly^{14}-Cys^{15}-Ser^{16}$ | 141 |
| N65 | C4:C12, C7:C15 | $Glu^1-Asp^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Ser^{16}$ | 142 |
| N66 | C4:C12, C7:C15 | $Glu^1-Asp^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Ser^{16}$ | 143 |
| N67 | C4:C12, C7:C15 | $Glu^1-Glu^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Ser^{16}$ | 144 |
| N68 | C4:C12, C7:C15 | $Glu^1-Glu^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 145 |
| N69 | C4:C12, C7:C15 | $Asp^1-Asp^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 146 |
| N70 | C4:C12, C7:C15 | $Asp^1-Asp^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 147 |
| N71 | C4:C12, C7:C15 | $Asp^1-Glu^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 148 |
| N72 | C4:C12, C7:C15 | $Asp^1-Glu^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 149 |
| N73 | C4:C12, C7:C15 | $Gln^1-Asp^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 150 |
| N74 | C4:C12, C7:C15 | $Gln^1-Asp^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 151 |
| N75 | C4:C12, C7:C15 | $Gln^1-Glu^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 152 |
| N76 | C4:C12, C7:C15 | $Gln^1-Glu^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 153 |
| N77 | C4:C12, C7:C15 | $Lys^1-Asp^2-Asp^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 154 |
| N78 | C4:C12, C7:C15 | $Lys^1-Asp^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 155 |
| N79 | C4:C12, C7:C15 | $Lys^1-Glu^2-Glu^3-Cys^4-Glu^5-Leu^6-Cys^7-Ile^8-Asn^9-Met^{10}-Ala^{11}-Cys^{12}-Thr^{13}-Gly^{14}-Cys^{15}-Leu^{16}$ | 156 |

TABLE IV-continued

SP-304 Analogs, Uroguanylin, and Uroguanylin Analogs

| Name | Position of Disulfide bonds | Structure | SEQ ID NO |
|---|---|---|---|
| N80 | C4:C12, C7:C15 | Lys$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 157 |
| N81 | C4:C12, C7:C15 | Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 158 |
| N82 | C4:C12, C7:C15 | Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 159 |
| N83 | C4:C12, C7:C15 | Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 160 |
| N84 | C4:C12, C7:C15 | Glu$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 161 |
| N85 | C4:C12, C7:C15 | Asp$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 162 |
| N86 | C4:C12, C7:C15 | Asp$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 163 |
| N87 | C4:C12, C7:C15 | Asp$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 164 |
| N88 | C4:C12, C7:C15 | Asp$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 165 |
| N89 | C4:C12, C7:C15 | Gln$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 166 |
| N90 | C4:C12, C7:C15 | Gln$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 167 |
| N91 | C4:C12, C7:C15 | Gln$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 168 |
| N92 | C4:C12, C7:C15 | Gln$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 169 |
| N93 | C4:C12, C7:C15 | Lys$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 170 |
| N94 | C4:C12, C7:C15 | Lys$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 171 |
| N95 | C4:C12, C7:C15 | Lys$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 172 |
| N96 | C4:C12, C7:C15 | Lys$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 173 |

TABLE V

Guanylin and Analogs

| Name | Position of Disulfide bonds | Structure | SEQ ID NO |
|---|---|---|---|
| Formula XIX | 4:12, 7:15 C7:C15 | $Xaa^1$-$Xaa^2$-$Xaa^3$-$Maa^4$-$Xaa^5$-$Xaa^6$-$Maa^7$-$Xaa^8$-$Xaa^9$-$Xaa^{10}$-$Xaa^{11}$-$Maa^{12}$-$Xaa^{13}$-$Xaa^{14}$-$Maa^{15}$ | 174 |
| Guanylin | C4:C12, C7:C15 | $Ser^1$-$His^2$-$Thr^3$-$Cys^4$-$Glu^5$-$Ile^6$-$Cys^7$-$Ala^8$-$Phe^9$-$Ala^{10}$-$Ala^{11}$-$Cys^{12}$-$Ala^{13}$-$Gly^{14}$-$Cys^{15}$ | 175 |
| N97 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 176 |
| N98 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 177 |
| N99 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 178 |
| N100 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 179 |
| N101 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 180 |
| N102 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 181 |
| N103 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 182 |
| N104 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 183 |
| N105 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 184 |
| N106 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 185 |
| N107 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 186 |
| N108 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 187 |
| N109 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 188 |
| N110 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 189 |
| N111 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 190 |
| N112 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 191 |
| N113 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 192 |
| N114 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 193 |
| N115 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 194 |
| N116 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 195 |
| N117 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 196 |
| N118 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 197 |
| N119 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 198 |

TABLE V-continued

Guanylin and Analogs

| Name | Position of Disulfide bonds | Structure | SEQ ID NO |
|---|---|---|---|
| N120 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 199 |
| N121 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 200 |
| N122 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 201 |
| N123 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 202 |
| N124 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 203 |
| N125 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 204 |
| N126 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 205 |
| N127 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 206 |
| N128 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 207 |

TABLE VI

Lymphoguanylin and Analogs

| Name | Position of Disulfide bonds | Structure | SEQ ID NO |
|---|---|---|---|
| Formula XX | 4:12, 7:15 | $Xaa^1$-$Xaa^2$-$Xaa^3$-$Maa^4$-$Xaa^5$-$Xaa^6$-$Maa^7$-$Xaa^8$-$Xaa^9$-$Xaa^{10}$-$Xaa^{11}$-$Maa^{12}$-$Xaa^{13}$-$Xaa^{14}$-$Xaa_{n1}^{15}$ | 208 |
| Lymphoguanylin | C4:C12 | $Gln^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 209 |
| N129 | C4:C12 | $Gln^1$-$Glu^2$-$Glu^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 210 |
| N130 | C4:C12 | $Gln^1$-$Asp^2$-$Glu^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 211 |
| N131 | C4:C12 | $Gln^1$-$Asp^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 212 |
| N132 | C4:C12 | $Gln^1$-$Glu^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 213 |
| N133 | C4:C12 | $Gln^1$-$Glu^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 214 |
| N134 | C4:C12 | $Gln^1$-$Asp^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 215 |
| N135 | C4:C12 | $Gln^1$-$Asp^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 216 |
| N136 | C4:C12 | $Gln^1$-$Glu^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 217 |
| N137 | C4:C12 | $Gln^1$-$Glu^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 218 |
| N138 | C4:C12 | $Gln^1$-$Asp^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 219 |

TABLE VI-continued

Lymphoguanylin and Analogs

| Name | Position of Disulfide bonds | Structure | SEQ ID NO |
|---|---|---|---|
| N139 | C4:C12 | Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 220 |
| N140 | C4:C12 | Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 221 |
| N141 | C4:C12 | Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 222 |
| N142 | C4:C12 | Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 223 |
| N143 | C4:C12 | Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 224 |
| N144 | C4:C12 | Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 225 |
| N145 | C4:C12, C7:C15 | Gln$^1$-Glu$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 226 |
| N146 | C4:C12, C7:C15 | Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 227 |
| N147 | C4:C12, C7:C15 | Gln$^1$-Asp$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 228 |
| N148 | C4:C12, C7:C15 | Gln$^1$-Glu$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 229 |
| N149 | C4:C12, C7:C15 | Gln$^1$-Glu$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 230 |
| N150 | C4:C12, C7:C15 | Gln$^1$-Asp$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser | 231 |
| N151 | C4:C12, C7:C15 | Gln$^1$-Asp$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 232 |
| N152 | C4:C12, C7:C15 | Gln$^1$-Glu$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 233 |
| N153 | C4:C12, C7:C15 | Gln$^1$-Glu$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 234 |
| N154 | C4:C12, C7:C15 | Gln$^1$-Asp$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 235 |
| N155 | C4:C12, C7:C15 | Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 236 |
| N156 | C4:C12, C7:C15 | Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 237 |
| N157 | C4:C12, C7:C15 | Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 238 |
| N158 | C4:C12, C7:C15 | Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 239 |
| N159 | C4:C12, C7:C15 | Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 240 |
| N160 | C4:C12, C7:C15 | Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 241 |

TABLE VII

ST Peptide and Analogues

| Name | Position of Disulfide bonds | Structure | SEQ ID NO |
|---|---|---|---|
| ST Peptide | C3:C8, C4:C12, C7:15 | $Asn^1$-$Ser^2$-$Ser^3$-$Asn^4$-$Ser^5$-$Ser^6$-$Asn^7$-$Tyr^8$-$Cys^9$-$Cys^{10}$-$Glu^{11}$-$Lys^{12}$-$Cys^{13}$-$Cys^{14}$-$Asn^{15}$-$Pro^{16}$-$Ala^{17}$-$Cys^{18}$-$Thr^{19}$-$Gly^{20}$-$Cys^{21}$-$Tyr^{22}$ | 242 |
| N161 | C3:C8, C4:C12, C7:15 | PEG3-$Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 243 |
| N162 | C3:C8, C4:C12, C7:15 | PEG3-$Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 244 |
| N163 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 245 |
| N164 | C3:C8, C4:C12, C7:15 | $Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 246 |
| N165 | C3:C8, C4:C12, C7:15 | $dAsn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 247 |
| N166 | C3:C8, C4:C12, C7:15 | $Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 248 |
| N167 | C3:C8, C4:C12, C7:15 | $dAsn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 249 |

1.3 Methods of Use

The invention provides methods for treating or preventing gastrointestinal disorders and increasing gastrointestinal motility in a subject in need thereof by administering an effective amount of a GCC agonist formulation to the subject. Non-limiting examples of gastrointestinal disorders that can be treated or prevented according to the methods of the invention include irritable bowel syndrome (IBS), non-ulcer dyspepsia, chronic intestinal pseudo-obstruction, functional dyspepsia, colonic pseudo-obstruction, duodenogastric reflux, gastroesophageal reflux disease (GERD), ileus (e.g., post-operative ileus), gastroparesis, heartburn (high acidity in the GI tract), constipation (e.g., constipation associated with use of medications such as opioids, osteoarthritis drugs, or osteoporosis drugs); post surgical constipation, constipation associated with neuropathic disorders, Crohn's disease, and ulcerative colitis.

In one embodiment, the invention provides methods for treating or preventing gastrointestinal motility disorder, irritable bowel syndrome, a functional gastrointestinal disorder, gastroesophageal reflux disease, duodenogastric reflux, functional heartburn, dyspepsia, functional dyspepsia, non-ulcer dyspepsia, gastroparesis, chronic intestinal pseudo-obstruction, colonic pseudo-obstruction, obesity, congestive heart failure, or benign prostatic hyperplasia.

In one embodiment, the invention provides methods for treating or preventing constipation and/or increasing gastrointestinal motility in a subject in need thereof by administering an effective amount of a GCC agonist formulation to the subject. Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining (Schiller 2001 Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple sclerosis, Parkinson's disease, spinal cord lesions, Neurofibromatosis, autonomic neuropathy, Chagas disease, Hirschsprung disease and cystic fibrosis. Constipation may also be the result of surgery or due to the use of drugs such as analgesics (like opioids), antihypertensives, anticonvulsants, antidepressants, antispasmodics and antipsychotics.

In various embodiments, the constipation is associated with use of a therapeutic agent; the constipation is associated with a neuropathic disorder; the constipation is postsurgical constipation; the constipation is associated with a gastrointestinal disorder; the constipation is idiopathic (functional constipation or slow transit constipation); the constipation is associated with neuropathic, metabolic or endocrine disorder (e.g., diabetes mellitus, hypothyroidism, hyperthyroidism, hypocalcaemia, Multiple Sclerosis, Parkinson's disease, spinal cord lesions, neurofibromatosis, autonomic neuropathy, Chagas disease, Hirschsprung disease or cystic fibrosis). Constipation may also be the result of surgery or due to the use of drugs such as analgesics (e.g., opioids), antihypertensives, anticonvulsants, antidepressants, antispasmodics and antipsychotics.

In one embodiment, the invention provides methods for treating or preventing chronic idiopathic constipation and increasing gastrointestinal motility in a subject in need thereof by administering an effective amount of a GCC agonist formulation to the subject.

The term "treating" as used herein refers to a reduction, a partial improvement, amelioration, or a mitigation of at least one clinical symptom associated with the gastrointestinal disorders being treated. The term "preventing" refers to an inhibition or delay in the onset or progression of at least one clinical symptom associated with the gastrointestinal disorders to be prevented. The term "effective amount" as used herein refers to an amount that provides some improvement or benefit to the subject. In certain embodiments, an effective amount is an amount that provides some alleviation, mitigation, and/or decrease in at least one clinical symptom of the gastrointestinal disorder to be treated. In other embodiments, the effective amount is the amount that provides some inhibition or delay in the onset or progression of at least one clinical symptom associated with the gastrointestinal disorder to be prevented. The therapeutic effects need not be complete or curative, as long as some benefit is provided to the subject. The term "subject" preferably refers to a human subject but may also refer to a non-human primate or other mammal preferably selected from among a mouse, a rat, a dog, a cat, a cow, a horse, or a pig.

The invention also provides methods for treating gastrointestinal cancer in a subject in need thereof by administering an effective amount of a GCC agonist formulation to the subject. Non-limiting examples of gastrointestinal cancers that can be treated according to the methods of the invention include gastric cancer, esophageal cancer, pancreatic cancer, colorectal cancer, intestinal cancer, anal cancer, liver cancer, gallbladder cancer, or colon cancer.

The invention also provides methods for treating lipid metabolism disorders, biliary disorders, inflammatory disorders, lung disorders, cancer, cardiac disorders including cardiovascular disorders, eye disorders, oral disorders, blood disorders, liver disorders, skin disorders, prostate disorders, endocrine disorders, and obesity.

Lipid metabolism disorders include, but are not limited to, dyslipidemia, hyperlipidemia, hypercholesterolemia, hypertriglyceridemia, sitosterolemia, familial hypercholesterolemia, xanthoma, combined hyperlipidemia, lecithin cholesterol acyltransferase deficiency, tangier disease, abetalipoproteinemia, erectile dysfunction, fatty liver disease, and hepatitis.

Billary disorders include gallbladder disorders such as for example, gallstones, gall bladder cancer cholangitis, or primary sclerosing cholangitis; or bile duct disorders such as for example, cholecystitis, bile duct cancer or fascioliasis.

Inflammatory disorders include tissue and organ inflammation such as kidney inflammation (e.g., nephritis), gastrointestinal system inflammation (e.g., Crohn's disease and ulcerative colitis); necrotizing enterocolitis (NEC); pancreatic inflammation (e.g., pancreatis), lung inflammation (e.g., bronchitis or asthma) or skin inflammation (e.g., psoriasis, eczema).

Lung Disorders include for example chronic obstructive pulmonary disease (COPD), and fibrosis.

Cancer includes tissue and organ carcinogenesis including metastases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer.

Cardiac disorders include for example, congestive heart failure, trachea cardia hypertension, high cholesterol, or high triglycerides. Cardiovascular disorders include for example aneurysm, angina, atherosclerosis, cerebrovascular accident (stroke), cerebrovasculardisease, congestive heart failure, coronary artery disease, myocardial infarction (heart attack), or peripheral vascular disease.

Liver disorders include for example cirrhosis and fibrosis. In addition, GC-C agonist may also be useful to facilitate liver regeneration in liver transplant patients. Eye disorders include for example increased intra-ocular pressure, glaucoma, dry eyes retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example benign prostatic hyperplasia (BPH). Endocrine disorders include for example diabetes mellitus, hyperthyroidism, hypothyroidism, and cystic fibrosis.

1.3.1 Therapeutically Effective Dosages

Disorders are treated, prevented or alleviated by administering to a subject, e.g., a mammal such as a human in need thereof, a therapeutically effective dose of a GCC agonist peptide. The present invention is based in part on the unexpected results of clinical trials in humans which demonstrated that the formulations of the invention are therapeutically effective at much lower doses than predicted based on animal studies. In accordance with one aspect of the invention, the therapeutically effective dose is between 0.01 milligrams (mg) and 10 mg per unit dose. The term "unit dose" refers to a single drug delivery entity, e.g., a tablet, capsule, solution or inhalation formulation. In one embodiment, the effective dose is between 0.01 mg and 9 mg. In another embodiment, the effective dose is between 0.01 mg and 5 mg. In another embodiment, the effective dose is between 0.01 mg and 3 mg. In another embodiment, the effective dose is between 0.10 mg and 5 mg. In another embodiment, the effective dose is between 0.10 mg and 3 mg. In one embodiment, the unit dose is 0.01 mg, 0.05 mg, 0.1 mg, 0.2 mg, 0.3 mg, 0.5 mg, 1.0 mg, 1.5 mg, 2.0 mg, 2.5 mg, 3.0 mg, 5 mg, or 10 mg. In one embodiment, the unit dose is 0.3 mg, 1.0 mg, 3.0 mg, 9.0 mg, or 9.5 mg.

The GCC agonist peptides may be in a pharmaceutical composition in unit dose form, together with one or more pharmaceutically acceptable excipients. The amount of peptide present should be sufficient to have a positive therapeutic effect when administered to a patient. What constitutes a "positive therapeutic effect" will depend upon the particular condition being treated and will include any significant improvement in a condition readily recognized by one of skill in the art.

The GCC agonists for use in the methods described above are preferably administered orally. Dosage forms include solutions, suspensions, emulsions, tablets, and capsules.

The total daily dose can be administered to the patient in a single dose, or in multiple sub-doses. Typically, sub-doses can be administered two to six times per day, preferably two to four times per day, and even more preferably two to three times per day. Preferably, a single daily dose is administered.

The GCC agonists may be administered as either the sole active agent or in combination with one or more additional active agents. In all cases, additional active agents should be administered at a dosage that is therapeutically effective using the existing art as a guide. The GCC agonists may be administered in a single composition or sequentially with the one or more additional active agents. In one embodiment, the GCC agonist is administered in combination with one or more inhibitors of cGMP dependent phosphodiesterase such as suldinac sulfone, zaprinast, motapizone, vardenafil, or sildenifil. In another embodiment, the GCC agonist is administered in combination with one or more chemotherapeutic agents. In another embodiment, the GCC agonist is administered in combination with one or more or anti-inflammatory drugs such as steroids or non-steroidal anti-inflammatory drugs (NSAIDS), such as aspirin.

Combination therapy can be achieved by administering two or more agents, e.g., a GCC agonist peptide described herein and another compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The GCC agonist peptides described herein may be combined with phosphodiesterase inhibitors, e.g., sulindae sulfone, Zaprinast, sildenafil, vardenafil or tadalafil to further enhance levels of cGMP in the target tissues or organs.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

1.3.2 Exemplary Agents for Combination Therapy

The GCC agonist formulations of the invention may be administered alone or in combination with one or more additional therapeutic agents as part of a therapeutic regimen for the treatment or prevention of a gastrointestinal disease or disorder. In some embodiments, the GCC agonist formulation comprises one or more additional therapeutic agents. In other embodiments, the GCC agonist is formulated separately from the one or more additional therapeutic agents. In accordance with this embodiment, the GCC agonist is administered either simultaneously, sequentially, or at a different time than the one or more additional therapeutic agents. In one embodiment, the GCC agonist formulation is administered in combination with one or more additional therapeutic agents selected from the group consisting of phosphodiesterase inhibitors, cyclic nucleotides (such as cGMP and cAMP), a laxative (such as SENNA or METAMUCIL), a stool softner, an anti-tumor necrosis factor alpha therapy for IBD (such as REMICADE, ENBREL, or HUMIRA), and anti-inflammatory drugs (such as COX-2 inhibitors, sulfasalazine, 5-ASA derivatives and NSAIDS). In certain embodiments, the GCC agonist formulation is administered in combination with an effective dose of an inhibitor of cGMP-specific phosphodiesterase (cGMP-PDE) either concurrently or sequentially with said GCC agonist. cGMP-PDE inhibitors include, for example, suldinac sulfone, zaprinast, motapizone, vardenifil, and sildenafil. In another embodiment, the GCC agonist formulation is administered in combination with inhibitors of cyclic nucleotide transporters. Further examples of therapeutic agents that may be administered in combination with the GCC agonist formulations of the invention are given in the following sections.

1.3.2.1 Agents to Treat Gastrointestinal Cancers

The GCC agonist formulations described herein can be used in combination with one or more antitumor agents including but not limited to alkylating agents, epipodophyllotoxins, nitrosoureas, anti-metabolites, *vinca* alkaloids, anthracycline antibiotics, nitrogen mustard agents, and the like. Particular antitumor agents include tamoxifen, taxol, etoposide, and 5-fluorouracil. In one embodiment, the GCC agonist formulations are used in combination with an antiviral agent or a monoclonal antibody.

Non-limiting examples of antitumor agents that can be used in combination with the GCC agonist formulations of the invention for the treatment of colon cancer include anti-proliferative agents, agents for DNA modification or repair, DNA synthesis inhibitors, DNA/RNA transcription regulators, RNA processing inhibitors, agents that affect protein expression, synthesis and stability, agents that affect protein localization or their ability to exert their physiological action, agents that interfere with protein-protein or protein-nucleic acid interactions, agents that act by RNA interference, receptor binding molecules of any chemical nature (including small molecules and antibodies), targeted toxins, enzyme activators, enzyme inhibitors, gene regulators, HSP-90 inhibitors, molecules interfering with microtubules or other cytoskeletal components or cell adhesion and motility, agents for phototherapy, and therapy adjuncts.

Representative anti-proliferative agents include N-acetyl-D-sphingosine (C.sub.2 ceramide), apigenin, berberine chloride, dichloromethylenediphosphonic acid disodium salt, loe-emodine, emodin, HA 14-1, N-hexanoyl-D-sphingosine (C.sub.6 ceramide), 7b-hydroxycholesterol, 25-hydroxycholesterol, hyperforin, parthenolide, and rapamycin.

Representative agents for DNA modification and repair include aphidicolin, bleomycin sulfate, carboplatin, carmustine, chlorambucil, cyclophosphamide monohydrate, cyclophosphamide monohydrate ISOPAC®, cis-diammineplatinum(II) dichloride (Cisplatin), esculetin, melphalan, methoxyamine hydrochloride, mitomycin C, mitoxantrone dihydrochloride, oxaliplatin, and streptozocin.

Representative DNA synthesis inhibitors include (.+−.) amethopterin (methotrexate), 3-amino-1,2,4-benzotriazine 1,4-dioxide, aminopterin, cytosine b-D-arabinofurdnoside (Ara-C), cytosine b-D-arabinofuranoside (Ara-C) hydrochloride, 2-fluoroadenine-9-b-D-arabinofuranoside (Fludarabine des-phosphate; F-ara-A), 5-fluoro-5'-deoxyuridine, 5-fluorouracil, ganciclovir, hydroxyurea, 6-mercaptopurine, and 6-thioguanine.

Representative DNA/RNA transcription regulators include actinomycin D, daunorubicin hydrochloride, 5,6-dichlorobenzimidazole 1-b-D-ribofuranoside, doxorubicin hydrochloride, homoharringtonine, and idarubicin hydrochloride.

Representative enzyme activators and inhibitors include forskolin, DL-aminoglutethimide, apicidin, Bowman-Birk Inhibitor, butein, (S)-(+)-camptothecin, curcumin, (−)-deguelin, (−)-depudecin, doxycycline hyclate, etoposide, formestane, fostriecin sodium salt, hispidin, 2-imino-1-imidazolidineacetic acid (Cyclocreatine), oxamflatin, 4-phenylbutyric acid, roscovitine, sodium valproate, trichostatin A, tyrphostin AG 34, tyrphostin AG 879, urinary trypsin inhibitor fragment, valproic acid (2-propylpentanoic acid), and XK469.

Representative gene regulators include 5-aza-2'-deoxycytidine, 5-azacytidine, cholecalciferol (Vitamin D3), cigliti-zone, cyproterone acetate, 15-deoxy-D.sup.12,14-prostaglandin J.sub.2, epitestosterone, flutamide, glycyrrhizic acid ammonium salt (glycyrrhizin), 4-hydroxytamoxifen, mifepristone, procainamide hydrochloride, raloxifene hydrochloride, all trans-retinal (vitamin A aldehyde), retinoic acid (vitamin A acid), 9-cis-retinoic acid, 13-cis-retinoic acid, retinoic acid p-hydroxyanilide, retinol (Vitamin A), tamoxifen, tamoxifen citrate salt, tetradecylthioacetic acid, and troglitazone.

Representative HSP-90 inhibitors include 17-(allylamino)-17-demethoxygeldanamycin and geldanamycin.

Representative microtubule inhibitors include colchicines, dolastatin 15, nocodazole, taxanes and in particular paclitaxel, podophyllotoxin, rhizoxin, vinblastine sulfate salt, vincristine sulfate salt, and vindesine sulfate salt and vinorelbine (Navelbine) ditartrate salt.

Representative agents for performing phototherapy include photoactive porphyrin rings, hypericin, 5-methoxypsoralen, 8-methoxypsoralen, psoralen and ursodeoxycholic acid.

Representative agents used as therapy adjuncts include amifostine, 4-amino-1,8-naphthalimide, brefeldin A, cimetidine, phosphomycin disodium salt, leuprolide (leuprorelin) acetate salt, luteinizing hormone-releasing hormone (LH-RH) acetate salt, lectin, papaverine hydrochloride, pifithrin-a, (−)-scopolamine hydrobromide, and thapsigargin.

The agents can also be anti-VEGF (vascular endothelial growth factor) agents, as such are known in the art. Several antibodies and small molecules are currently in clinical trials or have been approved that function by inhibiting VEGF, such as Avastin (Bevacizumab), SU5416, SU11248 and BAY 43-9006. The agents can also be directed against growth factor receptors such as those of the EGF/Erb-B family such as EGF Receptor (Iressa or Gefitinib, and Tarceva or Erlotinib), Erb-B2, receptor (Herceptin or Trastuzumab), other receptors (such as Rituximab or Rituxan/MabThera), tyrosine kinases, non-receptor tyrosine kinases, cellular serine/threonine kinases (including MAP kinases), and various other proteins whose deregulation contribute to oncogenesis (such as small/Ras family and large/heterotrimeric G proteins). Several antibodies and small molecules targeting those molecules are currently at various stages of development (including approved for treatment or in clinical trials).

In a preferred embodiment, the invention provides a method for treating colon cancer in a subject in need thereof by administering to the subject a GCC agonist formulation in combination with one or more antitumor agent selected from the group consisting of paclitaxel, docetaxel, tamoxifen, vinorelbine, gemcitabine, cisplatin, etoposide, topotecan, irinotecan, anastrozole, rituximab, trastuzumab, fludarabine, cyclophosphamide, gentuzumab, carboplatin, interferons, and doxorubicin. In a particular embodiment the antitumor agent is paclitaxel. In a further embodiment, the method further comprises an antitumor agent selected from the group consisting of 5-FU, doxorubicin, vinorelbine, cytoxan, and cisplatin.

1.3.2.2 Agents that Treat Crohn's Disease

In one embodiment, a GCC agonist formulation of the invention is administered as part of a combination therapy with one or more additional therapeutic agents for the treatment of Crohn's disease. Non-limiting examples of the one or more additional therapeutic agents include sulfasalazine and other mesalamine-containing drugs, generally known as 5-ASA agents, such as Asacol, Dipentum, or Pentasa, or infliximab (REMICADE). In certain embodiments, the one or more additional agents is a corticosteroid or an immunosuppressive agent such as 6-mercaptopurine or azathioprine. In another embodiment, the one or more additional agents is an antidiarrheal agent such as diphenoxylate, loperamide, or codeine.

1.3.2.3 Agents that Treat Ulcerative Colitis

In one embodiment, a GCC agonist formulation of the invention is administered as part of a combination therapy with one or more additional therapeutic agents for the treatment of ulcerative colitis. The agents that are used to treat ulcerative colitis overlap with those used to treat Chrohn's Disease. Non-limiting examples of the one or more additional therapeutic agents that can be used in combination with a GCC agonist formulation of the invention include aminosalicylates (drugs that contain 5-aminosalicyclic acid (5-ASA)) such as sulfasalazine, olsalazine, mesalamine, and balsalazide. Other therapeutic agents that can be used include corticosteroids, such as prednisone and hydrocortisone, immunomodulators, such as azathioprine, 6-mercapto-purine (6-MP), cytokines, interleukins, and lymphokines, and anti-TNF-alpha agents, including the thiazolidinediones or glitazones such as rosiglitazone and pioglitazone. In one embodiment, the one or more additional therapeutic agents includes both cyclosporine A and 6-MP or azathioprine for the treatment of active, severe ulcerative colitis.

1.3.2.4 Agents that Treat Constipation/Irritable Bowel Syndrome

In one embodiment, a GCC agonist formulation of the invention is administered as part of a combination therapy with one or more additional therapeutic agents for the treatment of constipation, such as that associated with irritable bowel syndrome. Non-limiting examples of the one or more additional therapeutic agents include laxatives such as SENNA, MIRALAX, LACTULOSE, PEG, or calcium polycarbophil), stool softeners (such as mineral oil or COLACE), bulking agents (such as METAMUCIL or bran), agents such as ZELNORM (also called tegaserod), and anticholinergic medications such as BENTYL and LEVSIN.

1.3.2.5 Agents for the Treatment of Postoperative Ileus

In one embodiment, a GCC agonist formulation of the invention is administered as part of a combination therapy with one or more additional therapeutic agents for the treatment of postoperative ileus. Non-limiting examples of the one or more additional therapeutic agents include ENTEREG (alvimopan; formerly called ado lor/ADL 8-2698), conivaptan, and related agents describes in U.S. Pat. No. 6,645,959.

1.3.2.6 Anti-Obesity Agents

In one embodiment, a GCC agonist formulation of the invention is administered as part of a combination therapy with one or more additional therapeutic agents for the treatment of obesity. Non-limiting examples of the one or more additional therapeutic agents include 1 1β HSD-I (11-beta hydroxy steroid dehydrogenase type 1) inhibitors, such as BVT 3498, BVT 2733, 3-(l-adamantyl)-4-ethyl-5-(ethylthio)-4H-1,2,4-triazole, 3-(l-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO01/90091, WOO 1/90090, WOO 1/90092 and WO02/072084; 5HT antagonists such as those in WO03/037871, WO03/037887, and the like; 5HTIa modulators such as carbidopa, benserazide and those disclosed in U.S. Pat. No. 6,207,699, WO03/031439, and the like; 5HT2c (serotonin receptor 2c) agonists, such as BVT933, DPCA37215, IK264, PNU 22394, WAY161503, R-1065, SB 243213 (Glaxo Smith Kline) and YM 348 and those disclosed in U.S. Pat. No. 3,914,250, WO00/77010, WO02/36596, WO02/48124, WO02/10169, WO01/66548, WO02/44152, WO02/51844, WO02/40456, and WO02/40457; 5HT6 receptor modulators, such as those in WO03/030901, WO03/035061, WO03/039547, and the like; acyl-estrogens, such as oleoyl-estrone, disclosed in del Mar-Grasa, M. et al, Obesity Research, 9:202-9 (2001) and Japanese Patent Application No. JP 2000256190; anorectic bicyclic compounds such as 1426 (Aventis) and 1954 (Aventis), and the compounds disclosed in WO00/18749, WO01/32638, WO01/62746, WO01/62747, and WO03/015769; CB 1 (cannabinoid-1 receptor) antagonist/inverse agonists such as rimonabant (Acomplia; Sanofi), SR-147778 (Sanofi), SR-141716 (Sanofi), BAY 65-2520 (Bayer), and SLV 319 (Solvay), and those disclosed in patent publications U.S. Pat. Nos. 4,973,587, 5,013,837, 5,081,122, 5,112,820, 5,292,736, 5,532,237, 5,624,941, 6,028,084, 6,509,367, 6,509,367, WO96/33159, WO97/29079, WO98/31227, WO98/33765, WO98/37061, WO98/41519, WO98/43635, WO98/43636, WO99/02499, WO00/10967, WO00/10968, WO01/09120, WO01/58869, WO01/64632, WO01/64633, WO01/64634, WO01/70700, WO01/96330, WO02/076949, WO03/006007, WO03/007887, WO03/020217, WO03/026647, WO03/026648, WO03/027069, WO03/027076, WO03/027114, WO03/037332, WO03/040107, WO03/086940, WO03/084943 and EP658546; CCK-A (cholecystokinin-A) agonists, such as AR-R 15849, GI 181771 (GSK), JMV-180, A-71378, A-71623 and SR146131 (Sanofi), and those described in U.S. Pat. No. 5,739,106; CNTF (Ciliary neurotrophic factors), such as GI-181771 (Glaxo-SmithKline), SR1 46131 (Sanofi Synthelabo), butabindide, PD 170,292, and PD 149164 (Pfizer); CNTF derivatives, such as Axokine® (Regeneron), and those disclosed in WO94/09134, WO98/22128, and WO99/43813; dipeptidyl peptidase IV (DP-IV) inhibitors, such as isoleucine thiazolidide, valine pyrrolidide, NVP-DPP728, LAF237, P93/01, P 3298, TSL 225 (tryptophyl-1,2,3,4-tetrahydroisoquinoline-3-carboxylic acid; disclosed by Yamada et al, Bioorg. & Med. Chem. Lett. 8 (1998) 1537-1540), TMC-2A/2B/2C, CD26 inhibitors, FE 999011, P9310/K364, VIP 0177, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) and the compounds disclosed patent publications. WO99/38501, WO99/46272, WO99/67279 (Probiodrug), WO99/67278 (Probiodrug), WO99/61431 (Probiodrug), WO02/083128, WO02/062764, WO03/000180, WO03/000181, WO03/000250, WO03/002530, WO03/002531, WO03/002553, WO03/002593, WO03/004498, WO03/004496, WO03/017936, WO03/024942, WO03/024965, WO03/033524, WO03/037327 and EP1258476; growth hormone secretagogue receptor agonists/antagonists, such as NN703, hexarelin, MK-0677 (Merck), SM-130686, CP-424391 (Pfizer), LY 444,711 (Eli Lilly), L-692,429 and L-163,255, and such as those disclosed in U.S. Ser. No. 09/662,448, U.S. provisional application 60/203,335, U.S. Pat. No. 6,358,951, US2002049196, US2002/022637, WO01/56592 and WO02/32888; H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO02/15905, WO03/024928 and WO03/024929; leptin derivatives, such as those disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519, and WO96/23520; leptin, including recombinant human leptin (PEG-OB, Hoffman La Roche) and recombinant methionyl human leptin (Amgen); lipase inhibitors, such as tetrahydrolipstatin (orlistat/Xenical®), Triton WR1 339, RHC80267, lipstatin, teasaponin, diethylumbelliferyl phosphate, FL-386, WAY-121898, Bay-N-3176, valilactone, esteracin, ebelactone A, ebelactone B, and RHC 80267, and those disclosed in patent publications WO01/77094, U.S. Pat. Nos. 4,598,089, 4,452,813, 5,512, 565, 5,391,571, 5,602,151, 4,405,644, 4,189,438, and 4,242, 453; lipid metabolism modulators such as maslinic acid, erythrodiol, ursolic acid uvaol, betulinic acid, betulin, and the like and compounds disclosed in WO03/011267; Mc4r (melanocortin 4 receptor) agonists, such as CHIR86036 (Chiron), ME-10142, ME-10145, and HS-131 (Melacure), and those disclosed in PCT publication Nos. WO99/64002, WO00/74679, WOO 1/991752, WOO 1/25192, WOO 1/52880, WOO 1/74844, WOO 1/70708, WO01/70337, WO01/91752, WO02/059095, WO02/059107, WO02/059108, WO02/059117, WO02/06276, WO02/12166, WO02/11715, WO02/12178, WO02/15909, WO02/38544, WO02/068387, WO02/068388, WO02/067869, WO02/081430, WO03/06604, WO03/007949, WO03/009847, WO03/009850, WO03/013509, and WO03/031410; Mc5r (melanocortin 5 receptor) modulators, such as those disclosed in WO97/19952, WO00/15826, WO00/15790, US20030092041; melanin-concentrating hormone 1 receptor (MCHR) antagonists, such as T-226296 (Takeda), SB 568849, SNP-7941 (Synaptic), and those disclosed in patent publications WOO 1/21169, WO01/82925, WO01/87834, WO02/051809, WO02/06245, WO02/076929, WO02/076947, WO02/04433, WO02/51809, WO02/083134, WO02/094799, WO03/004027, WO03/13574, WO03/15769, WO03/028641, WO03/035624, WO03/033476, WO03/033480, JP13226269, and JP1437059; mGluR5 modulators such as those disclosed in WO03/029210, WO03/047581, WO03/048137, WO03/051315, WO03/051833, WO03/053922, WO03/059904, and the like; serotoninergic agents, such as fenfluramine (such as Pondimin® (Benzeneethanamine, N-ethyl-alpha-methyl-3-(trifluoromethyl)-, hydrochloride), Robbins), dexfenfluramine (such as Redux® (Benzeneethanamine, N-ethyl-alpha-methyl-3-(trifluoromethyl)-, hydrochloride), Interneuron) and sibutramine ((Meridia®, Knoll/Reductil™) including racemic mixtures, as optically pure isomers (+) and (−), and pharmaceutically acceptable salts, solvents, hydrates, clathrates and prodrugs thereof including sibutramine hydrochloride monohydrate salts thereof, and those compounds disclosed in U.S. Pat. Nos. 4,746,680, 4,806,570, and 5,436, 272, US20020006964, WOO 1/27068, and WOO 1/62341; NE (norepinephrine) transport inhibitors, such as GW 320659, despiramine, talsupram, and nomifensine; NPY 1 antagonists, such as BIBP3226, J-115814, BIBO 3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; NPYS (neuropeptide Y Y5) antagonists, such as 152,804, GW-569180A, GW-594884A, GW-587081X, GW-548118X, FR235208, FR226928, FR240662, FR252384, 1229U91, GI-264879A, CGP71683A, LY-377897, LY-366377, PD-160170, SR-120562A, SR-120819A, JCF-104, and H409/22 and those compounds disclosed in patent publications U.S. Pat. Nos. 6,140,354, 6,191,160, 6,218,408, 6,258,837, 6,313, 298, 6,326,375, 6,329,395, 6,335,345, 6,337,332, 6,329,395, 6,340,683, EP01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO/0113917, WO01/09120, WO01/14376, WO01/85714, WO01/85730, WO01/07409, WO01/02379, WO01/23388, WO01/23389, WOO 1/44201, WO01/62737, WO01/62738, WO01/09120, WO02/20488, WO02/22592, WO02/48152, WO02/49648, WO02/051806, WO02/094789, WO03/009845, WO03/014083, WO03/022849, WO03/028726 and Norman et al, J. Med. Chem. 43:4288-4312 (2000); opioid antagonists, such as nalmefene (REVEX®), 3-methoxynaltrexone, methylnaltrexone, naloxone, and naltrexone (e.g. PT901; Pain Therapeutics, Inc.) and those disclosed in US20050004155 and WO00/21509; orexin antagonists, such as SB-334867-A and those disclosed in patent publications WO01/96302, WO01/68609, WO02/44172, WO02/51232, WO02/51838, WO02/089800, WO02/090355, WO03/023561, WO03/032991, and WO03/037847; PDE inhibitors (e.g. compounds which slow the degradation of cyclic AMP (cAMP) and/or cyclic GMP (cGMP) by inhibition of the phosphodiesterases, which can lead to a relative increase in the intracellular concentration of cAMP and cGMP; possible PDE inhibitors are primarily those substances which are to be numbered among the class consisting of the PDE3 inhibitors, the class consisting of the PDE4 inhibitors and/or the class consisting of the PDE5 inhibitors, in particular those substances which can be designated as mixed types of PDE3/4 inhibitors or as mixed types of PDE3/4/5 inhibitors such as those disclosed in patent publications DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EPO1 12987, EPO1 16948, EP0150937, EP0158380, EP0161632, EP0161918, EP0167121, EP0199127, EP0220044, EP0247725, EP0258191, EP0272910, EP0272914, EP0294647, EPO300726, EPO335386, EPO357788, EPO389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5,141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DE1 116676, DE2162096, EP0293063, EP0463756, EP0482208, EP0579496, EP0667345 U.S. Pat. No. 6,331,543, US20050004222 (including those disclosed in formulas I-XIII and paragraphs 37-39, 85-0545 and 557-577), WO9307124, EP0163965, EPO393500, EP0510562, EP0553174, WO9501338 and WO9603399, as well as PDE5 inhibitors (such as RX-RA-69, SCH-51866, KT-734, vesnarinone, zaprinast, SKF-96231, ER-21355, BF/GP-385, NM-702 and sildenafil (Viagra™)), PDE4 inhibitors (such as etazolate, ICI63197, RP73401, imazolidinone (RO-20-1724), MEM 1414 (R1533/R1500; Pharmacia Roche), denbufylline, rolipram, oxagrelate, nitraquazone, Y-590, DH-6471, SKF-94120, motapizone, lixazinone, indolidan, olprinone, atizoram, KS-506-G, dipamfylline, BMY-43351, atizoram, arofylline, filaminast, PDB-093, UCB-29646, CDP-840, SKF-107806, piclamilast, RS-17597, RS-25344-000, SB-207499, TIBENELAST, SB-210667, SB-211572, SB-211600, SB-212066, SB-212179, GW-3600, CDP-840, mopidamol, anagrelide, ibudilast, amrinone, pimobendan, cilostazol, quazinone and N-(3,5-dichloropyrid-4-yl)-3-cyclopropyl-methoxy4-difluoromethoxybenzamide; PDE3 inhibitors (such as ICI153, 100, bemorandane (RWJ 22867), MCI-154, UD-CG 212, sulmazole, ampizone, cilostamide, carbazeran, piroximone, imazodan, CI-930, siguazodan, adibendan, saterinone, SKF-95654, SDZ-MKS-492, 349-U-85, emoradan, EMD-53998, EMD-57033, NSP-306, NSP-307, revizinone, NM-702, WIN-62582 and WIN-63291, enoximone and milrinone, PDE3/4 inhibitors (such as benafentrine, trequinsin, ORG-30029, zardaverine, L-686398, SDZ-ISQ-844, ORG-20241, EMD-54622, and tolafentrine) and other PDE inhibitors (such as vinpocetin, papaverine, enprofylline, cilomilast, fenoximone, pentoxifylline, roflumilast, tadalafil (Cialis®), theophylline, and vardenafil (Levitra®); Neuropeptide Y2 (NPY2) agonists include but are not limited to: polypeptide YY and fragments and variants thereof (e.g. YY3-36 (PYY3-36)(N. Engl. J. Med. 349:941, 2003; IKPEAPGE DASPEELNRY YASL-RHYLNL VTRQRY (SEQ ID NO:XXX)) and PYY agonists such as those disclosed in WO02/47712, WO03/026591, WO03/057235, and WO03/027637; serotonin reuptake inhibitors, such as, paroxetine, fluoxetine (Prozac™), fluvoxamine, sertraline, citalopram, and imipramine, and those disclosed in U.S. Pat. Nos. 6,162,805, 6,365,633, WO03/00663, WOO 1/27060, and WOO 1/162341; thyroid hormone β agonists, such as KB-2611 (KaroBioBMS), and those disclosed in WO02/15845, WO97/21993, WO99/00353, GB98/284425, U.S. Provisional Application No. 60/183,223, and Japanese Patent Application No. JP 2000256190; UCP-I (uncoupling protein-1), 2, or 3 activators, such as phytanic acid, 4-[(E)-2-(5, 6,7,8-tetrahydro-5, 5,8,8-tetramethyl-2-napthalenyl)-1-propenyl]benzoic acid (TTNPB), retinoic acid, and those disclosed in WO99/00123; β3 (beta adrenergic receptor 3) agonists, such as AJ9677/TAK677 (Dainippon/Takeda), L750355 (Merck), CP331648 (Pfizer), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), SR 59119A, and those disclosed in U.S. Pat. Nos. 5,541,204, 5,770,615, 5,491,134, 5,776,983, US488064, U.S. Pat. Nos. 5,705,515, 5,451,677, WO94/18161, WO95/29159, WO97/46556, WO98/04526 and WO98/32753, WO01/74782, WO02/32897, WO03/014113, WO03/016276, WO03/016307, WO03/024948, WO03/024953 and WO03/037881; noradrenergic agents including, but not limited to, diethylpropion (such as Tenuate® (1-propanone, 2-(diethylamino)-1-phenyl-, hydrochloride), Merrell), dextroamphetamine (also known as dextroamphetamine sulfate, dexamphetamine, dexedrine, Dexampex, Ferndex, Oxydess II, Robese, Spancap #1), mazindol ((or 5-(p-chlorophenyl)-2,5-dihydro-3H-imidazo[2,1-a]isoindol-5-01) such as Sanorex®, Novartis or Mazanor®, Wyeth Ayerst), phenylpropanolamine (or Benzenemethanol, alpha-(1-aminoethyl)-, hydrochloride), phentermine ((or Phenol, 3-[[4,5-duhydro-1H-imidazol-2-yl) ethyl](4-methylpheny-1)amino], monohydrochloride) such as Adipex-P®, Lemmon, FASTIN®, Smith-Kline Beecham and Ionamin®, Medeva), phendimetrazine ((or (2S,3S)-3,4-Dimethyl-2phenylmorpholine L-(+)-tartrate (1:1)) such as Metra® (Forest), Plegine® (Wyeth-Ay erst), Prelu-2® (Boehringer Ingelheim), and Statobex® (Lemmon), phendamine tartrate (such as Thephorin® (2,3,4,9-Tetrahydro-2-methyl-9-phenyl-1H-indenol[2,1-c]pyridine L-(+)-tartrate (1:1)), Hoffmann-LaRoche), methamphetamine (such as Desoxyn®, Abbot ((S)-N, (alpha)-dimethylbenzeneethanamine hydrochloride)), and phendimetrazine tartrate (such as Bontril® Slow-Release Capsules, Amarin (-3,4-Dimethyl-2-phenylmorpholine Tartrate); fatty acid oxidation upregulator/inducers such as Famoxin® (Genset); monamine oxidase inhibitors including but not limited to befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO01/12176; and other anti-obesity agents such as 5HT-2 agonists, ACC (acetyl-CoA carboxylase) inhibitors such as those described in WO03/072197, alpha-lipoic acid (alpha-LA), AOD9604, appetite suppressants such as those in WO03/40107, ATL-962 (Alizyme PLC), benzocaine, benzphetamine hydrochloride (Didrex), bladderwrack (focus vesiculosus), BRS3 (bombesin receptor subtype 3) agonists, bupropion, caffeine, CCK agonists, chitosan, chromium, conjugated linoleic acid, corticotropin-releasing hormone agonists, dehydroepiandrosterone, DGAT1 (diacylglycerol acyltransferase 1) inhibitors, DGAT2 (diacylglycerol acyltransferase 2) inhibitors, dicarboxylate transporter inhibitors, ephedra, exendin-4 (an inhibitor of glp-1) FAS (fatty acid synthase) inhibitors (such as Cerulenin and C75), fat resorption inhibitors (such as those in WO03/053451, and the like), fatty acid transporter inhibitors, natural water soluble fibers (such as *psyllium, plantago*, guar, oat, pectin), galanin antagonists, galega (Goat's Rue, French Lilac), *garcinia cambogia*, germander (*teucrium chamaedrys*), ghrelin antibodies and ghrelin antagonists (such as those disclosed in WO01/87335, and WO02/08250), polypeptide hormones and variants thereof which affect the islet cell secretion, such as the hormones of the secretin/gastric inhibitory polypeptide (GIP)/vasoactive intestinal polypeptide (VIP)/pituitary adenylate cyclase activating polypeptide (PACAP)/glucagon-like polypeptide II (GLP-II)/glicentin/glucagon gene family and/or those of the adrenomedullin/amylin/calcitonin gene related polypeptide (CGRP) gene family including GLP-1 (glucagon-like polypeptide 1) agonists (e.g. (1) exendin-4, (2) those GLP-I molecules described in US20050130891 including GLP-1(7-34), GLP-1(7-35), GLP-1(7-36) or GLP-1(7-37) in its C-terminally carboxylated or amidated form or as modified GLP-I polypeptides and modifications thereof including those described in paragraphs 17-44 of US20050130891, and derivatives derived from GLP-1-(7-34)COOH and the corresponding acid amide are employed which have the following general formula: R—NH-HAEGTFTSDVSYLEGQAAKEFI-AWLVK—CONH$_2$ wherein R=H or an organic compound having from 1 to 10 carbon atoms. Preferably, R is the residue of a carboxylic acid. Particularly preferred are the following carboxylic acid residues: formyl, acetyl, propionyl, isopropionyl, methyl, ethyl, propyl, isopropyl, n-butyl, sec-butyl, tert-butyl.) and glp-1 (glucagon-like polypeptide-1), glucocorticoid antagonists, glucose transporter inhibitors, growth hormone secretagogues (such as those disclosed and specifically described in U.S. Pat. No. 5,536,716), interleukin-6 (IL-6) and modulators thereof (as in WO03/057237, and the like), L-carnitine, Mc3r (melanocortin 3 receptor) agonists, MCH2R (melanin concentrating hormone 2R) agonist/antagonists, melanin concentrating hormone antagonists, melanocortin agonists (such as Melanotan II or those described in WO 99/64002 and WO 00/74679), nomame herba, phosphate transporter inhibitors, phytopharm compound 57 (CP 644,673), pyruvate, SCD-I (stearoyl-CoA desaturase-1) inhibitors, T71 (Tularik, Inc., Boulder Colo.), Topiramate (Topimax®, indicated as an anti-convulsant which has been shown to increase weight loss), transcription factor modulators (such as those disclosed in WO03/026576), β-hydroxy steroid dehydrogenase-1 inhibitors (β-HSD-I), β-hydroxy-β-methylbutyrate, p57 (Pfizer), Zonisamide (Zonegran™ indicated as an antiepileptic which has been shown to lead to weight loss), and the agents disclosed in US20030119428 paragraphs 20-26.

1.3.2.7 Phosphodiesterase Inhibitors

In certain embodiments, the regimen of combination therapy includes the administration of one or more phosphodiesterase ("PDE") inhibitors. PDE inhibitors slow the degradation of cyclic AMP (cAMP) and/or cyclic GMP (cGMP) by inhibiting phosphodiesterases, which can lead to a relative increase in the intracellular concentration of cAMP and/or cGMP. Non-limiting examples of PDE inhibitors that can be used in combination with the GCC agonists of the invention include PDE3 inhibitors, PDE4 inhibitors and/or PDE5 inhibitors, in particular those substances which can be designated as mixed types of PDE3/4 inhibitors or as mixed types of PDE3/4/5 inhibitors. Non-limiting examples of such PDE inhibitors are described in the following patent applications and patents: DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EPO1 12987, EPO1 16948, EP0150937, EP0158380, EP0161632, EP0161918, EP0167121, EP0199127, EP0220044, EP0247725, EP0258191, EP0272910, EP0272914, EP0294647, EPO300726, EPO335386, EPO357788, EPO389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5,141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DE1 116676, DE2162096, EP0293063, EP0463756, EP0482208, EP0579496, EP0667345 U.S. Pat. No. 6,331,543, US20050004222 (including those disclosed in formulas I-XIII and paragraphs 37-39, 85-0545 and 557-577) and WO9307124, EP0163965, EPO393500, EP0510562, EP0553174, WO9501338 and WO9603399. PDE5 inhibitors which may be mentioned by way of example are RX-RA-69, SCH-51866, KT-734, vesnarinone, zaprinast, SKF-96231, ER-21355, BF/GP-385, NM-702 and sildenafil (Viagra®). PDE4 inhibitors which may be mentioned by way of example are RO-20-1724, MEM 1414 (R1533/R1500; Pharmacia Roche), DENBUFYLLINE, ROLIPRAM, OXAGRELATE, NITRAQUAZONE, Y-590, DH-6471, SKF-94120, MOTAPIZONE, LIXAZINONE, INDOLIDAN, OLPRINONE, ATIZORAM, KS-506-G, DIPAMFYLLINE, BMY-43351, ATIZORAM, AROFYLLINE, FILAMINAST, PDB-093, UCB-29646, CDP-840, SKF-107806, PICLAMILAST, RS-17597, RS-25344-000, SB-207499, TIBENELAST, SB-210667, SB-211572, SB-211600, SB-212066, SB-212179, GW-3600, CDP-840, MOPIDAMOL, ANAGRELIDE, IBUDILAST, AMRINONE, PIMOBENDAN, CILOSTAZOL, QUAZINONE and N-(3,5-dichloropyrid-4-yl)-3-cyclopropylmethoxy4-difluoromethoxybenzamide. PDE3 inhibitors which may be mentioned by way of example are SULMAZOLE, AMPIZONE, CILOSTAMIDE, CARBAZERAN, PIROXIMONE, IMAZODAN, CI-930, SIGUAZODAN, ADIBENDAN, SATERINONE, SKF-95654, SDZ-MKS-492, 349-U-85, EMORADAN, EMD-53998, EMD-57033, NSP-306, NSP-307, REVIZINONE, NM-702, WIN-62582 and WIN-63291, ENOXIMONE and MILRINONE. PDE3/4 inhibitors which may be mentioned by way of example are BENAFENTRINE, TREQUINSIN, ORG-30029, ZARDAVERINE, L-686398, SDZ-ISQ-844, ORG-20241, EMD-54622, and TOLAFENTRINE. Other PDE inhibitors include: cilomilast, pentoxifylline, roflumilast, tadalafil (Cialis®), theophylline, and vardenafil (Levitra®), zaprinast (PDE5 specific).

GCC AGONIST 1.3.2.8 Analgesic Agents

In certain embodiments, the regimen of combination therapy includes the administration of one or more analgesic agents, e.g., an analgesic compound or an analgesic polypeptide. In some embodiments, the GCC agonist formulation is administered simultaneously or sequentially with one or more analgesic agents. In other embodiments, the GCC agonist is covalently linked or attached to an analgesic agent to create a therapeutic conjugate. Non-limiting examples of analgesic agents that can be used include calcium channel blockers, 5HT receptor antagonists (for example 5HT3, 5HT4 and 5HT1 receptor antagonists), opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSRI), vanilloid and cannabanoid receptor agonists, and sialorphin. Further examples of analgesic agents in the various classes are known in the art.

In one embodiment, the analgesic agent is an analgesic polypeptide selected from the group consisting of sialorphin-related polypeptides, including those comprising the amino acid sequence QHNPR (SEQ ID NO: 239), including: VQHNPR (SEQ ID NO: 240); VRQHNPR (SEQ ID NO: 241); VRGQHNPR (SEQ ID NO: 242); VRGPQHNPR (SEQ ID NO: 243); VRGPRQHNPR (SEQ ID NO: 244); VRGPRRQHNPR (SEQ ID NO: 245); and RQHNPR (SEQ ID NO: 246). Sialorphin-related polypeptides bind to neprilysin and inhibit neprilysin-mediated breakdown of substance P and Met-enkephalin. Thus, compounds or polypeptides that are inhibitors of neprilysin are useful analgesic agents which can be administered with the GCC agonists described herein or covalently linked to a GCC agonist to form a therapeutic conjugate. Sialorphin and related polypeptides are described in U.S. Pat. No. 6,589,750; U.S. 20030078200 A1; and WO 02/051435 A2.

In another embodiment, a GCC agonist formulation of the invention is administered as part of a regimen of combination therapy with an opioid receptor antagonist or agonist. In one embodiment, the GCC agonist and the opioid receptor antagonist or agonist are linked via a covalent bond. Non-limiting examples of opioid receptor antagonists include naloxone, naltrexone, methyl nalozone, nalmefene, cypridime, beta funaltrexamine, naloxonazine, naltrindole, nor-binaltorphimine, enkephalin pentapeptide (HOE825; Tyr-D-Lys-Gly-Phe-L-homoserine), trimebutine, vasoactive intestinal polypeptide, gastrin, glucagons. Non-limiting examples of opioid receptor agonists include fedotozine, asimadoline, and ketocyclazocine, the compounds described in WO03/097051 and WO05/007626, morphine, diphenyloxylate, frakefamide (H-Tyr-D-Ala-Phe(F)-Phe-NH 2; WO 01/019849 A1), and loperamide.

Further non-limiting examples of analgesic agents that can be used in a regimen of combination therapy along with the GCC agonist formulations of the invention include the dipeptide Tyr-Arg (kyotorphin); the chromogranin-derived polypeptide (CgA 47-66; See, e.g., Ghia et al. 2004 Regulatory polypeptides 119:199); CCK receptor agonists such as caerulein; conotoxin polypeptides; peptide analogs of thymulin (FR Application 2830451); CCK (CCKa or CCKb) receptor antagonists, including loxiglumide and dexloxiglumide (the R-isomer of loxiglumide) (WO 88/05774); 5-HT4 agonists such as tegaserod (Zelnorm®), mosapride, metoclopramide, zacopride, cisapride, renzapride, benzimidazolone derivatives such as BIMU 1 and BIMU 8, and lirexapride; calcium channel blockers such as ziconotide and related compounds described in, for example, EP625162B1, U.S. Pat. Nos. 5,364,842, 5,587,454, 5,824,645, 5,859,186, 5,994,305, 6,087,091, 6,136,786, WO 93/13128 A1, EP 1336409 A1, EP 835126 A1, EP 835126 B1, U.S. Pat. Nos. 5,795,864, 5,891,849, 6,054,429, WO 97/01351 A1; NK-I, receptor antagonists such as aprepitant (Merck & Co Inc), vofopitant, ezlopitant (Pfizer, Inc.), R-673 (Hoffmann-La Roche Ltd), SR-48968 (Sanofi Synthelabo), CP-122,721 (Pfizer, Inc.), GW679769 (Glaxo Smith Kline), TAK-637 (Takeda/Abbot), SR-14033, and related compounds described in, for example, EP 873753 A1, US 20010006972 A1, US 20030109417 A1, WO 01/52844 A1 (for a review see Giardina et al. 2003. Drugs 6:758); NK-2 receptor antagonists such as nepadutant (Menarini Ricerche SpA), saredutant (Sanoft-Synthelabo), GW597599 (Glaxo Smith Kline), SR-144190 (Sanofi-Synthelabo) and UK-290795 (Pfizer Inc); NK3 receptor antagonists such as osanetant (SR-142801; Sanoft-Synthelabo), SSR-241586, talnetant and related compounds described in, for example, WO 02/094187 A2, EP 876347 A1, WO 97/21680 A1, U.S. Pat. No. 6,277,862, WO 98/1 1090, WO 95/28418, WO 97/19927, and Boden et al. (J Med Chem. 39:1664-75, 1996); norepinephrine-serotonin reuptake inhibitors (NSRI) such as milnacipran and related compounds described in WO 03/077897; and vanilloid receptor antagonists such as arvanil and related compounds described in WO 01/64212 A1.

In addition to sialorphin-related polypeptides, analgesic polypeptides include: AspPhe, endomorphin-1, endomorphin-2, nocistatin, dalargin, lupron, ziconotide, and substance P.

1.3.2.9 Insulin and Insulin Modulating Agents

The GCC agonist peptides described herein can be used in combination therapy with insulin and related compounds including primate, rodent, or rabbit insulin including biologically active variants thereof including allelic variants, more preferably human insulin available in recombinant form. Sources of human insulin include pharmaceutically acceptable and sterile formulations such as those available from Eli Lilly (Indianapolis, Ind. 46285) as Humulin™ (human insulin rDNA origin). See, the THE PHYSICIAN'S DESK REFERENCE, 55.sup.th Ed. (2001) Medical Economics, Thomson Healthcare (disclosing other suitable human insulins).

The GCC peptides described herein can also be used in combination therapy with agents that can boost insulin effects or levels of a subject upon administration, e.g.

glipizide and/or rosiglitazone. The polypeptides and agonists described herein can be used in combitherapy with SYMLIN® (pramlintide acetate) and Exenatide® (synthetic exendin-4; a 39 aa polypeptide).

1.3.2.10 Anti-Hypertensive Agents

The GCC agonist peptides described herein can be used in combination therapy with an anti-hypertensive agent including but not limited to: (1) diuretics, such as thiazides, including chlorthalidone, chlorthiazide, dichlorophenamide, hydroflumethiazide, indapamide, polythiazide, and hydrochlorothiazide; loop diuretics, such as bumetanide, ethacrynic acid, furosemide, and torsemide; potassium sparing agents, such as amiloride, and triamterene; carbonic anhydrase inhibitors, osmotics (such as glycerin) and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; ceranapril; cilazapril; delapril; enalapril; enalopril; fosinopril; imidapril; lisinopril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as aprosartan, candesartan, eprosartan, irbesartan, losartan, olmesartan, pratosartan, tasosartan, telmisartan, valsartan, and EXP-3137, FI6828K, and RNH6270, and the like; (9) α/β adrenergic blockers such as nipradilol, arotinolol and amosulalol, and the like; (10) alpha 1 blockers, such as terazosin, urapidil, prazosin, tamsulosin, bunazosin, trimazosin, doxazosin, naftopidil, indoramin, WHP 164, and XENOIO, and the like; (11) alpha 2 agonists such as lofexidine, tiamenidine, moxonidine, rilmenidine and guanobenz, and the like; (12) aldosterone inhibitors, and the like; and (13) angiopoietin-2-binding agents such as those disclosed in WO03/030833. Specific anti-hypertensive agents that can be used in combination with polypeptides and agonists described herein include, but are not limited to: diuretics, such as thiazides (e.g., chlorthalidone, cyclothiazide (CAS RN 2259-96-3), chlorthiazide (CAS RN 72956-09-3, which may be prepared as disclosed in U.S. Pat. No. 2,809,194), dichlorophenamide, hydroflumethiazide, indapamide, polythiazide, bendroflumethazide, methyclothazide, polythiazide, trichlormethazide, chlorthalidone, indapamide, metolazone, quinethazone, althiazide (CAS RN 5588-16-9, which may be prepared as disclosed in British Patent No. 902,658), benzthiazide (CAS RN 91-33-8, which may be prepared as disclosed in U.S. Pat. No. 3,108,097), buthiazide (which may be prepared as disclosed in British Patent Nos. 861,367), and hydrochlorothiazide), loop diuretics (e.g. bumetanide, ethacrynic acid, furosemide, and torasemide), potassium sparing agents (e.g. amiloride, and triamterene (CAS Number 396-01-O)), and aldosterone antagonists (e.g. spironolactone (CAS Number 52-01-7), epirenone, and the like); β-adrenergic blockers such as Amiodarone (Cordarone, Pacerone), bunolol hydrochloride (CAS RN 31969-05-8, Parke-Davis), acebutolol (±N-[3-Acetyl-4-[2-hydroxy-3-[(1 methylethyl)amino] propoxy]phenyl]-butanamide, or (±)-3'-Acetyl-4'-[2-hydroxy-3-(isopropylamino) propoxy]butyranilide), acebutolol hydrochloride (e.g. Sectral®, Wyeth-Ayerst), alprenolol hydrochloride (CAS RN 13707-88-5 see Netherlands Patent Application No. 6,605,692), atenolol (e.g. Tenormin®, AstraZeneca), carteolol hydrochloride (e.g. Cartrol® Filmtab®, Abbott), Celiprolol hydrochloride (CAS RN 57470-78-7, also see in U.S. Pat. No. 4,034,009), cetamolol hydrochloride (CAS RN 77590-95-5, see also U.S. Pat. No. 4,059,622), labetalol hydrochloride (e.g. Normodyne®, Schering), esmolol hydrochloride (e.g. Brevibloc®, Baxter), levobetaxolol hydrochloride (e.g. Betaxon™ Ophthalmic Suspension, Alcon), levobunolol hydrochloride (e.g. Betagan® Liquifilm® with C CAP® Compliance Cap, Allergan), nadolol (e.g. Nadolol, Mylan), practolol (CAS RN 6673-35-4, see also U.S. Pat. No. 3,408,387), propranolol hydrochloride (CAS RN 318-98-9), sotalol hydrochloride (e.g. Betapace AF™, Berlex), timolol (2-Propanol,1-[(1,1-dimethylethyl)amino]-3-[[4-4(4-morpholinyl)-1,2,5-thiadiazol-3-yl]oxy]-, hemihydrate, (S)-, CAS RN 91524-16-2), timolol maleate (S)—I-[(1,1-dimethylethyl)amino]-3-[[4-(4-morpholinyl)-1,2,5-thiadiazol-3-yl]oxy]-2-propanol (Z)-2-butenedioate (1:1) salt, CAS RN 26921-17-5), bisoprolol (2-Propanol, 1-[4-[[2-(1-methylethoxy)ethoxy]-methyl]phenoxyl]-3-[(1-meth-ylethyl) amino]-, (±), CAS RN 66722-44-9), bisoprolol fumarate (such as (±)-1-[4-[[2-(1-Methylethoxy) ethoxy]methyl]phenoxy]-3-[(1-methylethyl)amino]-2-propanol (E)-2-butenedioate (2:1) (salt), e.g., Zebeta™, Lederle Consumer), nebivalol (2H-1-Benzopyran-2-methanol, αα'-[iminobis (methylene)]bis[6-fluoro-3,4-dihydro-, CAS RN 99200-09-6 see also U.S. Pat. No. 4,654,362), ciclopolol hydrochloride, such 2-Propanol, 1-[4-[2-(cyclopropylmethoxy)ethoxy]phenoxy]-3-[1-methylethyl)amino]-, hydrochloride, A.A.S. RN 63686-79-3), dexpropranolol hydrochloride (2-Propanol, 1-[1-methylethy)-amino]-3-(1-naphthalenyloxy)-hydrochloride (CAS RN 13071-11-9), diacetolol hydrochloride (Acetamide, N-[3-acetyl-4-[2-hydroxy-3-[(1-methyl-ethyl)amino]propoxy][phenyl]-, monohydrochloride CAS RN 69796-04-9), dilevalol hydrochloride (Benzamide, 2-hydroxy-5-[1-hydroxy-2-(1-methyl-3-phenylpropyl) amino]ethyl]-, monohydrochloride, CAS RN 75659-08-4), exaprolol hydrochloride (2-Propanol, 1-(2-cyclohexylphenoxy)-3-[(1-methylethyl)amino]-, hydrochloride CAS RN 59333-90-3), flestolol sulfate (Benzoic acid, 2-fluro-,3-[[2-[aminocarbonyl)amino]- -dimethylethyl]amino]-2-hydroxypropyl ester, (+)-sulfate (1:1) (salt), CAS RN 88844-73-9; metalol hydrochloride (Methanesulfonamide, N-[4-[1-hydroxy-2-(methylamino)propyl]phenyl]-, monohydrochloride CAS RN 7701-65-7), metoprolol 2-Propanol, 1-[4-(2-methoxyethyl)phenoxy]-3-[1-methylethyl)amino]-; CAS RN 37350-58-6), metoprolol tartrate (such as 2-Propanol, 1-[4-(2-methoxyethyl)phenoxy]-3-[(1-methylethyl)amino]-, e.g., Lopressor®, Novartis), pamatolol sulfate (Carbamic acid, [2-[4-[2-hydroxy-3-[(1-methylethyl)amino]propoxyl] phenyl]-ethyl]-, methyl ester, (±) sulfate (salt) (2:1), CAS RN 59954-01-7), penbutolol sulfate (2-Propanol, 1-(2-cyclopentylphenoxy)-3-[1,1-dimethyle-thyl)amino]1, (S)-, sulfate (2:1) (salt), CAS RN 38363-32-5), practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl)amino]-3-[2-(methylthio)-phenoxy]-, hydrochloride, (±), CAS RN 39832-43-4), tolamolol (Benzamide, 4-[2-[[2-hydroxy-3-(2-methylphenoxy)-propyl]amino]ethoxyl]-, CAS RN 38103-61-6), bopindolol, indenolol, pindolol, propanolol, tertatolol, and tilisolol, and the like; calcium channel blockers such as besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, e.g., Norvasc®, Pfizer), clentiazem maleate (1,5-Benzothiazepin-4(5H)-one, 3-(acetyloxy)-8-chloro-5-[2-(dimethylamino)ethyl]-2,3-dihydro-2-(4-methoxyphenyl)-(2S-cis)-, (Z)-2-butenedioate (1:1), see also U.S. Pat. No. 4,567,195), isradipine (3,5-Pyridinedicarboxylic acid, 4-(4-benzofurazanyl)-1,4-dihydro-2,6-dimethyl-, methyl 1-methylethyl ester, (±)-4(4-benzofurazanyl)-1,4-dihydro-2,6-dimethyl-3,5-pyridinedicarboxylate, see also U.S. Pat. No. 4,466,972); nimodipine (such as is isopropyl (2-methoxyethyl) 1,4-dihydro-2,6-dimethyl-4-(3-nitrophenyl)-3,5-pyridine-dicarboxylate, e.g. Nimotop®, Bayer), felodipine (such as ethyl methyl 4-(2,3-dichlorophenyl)-1,4-dihydro-2,6-dimethyl-3,5-pyridinedicarboxylate-, e.g. Plendil® Extended-Release, AstraZeneca LP), nilvadipine (3,5-Pyridinedicarboxylic acid, 2-cyano-1,4-dihydro-6-methyl-4-(3-nitrophenyl)-,3-methyl 5-(1-methylethyl) ester, also see U.S. Pat. No. 3,799,934), nifedipine (such as 3, 5-pyridinedicarboxylic acid,1,4-dihydro-2,6-dimethyl-4-(2-nitrophenyl)-, dimethyl ester, e.g., Procardia XL® Extended Release Tablets, Pfizer), diltiazem hydrochloride (such as 1,5-Benzothiazepin-4(5H)-one,3-(acetyloxy)-5[2-(dimethylamino)ethyl]-2,-3-dihydro-2(4-methoxyphenyl)-, monohydrochloride, (+)-cis., e.g., Tiazac®, Forest), verapamil hydrochloride (such as benzeneacetonitrile, (alpha)-[[3-[[2-(3,4-dimethoxyphenyl)ethyl]methylamino]propyl]-3,4-dimethoxy-(alpha)-(1-methylethyl) hydrochloride, e.g., Isoptin® SR, Knoll Labs), teludipine hydrochloride (3,5-Pyridinedicarboxylic acid, 2-[(dimethylamino)methyl]4-[2-[(1E)-3-(1,1-dimethylethoxy)-3-oxo-1-propenyl]phenyl]-1, 4-dihydro-6-methyl-, diethyl ester, monohydrochloride) CAS RN 108700-03-4), belfosdil (Phosphonic acid, [2-(2-phenoxy ethyl)-1,3-propane-diyl]bis-, tetrabutyl ester CAS RN 103486-79-9), fostedil (Phosphonic acid, [[4-(2-benzothiazolyl)phenyl]methyl]-, diethyl ester CAS RN 75889-62-2), aranidipine, azelnidipine, barnidipine, benidipine, bepridil, cinaldipine, clevidipine, efonidipine, gallopamil, lacidipine, lemildipine, lercanidipine, monatepil maleate (1-Piperazinebutanamide, N-(6, 11-dihydrodibenzo(b,e)thiepin-11-yl)4-(4-fluorophenyl)-, (+)-, (Z)-2-butenedioate (1:1) (±)-N-(6,11-Dihydrodibenzo(b,e)thiep-in-11-yl)-4-(p-fluorophenyl)-1-piperazinebutyramide maleate (1:1) CAS RN 132046-06-1), nicardipine, nisoldipine, nitrendipine, manidipine, pranidipine, and the like; T-channel calcium antagonists such as mibefradil; angiotensin converting enzyme (ACE) inhibitors such as benazepril, benazepril hydrochloride (such as 3-[[1-(ethoxycarbonyl)-3-phenyl-(1S)-propyl]amino]-2,3,4,5-tetrahydro-2-oxo-1H-1-(3S)-benzazepine-1-acetic acid monohydrochloride, e.g., Lotrel®, Novartis), captopril (such as 1-[(2S)-3-mercapto-2-methylpropionyl]-L-proline, e.g., Captopril, Mylan, CAS RN 62571-86-2 and others disclosed in U.S. Pat. No. 4,046,889), ceranapril (and others disclosed in U.S. Pat. No. 4,452,790), cetapril (alaceptil, Dainippon disclosed in Eur. Therap. Res. 39:671 (1986); 40:543 (1986)), cilazapril (Hoffman-LaRoche) disclosed in J. Cardiovasc. Pharmacol. 9:39 (1987), indalapril (delapril hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); disclosed in U.S. Pat. No. 4,385,051), enalapril (and others disclosed in U.S. Pat. No. 4,374,829), enalapril, enaloprilat, fosinopril, ((such as L-proline, 4-cyclohexyl-1-[[[2-methyl-1-(1-oxopropoxy) propoxy](4-phenylbutyl) phosphinyl]acetyl]-, sodium salt, e.g., Monopril, Bristol-Myers Squibb and others disclosed in U.S. Pat. No. 4,168, 267), fosinopril sodium (L-Proline, 4-cyclohexyl-1-[[(R)-[(1S)-2-methyl-1-(1-ox-opropoxy)propox), imidapril, indolapril (Schering, disclosed in J. Cardiovasc. Pharmacol. 5:643, 655 (1983)), lisinopril (Merck), losinopril, moexipril, moexipril hydrochloride (3-Isoquinolinecarboxylic acid, 2-[(2S)-2-[[(1S)-1-(ethoxycarbonyl)-3-phenylpropyl] amino]-1-oxopropyl]-1,-2,3,4-tetrahydro-6,7-dimethoxy-, monohydrochloride, (3S)-CAS RN 82586-52-5), quinapril, quinaprilat, ramipril (Hoechsst) disclosed in EP 79022 and Curr. Ther. Res. 40:74 (1986), perindopril erbumine (such as 2S,3aS,7aS-1-[(S)—N-[(S)-1-Carboxybutyl]alanyl]hexahydro^-indolinecarboxylic acid, 1-ethyl ester, compound with tert-butylamine (1:1), e.g., Aceon®, Solvay), perindopril (Servier, disclosed in Eur. J. din. Pharmacol. 31:519 (1987)), quanipril (disclosed in U.S. Pat. No. 4,344,949), spirapril (Schering, disclosed in Acta. Pharmacol. Toxicol. 59 (Supp. 5): 173 (1986)), tenocapril, trandolapril, zofenopril (and others disclosed in U.S. Pat. No. 4,316,906), rentiapril (fentiapril, disclosed in Clin. Exp. Pharmacol. Physiol. 10:131 (1983)), pivopril, YS980, teprotide (Bradykinin potentiator BPP9a CAS RN 35115-60-7), BRL 36,378 (Smith Kline Beecham, see EP80822 and EP60668), MC-838 (Chugai, see CA. 102:72588v and Jap. J. Pharmacol. 40:373 (1986), CGS 14824 (Ciba-Geigy, 3-([1-ethoxycarbonyl-3-phenyl-(1S)-propyl]amino)-2,3,4,5-tetrahydro-2-ox-o-l-(3S)-benzazepine-1 acetic acid HCl, see U.K. Patent No. 2103614), CGS 16,617 (Ciba-Geigy, 3(S)-[[(1S)-5-amino-1-carboxypentyl]amino]-2,3,4,-5-tetrahydro-2-oxo-1H-1-benzazepine-1-ethanoic acid, see U.S. Pat. No. 4,473,575), Ru 44570 (Hoechst, see Arzneimittelforschung 34:1254 (1985)), R 31-2201 (Hoffman-LaRoche see FEBS Lett. 165:201 (1984)), CI925 (Pharmacologist 26:243, 266 (1984)), WY-44221 (Wyeth, see J. Med. Chem. 26:394 (1983)), and those disclosed in US2003006922 (paragraph 28), U.S. Pat. No. 4,337,201, U.S. Pat. No. 4,432,971 (phosphonamidates); neutral endopeptidase inhibitors such as omapatrilat (Vanlev®), CGS 30440, cadoxatril and ecadotril, fasidotril (also known as aladotril or alatriopril), sampatrilat, mixanpril, and gemopatrilat, AVE7688, ER4030, and those disclosed in U.S. Pat. Nos. 5,362,727, 5,366,973, 5,225,401, 4,722,810, 5,223,516, 4,749,688, 5,552,397, 5,504,080, 5,612,359, 5,525,723, EP0599444, EP0481522, EP0599444, EP0595610, EP0534363, EP534396, EP534492, EP0629627; endothelin antagonists such as tezosentan, A308165, and YM62899, and the like; vasodilators such as hydralazine (apresoline), clonidine (clonidine hydrochloride (1H-Imidazol-2-amine, N-(2,6-dichlorophenyl)4,5-dihydro-, monohydrochloride CAS RN 4205-91-8), catapres, minoxidil (loniten), nicotinyl alcohol (roniacol), diltiazem hydrochloride (such as 1,5-Benzothiazepin-4(5H)-one,3-(acetyloxy)-5[2-(dimethylamino) ethyl]-2,-3-dihydro-2(4-methoxyphenyl) -, monohydrochloride, (+)-cis, e.g., Tiazac®, Forest), isosorbide dinitrate (such as 1,4:3,6-dianhydro-D-glucitol 2,5-dinitrate e.g., Isordil® Titradose®, Wyeth-Ayerst), sosorbide mononitrate (such as 1,4:3,6-dianhydro-D-glucito-1,5-nitrate, an organic nitrate, e.g., Ismo®, Wyeth-Ayerst), nitroglycerin (such as 2,3 propanetriol trinitrate, e.g., Nitrostat® Parke-Davis), verapamil hydrochloride (such as benzeneacetonitrile, (±)-(alpha)[3-[[2-(3,4 dimethoxyphenyl)ethyl]methylamino] propyl]-3,4-dimethoxy-(alpha)-(1-methylethyl) hydrochloride, e.g., Covera HS® Extended-Release, Searle), chromonar (which may be prepared as disclosed in U.S. Pat.

No. 3,282,938), clonitate (Annalen 1870 155), droprenilamine (which may be prepared as disclosed in DE2521113), lidoflazine (which may be prepared as disclosed in U.S. Pat. No. 3,267,104); prenylamine (which may be prepared as disclosed in U.S. Pat. No. 3,152,173), propatyl nitrate (which may be prepared as disclosed in French Patent No. 1,103,113), mioflazine hydrochloride (1-Piperazineacetamide, 3-(aminocarbonyl)4-[4,4-bis(4-fluorophenyl)butyl]-N-(2,6-dichlorophenyl)-, dihydrochloride CAS RN 83898-67-3), mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3, 4-dimethoxyphenethyl)imino]pyrrolidine CAS RN 27737-38-8), molsidomine (1,2,3-Oxadiazolium, 5-Rethoxycarbonyl)amino]-3-(4-morpholinyl)-, inner salt CAS RN 25717-80-0), isosorbide mononitrate (D-Glucitol, 1,4:3,6-dianhydro-, 5-nitrate CAS RN 16051-77-7), erythrityl tetranitrate (1,2,3,4-Butanetetrol, tetranitrate, (2R,3S)-rel-CAS RN 7297-25-8), clonitrate (1,2-Propanediol, 3-chloro-, dinitrate (7CI, 8CI, 9CI) CAS RN 2612-33-1), dipyridamole Ethanol, 2,2',2'',2'''-[(4,8-di-1-piperidinylpyrimido[5,4-d]pyrimidine-2,6-diyl)dinitrilo]tetrakis-CAS RN 58-32-2), nicorandil (CAS RN 65141-46-0 3-), pyridinecarboxamide (N-[2-(nitrooxy)ethyl]-Nisoldipine3,5-Pyridinedicarboxylic acid, 1,4-dihydro-2,6-dimethyl-4-(2-nitrophenyl)-, methyl 2-methylpropyl ester CAS RN 63675-72-9), nifedipine3,5-Pyridinedicarboxylic acid, 1,4-dihydro-2,6-dimethyl-4-(2-nitrophenyl)-, dimethyl ester CAS RN 21829-25-4), perhexiline maleate (Piperidine, 2-(2,2-dicyclohexylethyl)-, (2Z)-2-butenedioate (1:1) CAS RN 6724-53-4), oxprenolol hydrochloride (2-Propanol, 1-[(1-methylethyl)amino]-3-[2-(2-propenyloxy)phenoxy]-, hydrochloride CAS RN 6452-73-9), pentrinitrol (1,3-Propanediol, 2,2-bis[(nitrooxy)methyl]-, mononitrate (ester) CAS RN 1607-17-6), verapamil (Benzeneacetonitrile, α-[3-[[2-(3,4-dimethoxyphenyl)ethyl]-methylamino]propyl]-3,4-dimethoxy-α-(1-methylethyl)-CAS RN 52-53-9) and the like; angiotensin II receptor antagonists such as, aprosartan, zolasartan, olmesartan, pratosartan, FI6828K, RNH6270, candesartan (1H-Benzimidazole-7-carboxylic acid, 2-ethoxy-1-[[2'-(1H-tetrazol-5-yl)[1,1'-biphenyl]4-yl]methyl]-CAS RN 139481-59-7), candesartan cilexetil ((+/−)-1-(cyclohexylcarbonyloxy)ethyl-2-ethoxy-1-[[2'-(1H-tetrazol-5-yl)biphenyl-4-yl]-1H-benzimidazole carboxylate, CAS RN 145040-37-5, U.S. Pat. Nos. 5,703,110 and 5,196,444), eprosartan (3-(1-4-carboxyphenylmethyl)-2-n-butyl-imidazol-5-yl]-(2-thienylmethyl) propenoic acid, U.S. Pat. No. 5,185,351 and U.S. Pat. No. 5,650,650), irbesartan (2-n-butyl-3-[[2'-(1h-tetrazol-5-yl)biphenyl-4-yl]methyl]1,3-diazazspiro[4,4]non-1-en-4-one, U.S. Pat. Nos. 5,270,317 and 5,352,788), losartan (2-N-butyl-4-chloro-5-hydroxymethyl-1-[(2'-(1H-tetrazol-5-yl)biphenyl-4-yl)-methyl]imidazole, potassium salt, U.S. Pat. Nos. 5,138,069, 5,153,197 and 5,128,355), tasosartan (5,8-dihydro-2,4-dimethyl-8-[(2'-(1H-tetrazol-5-yl)[1,r-biphenyl]4-yl)methyl]-pyrido[2,3-d]pyrimidin-7(6H)-one, U.S. Pat. No. 5,149,699), telmisartan (4'-[(1,4-dimethyl-2'-propyl-(2, 6'-bi-1H-benzimidazol)-r-yl)]-[1,1'-biphenyl]-2-carboxylic acid, CAS RN 144701-48-4, U.S. Pat. No. 5,591,762), milfasartan, abitesartan, valsartan (Diovan® (Novartis), (S)—N-valeryl-N-[[2'-(1H-tetrazol-5-yl)biphenyl-4-yl) methyl]valine, U.S. Pat. No. 5,399,578), EXP-3137 (2-N-butyl-4-chloro-1-[(2'-(1H-tetrazol-5-yl)biphenyl-4-yl)-methyl]imidazole-5-carboxylic acid, U.S. Pat. Nos. 5,138, 069, 5,153,197 and 5,128,355), 3-(2'-(tetrazol-5-yl)-1,r-biphen-4-yl)methyl-5,7-dimethyl-2-ethyl-3H-imidazo[4,5-b]pyridine, 4'[2-ethyl-4-methyl-6-(5,6,7,8-tetrahydroimidazo[1,2-a]pyridin-2-yl]-benzimidazol-1-yl]-methyl]-l,r-biphenyl]-2-carboxylic acid, 2-butyl-6-(1-methoxy-1-methylethyl)-2-[2'-)1H-tetrazol-5-yl)biphenyl-4-yl)methyl]guinazolin-4(3H)-one, 3-[2'-carboxybiphenyl-4-yl)methyl]-2-cyclopropyl-7-methyl-3H-imidazo[4,5-b] pyridine, 2-butyl-4-chloro-1-[(2'-tetrazol-5-yl)biphenyl-4-yl)methyl]imidazole-carboxylic acid, 2-butyl-4-chloro-1-[[2'-(1H-tetrazol-5-yl) [1,1'-biphenyl]-4-yl]methyl]-1H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]-sulfonyl](1,1'-biphenyl)-4-yl]methyl]-1H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl]methyl]-3-thiophencarboxylate, 5-[(3,5-dibutyl-1H-1,2,4-triazol-1-yl) methyl]-2-[2-(1H-tetrazol-5-ylphenyl))pyridine, 6-butyl-2-(2-phenylethyl)-5[[2'-(I H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1,2, 4]-triazolo[1,5-c]pyrimidin-2(3H)-one, 2,7-diethyl-5-[[2'-(5-tetrazoly)biphenyl-4-yl]methyl]-5H-pyrazolo[1,5-b][1,2, 4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]benzoic acid, ethyl ester, potassium salt, 3-methoxy-2,6-dimethyl-4-[[2'(1H-tetrazol-5-yl)-1,1'-biphenyl-4-yl]methoxy]pyridine, 2-ethoxy-1-[[2'-(5-oxo-2, 5-dihydro-1,2,4-oxadiazol-3-yl)biphenyl-4-yl]methyl]-1H-benzimidazole-7-carboxylic acid, 1-[N-(2'-(1H-tetrazol-5-yl)biphenyl-4-yl-methyl)-N-valerolylaminomethyl) cyclopentane-1-carboxylic acid, 7-methyl-2n-propyl-3-[[2' 1H-tetrazol-5-yl)biphenyl-4-yl]methyl]-3H-imidazo[4,5-6] pyridine, 2-[5-[(2-ethyl-5,7-dimethyl-3H-imidazo[4,5-b] pyridine-3-yl)methyl]-2-quinolinyl]sodium benzoate, 2-butyl-6-chloro-4-hydroxymethyl-5-methyl-3-[[2'-(1H-tetrazol-5-yl)biphenyl-4-yl]methyl]pyridine, 2-[[[2-butyl-1-[(4-carboxyphenyl)methyl]-1H-imidazol-5-yl]methyl] amino]benzoic acid tetrazol-5-yl)biphenyl-4-yl]methyl] pyrimidin-6-one, 4(S)-[4-(carboxymethyl)phenoxy]-N-[2 (R)-[4-(2-sulfobenzamido)imidazol-1-yl]octanoyl]-L-proline, 1-(2,6-dimethylphenyl)-4-butyl-1,3-dihydro-3-[[6-[2-(1H-tetrazol-5-yl)phenyl]-3-pyridinyl]methyl]-2H-imidazol-2-one, 5,8-ethano-5,8-dimethyl-2-n-propyl-5,6,7, 8-tetrahydro-1-[[2'(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7, 8-tetrahydro-2-trifylquinazoline, 2-(2-chlorobenzoyl)imino-5-ethyl-3-[2'-(1H-tetrazole-5-yl)biphenyl-4-yl)methyl-1,3, 4-thiadiazoline, 2-[5-ethyl-3-[2-(1H-tetrazole-5-yl) biphenyl-4-yl]methyl-1,3,4-thiazoline-2-ylidene] aminocarbonyl-1-cyclopentencarboxylic acid dipotassium salt, and 2-butyl-4-[N-methyl-N-(3-methylcrotonoyl) amino]-1-[[2'-(1H-tetrazol-5-yl)biphenyl-4-yl]methyl]-1H-imidzole-5-carboxylic acid 1-ethoxycarbonyloxyethyl ester, those disclosed in patent publications EP475206, EP497150, EP539086, EP539713, EP535463, EP535465, EP542059, EP497121, EP535420, EP407342, EP415886, EP424317, EP435827, EP433983, EP475898, EP490820, EP528762, EP324377, EP323841, EP420237, EP500297, EP426021, EP480204, EP429257, EP430709, EP434249, EP446062, EP505954, EP524217, EP514197, EP514198, EP514193, EP514192, EP450566, EP468372, EP485929, EP503162, EP533058, EP467207 EP399731, EP399732, EP412848, EP453210, EP456442, EP470794, EP470795, EP495626, EP495627, EP499414, EP499416, EP499415, EP511791, EP516392, EP520723, EP520724, EP539066, EP438869, EP505893, EP530702, EP400835, EP400974, EP401030, EP407102, EP411766, EP409332, EP412594, EP419048, EP480659, EP481614, EP490587, EP467715, EP479479, EP502725, EP503838, EP505098, EP505111 EP513,979 EP507594, EP510812, EP511767, EP512675, EP512676, EP512870, EP517357, EP537937, EP534706, EP527534, EP540356, EP461040, EP540039, EP465368, EP498723, EP498722, EP498721, EP515265, EP503785, EP501892, EP519831, EP532410, EP498361, EP432737, EP504888, EP508393, EP508445, EP403159, EP403158, EP425211, EP427463, EP437103, EP481448, EP488532, EP501269, EP500409, EP540400, EP005528, EP028834, EP028833, EP411507, EP425921, EP430300, EP434038, EP442473, EP443568, EP445811, EP459136, EP483683, EP518033, EP520423, EP531876, EP531874, EP392317, EP468470, EP470543, EP502314, EP529253, EP543263, EP540209, EP449699, EP465323, EP521768, EP415594, WO92/14468, WO93/08171, WO93/08169, WO91/00277, WO91/00281, WO91/14367, WO92/00067, WO92/00977, WO92/20342, WO93/04045, WO93/04046, WO91/15206, WO92/14714, WO92/09600, WO92/16552, WO93/05025, WO93/03018, WO91/07404, WO92/02508, WO92/13853, WO91/19697, WO91/11909, WO91/12001, WO91/11999, WO91/15209, WO91/15479, WO92/20687, WO92/20662, WO92/20661, WO93/01177, WO91/14679, WO91/13063, WO92/13564, WO91/17148, WO91/18888, WO91/19715, WO92/02257, WO92/04335, WO92/05161, WO92/07852, WO92/15577, WO93/03033, WO91/16313, WO92/00068, WO92/02510, WO92/09278, WO92/10179, WO92/10180, WO92/10186, WO92/10181, WO92/10097, WO92/10183, WO92/10182, WO92/10187, WO92/10184, WO92/10188, WO92/10180, WO92/10185, WO92/20651, WO93/03722, WO93/06828, WO93/03040, WO92/19211, WO92/22533, WO92/06081, WO92/05784, WO93/00341, WO92/04343, WO92/04059, U.S. Pat. Nos. 5,104,877, 5,187,168, 5,149,699, 5,185,340, 4,880,804, 5,138,069, 4,916,129, 5,153,197, 5,173,494, 5,137,906, 5,155,126, 5,140,037, 5,137,902, 5,157,026, 5,053,329, 5,132,216, 5,057,522, 5,066,586, 5,089,626, 5,049,565, 5,087,702, 5,124,335, 5,102,880, 5,128,327, 5,151,435, 5,202,322, 5,187,159, 5,198,438, 5,182,288, 5,036,048, 5,140,036, 5,087,634, 5,196,537, 5,153,347, 5,191,086, 5,190,942, 5,177,097, 5,212,177, 5,208,234, 5,208,235, 5,212,195, 5,130,439, 5,045,540, 5,041,152, and 5,210,204, and pharmaceutically acceptable salts and esters thereof; α/β adrenergic blockers such as nipradilol, arotinolol, amosulalol, bretylium tosylate (CAS RN: 61-75-6), dihydroergtamine mesylate (such as ergotaman-3',6',18-trione,9,-10-dihydro-12'-hydroxy-2'-methyl-5'-(phenylmethyl)-, (5'(α))-, monomethanesulfonate, e.g., DHE 45® Injection, Novartis), carvedilol (such as (±)-1-(Carbazol-4-yloxy)-3-[[2-(o-methoxyphenoxy)ethyl] amino]-2-propanol, e.g., Coreg®, SmithKline Beecham), labetalol (such as 5-[1-hydroxy-2-[(1-methyl-3-phenylpropyl)amino]ethyl]salicylamide monohydrochloride, e.g., Normodyne®, Schering), bretylium tosylate (Benzenemethanaminium, 2-bromo-N-ethyl-N,N-dimethyl-, salt with 4-methylbenzenesulfonic acid (1:1) CAS RN 61-75-6), phentolamine mesylate (Phenol, 3-[[(4,5-dihydro-1H-imidazol-2-yl)methyl](4-methylphenyl)amino]-, monomethanesulfonate (salt) CAS RN 65-28-1), solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5), zolertine hydrochloride (Piperazine, 1-phenyl4-[2-(1H-tetrazol-5-yl)ethyl]-, monohydrochloride (8Cl, 9Cl) CAS RN 7241-94-3) and the like; α adrenergic receptor blockers, such as alfuzosin (CAS RN: 81403-68-1), terazosin, urapidil, prazosin (Minipress®), tamsulosin, bunazosin, trimazosin, doxazosin, naftopidil, indoramin, WHP 164, XENOIO, fenspiride hydrochloride (which may be prepared as disclosed in U.S. Pat. No. 3,399,192), proroxan (CAS RN 33743-96-3), and labetalol hydrochloride and combinations thereof; α 2 agonists such as methyldopa, methyldopa HCL, lofexidine, tiamenidine, moxonidine, rilmenidine, guanobenz, and the like; aldosterone inhibitors, and the like; renin inhibitors including Aliskiren (SPP100; Novartis/Speedel); angiopoietin-2-binding agents such as those disclosed in WO03/030833; anti-angina agents such as ranolazine (hydrochloride 1-Piperazineacetamide, N-(2,6-dimethylphenyl)-4-[2-hydroxy-3-(2-methoxyphenoxy)propyl]-, dihydrochloride CAS RN 95635-56-6), betaxolol hydrochloride (2-Propanol, 1-[4-[2 (cyclopropylmethoxy)ethyl]phenoxy]-3-[(1-methylethyl) amino]-, hydrochloride CAS RN 63659-19-8), butoprozine hydrochloride (Methanone, [4-[3(dibutylamino)propoxy] phenyl](2-ethyl-3-indolizinyl)-, monohydrochloride CAS RN 62134-34-3), cinepazet maleatel-Piperazineacetic acid, 4-[1-oxo-3-(3,4,5-trimethoxyphenyl)-2-propenyl]-, ethyl ester, (2Z)-2-butenedioate (1:1) CAS RN 50679-07-7), tosifen (Benzenesulfonamide, 4-methyl-N-[[[(1S)-1-methyl-2-phenylethyl]amino]carbonyl]-CAS RN 32295-184), verapamilhydrochloride (Benzeneacetonitrile, α-[3-[[2-(3,4-dimethoxyphenyl)ethyl]methylamino]propyl]-3,4-dimethoxy-α-(1-methylethyl)-, monohydrochloride CAS RN 152-114), molsidomine (1,2,3-Oxadiazolium, 5-[(ethoxycarbonyl)amino]-3-(4-morpholinyl)-, inner salt CAS RN 25717-80-0), and ranolazine hydrochloride (1-Piperazineacetamide, N-(2,6-dimethylphenyl)4-[2-hydroxy-3-(2-meth-oxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-184); adrenergic stimulants such as guanfacine hydrochloride (such as N-amidino-2-(2,6-dichlorophenyl) acetamide hydrochloride, e.g., Tenex® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2H-1,2,4-benzothiadiazine-7-sulfonamide 1,1-dioxide, e.g., the combination as, e.g., Aldoril® Tablets available from Merck), methyldopa-chlorothiazide (such as 6-chloro-2H-1, 2,4-benzothiadiazine-7-sulfonamide 1,1-dioxide and methyldopa as described above, e.g., Aldoclor®, Merck), clonidine hydrochloride (such as 2-(2,6-dichlorophenylamino)-2-imidazoline hydrochloride and chlorthalidone (such as 2-chloro-5-(1-hydroxy-3-oxo-1-isoindolinyl)benzenesulfonamide), e.g., Combipres®, Boehringer Ingelheim), clonidine hydrochloride (such as 2-(2,6-dichlorophenylamino)-2-imidazoline hydrochloride, e.g., Catapres®, Boehringer Ingelheim), clonidine (1H-Imidazol-2-amine, N-(2,6-dichlorophenyl)4,5-dihydro-CAS RN 4205-90-7), Hyzaar (Merck; a combination of losartan and hydrochlorothiazide), Co-Diovan (Novartis; a combination of valsartan and hydrochlorothiazide, Lotrel (Novartis; a combination of benazepril and amlodipine) and Caduet (Pfizer; a combination of amlodipine and atorvastatin), and those agents disclosed in US20030069221.

1.3.2.11 Agents for the Treatment of Respiratory Disorders

The GCC agonist peptides described herein can be used in combination therapy with one or more of the following agents useful in the treatment of respiratory and other disorders including but not limited to: (1) β-agonists including but not limited to: albuterol (PRO VENTIL®, S ALBUT AMOK), VENTOLIN®), bambuterol, bitoterol, clenbuterol, fenoterol, formoterol, isoetharine (BRONKOSOL®, BRONKOMETER®), metaproterenol (ALUPENT®, METAPREL®), pirbuterol (MAXAIR®), reproterol, rimiterol, salmeterol, terbutaline (BRETHAIRE®, BRETHINE®, BRICANYL®), adrenalin, isoproterenol (ISUPREL®), epinephrine bitartrate (PRIMATENE®), ephedrine, orciprenline, fenoterol and isoetharine; (2) steroids, including but not limited to beclomethasone, beclomethasone dipropionate, betamethasone, budesonide, bunedoside, butixocort, dexamethasone, flunisolide, fluocortin, fluticasone, hydrocortisone, methyl prednisone, mometasone, predonisolone, predonisone, tipredane, tixocortal, triamcinolone, and triamcinolone acetonide; (3) β2-agonist-corticosteroid combinations [e.g., salmeterol-fluticasone (AD V AIR®), formoterol-budesonid (S YMBICORT®)]; (4) leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafhiukast, montelukast, montelukast sodium (SINGULAIR®), pranlukast, iralukast, pobilukast, SKB-106,203 and compounds described as having LTD4 antagonizing activity described in U.S. Pat. No. 5,565,473; (5) 5-lipoxygenase inhibitors and/or leukotriene biosynthesis inhibitors [e.g., zileuton and BAY1005 (CA registry 128253-31-6)]; (6) histamine Hl receptor antagonists/antihistamines (i.e., any compound that is capable of blocking, inhibiting, reducing or otherwise interrupting the interaction between histamine and its receptor) including but not limited to: astemizole, acrivastine, antazoline, azatadine, azelastine, astamizole, bromopheniramine, bromopheniramine maleate, carbinoxamine, carebastine, cetirizine, chlorpheniramine, chlorpheniramine maleate, cimetidine clemastine, cyclizine, cyproheptadine, descarboethoxyloratadine, dexchlorpheniramine, dimethindene, diphenhydramine, diphenylpyraline, doxylamine succinate, doxylarnine, ebastine, efletirizine, epinastine, famotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; (7) an anticholinergic including but not limited to: atropine, benztropine, biperiden, flutropium, hyoscyamine (e.g. Levsin®; Levbid®; Levsin/SLC), Anaspaz®, Levsinex Timecaps®, NuLev®), ilutropium, ipratropium, ipratropium bromide, methscopolamine, oxybutinin, rispenzepine, scopolamine, and tiotropium; (8) an anti-tussive including but not limited to: dextromethorphan, codeine, and hydromorphone; (9) a decongestant including but not limited to: pseudoephedrine and phenylpropanolamine; (10) an expectorant including but not limited to: guafenesin, guaicolsulfate, terpin, ammonium chloride, glycerol guaicolate, and iodinated glycerol; (11) a bronchodilator including but not limited to: theophylline and aminophylline; (12) an anti-inflammatory including but not limited to: fluribiprofen, diclophenac, indomethacin, ketoprofen, S-ketroprophen, tenoxicam; (13) a PDE (phosphodiesterase) inhibitor including but not limited to those disclosed herein; (14) a recombinant humanized monoclonal antibody [e.g. xolair (also called omalizumab), rhuMab, and talizumab]; (15) a humanized lung surfactant including recombinant forms of surfactant proteins SP-B, SP-C or SP-D [e.g. SURFAXIN®, formerly known as dsc-104 (Discovery Laboratories)], (16) agents that inhibit epithelial sodium channels (ENaC) such as amiloride and related compounds; (17) antimicrobial agents used to treat pulmonary infections such as acyclovir, amikacin, amoxicillin, doxycycline, trimethoprin sulfamethoxazole, amphotericin B, azithromycin, clarithromycin, roxithromycin, clarithromycin, cephalosporins (ceffoxitin, cefmetazole etc), ciprofloxacin, ethambutol, gentimycin, ganciclovir, imipenem, isoniazid, itraconazole, penicillin, ribavirin, rifampin, rifabutin, amantadine, rimantidine, streptomycin, tobramycin, and vancomycin; (18) agents that activate chloride secretion through Ca++ dependent chloride channels (such as puringergic receptor (P2Y(2) agonists); (19) agents that decrease sputum viscosity, such as human recombinant DNase 1, (Pulmozyme®); (20) nonsteroidal anti-inflammatory agents (acemetacin, acetaminophen, acetyl salicylic acid, alclofenac, alminoprofen, apazone, aspirin, benoxaprofen, bezpiperylon, bucloxic acid, carprofen, clidanac, diclofenac, diclofenac, diflunisal, diflusinal, etodolac, fenbufen, fenbufen, fenclofenac, fenclozic acid, fenoprofen, fentiazac, feprazone, flufenamic acid, flufenisal, flufenisal, fluprofen, flurbiprofen, flurbiprofen, furofenac, ibufenac, ibuprofen, indomethacin, indomethacin, indoprofen, isoxepac, isoxicam, ketoprofen, ketoprofen, ketorolac, meclofenamic acid, meclofenamic acid, mefenamic acid, mefenamic acid, miroprofen, mofebutazone, nabumetone oxaprozin, naproxen, naproxen, niflumic acid, oxaprozin, oxpinac, oxyphenbutazone, phenacetin, phenylbutazone, phenylbutazone, piroxicam, piroxicam, pirprofen, pranoprofen, sudoxicam, tenoxican, sulfasalazine, sulindac, sulindac, suprofen, tiaprofenic acid, tiopinac, tioxaprofen, tolfenamic acid, tolmetin, tolmetin, zidometacin, zomepirac, and zomepirac); and (21) aerosolized antioxidant therapeutics such as S-Nitrosoglutathione.

1.3.2.12 Anti-Diabetic Agents

The GCC agonist peptides described herein can be used in therapeutic combination with one or more anti-diabetic agents, including but not limited to: PPARγ agonists such as glitazones (e.g., WAY-120,744, AD 5075, balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), rivoglitazone (CS-011, Sankyo), GL-262570 (Glaxo Welcome), BRL49653 (disclosed in WO98/05331), CLX-0921, 5-BTZD, GW-0207, LG-100641, JJT-501 (JPNT/P&U), L-895645 (Merck), R-119702 (Sankyo/Pfizer), NN-2344 (Dr. Reddy/NN), YM-440 (Yamanouchi), LY-300512, LY-519818, R483 (Roche), T131 (Tularik), and the like and compounds disclosed in U.S. Pat. Nos. 4,687,777, 5,002,953, 5,741,803, 5,965,584, 6,150,383, 6,150,384, 6,166,042, 6,166,043, 6,172,090, 6,211,205, 6,271,243, 6,288,095, 6,303,640, 6,329,404, 5,994,554, WO97/10813, WO97/27857, WO97/28115, WO97/28137, WO97/27847, WO00/76488, WO03/000685, WO03/027112, WO03/035602, WO03/048130, WO03/055867, and pharmaceutically acceptable salts thereof; biguanides such as metformin hydrochloride (N,N-dimethylimidodicarbonimidic diamide hydrochloride, such as Glucophage™, Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A. G.); other metformin salt forms (including where the salt is chosen from the group of, acetate, benzoate, citrate, ftimarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octanoate, decanoate, hexadecanoate, octodecanoate, benzenesulphonate, trimethoxybenzoate, paratoluenesulphonate, adamantanecarboxylate, glycoxylate, glutamate, pyrrolidonecarboxylate, naphthalenesulphonate, 1-glucosephosphate, nitrate, sulphite, dithionate and phosphate), and phenformin; protein tyrosine phosphatase-IB (PTP-IB) inhibitors, such as A-401,674, KR 61639, OC-060062, OC-83839, OC-297962, MC52445, MC52453, ISIS 113715, and those disclosed in WO99/585521, WO99/58518, WO99/58522, WO99/61435, WO03/032916, WO03/032982, WO03/041729, WO03/055883, WO02/26707, WO02/26743, JP2002114768, and pharmaceutically acceptable salts and esters thereof; sulfonylureas such as acetohexamide (e.g. Dymelor, Eli Lilly), carbutamide, chlorpropamide (e.g. Diabinese®, Pfizer), gliamilide (Pfizer), gliclazide (e.g. Diamcron, Servier Canada Inc), glimepiride (e.g. disclosed in U.S. Pat. No. 4,379,785, such as Amaryl, Aventis), glipentide, glipizide (e.g. Glucotrol or Glucotrol XL Extended Release, Pfizer), gliquidone, glisolamide, glyburide/glibenclamide (e.g. Micronase or Glynase Prestab, Pharmacia & Upjohn and Diabeta, Aventis), tolazamide (e.g. Tolinase), and tolbutamide (e.g. Orinase), and pharmaceutically acceptable salts and esters thereof; meglitinides such as repaglinide (e.g. Pranidin®, Novo Nordisk), KAD1229 (PF/Kissei), and nateglinide (e.g. Starlix®, Novartis), and pharmaceutically acceptable salts and esters thereof; a glucoside hydrolase inhibitors (or glucoside inhibitors) such as acarbose (e.g. Precose™, Bayer disclosed in U.S. Pat. No. 4,904,769), miglitol (such as GLYSET™, Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-alpha-D-glucopyranoside, Marion Merrell Dow), voglibose (Takeda), adiposine, emiglitate, pradimicin-Q, salbostatin, CKD-711, MDL-25,637, MDL-73,945, and MOR 14, and the compounds disclosed in U.S. Pat. Nos. 4,062,950, 4,174,439, 4,254,256, 4,701,559, 4,639,436, 5,192,772, 4,634,765, 5,157,116, 5,504,078, 5,091,418, 5,217,877, 51,091 and WOO 1/47528 (polyamines); α-amylase inhibitors such as tendamistat, trestatin, and A1-3688, and the compounds disclosed in U.S. Pat. Nos. 4,451,455, 4,623,714, and 4,273,765; SGLT2 inhibitors including those disclosed in U.S. Pat. Nos. 6,414,126 and 6,515,117; an aP2 inhibitor such as disclosed in U.S. Pat. No. 6,548,529; insulin secretagogues such as linogliride, A-4166, forskilin, dibutyrl cAMP, isobutylmethylxanthine (IBMX), and pharmaceutically acceptable salts and esters thereof; fatty acid oxidation inhibitors, such as clomoxir, and etomoxir, and pharmaceutically acceptable salts and esters thereof; A2 antagonists, such as midaglizole, isaglidole, deriglidole, idazoxan, earoxan, and fluparoxan, and pharmaceutically acceptable salts and esters thereof; insulin and related compounds (e.g. insulin mimetics) such as biota, LP-100, novarapid, insulin detemir, insulin lispro, insulin glargine, insulin zinc suspension (lente and ultralente), Lys-Pro insulin, GLP-I (1-36) amide, GLP-I (73-7) (insulintropin, disclosed in U.S. Pat. No. 5,614,492), LY-315902 (Lilly), GLP-I (7-36)-NH2), AL-401 (Autoimmune), certain compositions as disclosed in U.S. Pat. Nos. 4,579,730, 4,849,405, 4,963,526, 5,642,868, 5,763,396, 5,824,638, 5,843,866, 6,153,632, 6,191,105, and WO 85/05029, and primate, rodent, or rabbit insulin including biologically active variants thereof including allelic variants, more preferably human insulin available in recombinant form (sources of human insulin include pharmaceutically acceptable and sterile formulations such as those available from Eli Lilly (Indianapolis, Ind. 46285) as Humulin™ (human insulin rDNA origin), also see the THE PHYSICIAN'S DESK REFERENCE, 55.sup.th Ed. (2001) Medical Economics, Thomson Healthcare (disclosing other suitable human insulins); non-thiazolidinediones such as JT-501 and farglitazar (GW-2570/GI-262579), and pharmaceutically acceptable salts and esters thereof; PPARα/γ dual agonists such as AR-H039242 (Aztrazeneca), GW-409544 (Glaxo-Wellcome), BVT-142, CLX-0940, GW-1536, GW-1929, GW-2433, KRP-297 (Kyorin Merck; 5-[(2,4-Dioxo thiazolidinyl)methyl]methoxy-N-[[4-(trifluoromethyl)phenyl]methyl]benzamide), L-796449, LR-90, MK-0767 (Merck/Kyorin/Banyu), SB 219994, muraglitazar (BMS), tesaglitzar (Astrazeneca), reglitazar (JTT-501) and those disclosed in WO99/16758, WO99/19313, WO99/20614, WO99/38850, WO00/23415, WO00/23417, WO00/23445, WO00/50414, WO01/00579, WO01/79150, WO02/062799, WO03/004458, WO03/016265, WO03/018010, WO03/033481, WO03/033450, WO03/033453, WO03/043985, WO 031053976, U.S. application Ser. No. 09/664,598, filed Sep. 18, 2000, Murakami et al. Diabetes 47, 1841-1847 (1998), and pharmaceutically acceptable salts and esters thereof; other insulin sensitizing drugs; VPAC2 receptor agonists; GLK modulators, such as those disclosed in WO03/015774; retinoid modulators such as those disclosed in WO03/000249; GSK 3β/GSK 3 inhibitors such as 4-[2-(2-bromophenyl)-4-(4-fluorophenyl-1H-imidazol-5-yl]pyridine and those compounds disclosed in WO03/024447, WO03/037869, WO03/037877, WO03/037891, WO03/068773, EP1295884, EP1295885, and the like; glycogen phosphorylase (HGLPa) inhibitors such as CP-368,296, CP-316,819, BAYR3401, and compounds disclosed in WOO 1/94300, WO02/20530, WO03/037864, and pharmaceutically acceptable salts or esters thereof; ATP consumption promotors such as those disclosed in WO03/007990; TRB3 inhibitors; vanilloid receptor ligands such as those disclosed in WO03/049702; hypoglycemic agents such as those disclosed in WO03/015781 and WO03/040114; glycogen synthase kinase 3 inhibitors such as those disclosed in WO03/035663 agents such as those disclosed in WO99/51225, US20030134890, WO01/24786, and WO03/059870; insulin-responsive DNA binding protein-1 (IRDBP-I) as disclosed in WO03/057827, and the like; adenosine A2 antagonists such as those disclosed in WO03/035639, WO03/035640, and the like; PPARδ agonists such as GW 501516, GW 590735, and compounds disclosed in JP10237049 and WO02/14291; dipeptidyl peptidase IV (DP-IV) inhibitors, such as isoleucine thiazolidide, NVP-DPP728A (1-[[[2-[(5-cyanopyridin-2-yl)amino]ethyl]amino]acetyl]-2-cyano-(S)-pyrrolidine, disclosed by Hughes et al, Biochemistry, 38(36), 11597-11603, 1999), P32/98, NVP-LAF-237, P3298, TSL225 (tryptophyl-1,2,3,4-tetrahydro-isoquinoline-3-carboxylic acid, disclosed by Yamada et al, Bioorg. & Med. Chem. Lett. 8 (1998) 1537-1540), valine pyrrolidide, TMC-2A/2B/2C, CD-26 inhibitors, FE999011, P9310/K364, VIP 0177, DPP4, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996), and the compounds disclosed in U.S. Pat. Nos. 6,395,767, 6,573,287, 6,395,767 (compounds disclosed include BMS-477118, BMS-471211 and BMS 538,305), WO99/38501, WO99/46272, WO99/67279, WO99/67278, WO99/61431 WO03/004498, WO03/004496, EP1258476, WO02/083128, WO02/062764, WO03/000250, WO03/002530, WO03/002531, WO03/002553, WO03/002593, WO03/000180, and WO03/000181; GLP-I agonists such as exendin-3 and exendin-4 (including the 39 aa polypeptide synthetic exendin-4 called Exenatide®), and compounds disclosed in US2003087821 and NZ 504256, and pharmaceutically acceptable salts and esters thereof; peptides including amlintide and Symlin® (pramlintide acetate); and glycokinase activators such as those disclosed in US2002103199 (fused heteroaromatic compounds) and WO02/48106 (isoindolin-1-one-substituted propionamide compounds).

EXAMPLES

Example 1

Clinical Study for Safety and Efficacy in Humans for the Treatment of Chronic Idiopathic Constipation A randomized, double-blind, placebo-controlled, 14-day repeat oral, dose ranging study was conducted in patients with chronic idiopathic constipation (CIC). The primary objective of this study was to evaluate the safety of SP-304 (1.0 mg, 3.0 mg, 9.0 mg and 0.3 mg) for 14 days in patients with CIC. One secondary objective was to assess the pharmacokinetic profile of SP-304 in plasma. Other secondary objectives included evaluations of pharmacodynamic effects (efficacy) on parameters such as the time to first bowel movement after daily dosing with SP-304, bowel habits over time—for example, spontaneous bowel movements (SBMs), complete spontaneous bowel movements (CSBMs), and stool consistency [using Bristol Stool Form Scale (BSFS)]—and other patient reported outcomes such as abdominal discomfort.

The study included five arms with assigned interventions as indicated in the table below.

| Arms | Interventions |
|---|---|
| SP-304 1.0 mg: Experimental | Subjects receiving SP-304 1.0 mg for 14 consecutive days |
| SP-304 3.0 mg: Experimental | Subjects receiving SP-304 3.0 mg for 14 consecutive days |
| SP-304 9.0 mg: Experimental | Subjects receiving SP-304 9.0 mg for 14 consecutive days |
| Placebo: Placebo Comparator | Subjects receiving Placebo for 14 consecutive days |
| SP-304 0.3 mg: Experimental | Subjects receiving SP-304 0.3 mg for 14 consecutive days |

Subjects diagnosed with CIC were screened for the anticipated 4 cohorts to yield 80 randomized subjects for enrollment. There were four dose cohorts (1.0 mg, 3.0 mg, 9.0 mg and 0.3 mg) with 20 subjects per dose cohort [randomization ratio 3:1 (15 receive SP-304:5 receive placebo)]. Subjects who continued to meet all the entry criteria and complete the pre-treatment bowel movement (BM) diary received, in a double-blind, randomized fashion, SP-304 or matching placebo. The entry criteria included (1) meeting modified ROME III criteria for chronic constipation (CC); (2) no significant finding in colonoscopy within past 5 years; (3) good health as determined by physical examination, medical history, vital signs, ECG, clinical chemistry, hematology, urinalysis, drug screen and serology assessments; and (4) during 14-day pre-treatment period, subjects reporting <6 SBM and <3 CSBM in each pre-treatment week. All subjects receiving at least one dose of SP-304 or matching placebo were considered evaluable for the safety endpoints (78 total). If a subject did not have a major protocol deviation, had at least 5 days of study treatment each week and corresponding entries for bowel habits, he/she was considered evaluable for efficacy parameters (54-55 total).

The demographics of the subjects in the study are summarized in the table below.

|  | Placebo | 0.3 mg | 1.0 mg | 3.0 mg | 9.0 mg |
|---|---|---|---|---|---|
|  | Age | | | | |
|  | 47.7 (14.6) | 51.1 (12.0) | 50.5 (10.6) | 48.5 (16.1) | 47.3 (12.7) |
|  | Gender | | | | |
| Female | 18 (90.0%) | 12 (85.7%) | 14 (100%) | 13 (86.7) | 12 (80%) |
| Male | 2 (10.0%) | 2 (14.3%) | 0 | 2 (13.3%) | 3 (20%) |
|  | Race | | | | |
| White | 17 (85.0%) | 13 (92.9%) | 12 (85.7%) | 14 (93.3%) | 12 (80.0%) |
| African American | 1 (5.0%) | 0 | 1 (7.1%) | 0 | 2 (13.3%) |
| Asian | 1 (5.0%) | 1 (7.1%) | 1 (7.1%) | 0 | 1 (6.7%) |
| American Indian | 1 (5.0%) | 0 | 0 | 0 | 0 |
| Other | 0 | 0 | 0 | 1 (6.7%) | 0 |

Values for age are the mean (standard deviation); values for gender and race are the number (percentage of experimental arm).

Results

Pharmacokinetics and Safety:

There was no detectable systemic absorption of plecanatide (assay sensitivity ≥10 ng/mL). No serious adverse events (SAE) were reported in subjects receiving plecanatide and no deaths reported in this study. 10% (2/20) subjects who received placebo and 17.2% (10/58) subjects who received SP-304 reported adverse events considered as related to the treatment. The majority of adverse events were mild/moderate and transient in nature. 10% (2/20) subjects who received placebo and 5.2% (3/58) subjects who received SP-304 reported GI-related adverse events considered as related to treatment. There was no diarrhea reported for any subject receiving SP-304. The table below is a GI-related adverse event (AE) summary.

|  | Placebo n = 20 | 0.3 mg n = 14 | 1.0 mg n = 14 | 3.0 mg n = 15 | 9.0 mg n = 15 |
|---|---|---|---|---|---|
| Abdominal Cramping | 1 (5.0%) | 0 | 0 | 0 | 0 |
| Abdominal Pain | 1 (5.0%) | 0 | 0 | 0 | 0 |
| Bloating | 0 | 0 | 0 | 0 | 1 (6.7%) |
| Diarrhea | 1 (5.0%) | 0 | 0 | 0 | 0 |
| Flatulence | 2 (10.0%) | 0 | 0 | 0 | 0 |
| Nausea | 0 | 1 (7.1%) | 0 | 0 | 0 |
| Upset Stomach | 0 | 0 | 0 | 1 (6.7%) | 0 |

Values are the number (percentage of experimental arm).

Figure 2:
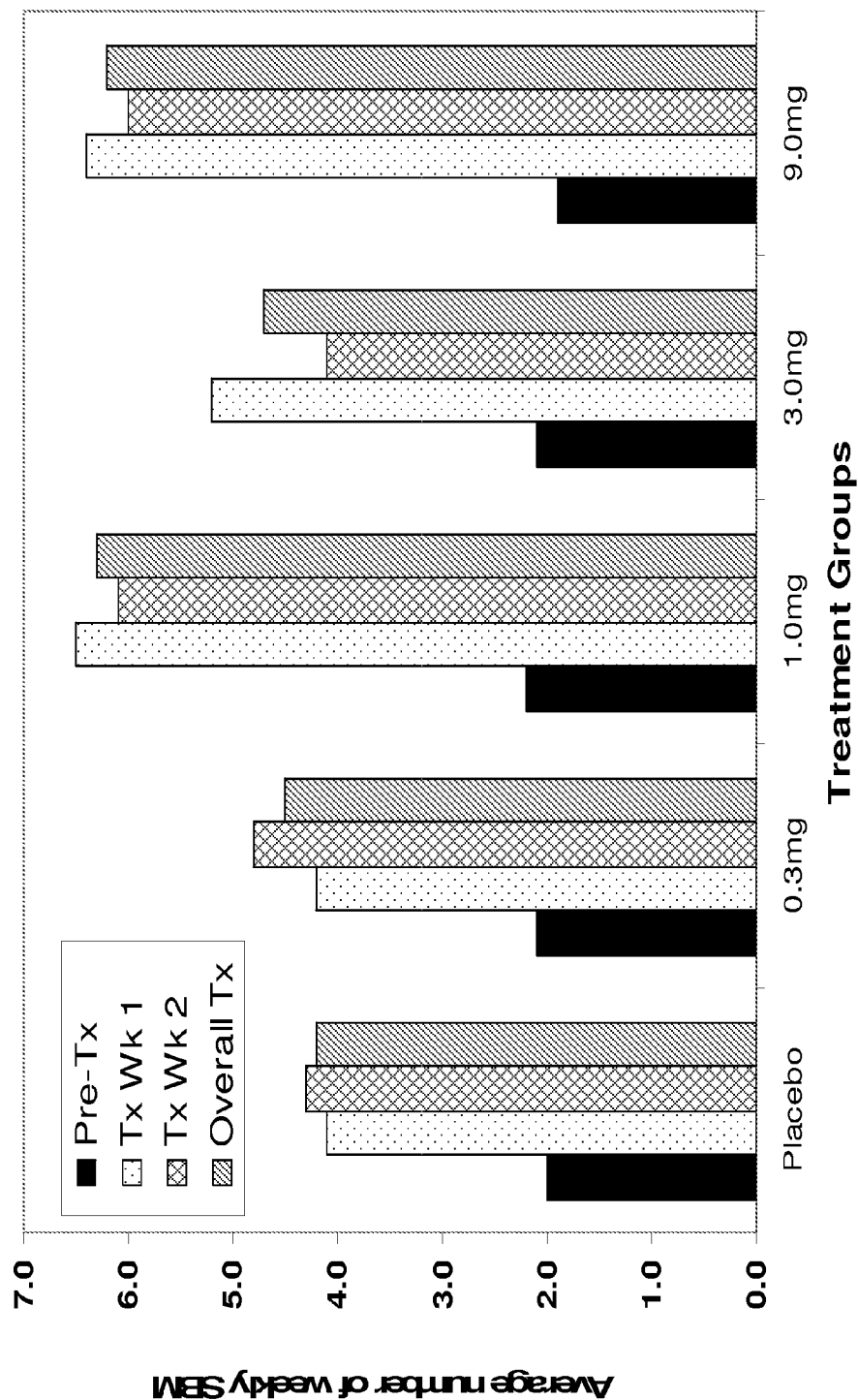
FIG. 2: Effect of daily treatment with plecanatide on spontaneous bowel movements (SBM) in chronic constipation patients.
Figure 3:
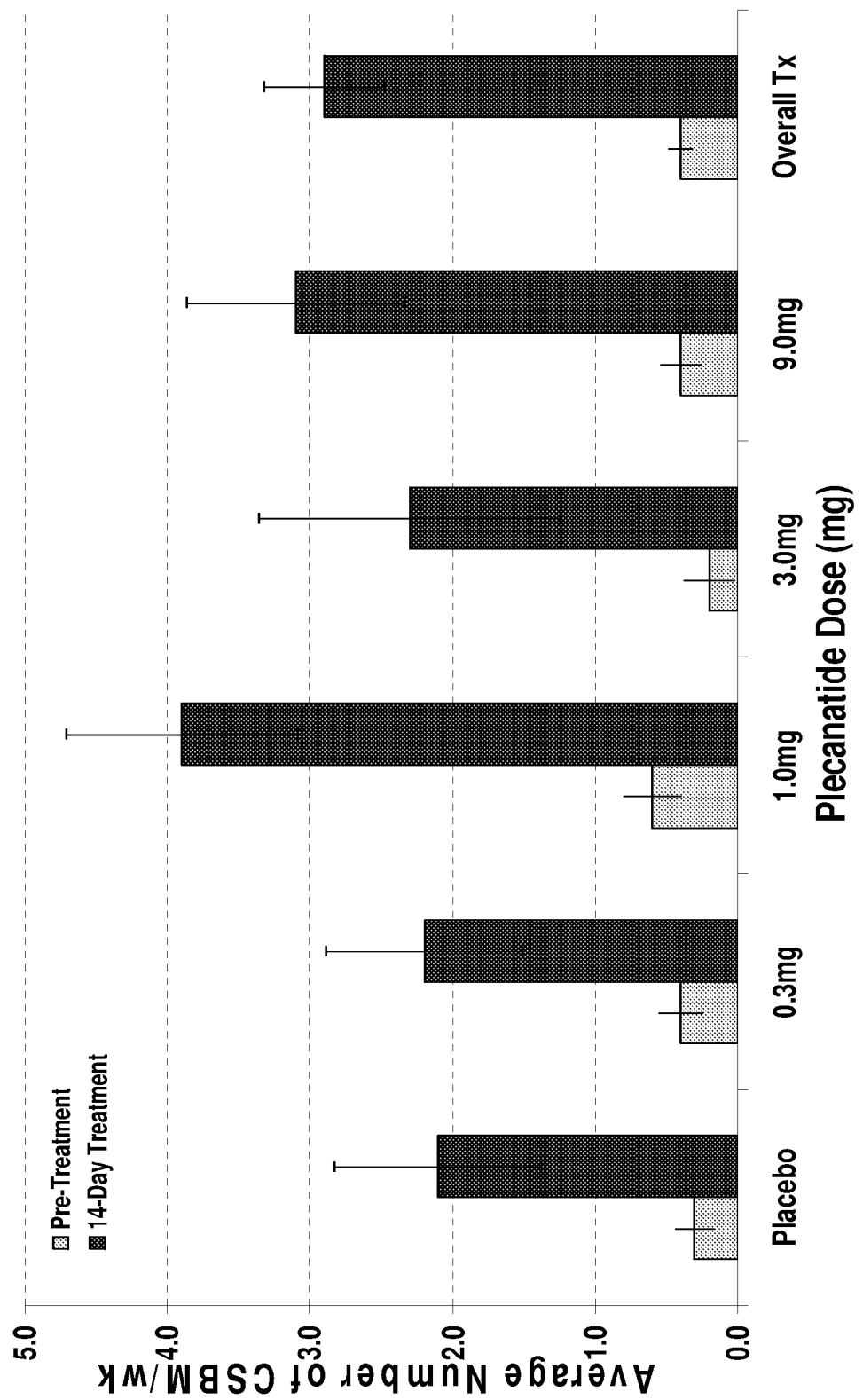
FIG. 3: Effect of daily treatment with plecanatide on complete spontaneous bowel movements (CSBM) in chronic constipation patients.
Figure 4:
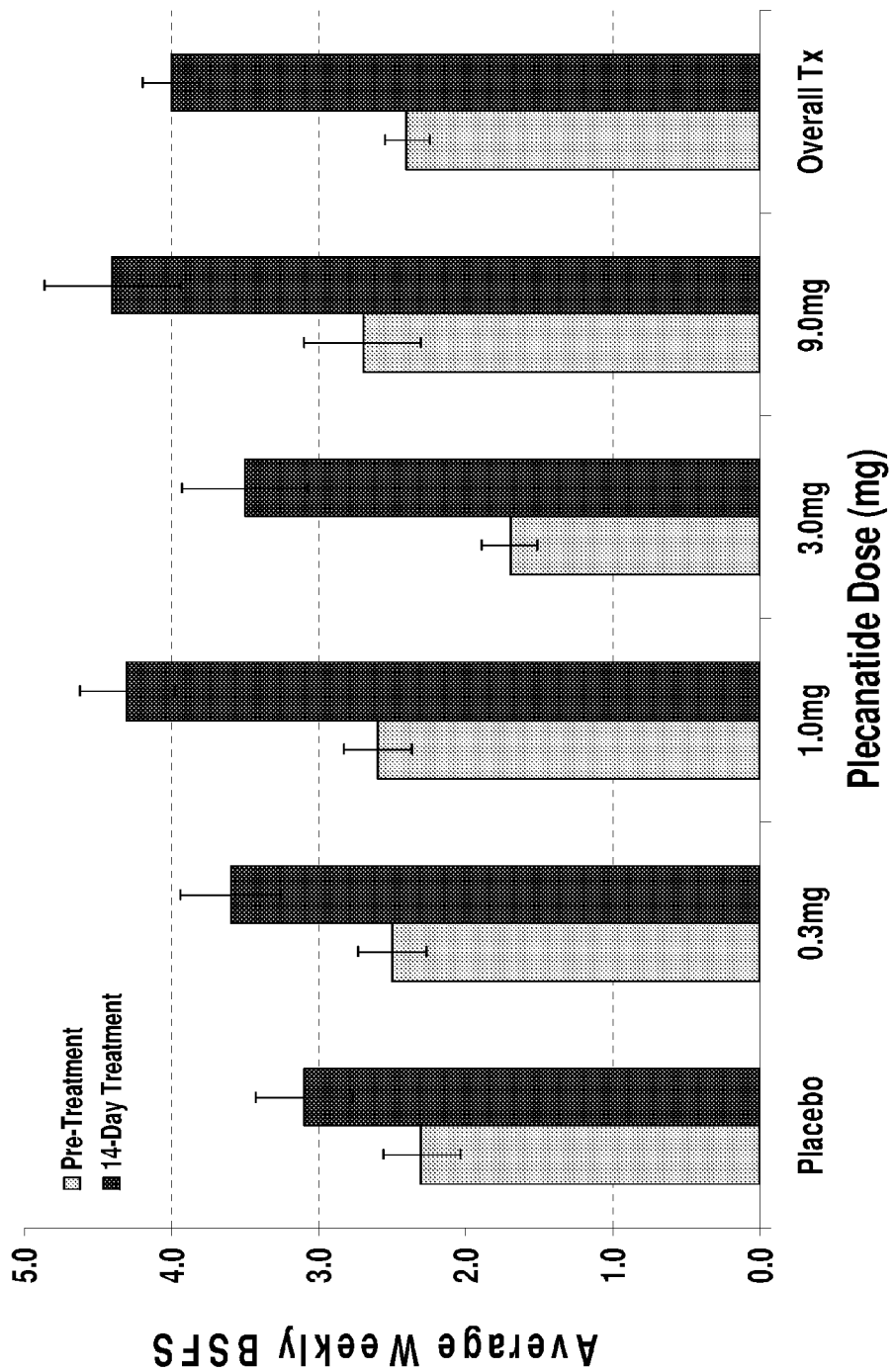
FIG. 4: Effect of daily treatment with plecanatide on Bristol Stool Form Scores (BSFS) in chronic constipation patients.
Figure 5:
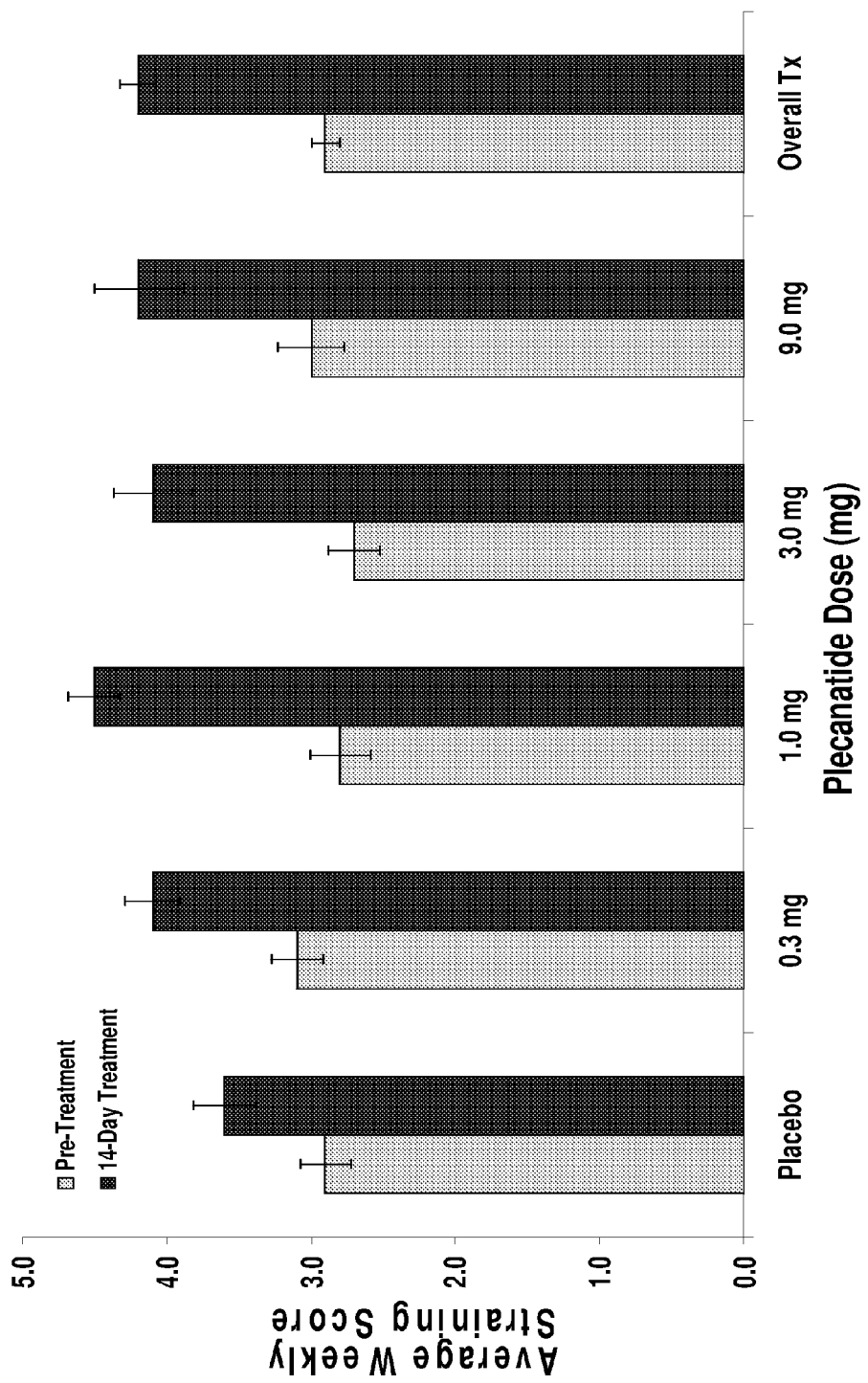
FIG. 5: Effect of daily treatment with plecanatide on straining scores in chronic constipation patients
Figure 6:
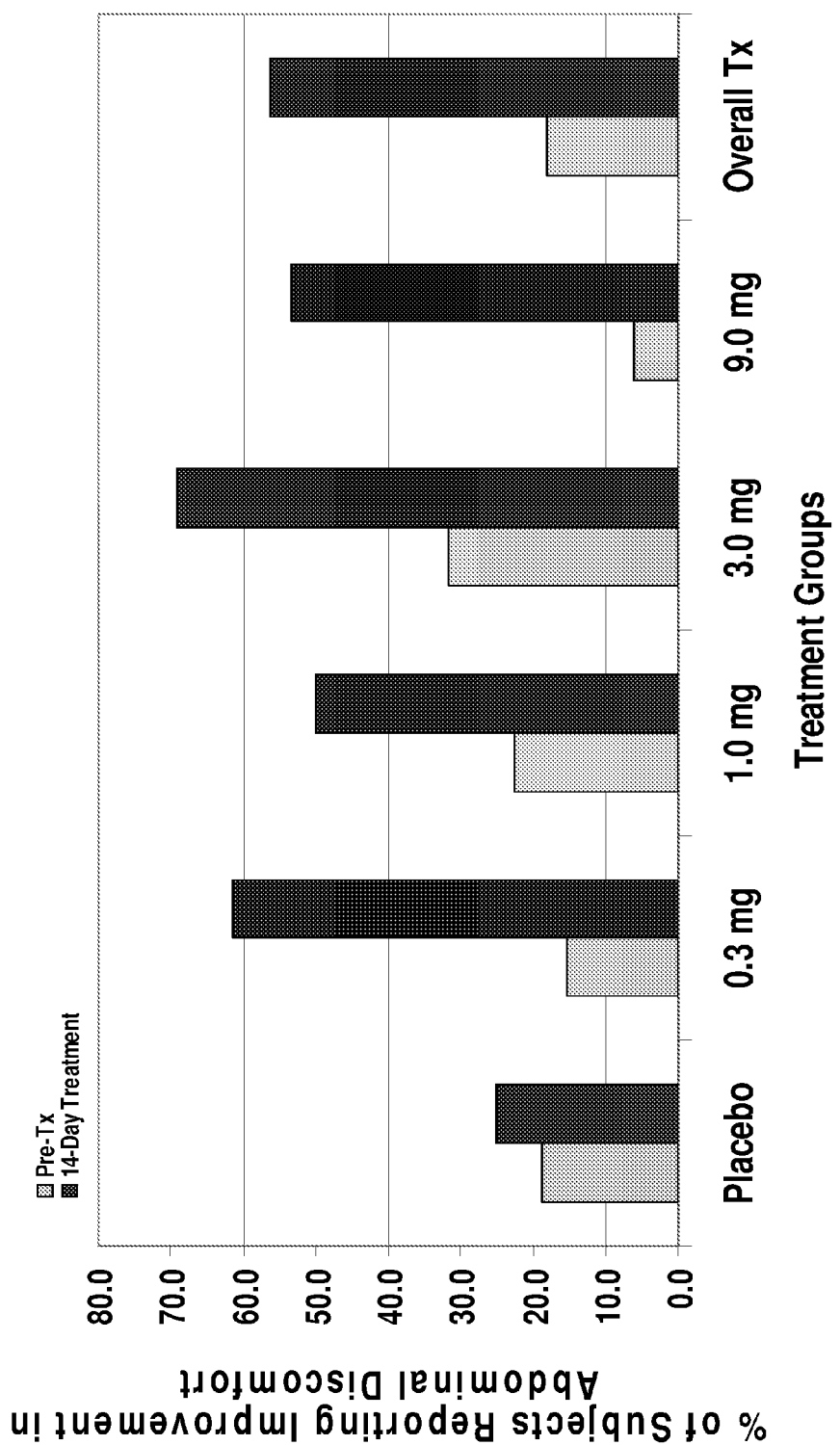
FIG. 6: Percentage of subjects reporting improvements in abdominal discomfort scores after 14-days of daily treatment with plecanatide.

Efficacy:

SP-304 (plecanatide) treatment decreased the time to first bowel movement, increased stool frequency (SBM and CSBM), improved stool consistency, and reduced straining and abdominal discomfort. See FIGS. 1-6.

Example 2

Composition of Wet Granulation Batch 10005

| Item No. | Ingredient | Use | Concentration % w/w |
|---|---|---|---|
| 1 | SP304 | | 0.23 |
| 2 | Mannogem EZ, USP/EP (Mannitol) | Diluent | 79.77 |
| 3 | PROSOLV SMCC 90 LM (silicified microcrystalline cellulose) | Binder | 15.0 |
| 4 | Purified Water (chilled to 5° C.), USP | vehicle | n/a |
| 5 | Purified Water (chilled to 5° C.), USP | | n/a |
| 6 | Explotab (Sodium Starch Glycolate) | Disintregant | 4.0 |
| 7 | Pruv (sodium stearyl fumarate) | Lubricant | 1.0 |
| | Total | | 100 |

Example 3

Composition of Wet Granulation Batch 10007

| Item No. | Ingredient | Use | Concentration % w/w |
|---|---|---|---|
| 1 | SP304 | | 0.3 |
| 3 | PROSOLV SMCC 90 HD (silicified microcrystalline cellulose) | Binder | 95.7 |
| 4 | Purified Water (chilled to 5° C.), USP | vehicle | n/a |
| 5 | Purified Water (chilled to 5° C.), USP | | n/a |
| 6 | Explotab (Sodium Starch Glycolate) | Disintregant | 4.0 |
| | Total | | 100 |

Example 4

Excipient Compatibility

Binary mixtures of SP-304 were prepared and stored in glass vials. For solid excipients the binary mixtures were comprised of 9.1% or 50% excipient. Glass vials were stored at 40 C/75RH open or closed. The percent purity (measured by HPLC) of the GCC agonist peptide (SP-304) after storage for the time indicated in each column (i.e., 1, 2, or 3 months for the closed vial and 0.5, 1, 2, or 3 months for the open vials) is indicated by numerical values.

| | | Closed | | | Open | | | |
|---|---|---|---|---|---|---|---|---|
| PURPOSE | EXCIPIENT | 1 M | 2 M | 3 M | 0.5 M | 1 M | 2 M | 3 M |
| None | None | 91.4 | 88.2 | 84.1 | 93.7 | 91.2 | 88.2 | 84.8 |
| Diluent | Sorbitol | 92.4 | 90.1 | 87.2 | 92.2 | 90.8 | 87.1 | 80.9 |
| | Mannitol | 91.9 | 88.4 | 85.1 | 92.6 | 90.5 | 87.9 | 83.8 |
| | Prosolv | 92.2 | 89.6 | 86.3 | 93 | 90.5 | 87.8 | 83.7 |
| | Starch | 91.4 | 88.7 | 85.4 | 92.5 | 90.5 | 87.9 | 83.7 |
| Binder | Emdex | 91.3 | 88.7 | 85.2 | 91.8 | 90.7 | 87.9 | 81.9 |
| | Plasdone | 92.8 | 90.6 | 85.6 | 93.1 | 90.4 | 87.3 | 83 |
| Disintegrant | Explotab | 91.9 | 89.4 | 87.1 | 92.2 | 90.3 | 84.7 | 78.3 |
| | Polyplasdone | 92 | 89 | 85.6 | 93.5 | 90.3 | 87.4 | 83.1 |
| Glidant | Cabosil | 92.1 | 88.3 | 85.6 | 92.6 | 90.5 | 87.3 | 84 |
| Lubricant | Mg stearte | 91.5 | 87.7 | 84.6 | 92.6 | 90.6 | 87.6 | 83.8 |
| | PRUV | 92 | 88.3 | 85.7 | 92.2 | 90.5 | 87.5 | 83.8 |
| | compritol | 90.8 | 87.1 | 84.4 | 92 | 90.5 | 86.7 | 84.1 |
| Excipient | PEG 3350 | 90.9 | 87 | 83.3 | 91.5 | 89.4 | 84.4 | 77.5 |
| Antioxidant | Ascorbic acid | 91.3 | 86.9 | 83 | 92.8 | 90 | 85.7 | 83.8 |
| | BHA | 91.9 | 88.9 | 85.9 | 93.5 | 90.8 | 87.4 | 85.8 |
| | BHT | 90.8 | 87.2 | 84.6 | 92.4 | 90.3 | 86.6 | 83.6 |
| | EDTA | 90.9 | 87.5 | 84.1 | 92.3 | 90.4 | 86.7 | 84.6 |
| Capsule | HPMC capsule | 92.2 | 89 | 85.2 | 92.3 | 90.2 | 86.4 | 83.5 |
| | Gelatin capsule | 91.5 | 88.3 | 84.3 | 84.3 | 90.5 | 86.7 | 83.6 |
| Liquid for liquid filled capsule | Medium chain trig | | 90.4 | | | | | |
| | PG dicaprylocaprate | | 89.3 | | | | | |
| | Vit E | | 90 | | | | | |
| | Soybean oil | | 89.6 | | | | | |
| | Cremaphor | | 79.7 | | | | | |
| | PG | | 3.4 | | | | | |
| | PG 400 | | 0.7 | | | | | |

Example 5

Geometric Dry Mix for 0.3 mg Capsule

Place 12 g mannitol in mortar. Add 4 g SP-304 and gently mix until a visually uniform powder is obtained. Transfer to Turbula mixer. Rinse mortar with mannitol and transfer to Turbula mixer and mix at high speed for 10 minutes. Add about 150 g of mannitol to 4 quart V-shell mixer. Transfer the contents of the Turbula mixer to the V-shell and add 150 g of mannitol mix. Discharge v-shell contents and screen through 40 mesh and return to mixer. Add 586 g of mannitol to mixer and mix for 20 minutes.

Example 6

Wet Granulation Process

Batch 017-10005 comprised of mannitol and low-moisture (2.4%) PROSOLV LM90 (0.33 g/mL) was sprayed with SP-304 solution and fluid bed dried resulted in granulation water content of 0.35%. The final blend contained 1% water, flowed well, and filled capsules well. The 2nd prototype 017-1006 comprised of the same components was adjusted to obtain a target capsule fill weight of 100 mg based on the results of the 1st batch. Water was sprayed onto powder blend with SP-304. The inlet temperature was 50 C and the granulation was dried for 1.5 hours and stopped when the product temperature reached 36 C. The 3rd (batch 017-10006) and 4th (batch 017-10007) capsule prototypes will use PROSOLV HD90, which is a higher density material with superior flow properties and higher moisture content of 5.5% than the PROSOLV LM90. The moisture content of the PROS OLV HD90 is readily removed by fluid bed drying. The density of PROSOLV HD90 is about 0.55 g/mL. The PRUV lubricant will be removed for these batches.

Example 7

Wet Granulation Stability

SP-304 was extracted from the capsules by sonication at either at room temperature (RT) or cold temperature and the amount of peptide was determined by HPLC. Initial percentages are based on the amount stated on the label.

| Batch | % peptide (initial) | % peptide (1 mos at RT) |
|---|---|---|
| 017-10006 | 101.1 (sonicated RT) | 97.6 (sonicated cold) |
| 017-10008 | 97.5 (sonicated RT) | 108.2 (sonicated cold) |

Example 8

1M Capsule Stability in HDPE Bottles

Capsules contained 0.3 mg SP-304 with the remainder of the fill weight (up to 5 mg) made up by mannitol (Perlitol 300 DC). Each capsule contained 1.5% by weight SP-304 and 98.5% mannitol. The capsule shell was composed of HPMC. Amounts are relative to the amount specified on the label (i.e., 0.30 mg peptide). The indicated number of capsules was placed in a high density polyethylene bottle with an induction seal and molecular sieve desiccant for 1 month at either 2-8 C (first two columns) or 25 C and 60% relative humidity (last two columns). The initial amount of peptide present was 101% of the label claim. The last row gives the amount of peptide remaining after 1 month storage at the indicated temperature as determined by HPLC.

| 2-8 C. 1-capsule per bottle | 2-8 C. 6-capsules per bottle | 25 C./60 RH 1-capsule per bottle | 25 C./60 RH 6-capsules per bottle |
|---|---|---|---|
| 100% | 92% | 92% | 98% |

Example 9

Composition of Batch 1528-2855-RD (Capsules) and Spray Coating and Drying Process

| Item No. | Ingredient | Amount per unit (mg) | Concentration % w/w |
|---|---|---|---|
| 1 | SP-304 | 0.3246 | 0.3246 |
| 2 | Microcrystalline cellulose (Celphere SCP-100) | 99.10 | 99.10 |
| 3 | Calcium chloride dihydrate | 0.2622 | 0.2622 |
| 4 | Leucine USP | 0.1171 | 0.1171 |
| 5 | Hypromellose (Methocel E5 PremLV) | 0.2000 | 0.2000 |
| 6 | Purified Water, USP | 7.2 mL* | n/a |
| | Total | 100 | 100 |

*The amount of water is calculated based on use of 119.0 mL purified water for the whole batch containing 5.356 g SP-304.

The spray drying process of making the batch 2855-RD is described below.

Preparation of Coating Dispersion:

Purified water was added to a glass container and stirred such that a liquid vortex was produced without introducing air. Then calcium chloride dihydrate was slowly added into the water. The mixture was stirred until the salt was dissolved or well dispersed. Next, leucine was slowly added and the resulting mixture was stirred until the amino acid was dissolved or well dispersed. Afterward, methocel was slowly added and the mixture was stirred until methocel was completely dissolved. The solution could be warmed up to dissolve methocel, if necessary. The resulting excipient solution was allowed to cool to room temperature and pass through 80 mesh screen. Then, 127.9 g of screened excipient solution was added to a glass container and placed in an ice bath for 0.5 to 1 hour until the solution reached 0° C. Next, SP-304 was added into the cold excipient solution. The mixture was stir vigorously to allow the peptide to dissolve in the cold solution. The resulting peptide solution was kept cold in the ice bath as a spraying/coating solution.

Drug Layering

A Glatt GPCG-2 fluid bed processor (with top spray tower) with a Wurster insert was set up for drug layering onto Celphere SCP-100 beads. After loading the Wurster column with Celphere SCP-100 beads, bed temperature was raised to 35° C. and maintained for 30 minutes with minimum fluidization of the beads. The bed temperature was reduced until an exhaust temperature of 35° C. was achieved. The pump tubing of the peristaltic pump used was primed by circulating the spraying solution mentioned above. After the spraying apparatus was adjusted to obtain a satisfactory spray pattern, the coating solution was sprayed onto Celphere SCP-100 beads until all coating solution was sprayed. Operating parameters were recorded. The bed temperature and fluidization were maintained until the beads were sufficiently dry. The fluidization was then reduced while the bed temperature was maintained at 35° C. for 10 minutes. 2 g of beads were sampled for moisture analysis when the bed temperature was kept at 35° C. When the moisture of the sampled beads reached <5% moisture, the coated beads were discharged and loaded into a dry container. LOD (loss on drying) 2.399%.

Example 10

Composition of Batch 1528-2851-RD (Tablets) and Spray Coating and Drying Process

| Item No. | Ingredient | Amount per unit (mg) | Concentration % w/w |
|---|---|---|---|
| 1 | SP-304 | 0.3246 | 0.3607 |
| 2 | Microcrystalline cellulose (Avicel PH 102) | 88.88 | 98.75 |
| 3 | Calcium chloride dihydrate | 0.2622 | 0.2913 |
| 4 | Leucine USP | 0.1171 | 0.1301 |
| 5 | Hypromellose (Methocel E5 PremLV) | 0.2000 | 0.2222 |
| 6 | Magnesium stearate | 0.225 | 0.2500 |
| 7 | Purified Water, USP | 7.2 mL* | n/a |
|  | Total | 90.0 | 100 |

*The amount of water is calculated based on use of 119.0 mL purified water for the whole batch containing 5.356 g SP-304.

The spray coating and drying process of making the batch 2851-RD is described below.
Preparation of Coating Dispersion:
Purified water was added to a glass container and stirred such that a liquid vortex was produced without introducing air. Then calcium chloride dihydrate was slowly added into the water. The mixture was stirred until the salt was dissolved or well dispersed. Next, leucine was slowly added and the resulting mixture was stirred until the amino acid was dissolved or well dispersed. Afterward, methocel was slowly added and the mixture was stirred until methocel was completely dissolved. The solution could be warmed up to dissolve methocel, if necessary. The resulting excipient solution was allowed to cool to room temperature and pass through 80 mesh screen. Then, 127.9 g of screened excipient solution was added to a glass container and placed in an ice bath for 0.5 to 1 hour until the solution reached 0° C. Next, SP-304 was added into the cold excipient solution. The mixture was stir vigorously to allow the peptide to dissolve in the cold solution. The resulting peptide solution was kept cold in the ice bath as a spraying/coating solution.
Drug Layering
A Glatt GPCG-2 fluid bed processor (with top spray tower) with a Wurster insert was set up for drug layering onto Avicel PH 102 beads. After loading the Wurster column with Avicel PH 102 beads, temperature was raised to 35° C. and maintained for 30 minutes with minimum fluidization of the beads. The bed temperature was reduced until an exhaust temperature of 35° C. was achieved. The pump tubing of the peristaltic pump used was primed by circulating the spraying solution mentioned above. After the spraying apparatus was adjusted to obtain a satisfactory spray pattern, the coating solution was sprayed onto Avicel PH 102 beads until all coating solution was sprayed. Operating parameters were recorded. The bed temperature and fluidization were maintained until the beads were sufficiently dry. The fluidization was then reduced while the bed temperature was maintained at 35° C. for 10 minutes. 2 g of beads were sampled for moisture analysis when the bed temperature was kept at 35° C. When the moisture of the sampled beads reached <5% moisture, the coated beads were discharged and loaded into a dry container. LOD (loss on drying)<5%.

The net weight of the coated blend was determined for calculation of the amount of magnesium stearate needed to lubricate the blend. Then the magnesium stearate was added to the coated blend and the mixture was blended for 1 minute.
Compression
A Fette tablet press was set up. Then the blend mixture was loaded into the powder hopper and tooling was installed. The weight of each tablet was set to be 90 mg±5% and hardness to be 4-6 Kp. The weight, hardness and thickness of tablets were measured and recorded every 5 to 10 minutes. Friability measurement was also performed to ensure satisfactory product.

Example 11

Composition of Batch 1528-2850-RD (Capsules) and Process

| Item No. | Ingredient | Concentration % w/w |
|---|---|---|
| 1 | SP-304 | 0.3246 |
| 2 | Microcrystalline cellulose (Avicel PH 102) | 99.43 |
| 3 | Magnesium stearate | 0.2500 |
| 4 | HPMC capsule shells | n/a |
|  | Total | 100 |

The dry blend process of making the batch 2850-RD is described below.
Blending:
Avicel PH 102 was screened through a 60 mesh screen. V-blenders (1 Qt, 4 Qt, and 16 Qt) were then dusted by the screened Avicel PH 102. SP-304 was screened through a 200 mesh screen and loaded into the 1-Qt V-blender. Then, about 80 g Avicel PH 102 was added into the 1-Qt blender and the mixture was blended for 10 minutes at 25 rpm. The mixture was then transferred to the 4-Qt V-blender which was pre-dusted by the screened Avicel PH 102. The 1-Qt blender was rinsed with Avicel and the rinse material was transferred to the 4-Qt blender. The rinsing was repeated until all SP-304 was transferred to the 4-Qt blender. About 200 g Avicel was added to the 4-Qt V-blender and the mixture was blended for 10 minutes. The resulting blend was then screened through a 60 mesh screen and then transferred into the pre-dusted 16-Qt blender (dusted with 1500 g Avicel). The 4-Qt blender was rinsed with Avicel and the rinse material was transferred to the 16-Qt blender. The remaining Avicel was added to the 16-Qt blender and the mixture was blended for 10 minutes. The resulting blend was passed through Comil and then returned to the 16-Qt blender and was further blended for 5 minutes. Proper amount of magnesium stearate was weighed, screened through a 60 mesh screen, and added into the 16-Qt blender. The resulting mixture was blended for 2 minutes.

Encapsulation

A MG2 Planeta capsule filler was set up. Average weight of the empty capsule shells was determined and target capsule fill weight was calculated (±5%). The blend from the above process was added into the hopper of the capsule filler and encapsulation was started. Run weight parameters were manually adjusted. Resulting capsules were then sorted according to the target fill weight.

Example 12

Composition of Batch 1528-2850B-RD (Tablets) and Process

| Item No. | Ingredient | Concentration % w/w |
|---|---|---|
| 1 | SP-304 | 0.3246 |
| 2 | Microcrystalline cellulose (Avicel PH 102) | 99.43 |
| 3 | Magnesium stearate | 0.2500 |
| | Total | 100 |

The dry blend process of making the batch 2850B-RD is described below.

Blending:

Avicel PH 102 was screened through a 60 mesh screen. V-blenders (1 Qt, 4 Qt, and 16 Qt) were then dusted by the screened Avicel PH 102. SP-304 was screened through a 200 mesh screen and loaded into the 1-Qt V-blender. Then, about 80 g Avicel PH 102 was added into the 1-Qt blender and the mixture was blended for 10 minutes at 25 rpm. The mixture was then transferred to the 4-Qt V-blender which was pre-dusted by the screened Avicel PH 102. The 1-Qt blender was rinsed with Avicel and the rinse material was transferred to the 4-Qt blender. The rinsing was repeated until all SP-304 was transferred to the 4-Qt blender. About 200 g Avicel was added to 4-Qt V-blender and the mixture was blended for 10 minutes. The resulting blend was then screened through a 60 mesh screen and then transferred into the pre-dusted 16-Qt blender (dusted with 1500 g Avicel). The 4-Qt blender was rinsed with Avicel and the rinse material was transferred to the 16-Qt blender. The remaining Avicel was added to the 16-Qt blender and the mixture was blended for 10 minutes. The resulting blend was passed through Comil and then returned to the 16-Qt blender and was further blended for 5 minutes. Proper amount of magnesium stearate was weighed, screened through a 60 mesh screen, and added into the 16-Qt blender. The resulting mixture was blended for 2 minutes.

Compression

A Fette tablet press was set up. Then the blend mixture was loaded into the powder hopper and tooling was installed. The weight of each tablet was set to be 90 mg±5% and hardness to be 4-6 Kp. The weight, hardness, and thickness of tablets were measured and recorded every 5 to 10 minutes. Friability measurement was also performed to ensure satisfactory product.

Example 13

Composition of Dry Blend Tablet Formulation 1528-3161-RD, 1 mg for Vacuum Drying

| Item No. | Ingredient | Concentration % w/w |
|---|---|---|
| 1 | SP-304 | 1.176 |
| 2 | Microcrystalline cellulose (Avicel PH 102) | 98.57 |
| 3 | Magnesium stearate | 0.2500 |
| | Total | 100 |

Example 14

Composition of Dry Blend Tablet Formulation 1528-3162-RD, 1 mg with Low-Moisture Cellulose

| Item No. | Ingredient | Concentration % w/w |
|---|---|---|
| 1 | SP-304 | 1.176 |
| 2 | Microcrystalline cellulose (Avicel PH 112) | 97.09 |
| 3 | Magnesium stearate | 0.2500 |
| | Total | 100 |

Example 15

Composition of Spray Coated Trehalose Granules Tablet Formulation 1528-3170-RD, 1 mg

| Item No. | Ingredient | Concentration % w/w |
|---|---|---|
| 1 | SP-304 | 1.176 |
| 2 | Trehalose granules | 70.48 |
| 3 | Methocel ES Premium LV | 0.50 |
| 4 | Histidine (in coating solution) | 0.9225 |
| 5 | Calcium ascorbate | 0.100 |
| 6 | Purified water | N/A |
| 7 | Trehalose powder (in coating solution) | 1.0176 |
| 8 | Microcrystalline cellulose (Avicel PH 200) | 25.00 |
| 9 | Histidine | 0.5535 |
| 10 | Magnesium stearate | 0.2500 |
| | Total | 100 |

The process for making spray coated trehalose Granules tablet formulation 1528-3170-RD is described below.

Preparation of the Coating Dispersion

Add purified water to labeled container and begin stiffing. Stir such that a liquid vortex is produced without introducing air into liquid. Slowly add Methocel to solution. Stir until methocel is completely dissolved. Warm the solution if necessary to dissolve Methocel (≤50° C.). Solution must be cooled before adding other materials. Add Trehalose to solution. Stir until materials are dissolved. Add Calcium Ascorbate to solution. Stir until materials are dissolved. Adjust pH to 7.0 with 1N NaOH solution if pH >7.0. Record adjusted pH. Place the Coating Solution in an ice bath and allow it stay in the batch for 0.5 to 1 hour until it reaches the ice temperature. Check with a thermometer to ensure at ice temperature. Weigh portions of required amount of API on a weighing boat and add each portion carefully to the cold Excipient Solution. Stir vigorously to allow peptide wetting and dissolving in the cold solution. Total amount of peptide must equal 14.107 g. Continue stiffing solution such that a liquid vortex is produced without introducing air into liquid. Stir until PLECANATIDE is completely dissolved. Keep peptide solution cold all the time in the ice bath. Add Histidine to solution. Stir not more than 10 min to dissolve the material. Obtain final pH of the Coating Solution. Obtain net weight of the Coating Solution. Coating Solution must be used within 30 min to avoid coloration.

Drug Layering

Setup Glatt GPCG2 with Wurster insert according to SOP EQP-OCM-064 for drug layering onto Trehalose Granules with coating dispersion. Use Glatt GPCG2 In-process form, "EQP-OCM-064-F1," to record in-process information. Turn unit on and preheat column. Fluid Bed Processor: Glatt GPCG-2. Filter: 200 micron screen. Product Container: 4" wurster, stainless steel. Insert height from bottom: 1". Spray direction: Top Spray. Fluid Nozzle Size/Type: 1 mm. Pump: Peristaltic, Master Flex LS. Tubing: Nalge #14 Silicon. Bed Temperature: ≤40° C. Inlet air temperature: Adjust to meet bed temperature target. Outlet air temperature: Monitor & record. Spray rate: initial rate 4-6 g/min, adjust as required. Atomizing air pressure: 20 psi. Air flow: 60 cmh and adjust for fluidization. Prepare double polyethylene bags large enough to hold drug layered Granules. Load column with Trehalose. Increase bed temperature to 35° C. and maintain for 30 minutes with minimum fluidization of the Granules. Reduce bed temperature until an exhaust temperature of 35° C. is achieved. Prime pump tubing by circulating spraying solution; must not use more than 40 g for tubing priming. Adjust the spraying apparatus to obtain satisfactory spray pattern. Coating Solution Weight after priming should >317 g. Record initial weight below before spraying onto trehalose. Start spraying the coating solution onto Trehalose Granules. Record operating parameters on fluid bed processing form. Stop spraying when 297.2 g of coating solution has been sprayed. Maintain bed temperature and continue fluidization until Granules are sufficiently dry. Reduce fluidization and maintain bed temperature at 35° C. for 10 minutes. Do not cool down the Granules. Sample 2 g for moisture analysis until moisture is below 1%. Discharge coated Granules into pre-prepared and labeled container (with tare weight) lined with double polyethylene bag. Calculate net weight of drug layered Granules. Setup Lyophilizer per SOP EQP-OCM-00002. Load drug layered granules into a Lyoguard tray (Save bags). Use recipe 3 to dry blend overnight. Discharge dried blend into saved polyethylene bags. Obtain final moisture of the dried granules. Record final Moisture (<1%). Calculate net weight of dried Granules.

Blending

Screen required Avicel and pass through 60 mesh screen. Setup 4 qt V-blender per SOP EQP-OCM-00056. Weigh amount of Histidine needed and blend with small amount of Avicel weighed. Charge into 4 qt. V-blender. Transfer Plecanatide Dried Granules into the V-Blender. Rinse 2-3 times the Lyoguard tray from Step 24 with adequate amount of Weighed Avicel Transfer rinses into 4 qt. V-blender. Transfer all remaining Pre-weighed/screened Avicel into the V-Blender. Mix for 15 minutes. Weigh and screen Magnesium Stearate through a 60 mesh screen. Charge Magnesium Stearate to the 4 qt V-Blender. Ensure the cover is securely closed with no potential powder leakage during blending. Blend for 2 minutes.

Compression

Set-up Korsch press per SOP EQP-OCM-00087. Install 0.250" Standard Concave Round Plain tolling. Obtain blend Assay results and calculate Target Tablet Weight. Acceptable weight range of tablets is ±5.0%. Load the Final Blend into the powder hopper. Refill as necessary. Adjust fill weight to obtain tablets in the range of 95.0-105.0 mg and hardness in the range of 4-6 kP. Verify friability is NMT 1.0%. Check 5 tablet weights periodically every 5-10 min to ensure tablet weight is within the range and record on form QRA-DOC-00011-F6. After tablet weights are recorded, obtain and record 3 tablet hardness and thickness during the periodic weight check. Continue to compress acceptable tablets until the blend is used up. Once press is running properly to achieve specifications above, perform final Friability test and record results (Spec: NMT 1.0%).

Example 16

Composition of Spray Coated Trehalose Granules Tablet Formulation 1528-3171-RD, 1 mg

| Item No. | Ingredient | Concentration % w/w |
|---|---|---|
| 1 | SP-304 | 1.167 |
| 2 | Trehalose granules | 70.31 |
| 3 | Methocel ES Premium LV | 0.50 |
| 4 | Arginine | 1.657 |
| 5 | Calcium ascorbate | 0.100 |
| 6 | Water for injection | N/A |
| 7 | Trehalose powder (in coating solution) | 1.0176 |
| 8 | Microcrystalline cellulose (Avicel PH 200) | 25.00 |
| 9 | Magnesium stearate | 0.2500 |
| | Total | 100 |

The process for making spray coated trehalose Granules tablet formulation 1528-3171-RD is described below.

Preparation of Coating Solution

Add purified water (Item 6) to labeled container and begin stirring. Stir such that a liquid vortex is produced without introducing air into liquid. Slowly add Methocel to solution. Stir until methocel is completely dissolved. Warm the solution if necessary to dissolve Methocel (≤50° C.). Record appearance of solution. Solution must be cooled before adding other materials. Add Trehalose to solution. Stir until materials are dissolved. Record appearance of solution. Add Arginine to solution. Stir until materials are dissolved. Record appearance of solution. Add Calcium Ascorbate to solution. Stir until materials are dissolved. Record appearance of solution. Adjust solution pH to pH 8.5-8.6 with concentrated HCl followed by adjust pH to 8.3-8.4 with 10N HCl. Record final adjusted pH. Place the Coating Solution in an ice bath and allow it stay in the batch for 0.5 to 1 hour until it reaches the ice temperature. Check with a thermometer to ensure at ice temperature. Weigh portions of required amount of API on a weighing boat and add each portion carefully to the cold Excipient Solution. Stir vigorously to allow peptide wetting and dissolving in the cold solution. Total amount of peptide must equal 14.006 g. Continue stirring solution such that a liquid vortex is produced without introducing air into liquid. Stir until PLECANATIDE is completely dissolved. Keep peptide solution cold all the time in the ice bath. Weigh 5.0 g of WFI to rinse API container. Carefully rinse the side of coating solution container and completely transfer the rinse back to the coating solution container. Obtain final pH of the Coating Solution. Obtain net weight of the Coating Solution (360.3 g). Coating Solution must be used within as soon as possible.

Drug Layering

Setup Glatt GPCG2 with Wurster insert according to SOP EQP-OCM-064 for drug layering onto Trehalose Granules with coating dispersion. Use Glatt GPCG2 In-process form, "EQP-OCM-064-F1," to record in-process information. Turn unit on and preheat column.

Fluid Bed Processor: Glatt GPCG-2. Filter: 200 micron screen. Product Container: 4" wurster, stainless steel. Insert height from bottom: 1". Spray direction: Top Spray. Fluid Nozzle Size/Type: 1 mm. Pump: Peristaltic, Master Flex LS. Tubing: Nalge #14 Silicon. Bed Temperature: ≤40° C. Inlet air temperature: Adjust to meet bed temperature target. Outlet air temperature: Monitor & record. Spray rate: initial rate 4-6 g/min, adjust as required. Atomizing air pressure: 20 psi. Air flow: 60 cmh and adjust for fluidization. Load column with Trehalose G. Increase bed temperature to 35° C. and maintain for 30 minutes with minimum fluidization of the Granules. Reduce bed temperature until an exhaust temperature of 35° C. is achieved. Prime pump tubing with coating solution. Must not use more than 40 g for tubing priming. Adjust the spraying apparatus to obtain satisfactory spray pattern. Record initial weight below before spraying onto trehalose. Start spraying the coating solution onto Trehalose Granules. Record operating parameters on fluid bed processing form. Stop spraying when 300.3 g of coating solution has been sprayed. Maintain bed temperature and continue fluidization until Granules are sufficiently dry. Reduce fluidization and maintain bed temperature at 35° C. for 10 minutes. Do not cool down the Granules. Sample 2 g for moisture analysis until moisture is below 1%. Discharge coated Granules into pre-prepared and labeled container (with tare weight) lined with double polyethylene bag. Calculate net weight of drug layered Granules. If moisture is >1%, vacuum dry blend as follows: Setup Lyophilizer per SOP EQP-OCM-00002. Load drug layered granules into a Lyoguard tray. Use recipe 3 to dry blend overnight. Discharge dried blend into saved polyethylene bags. Obtain final moisture of the dried granules. Calculate net weight of dried Granules.

Blending

Screen required Avicel and pass through 60 mesh screen. Setup 4 qt V-blender. Transfer Plecanatide Dried Granules into the V-Blender. Save bag for discharging final blend. Rinse 2-3 times the Lyoguard tray and bag with adequate amount of Weighed Avicel. Transfer rinses into 4 qt. V-blender. Transfer all remaining Pre-weighed/screened Avicel into the V-Blender. Mix for 20 minutes. Weigh and screen Magnesium Stearate through a 60 mesh screen. Charge Magnesium Stearate to the 4 qt V-Blender. Ensure the cover is securely closed with no potential powder leakage during blending. Blend for 2 minutes. Sample 3×350 mg of blend at three locations. Obtain exact weight of each sample that has been transferred into the sampling bottle.

Compression

Set-up Korsch press per SOP EQP-OCM-00087. Install 0.250" Standard Concave Round Plain tolling. Obtain blend Assay results and calculate Target Tablet Weight. Acceptable weight range of tablets is ±5.0%. Load the Final Blend into the powder hopper. Refill as necessary. Adjust fill weight to obtain tablets in the range of 95.0-105.0 mg and hardness in the range of 4-6 kP. Verify friability is NMT 1.0%. Check 5 tablet weights periodically every 5-10 min to ensure tablet weight is within the range. After tablet weights are recorded, obtain and record 3 tablet hardness and thickness during the periodic weight check. Continue to compress acceptable tablets until the blend is used up. Once press is running properly to achieve specifications above, perform final Friability test and record results (Spec: NMT 1.0%).

Example 17

Composition of Spray Coated Trehalose Granules Tablet Formulation 1528-3172, 1 mg

| Item No. | Ingredient | Concentration % w/w |
|---|---|---|
| 1 | SP-304 | 1.167 |
| 2 | Trehalose granules | 70.81 |
| 3 | Methocel ES Premium LV | 0.50 |
| 4 | TRIS | 1.1524 |
| 5 | Calcium ascorbate | 0.100 |
| 6 | Water for injection | N/A |
| 7 | Trehalose powder (in coating solution) | 1.0176 |
| 8 | Microcrystalline cellulose (Avicel PH 200) | 25.00 |
| 9 | Magnesium stearate | 0.2500 |
| | Total | 100 |

The process for making spray coated trehalose granules tablet formulation 1528-3172-RD is described below.

Preparation of Coating Solution

Add purified water to labeled container and begin stirring. Stir such that a liquid vortex is produced without introducing air into liquid. Slowly add Methocel to solution. Stir until methocel is completely dissolved. Warm the solution if necessary to dissolve Methocel (≤50° C.). Record appearance of solution.

Solution must be cooled before adding other materials. Add Trehalose to solution. Stir until materials are dissolved. Record appearance of solution. Add TRIS to solution. Stir until materials are dissolved. Record appearance of solution. Add Calcium Ascorbate to solution. Stir until materials are dissolved. Record appearance of solution. Obtain solution pH: Adjust pH to pH 7.8-7.9 with concentrated HCl followed by adjust pH to 7.7-7.6 with 10N HCl. Record final adjusted pH. Place the Coating Solution in an ice bath and allow it stay in the batch for 0.5 to 1 hour until it reaches the ice temperature. Check with a thermometer to ensure at ice temperature. Weigh portions of required amount of API on a weighing boat and add each portion carefully to the cold Excipient Solution. Stir vigorously to allow peptide wetting and dissolving in the cold solution. Total amount of peptide must equal 14.006 g. Continue stirring solution such that a liquid vortex is produced without introducing air into liquid. Stir until PLECANATIDE is completely dissolved. Keep peptide solution cold all the time in the ice bath. Weigh 5.0 g of WFI to rinse API container. Carefully rinse the side of coating solution container and completely transfer the rinse back to the coating solution container. Obtain final pH of the Coating Solution. Obtain net weight of the Coating Solution (~354.2 g). Coating Solution must be used as soon as possible.

The blending and compression processes for batch 1528-3172-RD are similar to that described above for batch 1528-3171-RD.

Example 18

Composition of 1 mg Dry Blend Tablet Formulation 1528-2925-RD

| Item No. | Ingredient | Concentration % w/w |
|---|---|---|
| 1 | SP-304 | 1.106 |
| 2 | Microcrystalline cellulose (Avicel PH 102) | 98.64 |
| 3 | Magnesium stearate | 0.2500 |
| | Total | 100 |

Example 19

Composition of 3 mg Dry Blend Tablet Formulation 1528-2926-RD

| Item No. | Ingredient | Concentration % w/w |
|---|---|---|
| 1 | SP-304 | 3.318 |
| 2 | Microcrystalline cellulose (Avicel PH 102) | 96.43 |
| 3 | Magnesium stearate | 0.2500 |
| | Total | 100 |

Other batches were prepared by the processes similar to those described in Examples 9-12. Their compositions are listed below.

Batch 500-55: 0.33% plecanatide, 95.17% microcyrstalline cellulose, 4.0% sodium starch glycolate, and 0.5% magnesium stearate.

Batches 1528-2907-RD and 2010F100A: 3.318% plecanatide, 96.43% Avicel, and 0.25% Mg stearate.

Batches 1528-2906-RD and 2010F099A: 1.106% plecanatide, 98.65% Avicel, and 0.25% Mg stearate.

Batches 1528-2890-RD and 2010F101A: 0.3246% plecanatide, 99.43% Avicel, and 0.25% Mg stearate.

Formula compositions for batches 11H141, 11H152, and 11H140 in this table below (not previously disclosed) are the same as the formula compositions for GMP stability batches 2010F101A, 2010F099A, and 2010F100A, respectively.

Example 20

Plecanatide Tablet and Capsule Stability

Capsules and tablets of different batches were tested for their stability and the results were provided. Unless otherwise specified, 1M, 2M, 3M, or 4M in the tables below denotes that the measurements were carried out at the end of 1, 2, 3, or 4 month(s) of the storage period.

Potency Summary: This test was performed by taking a composite sample of about 5 units to determine the average potency of the sample. The table below shows the stability of capsules or tablets in terms of potency (% of label claim).

| | | | | Potency (% Label Claim) | | | | | | | | |
|---|---|---|---|---|---|---|---|---|---|---|---|---|
| | | | | | | Storage Condition | | | | | | |
| Lot | | | | 40 C./75 RH | | | 30 C./65 RH | | | 25 C./60 RH | | |
| (description) | Bulk* | Package | Initial | 1 M | 2 M | 3 M | 1 M | 2 M | 3 M | 1 M | 2 M | 3 M |
| 1528-2850-RD (0.3 mg dry blend capsules) | 88 | HDPE bottle | | 89 | | 87 | | | 89 | | | 91 |
| | | Oxyguard bottle | | 91 | | 91 | | | 92 | | | 91 |
| | | Blister strip | 90 | 90 | | 85 | | | 88 | | | 91 |
| 1528-2855-RD (0.3 mg coated bead capsule) | 94 | HDPE bottle | | 101 | | 100 | | | 96 | | | 102 |
| | | Oxyguard bottle | | 101 | | 96 | | | 99 | | | 104 |
| | | Blister strip | | 97 | | 103 | | | 99 | | | 98 |
| 500-55 (0.3 mg dry blend capsule) | 97 | HDPE bottle | | 97 | | 94 | | | 95 | | | 96 |
| | | Oxyguard bottle | | 98 | | 96 | | | 96 | | | 102 |
| | | Blister strip | 93 | 97 | | 93 | | | 95 | | | 106 |
| 1528-2850B-RD (0.3 mg dry blend tablet) | 76 | HDPE bottle | | 85 | | 88 | | | 94 | | | 83 |
| | | Oxyguard bottle | | 84 | | 84 | | | 88 | | | 74 |
| 1528-2851-RD (0.3 mg coated particle tablet) | 96 | HDPE bottle | | 115 | | 72 | | | 90 | | | 99 |
| | | Oxyguard bottle | | 81 | | 88 | | | 83 | | | 111 |
| 2010F100A (3 mg dry blend capsule) | 101 | Blister strip | 97 | 95 | 94 | 91 | 95 | 95 | 92 | 97 | 95 | 93 |
| 2010F101A (0.3 mg dry blend capsule) | 97 | Blister strip | 92 | 91 | 91 | 86 | 94 | 92 | 85 | 95 | 93 | 88 |

-continued

| Lot (description) | | | | | | | | | | | | |
|---|---|---|---|---|---|---|---|---|---|---|---|---|
| 2010F099A (1 mg dry blend capsule) | 98 | Blister strip | 94 | 92 | 91 | 89 | 93 | 94 | 89 | 94 | 94 | 91 |
| 11H141 (0.3 mg dry blend capsule) | 103 | Blister strip | 101 | 95 | 92 | 87 | 98 | 93 | 92 | 96 | 92 | 95 |
| 11H152 (1 mg dry blend capsule) | 102 | Blister strip | 97 | 91 | 91 | 93 | 94 | 95 | 96 | 96 | 95 | 96 |
| 11H140 (3 mg dry blend capsule) | 105 | Blister strip | 99 | 94 | 95 | 94 | 95 | 94 | 97 | 99 | 95 | 97 |
| 1528-2925-RD (1 mg dry blend tablet) | 99 | Oxyguard 40 cc with PharmaKeep | | | | | | | | | | |
| 1528-2926-RD (3 mg dry blend tablet) | 100 | Oxyguard 40 cc with PharmaKeep | | | | | | | | | | |
| 1528-2907-RD (3 mg dry blend capsule) | 98 | | | | | | | | | | | |
| 1528-2906-RD (1 mg dry blend capsule) | 98 | | | | | | | | | | | |
| 1528-2890-RD (0.3 mg dry blend capsule) | 93 | | | | | | | | | | | |

| | | | Potency (% Label Claim) | | | | | | | |
|---|---|---|---|---|---|---|---|---|---|---|
| | | | Storage Condition | | | | | | | |
| Lot (description) | Bulk* | Package | 25 C./60 RH | | 5 C. | | | | | |
| | | | 7 M | 10 M | 1 M | 2 M | 3 M | 4 M | 7 M | 8.5 M |
| 1528-2850-RD (0.3 mg dry blend capsules) | 88 | HDPE bottle | | 80 | | | | 89.3 | | 89 |
| | | Oxyguard bottle | | 79 | | | | 88.9 | | 90 |
| | | Blister strip | 79 | | | | | | 90 | |
| 1528-2855-RD (0.3 mg coated bead capsule) | 94 | HDPE bottle | | 88 | | | | | | 98 |
| | | Oxyguard bottle | | 87 | | | | | | 100 |
| | | Blister strip | 87 | | | | | | 97 | |
| 500-55 (0.3 mg dry blend capsule) | 97 | HDPE bottle | 84 | | | | | | 98 | |
| | | Oxyguard bottle | | 83 | | | | | | 97 |
| | | Blister strip | | 83 | | | | | | 96 |
| 1528-2850B-RD (0.3 mg dry blend tablet) | 76 | HDPE bottle | | 67 | | | | | | 70 |
| | | Oxyguard bottle | | 74 | | | | | | 80 |
| 1528-2851-RD (0.3 mg coated particle tablet) | 96 | HDPE bottle | | 99 | | | | | | 78 |
| | | Oxyguard bottle | | 85 | | | | | | 96 |
| 2010F100A (3 mg dry blend capsule) | 101 | Blister strip | | | 97 | 94 | 94 | | | |
| 2010F101A (0.3 mg dry blend capsule) | 97 | Blister strip | | | 95 | 95 | 92 | | | |
| 2010F099A (1 mg dry blend capsule) | 98 | Blister strip | | | 95 | 94 | 92 | | | |
| 11H141 (0.3 mg dry blend capsule) | 103 | Blister strip | | | 100 | 97 | 97 | | | |

-continued

|  |  |  |  |  |  |  |
|---|---|---|---|---|---|---|
| 11H152 (1 mg dry blend capsule) | 102 | Blister strip |  | 97 | 95 | 97 |
| 11H140 (3 mg dry blend capsule) | 105 | Blister strip |  | 99 | 97 | 97 |
| 1528-2925-RD (1 mg dry blend tablet) | 99 | Oxyguard 40 cc with PharmaKeep | 99 |  |  | 103 |
| 1528-2926-RD (3 mg dry blend tablet) | 100 | Oxyguard 40 cc with PharmaKeep | 94 |  |  | 93 |
| 1528-2907-RD (3 mg dry blend capsule) | 98 |  |  |  |  |  |
| 1528-2906-RD (1 mg dry blend capsule) | 98 |  |  |  |  |  |
| 1528-2890-RD (0.3 mg dry blend capsule) | 93 |  |  |  |  |  |

*Blend

As demonstrated by the table above, there was little or no appreciable loss in potency after storage under accelerated conditions (40 C/75RH or 30 C/65RH), which suggests that these capsules or tablets could be stable at room temperature for 18 months or for longer times if refrigerated or stored at 25 C, Water content summary: The table below shows that the water content was stable over the testing period in the packages evaluated for various capsule/tablet compositions. This further demonstrated that products were stable,

| Lot | Water (in-process) | Packaging | Initial | Water packaged product | | | | | | | | |
|---|---|---|---|---|---|---|---|---|---|---|---|---|
|  |  |  |  | 40 C./75 RH | | | 30 C./65 RH | | | 25 C./60 RH | | |
|  |  |  |  | 1 M | 2 M | 3 M | 1 M | 2 M | 3 M | 1 M | 2 M | 3 M |
| 1528-2850-RD 0.3 mg dry blend capsule |  | 32-count, HDPE bottle, 60 cc, N2, 2 g mol. sieve |  | 5.03 |  | 5.64 |  |  | 3.00 |  |  | 2.22 |
|  |  | 32-count, Oxyguard bottle, 40 cc, PharmaKeep KD-20 |  | 5.07 |  | 5.24 |  |  | 4.28 |  |  | 5.33 |
|  |  | Blister, N2 | 4.21 | 4.87 |  | 5.80 |  |  | 4.76 |  |  | 4.31 |
| 1528-2855-RD 0.3 mg coated bead capsule | 2.40 | 32-count, HDPE bottle, 60 cc, N2, 2 g mol. sieve |  | 0.57 |  | 0.47 |  |  | 1.63 |  |  | 0.68 |
|  |  | 32-count, Oxyguard bottle, 40 cc, PharmaKeep KD-20 |  | 2.10 |  | 1.05 |  |  | 1.29 |  |  | 2.07 |
|  |  | Blister strip |  | 0.73 |  | 2.11 |  |  | 0.54 |  |  | 0.58 |
| 500-55 0.3 mg dry blend capsule |  | HDPE bottle |  | 5.63 |  | 4.19 |  |  | 5.51 |  |  | 5.79 |
|  |  | Oxyguard bottle |  | 5.78 |  | 4.69 |  |  | 5.90 |  |  | 5.66 |
|  |  | Blister strip | 4.09 | 5.78 |  | 4.17 |  |  | 5.53 |  |  | 6.16 |
| 1528-2850B-RD 0.3 mg dry blend tablet |  | 32-count, HDPE bottle, 60 cc, N2, 2 g mol. sieve |  | 4.09 |  | 4.03 |  |  | 6.28 |  |  | 6.10 |
|  |  | 32-count, Oxyguard bottle, 40 cc, PharmaKeep KD-20 |  | 4.81 |  | 4.91 |  |  | 6.15 |  |  | 6.30 |

-continued

| Lot | (in-process) | Packaging | | | | | | | | | | |
|---|---|---|---|---|---|---|---|---|---|---|---|---|
| 1528-2851-RD 0.3 mg coated particle tablet | 3.32 | 32-count, HDPE bottle, 60 cc, N2, 2 g mol. sieve | | 4.33 | | 4.50 | | | 5.09 | | | 5.90 |
| | | 32-count, Oxyguard bottle, 40 cc, PharmaKeep KD-20 | | 5.15 | | 4.88 | | | 5.82 | | | 6.02 |
| 2010F100A (3 mg dry blend capsule) | | Blister strip | 4.7 | 4.5 | 4.6 | 4.4 | 4.5 | 4.7 | 4.4 | 4.5 | 4.8 | 4.4 |
| 2010F101A (0.3 mg dry blend capsule) | | Blister strip | 4.5 | 4.8 | 4.7 | 4.7 | 4.5 | 4.7 | 4.3 | 4.4 | 4.7 | 4.3 |
| 2010F099A (1 mg dry blend capsule) | | Blister strip | 4.6 | 4.4 | 4.6 | 4.4 | 4.5 | 4.5 | 4.3 | 4.4 | 4.6 | 4.4 |
| 11H141 (0.3 mg dry blend capsule) | | Blister strip | 5 | 4.8 | 4.9 | 4.9 | 5.1 | 4.9 | 4.8 | 5.0 | 5.0 | 4.9 |
| 11H152 (1 mg dry blend capsule) | | Blister strip | 5.2 | 4.8 | 4.9 | 4.8 | 4.8 | 4.8 | 4.9 | 4.8 | 4.8 | 4.9 |
| 11H140 (3 mg dry blend capsule) | | Blister strip | 5.2 | 5.0 | 5.0 | 5.0 | 4.9 | 5.0 | 5.0 | 4.9 | 5.0 | 4.9 |
| 1528-2925-RD (1 mg dry blend tablet) | | Oxyguard 40 cc with PharmaKeep | | | | | | | | | | |
| 1528-2926-RD (3 mg dry blend capsule) | | Oxyguard 40 cc with PharmaKeep | | | | | | | | | | |
| 1528-2907-RD 3 mg dry blend capsule | | Bulk capsule | 4.78 | | | | | | | | | |
| 1528-2906-RD 1mg dry blend capsule | | Bulk capsule | 4.84 | | | | | | | | | |
| 1528-2890-RD | | Bulk capsule | 4.8 | | | | | | | | | |

| | Water | | Water packaged product | | | | | | | |
|---|---|---|---|---|---|---|---|---|---|---|
| | (in- | | 25 C./60 RH | | 5 C. | | | | | |
| Lot | process) | Packaging | 7 M | 10 M | 1 M | 2 M | 3 M | 4 M | 7 M | 8.5 M |
| 1528-2850-RD 0.3 mg dry blend capsule | | 32-count, HDPE bottle, 60 cc, N2, 2 g mol. sieve | | 2.39 | | | | 5.48 | | 1.8 |
| | | 32-count, Oxyguard bottle, 40 cc, PharmaKeep KD-20 | | 4.08 | | | | 5.31 | | 3.7 |
| | | Blister, N2 | | 4.09 | | | | | | 2.8 |
| 1528-2855-RD 0.3 mg coated bead capsule | 2.40 | 32-count, HDPE bottle, 60 cc, N2, 2 g mol. sieve | | 0.42 | | | | | | 0.2 |

-continued

| Sample | | Container | | | | | |
|---|---|---|---|---|---|---|---|
| | | 32-count, Oxyguard bottle, 40 cc, PharmaKeep KD-20 | 0.30 | | | | 0.8 |
| | | Blister strip | 0.32 | | | | 0.3 |
| 500-55 0.3 mg dry blend capsule | | HDPE bottle | 2.98 | | | | 2.7 |
| | | Oxyguard bottle | 2.99 | | | | 2.8 |
| | | Blister strip | 3.12 | | | | 2.9 |
| 1528-2850B-RD 0.3 mg dry blend tablet | | 32-count, HDPE bottle, 60 cc, N2, 2 g mol. sieve | 2.86 | | | | 2.1 |
| | | 32-count, Oxyguard bottle, 40 cc, PharmaKeep KD-20 | 4.05 | | | | 3.4 |
| 1528-2851-RD 0.3 mg coated particle tablet | 3.32 | 32-count, HDPE bottle, 60 cc, N2, 2 g mol. sieve | 2.55 | | | | 1.5 |
| | | 32-count, Oxyguard bottle, 40 cc, PharmaKeep KD-20 | 4.34 | | | | 3.0 |
| 2010F100A (3 mg dry blend capsule) | | Blister strip | | 4.5 | 4.8 | 4.5 | |
| 2010F101A (0.3 mg dry blend capsule) | | Blister strip | | 4.5 | 4.7 | 4.2 | |
| 2010F099A (1 mg dry blend capsule) | | Blister strip | | 4.2 | 4.7 | 4.3 | |
| 11H141 (0.3 mg dry blend capsule) | | Blister strip | | 5.0 | 4.9 | 4.9 | |
| 11H152 (1 mg dry blend capsule) | | Blister strip | | 5.0 | 4.9 | 4.8 | |
| 11H140 (3 mg dry blend capsule) | | Blister strip | | 4.9 | 4.9 | 4.8 | |
| 1528-2925-RD (1 mg dry blend tablet) | | Oxyguard 40 cc with PharmaKeep | 4.9 | | | | 4.0 |
| 1528-2926-RD (3 mg dry blend capsule) | | Oxyguard 40 cc with PhamaKeep | 4.0 | | | | 4.0 |
| 1528-2907-RD 3 mg dry blend capsule | | Bulk capsule | | | | | |
| 1528-2906-RD 1mg dry blend capsule | | Bulk capsule | | | | | |
| 1528-2890-RD | | Bulk capsule | | | | | |

Impurity summary: The table below shows the product stability in terms of HPLC or UPLC of total impurities as a function of time and storage condition. The data in the table suggest that the increase in total impurities in tested batches except batch 500-55 be no greater than 7% at room temperature after 18 months. It also suggest that the increase in total impurities in all tested 1528-2855-RD batch in different packages be no greater than 7% at 30° C. for 18 months. It was also observed that the 1528-2855-RD batch had less impurity increase than the 1528-2850-RD batch or was more stable than the 1528-2850-RD batch.

| | | | Total impurities % area | | | | | | | | |
|---|---|---|---|---|---|---|---|---|---|---|---|
| | | | 40 C./75 RH | | | 30 C./65 RH | | | 25 C./60 RH | | |
| Batch | Package | Initial | 1 M | 2 M | 3 M | 1 M | 2 M | 3 M | 1 M | 2 M | 3 M |
| 1528-2850-RD | HDPE bottle | 3.2 | 5.1 | | 5.9 | | | 4.4 | | | 3.8 |
| | Oxyguard bottle | | 5.7 | | 7.4 | | | 5.3 | | | 4.3 |
| | Blister strip | | 5.5 | | 7.0 | | | 5.0 | | | 4.3 |
| 1528-2855-RD | HDPE bottle | 3.5 | 3.6 | | 5.1 | | | 3.8 | | | 3.4 |
| | Oxyguard bottle | | 3.9 | | 4.4 | | | 4.1 | | | 3.7 |
| | Blister strip | | 4.0 | | 5.2 | | | 4.0 | | | 3.6 |
| 500-55 | HDPE bottle | 3.2 | 5.7 | | 8.4 | | | 5.4 | | | 4.4 |
| | Oxyguard bottle | | 5.6 | | 7.0 | | | 5.1 | | | 4.3 |
| | Blister strip | | 6.5 | | 8.0 | | | 5.7 | | | 4.8 |
| 1528-2850B-RD | HDPE bottle | 3.6 | 5.0 | | 6.5 | | | 4.5 | | | 3.9 |
| | Oxyguard bottle | | 5.6 | | 7.3 | | | 4.7 | | | 4.1 |
| 1528-2851-RD | HDPE bottle | 3.7 | 4.2 | | 5.1 | | | 4.0 | | | 3.8 |
| | Oxyguard bottle | | 4.9 | | 6.8 | | | 4.7 | | | 4.4 |
| 2010F101A (0.3 mg dry blend capsule) | Blister strip | 2.1 | 4.4 | 3.9 | 4.7 | 2.9 | 3.2 | 3.4 | 3.1 | 2.7 | 3.2 |
| 2010F099A (1 mg dry blend capsule) | Blister strip | 2.9 | 3.7 | 3.8 | 4.3 | 3.1 | 3.1 | 3.6 | 2.7 | 2.9 | 3.2 |
| 2010F100A (3 mg dry blend capsule) | Blister strip | 2.4 | 3.2 | 3.6 | 4.2 | 2.8 | 2.8 | 3.0 | 2.6 | 2.7 | 2.9 |
| 11H141 (0.3 mg dry blend capsule) | Blister strip | 1.3 | 3.3 | 4.2 | 4.5 | 2.5 | 3.6 | 3.3 | 2.0 | 2.8 | 2.9 |
| 11H152 (1 mg dry blend capsule) | Blister strip | 2.4 | 3.6 | 4.2 | 4.1 | 2.6 | 3.2 | 3.1 | 2.6 | 3.1 | 2.9 |
| 11H140 (3 mg dry blend capsule) | Blister strip | 2.1 | 3.5 | 3.7 | 4.5 | 2.6 | 2.7 | 3.3 | 2.5 | 2.7 | 2.9 |
| 1528-2925-RD (1 mg dry blend tablet) | Oxyguard 40cc with PharmaKeep | | | | | | | | | | |
| 1528-2926-RD (3 mg dry blend capsule) | Oxyguard 40cc with PharmaKeep | | | | | | | | | | |
| 1528-2906-RD | HDPE bottle | 1.83 | | 5.18 | | | | | | | |
| 1528-2907-RD | HDPE bottle | 1.85 | | 4.58 | | | | | | | |
| 1528-2890-RD | Bulk | 1.9 | | | | | | | | | |

-continued

|  |  | Total impurities % area ||||||||
|---|---|---|---|---|---|---|---|---|---|
|  |  | 25 C./60 RH || 5 C. ||||||
| Batch | Package | 7 M | 10 M | 1 M | 2 M | 3 M | 4 M | 7 M | 8.5 M |
| 1528-2850-RD | HDPE bottle |  | 4.8 |  |  |  | 3.1 |  | 3.7 |
|  | Oxyguard bottle |  | 5.3 |  |  |  | 3.1 |  | 3.5 |
|  | Blister strip |  | 5.5 |  |  |  |  |  | 3.7 |
| 1528-2855-RD | HDPE bottle |  | 4.4 |  |  |  |  |  | 3.4 |
|  | Oxyguard bottle |  | 4.0 |  |  |  |  |  | 3.7 |
|  | Blister strip |  | 4.2 |  |  |  |  |  | 3.8 |
| 500-55 | HDPE bottle |  | 6.0 |  |  |  |  |  | 3.5 |
|  | Oxyguard bottle |  | 5.6 |  |  |  |  |  | 3.5 |
|  | Blister strip |  | 6.5 |  |  |  |  |  | 3.6 |
| 1528-2850B-RD | HDPE bottle |  | 4.7 |  |  |  |  |  | 3.7 |
|  | Oxyguard bottle |  | 4.9 |  |  |  |  |  | 3.6 |
| 1528-2851-RD | HDPE bottle |  | 3.9 |  |  |  |  |  | 3.7 |
|  | Oxyguard bottle |  | 4.3 |  |  |  |  |  | 3.9 |
| 2010F101A (0.3 mg dry blend capsule) | Blister strip |  |  | 2.0 | 1.3 | 2.0 |  |  |  |
| 2010F099A (1 mg dry blend capsule) | Blister strip |  |  | 2.4 | 2.4 | 2.4 |  |  |  |
| 2010F100A (3 mg dry blend capsule) | Blister strip |  |  | 2.4 | 2.5 | 2.7 |  |  |  |
| 11H141 (0.3 mg dry blend capsule) | Blister strip |  |  | 1.4 | 1.5 | 1.8 |  |  |  |
| 11H152 (inig dry blend capsule) | Blister strip |  |  | 2.3 | 2.3 | 2.1 |  |  |  |
| 11H140 (3 mg dry blend capsule) | Blister strip |  |  | 2.3 | 2.2 | 1.8 |  |  |  |
| 1528-2925-RD (1 mg dry blend tablet) | Oxyguard 40cc with PharmaKeep | 2.7 |  |  |  |  |  | 1.7 |  |
| 1528-2926-RD (3 mg dry blend capsule) | Oxyguard 40cc with PharmaKeep | 2.6 |  |  |  |  |  |  |  |
| 1528-2906-RD | HDPE bottle |  |  |  |  |  |  |  |  |
| 1528-2907-RD | HDPE bottle |  |  |  |  |  |  |  |  |
| 1528-2890-RD | Bulk |  |  |  |  |  |  |  |  |

Content uniformity: This test was performed by placing 10 individual capsule/tablet units in 10 individual bottles and potency of each unit was measured to show whether individual capsules or tablets have uniform potency (% label claim or % LC).

| 0.3 mg Dry blend tablet 1528-2850B-RD | |
|---|---|
| Sample | % LC 1528-2850B-RD (dry tabs) |
| 1 | 78.62 |
| 2 | 91.43 |
| 3 | 86.52 |
| 4 | 90.9 |
| 5 | 84.83 |
| 6 | 95.29 |
| 7 | 75.69 |
| 8 | 76.87 |
| 9 | 84.92 |
| 10 | 86.9 |
| Mean | 85.2 |
| std. dev | 6.51 |
| % RSD | 7.64 |

| 0.3 mg Coated particle tablet 1528-2851-RD | | |
|---|---|---|
| Sample | Weight (mg) | % Label Claim |
| 1 | 88.86 | 69.55 |
| 2 | 89 | 94.41 |
| 3 | 88.89 | 94.34 |
| 4 | 88.6 | 72.18 |
| 5 | 88.37 | 142.52 |
| 6 | 88.76 | 149.44 |
| 7 | 89.42 | 78.8 |
| 8 | 88.56 | 131.08 |
| 9 | 89.08 | 102.55 |
| 10 | 88.78 | 99.13 |
| Mean | | 103.4 |
| St. Dev | | 28.53 |
| % RSD | | 27.59 |

| 0.3 mg Dry blend capsule 1528-2890 | | 3 mg Dry blend capsule 1528-2907-RD | | 1 mg Dry blend capsule 1528-2906-RD | |
|---|---|---|---|---|---|
| Sample | % LC | Sample | % LC | Sample | % LC |
| 1 | 87.2 | 1 | 94.5 | 1 | 98.1 |
| 2 | 94.6 | 2 | 101.2 | 2 | 101.8 |
| 3 | 92.6 | 3 | 97.9 | 3 | 93.1 |
| 4 | 94.2 | 4 | 94.5 | 4 | 97.5 |
| 5 | 93.5 | 5 | 95.9 | 5 | 97.9 |
| 6 | 91.7 | 6 | 95.2 | 6 | 97.1 |
| 7 | 91.6 | 7 | 96.1 | 7 | 94.5 |
| 8 | 99 | 8 | 99 | 8 | 100.1 |
| 9 | 91.8 | 9 | 93.8 | 9 | 98.1 |
| 10 | 92.1 | 10 | 93.4 | 10 | 97.9 |
| Mean | 92.8 | Mean | 96.2 | Mean | 97.6 |
| RSD | 3.20% | RSD | 2.60% | RSD | 2.50% |
| AV(10)*** | 12.8 | AV(10) | 8.4 | AV(10) | 6.8 |

***AV = acceptance value used for UPS <905> content uniformity. Idealy AV should be less than 15 to pass USP <905> content uniformity.

| 0.3 mg dry blend capsule 1528-2850-RD | | |
|---|---|---|
| Sample | Original % LC | Re-preparation % LC |
| 1 | 82.73 | 85.87 |
| 2 | 84.57 | 89.45 |
| 3 | 80.29 | 91.39 |
| 4 | 84.88 | 88.45 |
| 5 | 85.2 | 86.96 |
| 6 | 82.9 | 84.84 |
| 7 | 84.75 | 86.21 |
| 8 | 86.58 | 91.37 |
| 9 | 84.34 | 88.79 |
| 10 | 88.82 | 84.75 |
| Mean | 84.51 | 87.81 |
| std. dev | 2.288445 | 2.467121 |
| % RSD | 2.7 | 2.8 |

| Conte1528-2855-RD Sample | % LC | 1528-2850B-RD Sample | % LC |
|---|---|---|---|
| 1 | 88.82 | 1 | 78.62 |
| 2 | 93.73 | 2 | 91.43 |
| 3 | 89.06 | 3 | 86.52 |
| 4 | 84.94 | 4 | 90.9 |
| 5 | 89.93 | 5 | 84.83 |
| 6 | 88.7 | 6 | 95.29 |
| 7 | 88.71 | 7 | 75.69 |
| 8 | 86.85 | 8 | 76.87 |
| 9 | 86.92 | 9 | 84.92 |
| 10 | 91.33 | 10 | 86.9 |
| Mean | 88.9 | Mean | 85.2 |
| std. dev | 2.45 | std. dev | 6.51 |
| % RSD | 2.76 | % RSD | 7.64 |

| 500-55 | |
|---|---|
| Sample | % label claim |
| 1 | 96.90% |
| 2 | 99.40% |
| 3 | 103.20% |
| 4 | 96.90% |
| 5 | 100.00% |
| 6 | 99.60% |
| 7 | 96.90% |
| 8 | 102.80% |
| 9 | 96.80% |
| 10 | 93.90% |
| Mean | 98.60% |
| SD | 2.91 |
| RSD | 3.00% |
| AV | 7.1 (PASS) |

The data in the tables above show that all of the batches yield very good content uniformity acceptable for commercial product.

Dissolution 50-rpm summary: The tables below are summaries of the dissolution of drug from capsules or tablets in an unconventional small-volume apparatus needed to measure the small amount of drug in the units using slow stirring to look for changes in dissolution over time. The test was performed by placing one unit into a very small volume of water at 37 C with a paddle stirring at 50-rpm (which is slow) and data were collected at 15, 30 45, and 60 minutes to show the drug release rate over time. These tested products are "immediate release" oral solid dosage forms and a conventional requirement is to have about 75% released in about 45 minutes. The tables summarize the results at 45 minutes and indicate that dissolution was stable over time.

| Lot (description) | | Dissolution (% label claim at 45 minutes) | | | | | |
|---|---|---|---|---|---|---|---|
| | | Initial | 40 C./75 RH | | 30 C./65 RH | 25 C. | 5 C. |
| | | bulk | 0 M | 1 M | 2 M | 3 M | 3 M 4 M |
| 1528-2850-RD (dry blend V-Cap capsule HDPE bottle) | Vessel 1 | 85 | | 78 | 84 | 81 | 86 83 |
| | Vessel 2 | 87 | | 73 | 90 | 82 | 84 85 |
| | Vessel 3 | 88 | | 79 | 85 | 79 | 91 87 |
| | Vessel 4 | 84 | | 86 | 87 | 78 | 83 85 |
| | Vessel 5 | 89 | | 72 | 89 | 80 | 79 90 |
| | Vessel 6 | 88 | | 81 | 85 | 82 | 88 83 |
| | Average | 87 | | 78 | 87 | 80 | 85 85 |
| | RSD | 2 | | 6.4 | 2.7 | 2.1 | 5.0 2.9 |
| 1528-2850-RD (dry blend Vcap capsule OxyGuard bottle) | Vessel 1 | 85 | | 69 | 89 | 79 | 88 82 |
| | Vessel 2 | 87 | | 75 | 89 | 87 | 81 85 |
| | Vessel 3 | 88 | | 77 | 87 | 86 | 84 86 |
| | Vessel 4 | 84 | | 80 | 87 | 83 | 83 80 |
| | Vessel 5 | 89 | | 71 | 88 | 89 | 84 84 |
| | Vessel 6 | 88 | | 76 | 88 | 79 | 86 89 |
| | Average | 87 | | 75 | 88 | 84 | 84 84 |
| | RSD | 2 | | 5.3 | 1.2 | 5.2 | 3.1 3.6 |
| 1528-2850-RD (dry blend V-cap capsule blister strip) | Vessel 1 | 85 | 75 | 59 | 86 | 73 | 83 |
| | Vessel 2 | 87 | 89 | 77 | 79 | 81 | 81 |
| | Vessel 3 | 88 | 88 | 83 | 87 | 74 | 84 |
| | Vessel 4 | 84 | 89 | 67 | 93 | 85 | 83 |
| | Vessel 5 | 89 | 93 | 75 | 82 | 82 | 84 |
| | Vessel 6 | 88 | 90 | 82 | 90 | 67 | 87 |
| | Average | 87 | 87 | 74 | 86 | 77 | 84 |
| | RSD | 2 | 7 | 12.5 | 6.3 | 8.6 | 2.4 |

| Lot (description) | | Dissolution (% label claim at 45 minutes) | | | | |
|---|---|---|---|---|---|---|
| | | Initial | 40 C./75 RH | 30 C./65 RH | | 25 C. |
| | | bulk | 1 M | 2 M | 3 M | 3 M |
| 1528-2855-RD (coated bead V-Cap capsule HDPE bottle) | Vessel 1 | 104 | 85 | 100 | 79 | 83 |
| | Vessel 2 | 89 | 90 | 97 | 83 | 88 |
| | Vessel 3 | 91 | 84 | 71 | 91 | 50 |
| | Vessel 4 | 88 | 64 | 73 | 94 | 88 |
| | Vessel 5 | 94 | 75 | 72 | 75 | 92 |
| | Vessel 6 | 93 | 80 | 39 | 96 | 94 |
| | Average | 93 | 80 | 75 | 86 | 83 |
| | RSD | 6 | 12 | 29 | 9.7 | 20 |
| 1528-2855RD (coated bead V-cap capsule OxyGuard bottle) | Vessel 1 | 104 | 88 | 80 | 87 | 78 |
| | Vessel 2 | 89 | 79 | 91 | 86 | 94 |
| | Vessel 3 | 91 | 84 | 63 | 92 | 74 |
| | Vessel 4 | 88 | 92 | 98 | 90 | 98 |
| | Vessel 5 | 94 | 89 | 81 | 81 | 93 |
| | Vessel 6 | 93 | 44 | 99 | 81 | 78 |
| | Average | 93 | 79 | 85 | 86 | 86 |
| | RSD | 6 | 23 | 16 | 5.3 | 12.1 |

| Lot (description) | | Dissolution (% label claim at 45 minutes) | | | | |
|---|---|---|---|---|---|---|
| | | Initial | 40 C./75 RH | 30 C./65 RH | | 25 C. |
| | | bulk | 1 M | 2 M | 3 M | 3 M |
| 1528-2855-RD (coated bead V-cap capsule blister strip) | Vessel 1 | 104 | 85 | 98 | 100 | 81 |
| | Vessel 2 | 89 | 84 | 94 | 63 | 80 |
| | Vessel 3 | 91 | 97 | 96 | 82 | 87 |
| | Vessel 4 | 88 | 94 | 96 | 55 | 74 |
| | Vessel 5 | 94 | 64 | 75 | 95 | 66 |
| | Vessel 6 | 93 | 96 | 102 | 89 | 82 |
| | Average | 93 | 87 | 93 | 81 | 78 |
| | RSD | 6 | 14 | 10 | 22.4 | 9.2 |

| Lot (description) | | Dissolution (% label claim at 45 minutes) | | | |
|---|---|---|---|---|---|
| | | Initial | 40 C./75 RH | 30 C./65 RH | |
| | | bulk | 1M | 2M | 3M |
| 1528-2851-RD (coated particle tablet HDPE bottle) | Vessel 1 | 58% | 67 | 68 | 89 |
| | Vessel 2 | 77% | 84 | 78 | 124 |
| | Vessel 3 | 57% | 62 | 68 | 70 |
| | Vessel 4 | 96% | 110 | 84 | 105 |
| | Vessel 5 | 95% | 65 | 107 | 61 |
| | Vessel 6 | 64% | 103 | 76 | 51 |
| | Average | 74% | 82 | 80 | 83 |
| | RSD | 24% | 26 | 18 | 33 |
| 1528-2851-RD (coated particle tablet OxyGuard bottle) | Vessel 1 | 58% | 89 | 54 | 118 |
| | Vessel 2 | 77% | 73 | 101 | 69 |
| | Vessel 3 | 57% | 75 | 82 | 80 |
| | Vessel 4 | 96% | 68 | 67 | 73 |
| | Vessel 5 | 95% | 76 | 162 | 96 |
| | Vessel 6 | 64% | 97 | 82 | 95 |
| | Average | 74% | 80 | 91 | 89 |
| | RSD | 24% | 14 | 42 | 21 |

| Lot (description) | | Dissolution (% label claim at 45 minutes) | | | |
|---|---|---|---|---|---|
| | | Initial | 40 C./75 RH | 30 C./65 RH | |
| | | bulk | 1M | 2M | 3M |
| 1528-2850B-RD (dry blend tablet HDPE bottle) | Vessel 1 | 90% | 88 | 96 | 92 |
| | Vessel 2 | 69% | 79 | 82 | 92 |
| | Vessel 3 | 83% | 76 | 100 | 85 |
| | Vessel 4 | 94% | 96 | 86 | 94 |
| | Vessel 5 | 88% | 89 | 89 | 83 |
| | Vessel 6 | 92% | 83 | 97 | 83 |
| | Average | 86% | 85 | 92 | 88 |
| | RSD | 11% | 8.2 | 8 | 5.6 |
| 1528-2850B-RD (dry blend tablet OxyGuard bottle) | Vessel 1 | 90% | 74 | 80 | 91 |
| | Vessel 2 | 69% | 97 | 87 | 95 |
| | Vessel 3 | 83% | 91 | 86 | 90 |
| | Vessel 4 | 94% | 94 | 91 | 90 |
| | Vessel 5 | 88% | 83 | 91 | 89 |
| | Vessel 6 | 92% | 91 | 76 | 84 |
| | Average | 86% | 88 | 85 | 90 |
| | RSD | 11% | 9.6 | 7 | 4.0 |

| Lot (description) | | Initial bulk | 40 C./75 RH 0 M | 40 C./75 RH 1 M | 30 C./65 RH 2 M | 30 C./65 RH 3 M | 25 C. 3 M |
|---|---|---|---|---|---|---|---|
| 500-55 (dry blend V-Cap Plus capsule HDPE bottle) | Vessel 1 | 95 | | 90 | 92 | 91 | 89 |
| | Vessel 2 | 98 | | 85 | 98 | 97 | 98 |
| | Vessel 3 | 69 | | 85 | 96 | 94 | 76 |
| | Vessel 4 | 94 | | 89 | 95 | 100 | 97 |
| | Vessel 5 | 99 | | 89 | 97 | 98 | 86 |
| | Vessel 6 | 104 | | 100 | 99 | 94 | 92 |
| | Average | 93 | | 89 | 96 | 96 | 90 |
| | RSD | 13.1 | | 6.2 | 2.4 | 3.6 | 9.1 |
| 500-55 (dry blend V-Cap Plus capsule OxyGuard bottle) | Vessel 1 | 95 | | 84 | 103 | 99 | 94 |
| | Vessel 2 | 98 | | 97 | 101 | 95 | 103 |
| | Vessel 3 | 69 | | 97 | 99 | 98 | 97 |
| | Vessel 4 | 94 | | 92 | 97 | 92 | 96 |
| | Vessel 5 | 99 | | 91 | 100 | 95 | 101 |
| | Vessel 6 | 104 | | 96 | 95 | 93 | 91 |
| | Average | 93 | | 93 | 99 | 95 | 97 |
| | RSD | 13.1 | | 5.3 | 2.7 | 2.7 | 4.3 |
| 500-55 (dry blend V-Cap Plus capsule foil blister) | Vessel 1 | 95 | 98 | 99 | | 89 | 98 |
| | Vessel 2 | 98 | 101 | 88 | | 94 | 87 |
| | Vessel 3 | 69 | 107 | 90 | | 89 | 96 |
| | Vessel 4 | 94 | 96 | 90 | | 86 | 87 |
| | Vessel 5 | 99 | 99 | 68 | | 89 | 94 |
| | Vessel 6 | 104 | 99 | 90 | | 82 | 89 |
| | Average | 93 | 100 | 87 | | 88 | 92 |
| | RSD | 13.1 | 3.8 | 11.8 | | 4.3 | 5.5 |

| Dry blend 1 mg lot 1528-2906-RD 150-mL | | | | |
|---|---|---|---|---|
| | 15 min | 30 min | 45 min | 60 min |
| Vessel 1 | 65 | 92 | 96 | 99 |
| Vessel 2 | 49 | 91 | 95 | 96 |
| Vessel 3 | 46 | 88 | 96 | 97 |
| Vessel 4 | 44 | 96 | 101 | 102 |
| Vessel 5 | 39 | 78 | 93 | 99 |
| Vessel 6 | 57 | 90 | 95 | 96 |
| Average | 50 | 89 | 96 | 98 |
| RSD | 18.8 | 7 | 2.8 | 2.4 |

| Dry blend 0.3 mg lot 1528-2890-RD 50-mL | | | | |
|---|---|---|---|---|
| | 15 min | 30 min | 45 min | 60 min |
| Vessel 1 | 57 | 94 | 100 | 105 |
| Vessel 2 | 60 | 96 | 100 | 105 |
| Vessel 3 | 86 | 93 | 94 | 95 |
| Vessel 4 | 76 | 90 | 91 | 101 |
| Vessel 5 | 69 | 90 | 97 | 106 |
| Vessel 6 | 68 | 95 | 97 | 97 |
| Average | 69 | 93 | 97 | 102 |
| RSD | 15.6 | 2.8 | 3.4 | 4.5 |

| Capsule Dissolution at 45 minutes | | | | | | | | | | | | | |
|---|---|---|---|---|---|---|---|---|---|---|---|---|---|
| Lot | | 5 C. | | | 25 C. | | | 30 C. | | | 40 C. | | |
| (strength) | COA | 1 M | 2 M | 3 M | 1 M | 2 M | 3 M | 1 M | 2 M | 3 M | 1 M | 2 M | 3 M |
| 2011F101A (0.3 mg) | 98% | 99% | 95% | 95% | 95% | 92% | 95% | 94% | 93% | 97% | 93% | 90% | 92% |
| 2011F099A (1 mg) | 96% | 95% | 95% | 95% | 91% | 93% | 94% | 93% | 90% | 95% | 95% | 92% | 93% |
| 2011F100A (3 mg) | 99% | 101% | 97% | 97% | 100% | 95% | 95% | 98% | 95% | 95% | 96% | 93% | 95% |
| 11H141 (0.3 mg) | 101% | 102% | 101% | 101% | 105% | 96% | 106% | 102% | 97% | 103% | 99% | 96% | 98% |
| 11H152 (1 mg) | 96% | 96% | 99% | 97% | 96% | 99% | 97% | 96% | 96% | 98% | 96% | 96% | 98% |
| 11H140 (3 mg) | 102% | 102% | 102% | 101% | 105% | 100% | 97% | 102% | 99% | 102% | 101% | 99% | 96% |

| Dry blend 3 mg lot 1528-2907-RD 500-mL | | | | |
|---|---|---|---|---|
| | 15 min | 30 min | 45 min | 60 min |
| Vessel 1 | 91 | 96 | 97 | 96 |
| Vessel 2 | 96 | 95 | 97 | 96 |
| Vessel 3 | 96 | 97 | 97 | 97 |
| Vessel 4 | 95 | 102 | 100 | 100 |
| Vessel 5 | 97 | 96 | 96 | 97 |
| Vessel 6 | 92 | 99 | 98 | 98 |
| Average | 94 | 97 | 98 | 97 |
| RSD | 2.7 | 2.5 | 1.1 | 1.4 |

Dissolution 75-rpm: The tables below show a few examples where the stirring rate was increased slightly to 75-rpm to give more consistent results and indicates stable dissolution after accelerated storage of 1 or 2 months at 40 C 75% relative humidity.

| Dry blend 0.3 mg lot 1528-2850-RD 1M 40 C./75 RH 75-rpm 50-mL | | | | |
|---|---|---|---|---|
| | 15 min | 30 min | 45 min | 60 min |
| Vessel 1 | 75 | 80 | 80 | 81 |
| Vessel 2 | 61 | 75 | 80 | 82 |
| Vessel 3 | 65 | 81 | 83 | 84 |
| Vessel 4 | 78 | 86 | 84 | 85 |
| Vessel 5 | 66 | 79 | 83 | 84 |
| Vessel 6 | 62 | 79 | 84 | 86 |

2855-RD dissolution: The tables below are all the dissolution profiles of batch 1528-2850-RD and indicate stable drug release over time.

| | Dry blend 0.3 mg lot 1528-2850-RD 1M 40 C./75 RH 75-rpm 50-mL | | | |
|---|---|---|---|---|
| | 15 min | 30 min | 45 min | 60 min |
| Average | 68 | 80 | 82 | 84 |
| RSD | 10.3 | 4.5 | 2.3 | 2.2 |

| | Dry blend 1 mg lot 1528-2906A-RD 2M 40 C./75 RH 75-rpm 50-mL | | | |
|---|---|---|---|---|
| | 15 min | 30 min | 45 min | 60 min |
| Vessel 1 | 69 | 84 | 88 | 88 |
| Vessel 2 | 62 | 82 | 84 | 85 |
| Vessel 3 | 65 | 82 | 85 | 85 |
| Vessel 4 | 58 | 70 | 80 | 79 |
| Vessel 5 | 59 | 77 | 82 | 81 |
| Vessel 6 | 68 | 80 | 83 | 84 |
| Average | 64 | 79 | 84 | 84 |
| RSD | 7.2 | 6.4 | 3.3 | 3.8 |

| | Initial Percent Dissolved | | | |
|---|---|---|---|---|
| Vessel | 15 | 30 | 45 | 60 |
| 1 | 84% | 99% | 104% | 104% |
| 2 | 28% | 80% | 89% | 92% |
| 3 | 68% | 83% | 91% | 95% |
| 4 | 56% | 79% | 88% | 98% |
| 5 | 29% | 83% | 94% | 98% |
| 6 | 74% | 85% | 93% | 96% |
| Mean | 57% | 85% | 93% | 97% |
| RSD | 41.20% | 8.50% | 6.00% | 4.20% |

| | 1 M 40 C./75 RH OxyGuard Packaging | | | | 2 M 30 C./65 RH OxyGuard | | | | 3 M 30 C./65 RH OxyGuard | | | | 3 M 25 C./60 RH OxyGuard | | | |
|---|---|---|---|---|---|---|---|---|---|---|---|---|---|---|---|---|
| Vessel | 15 min | 30 min | 45 min | 60 min | 15 min | 30 min | 45 min | 60 min | 15 min | 30 min | 45 min | 60 min | 15 min | 30 min | 45 min | 60 min |
| 1 | 35 | 74 | 88 | 93 | 47 | 67 | 80 | 90 | 76 | 83 | 87 | 88 | 44 | 62 | 78 | 85 |
| 2 | 46 | 74 | 79 | 85 | 57 | 80 | 91 | 95 | 65 | 79 | 86 | 91 | 70 | 89 | 94 | 97 |
| 3 | 39 | 78 | 84 | 88 | 43 | 55 | 63 | 71 | 64 | 84 | 92 | 97 | 48 | 62 | 74 | 79 |
| 4 | 59 | 82 | 92 | 94 | 753 | 92 | 98 | 101 | 71 | 85 | 90 | 94 | 65 | 92 | 98 | 103 |
| 5 | 22 | 82 | 89 | 92 | 38 | 64 | 81 | 92 | 60 | 75 | 81 | 87 | 72 | 86 | 93 | 96 |
| 6 | 4 | 20 | 44 | 61 | 54 | 94 | 99 | 101 | 55 | 74 | 81 | 87 | 53 | 74 | 78 | 84 |
| Average | 34 | 68 | 79 | 86 | 52 | 75 | 85 | 92 | 65 | 80 | 86 | 91 | 59 | 78 | 86 | 91 |
| RSD | 57 | 35 | 23 | 14 | 25 | 21 | 16 | 12 | 11.7 | 5.7 | 5.3 | 4.6 | 20.1 | 17.4 | 12.1 | 10.4 |

| | 1 M 40 C./75 RH HDPE Bottle | | | | 2 M 30 C./65 RH HDPE | | | | 3 M 30 C./65 RH HDPE | | | | 3 M 25 C./60 RH HDPE | | | |
|---|---|---|---|---|---|---|---|---|---|---|---|---|---|---|---|---|
| Vessel | 15 min | 30 min | 45 min | 60 min | 15 min | 30 min | 45 min | 60 min | 15 min | 30 min | 45 min | 60 min | 15 min | 30 min | 45 min | 60 min |
| 1 | 61 | 78 | 85 | 89 | 78 | 97 | 100 | 103 | 58 | 72 | 79 | 85 | 54 | 70 | 83 | 92 |
| 2 | 63 | 83 | 90 | 92 | 77 | 93 | 97 | 98 | 51 | 72 | 83 | 90 | 66 | 81 | 88 | 92 |
| 3 | 66 | 79 | 84 | 91 | 41 | 59 | 71 | 78 | 53 | 84 | 91 | 94 | 10 | 29 | 50 | 66 |
| 4 | 25 | 44 | 64 | 77 | 50 | 65 | 73 | 78 | 66 | 89 | 94 | 95 | 69 | 81 | 88 | 92 |
| 5 | 47 | 67 | 75 | 80 | 37 | 59 | 72 | 83 | 48 | 66 | 75 | 81 | 68 | 83 | 92 | 97 |
| 6 | 57 | 71 | 80 | 85 | 6 | 21 | 39 | 52 | 85 | 94 | 96 | 99 | 82 | 91 | 94 | 97 |
| Average | 53 | 70 | 80 | 86 | 48 | 66 | 75 | 82 | 60 | 80 | 86 | 91 | 58 | 73 | 83 | 89 |
| RSD | 28 | 20 | 12 | 7 | 56 | 42 | 29 | 22 | 22.6 | 14 | 9.7 | 73 | 43 | 30.6 | 19.6 | 13.3 |

| | 1 M 40 C./75 RH Blister Packaging | | | | 2 M 30 C./65 RH Blister | | | | 3 M 30 C./65 RH Blister | | | | 3 M 25 C./60 RH Blister | | | |
|---|---|---|---|---|---|---|---|---|---|---|---|---|---|---|---|---|
| Vessel | 15 min | 30 min | 45 min | 60 min | 15 min | 30 min | 45 min | 60 min | 15 min | 30 min | 45 min | 60 min | 15 min | 30 min | 45 min | 60 min |
| 1 | 36 | 69 | 85 | 90 | 61 | 91 | 98 | 100 | 82 | 95 | 100 | 102 | 53 | 71 | 81 | 90 |
| 2 | 41 | 69 | 84 | 88 | 57 | 82 | 94 | 100 | 31 | 48 | 63 | 74 | 27 | 57 | 80 | 87 |
| 3 | 67 | 96 | 97 | 98 | 63 | 87 | 96 | 100 | 69 | 77 | 82 | 85 | 70 | 78 | 87 | 92 |
| 4 | 54 | 83 | 94 | 104 | 36 | 80 | 96 | 100 | 29 | 41 | 55 | 69 | 52 | 66 | 74 | 87 |
| 5 | 10 | 46 | 64 | 79 | 45 | 61 | 75 | 83 | 84 | 94 | 95 | 97 | 25 | 48 | 66 | 80 |
| 6 | 70 | 91 | 96 | 100 | 87 | 100 | 102 | 104 | 74 | 84 | 89 | 82 | 50 | 74 | 82 | 84 |
| Average | 47 | 76 | 87 | 93 | 58 | 83 | 93 | 98 | 62 | 73 | 81 | 85 | 46 | 66 | 78 | 87 |
| RSD | 48 | 25 | 14 | 10 | 30 | 16 | 10 | 8 | 40.5 | 32.1 | 22.4 | 14.9 | 37.0 | 17.0 | 9.2 | 5.3 |

Bathes 2850-RD, 2850B-RD, 2851-RD, and 500-55 were also tested in the similar fashion and all showed stable drug release over time.

---

We claim:

1. An oral dosage formulation of a Guanylate Cyclase-C (GCC) agonist peptide consisting of SEQ ID NO:1, wherein said peptide is a (4,12; 7,15) bicycle, an inert low moisture carrier and a lubricant, wherein the peptide has a chromatographic purity of no less than 91% after storage for at least three months.

2. The oral dosage formulation of claim 1, wherein the GCC agonist peptide has a chromatographic purity of no less than 92% to 95%.

3. The oral dosage formulation of claim 1, wherein the formulation contains less than 0.2% inorganic acids and carboxylic acids.

4. The oral dosage formulation of claim 1, wherein the formulation is a solid formulation and the unit dose is a powder, granule, sachet, troche, tablet, or capsule.

5. The oral dosage formulation of claim 1, wherein the GCC agonist peptide is stabilized against degradation for a period of at least 18 months at 30 ° C. and 65% relative humidity, or at least 18 months at 25 ° C. and 60% relative humidity, or at least 18 months at 2-8 ° C.

6. The oral dosage formulation of claim 1, wherein the formulation is in the form of a capsule or tablet.

7. The oral dosage formulation of claim 6, wherein the capsule or tablet is in a blister pack or strip.

8. The oral dosage formulation of claim 1, wherein the lubricant is magnesium stearate.

9. The oral dosage formulation of claim 1, wherein the lubricant is at 0.25% (w/w).

10. The oral dosage formulation of claim 1, wherein the inert carrier is microcrystalline cellulose.

11. The oral dosage formulation of claim 1, wherein the inert carrier is at least 96% (w/w).

12. The oral dosage formulation of claim 1, wherein the inert carrier has a particle size of from 50 to 900 microns.

* * * * *